US009828582B2

(12) United States Patent
Perez-Pinera et al.

(10) Patent No.: US 9,828,582 B2
(45) Date of Patent: Nov. 28, 2017

(54) COMPOSITIONS AND METHODS FOR THE INDUCTION AND TUNING OF GENE EXPRESSION

(71) Applicant: Duke University, Durham, NC (US)

(72) Inventors: Pablo Perez-Pinera, Durham, NC (US); Charles Gersbach, Durham, NC (US)

(73) Assignee: Duke University, Durham, NC (US)

( * ) Notice: Subject to any disclaimer, the term of this patent is extended or adjusted under 35 U.S.C. 154(b) by 0 days.

(21) Appl. No.: 14/220,116

(22) Filed: Mar. 19, 2014

(65) Prior Publication Data

US 2014/0309177 A1  Oct. 16, 2014

Related U.S. Application Data

(60) Provisional application No. 61/803,254, filed on Mar. 19, 2013.

(51) Int. Cl.
| | | |
|---|---|---|
| *C12N 15/63* | (2006.01) | |
| *C12N 5/071* | (2010.01) | |
| *A61K 38/17* | (2006.01) | |

(52) U.S. Cl.
CPC ........ *C12N 5/0602* (2013.01); *A61K 38/1709* (2013.01); *C12N 15/635* (2013.01); *C12N 2501/60* (2013.01)

(58) Field of Classification Search
CPC ................. C12N 15/63; C12N 15/85; C12N 2015/8518; C12N 15/62; A61K 48/005; A61K 48/00; C07K 2319/00
See application file for complete search history.

(56) References Cited

U.S. PATENT DOCUMENTS

| | | | |
|---|---|---|---|
| 5,593,972 | A | 1/1997 | Weiner et al. |
| 5,773,700 | A | 6/1998 | Van Grinsven et al. |
| 5,962,428 | A | 10/1999 | Carrano et al. |
| 2004/0175727 | A1 | 9/2004 | Draghia-Akli et al. |
| 2011/0197290 | A1 | 8/2011 | Fahrenkrug et al. |
| 2011/0301073 | A1* | 12/2011 | Gregory et al. ............... 514/1.1 |
| 2013/0274129 | A1* | 10/2013 | Katzen ............... C12N 15/1093 506/9 |
| 2014/0234975 | A1 | 8/2014 | Silva et al. |
| 2015/0159178 | A1 | 6/2015 | Green et al. |

FOREIGN PATENT DOCUMENTS

| | | | |
|---|---|---|---|
| CA | 2749305 | 7/2010 | |
| WO | WO 93/024640 | 12/1993 | |
| WO | WO 94/016737 | 8/1994 | |
| WO | WO 0183793 A2 * | 11/2001 | ......... C07K 14/4702 |
| WO | 2008/006028 | 1/2008 | |
| WO | 2011/036640 | 3/2011 | |
| WO | WO 2011/154427 | 12/2011 | |
| WO | WO 2013/163628 | 10/2013 | |

OTHER PUBLICATIONS

Verma et al. Gene therapy—promises, problems and prospects. Nature, vol. 389, pp. 239-242, 1997.*
Palù et al. In pursuit of new developments for gene therapy of human diseases. J. Biotechnol. vol. 68, pp. 1-13, 1999.*
Luo et al. Synthetic DNA delivery systems. Nature Biotechnology, vol. 18, pp. 33-37, 2000.*
Verma and Weitzman. Gene Therapy: Twenty-first century medicine. Annual Review of Biochemistry, vol. 74, pp. 711-738, 2005.*
Yan et al. Biochimica et Biophysica Acta, vol. 1835, No. 1, pp. 76-85, Jan. 2013.*
Edelstein et al. Gene therapy clinical trials worldwide 1989-2004—an overview. J. Gene Med. vol. 6, pp. 597-602, 2004.*
Latta-Mahieu et al. Gene transfer of a chimeric trans-activator is immunogenic and results in short-lived transgene expression. Human Gene Therapy, vol. 13, No. 13, pp. 1611-1620, Sep. 2002.*
Scholze et al. TAL effectors are remote controls for gene activation. Current Opinion in Microbiology, vol. 14, pp. 47-53, Jan. 2011.*
Perez-Pinera et al. Abstract 855. "Synergistic Transcriptional Activation by Combinations of Engineered TALEs" was publicly presented at the American Society of Gene & Cell Therapy's 15th Annual Meeting in Philadelphia, Pennsylvania during the Late Abstracts Poster Session III: Saturday, May 19, 2012.*
Perez-Pinera et al. Synergistic and tunable human gene activation by combinations of synthetic transcription factors. Nature Methods, vol. 10, No. 3, pp. 239-244, Feb. 3, 2013, including pp. 1/12-12-12 of Supplementary Material.*
Maeder et al. Robust, synergistic regulation of human gene expression using TALE activators. Nature Methods, vol. 10, No. 3, pp. 243-246, Feb. 10, 2013, including pp. 1/14-14/14 of Supplementary Material.*
Buler et al. Energy-sensing factors coactivator peroxisome proliferator-activated receptor gamma coactivator 1-alpha (PGC-1alpha) and AMP-activated protein kinase control expression of inflammatory mediators in liver. The Journal of Biological Chemistry, vol. 287, No. 3, pp. 1847-1860, Jan. 13, 2012.*
Lund et al. Promoter-targeted phage display selections with preassembled synthetic zinc finger libraries for endogenous gene regulation. Journal of Molecular Biology, vol. 340, pp. 599-613, 2004.*
Saito et al. Specific activation of microRNA-127 with downregulation of the proto-oncogene BCL6 by chromatin-modifying drugs in human cancer cells. Cancer Cell, vol. 9, pp. 435-443, Jun. 2006.*
Szyf, M. Epigenetics, DNA methylation, and chromatin modifying drugs. Annual Review of Pharmacology and Toxicology, vol. 49, pp. 243-263, 2009, published online Oct. 13, 2008.*
Seidel et al. Chromatin-modifygin agents in anti-cancer therapy. Biochimie, vol. 94, pp. 2264-2279, 2012.*
Aartsma-Rus, A. et al., "Antisense-mediated exon skipping: a versatile tool with therapeutic and research applications," RNA 13, 2007, 1609-1624.
Aartsma-Rus, A. et al., "Exploring the frontiers of therapeutic exon skipping for Duchenne muscular dystrophy by double targeting within one or multiple exons," Mol Ther, 2006, 14:401-407.
Aartsma-Rus, A. et al., "Theoretic applicability of antisense-mediated exon skipping for Duchenne muscular dystrophy mutations," Hum Mutat, 2009, 30:293-299.

(Continued)

*Primary Examiner* — Jennifer Dunston
(74) *Attorney, Agent, or Firm* — Michael Best & Friedrich LLP

(57) ABSTRACT

Disclosed herein are compositions of transcription activator-like effectors transcription factors and methods of using said compositions for inducing gene expression of mammalian genes.

1 Claim, 10 Drawing Sheets

(56) References Cited

OTHER PUBLICATIONS

Adler, A.F. et al., "Nonviral direct conversion of primary mouse embryonic fibroblasts to neuronal cells," Molecular therapy, 2012 Nucleic acids 1, e32.
Aiuti, A. et al., "Lentiviral hematopoietic stem cell gene therapy in patients with Wiskott-Aldrich syndrome," Science, 2013, 341(6148): p. 1233151.
Anders, S. et al., "Differential expression analysis for sequence count data," Genome biology 11, 2010, R106.
Anguela, X. M. et al., "Robust ZFN-mediated genome editing in adult hemophilic mice," Blood, 2013, 122:3283-3287.
Aoki, Y. et al., "Bodywide skipping of exons 45-55 in dystrophic mdx52 mice by systemic antisense delivery," Proc Natl Acad Sci USA, 2012, 109:13763-13768.
Bartsevich, V.V. et al., "Engineered zinc finger proteins for controlling stem cell fate," Stem Cells 21, 2003, 632-637.
Beerli, R. R. et al., "Chemically regulated zinc finger transcription factors," J Biol Chem, 2000, 275(42): p. 32617-27.
Beerli, R.R. et al., "Engineering polydactyl zinc-finger transcription factors," Nat Biotechnol 20, 2002, 135-141.
Beerli, R.R. et al., "Positive and negative regulation of endogenous genes by designed transcription factors," Proc Natl Acad Sci U S A 97, 2000, 1495-1500.
Beerli, R.R. et al., "Toward controlling gene expression at will: specific regulation of the erbB-2/HER-2 promoter by using polydactyl zinc finger proteins constructed from modular building blocks," Proc Natl Acad Sci U S A 95, 1998, 14628-14633.
Beltran, A. et al., "Re-activation of a dormant tumor suppressor gene maspin by designed transcription factors," Oncogene 26, 2007, 2791-2798.
Benedetti, S. et al., "Repair or Replace? Exploiting Novel Gene and Cell Therapy Strategies for Muscular Dystrophies," FEBS Journal (2013).
Berghella, L. et al., "Reversible immortalization of human myogenic cells by site-specific excision of a retrovirally transferred ondogene," Human gene therapy 10, 1999, 1607-1617.
Bhakta, M. S. et al., "Highly active zinc-finger nucleases by extended modular assembly," Genome Res, 2013, 530-538.
Bidou, L. et al., "Sense from nonsense: therapies for premature stop codon diseases," Trends in Molecular Medicine 18, 2012, 679-688.
Blancafort, P. et al., "Scanning the human genome with combinatorial transcription factor libraries," Nat Biotechnol 21, 2003, 269-274.
Boch, J. et al., "Breaking the code of DNA binding specificity of TAL-type III effectors," Science 326, 2009, 1509.
Bowles, D. E. et al., "Phase 1 Gene Therapy for Duchenne Muscular Dystrophy Using a Translation Optimized AAV Vector," Molecular Therapy 20, 2012, 443-455.
Brunet, E. et al., "Chromosomal translocations induced at specific loci in human stem cells," Proc Natl Acad Sci USA, 2009, 106:10620-10625.
Bultmann, S. et al., "Targeted transcriptional activation of silent oct4 pluripotency gene by combining designer TALEs and inhibition of epigenetic modifiers," Nucleic Acids Res 40, 2012, 5368-5377.
Cerletti, M. et al., "Highly efficient, functional engraftment of skeletal muscle stem cells in dystrophic muscles," Cell 134, 2008, 37-47.
Cermak, T. et al., "Efficient design and assembly of custom TALEN and other TAL effector-based constructs for DNA targeting," Nucleic Acids Res 30, 2011, e82.
Chapdelaine, P. et al., "Meganucleases can restore the reading frame of a mutual dystrophin," Gene therapy 17, 2010, 846-858.
Cheng, A. W. et al., "Multiplexed activation of endogenous genes by Crispr-on, an RNA-guided transcriptional activator system," Cell Res, 2013, 23(10): p. 1163-1171.
Cho, S. W. et al., "Analysis of off-target effects of CRISPR/Cas-derived RNA-guided endonucleases and nickases," Genome Res, 2014, 24:132-141.
Cho, S.W. et al., "Targeted genome engineering in human cells with the Cas9 RNA-guided endonuclease," Nat Biotechnol 31, 2013, 230-232.
Christian, M. et al., "Targeting DNA double-strand breaks with TAL effector nucleases," Genetics 186, 2010, 757-761.
Cirak, S. et al., "Exon skipping and dystrophin restoration in patients with Duchenne muscular dystrophy after systemic phosphorodiamidate morpholino oligomer treatment: an open-label, phase 2, dose-escalation study," Lancet 378, 2011, 595-605.
Cong, L. et al., "Multiplex Genome Engineering Using CRISPR/Cas Systems," Science 339, 2013, 819-823.
Cornu et al., "Quantification of zinc finger nuclease-associated toxicity," Meth Mol Biol, 2010, 649:237-245.
Cornu, T. I. et al., "DNA-binding specificity is a major determinant of the activity and toxicity of zinc-finger nucleases," Mol Ther, 2008, 16:352-358.
Cradick, T. J. et al., "CRISPR/Cas9 systems targeting beta-globin and CCR5 genes have substantial off-target activity," Nucleic Acids Res, 2013, 41(20): p. 9584-92.
Darabi, R. et al., "Human ES-and iPS-derived myogenic progenitors restore dystrophin and improve contractility upon transplantation in dystrophic mice," Cell Stem Cell 10, 2012, 610-619.
Dezawa, M. et al., "Bone marrow stromal cells generate muscle cells and repair muscle degeneration," Science Signaling 309, 2005, 314.
Ding, Q. et al., "A TALEN Genome-Editing System for Generating Human Stem Cell-Based Disease Models," 2013, Cell Stem Cell 12, 238-251.
Ding, Q. et al., "Enhanced efficiency of human pluripotent stem cell genome editing through replacing TALENs with CRISPRs," Cell Stem Cell, 2013, 12:393-394.
Doyle, E. L. et al., "TAL Effector-Nucleotide Targeter (TALE-NT) 2.0: tools for TAL effector design and target prediction," Nucleic Acids Res 40, 2012, W117-122.
Doyon, Y. et al., "Enhancing zinc-finger-nuclease activity with improved obligate heterodimeric architectures," Nat Methods 8, 2010, 74-79.
Esvelt et al., "Orthogonal Cas9 proteins for RNA-guided gene regulation and editing," Nature Methods 2013, 10(11): p. 1116-21.
Farinelli, G. et al., "Lentiviral vectors for the treatment of primary immunodeficiencies," J Inherit Metab Dis, 2014.
Farzadfard, F. et al., "Tunable and Multifunctional Eukaryotic Transcription Factors Based on CRISPR/Cas," ACS Synth Biol, 2013, 604-613.
Flanigan, K. M. et al., "Mutational spectrum of DMD mutations in dystrophinopathy patients: application of modern diagnostic techniques to a large cohort," Human mutation 30, 2009, 1657-1666.
Fonfara, I. et al., "Phylogeny of Cas9 determines funtional exchangeability of dual-RNA and Cas9 among orthologous type II CRISPR-Cas systems," Nucleic Acids Res, 2013.
Fu, Y., et al., "High-frequency off-target mutagenesis induced by CRISPR-Cas nucleases in humana cells," Nat Biotechnol, 2013, 31(9): p. 822-6.
Fu, Y., et al., "Improving CRISPR-Cas nuclease specificity using truncated guide RNAs," 2014, Nat Biotechnol 32, 279-284.
Gaj, T. et al., "Targeted gene knockout by direct delivery of zinc-finger nuclease proteins," Nature Methods, 2012.
Gaj, T. et al., "ZFN, TALEN, and CRISPR/Cas-based methods for genome engineering," Trends Biotechnol, 2013, 31:397-405.
Garg, A. et al., "Engineering synthetic TAL effectors with orthogonal target sites," Nucleic Acids Res 40, 2012, 7584-7595.
Gertz, J. et al., "Transposase mediated construction of RNA-seq libraries," Genome Res 22, 2012, 134-141.
Goemans, N. M. et al., "Systemic administration of PRO051 in Duchenne's muscular dystrophy," The New England journal of medicine 364, 2011, 1513-1522.
Gou, D. et al., "A novel approach for the construction of multiple shRNA expression vectors," J Gene Med, 2007, 9(9): p. 751-63.
Graslund, T. et al., "Exploring strategies for the design of artificial transcription factors: targeting sites proximal to known regulatory regions for the induction of gamma-globin expression and the treatment of sickle cell disease," J Biol Chem 280, 2005, 3707-3714.

(56) References Cited

OTHER PUBLICATIONS

Gregorevic, P. et al., "Systemic delivery of genes to striated muscles using adeno-associated viral vectors," Nat Med, 2004, 10:828-834.
Guo, J. et al., "Directed evolution of an enhanced and highly efficient FokI cleavage domain for zinc finger nucleases," J Mol Biol, 2010.
Guschin, D. Y. et al., "A rapid and general assay for monitoring endogenous gene modification," Methods Mol Biol 649, 2010, 247-256.
Hockemeyer, D. et al., "Efficient targeting of expressed and silent genes in human ESCs and iPSCs using zinc-finger nucleases," Nat Biotechnol, 2009, 27(9): p. 851-7.
Hockemeyer, D. et al., "Genetic engineering of human pluripotent cells using TALE nucleases," Nat Biotechnol 29, 2011, 731-734.
Hoffman, E. P. et al., "Dystrophin: the protein product of the Duchenne muscular dystrophy locus," Cell, 1987, 51:919.
Hou, Z. et al., "Efficient genome engineering in human pluripotent stem cells using Cas9 from Neisseria meningitidis," Proc Natl Acad Sci USA, 2013, 110:15644-15649.
Hsu et al., "DNA targeting specificity of RNA-guided Cas9 nucleases," Nature Biotechnology 31, 2013, 827-832 doi:10.1038/nbt.2647.
Hwang, W. Y. et al., "Efficient genome editing in zebrafish using CRISPR-Cas system," Nat Biotechnol, 2013, 31(3):p. 227-9.
International Search Report and Written Opinion for Application No. PCT/US13/38536 dated Nov. 29, 2013 (27 pages).
Jinek, M. et al., "A programmable dual-RNA-guided DNA endonuclease in adaptive bacterial immunity," Science 337, 2012, 816-821.
Jinek, M. et al., "RNA-programmed genome editing in human cells. eLife 2," e00471, 2013.
Jinek, M. et al., "Structures of Cas9 endonucleases reveal RNA-mediated conformational activation," Science, 2014, 343(6176): p. 1247997.
Joung, J. K. et al., "TALENs: a widely applicable technology for targeted genome editing," Nature Reviews Molecular Cell Biology 14, 2013, 49-55.
Kearns, N. A. et al., "Cas9 effector-mediated regulation of transcription and differentiation in human pluripotent stem cells," Development, 2014, 141(1): p. 219-23.
Kim, H. et al., "Surrogate reporters for enrichment of cells with nuclease-induced mutations," Nat Methods, 2011, 8:941-943.
Kim, Y. et al., "TALENs and ZFNs are associated with different mutation signatures," Nat Methods, 2013.
Kimura, E. et al., "Cell-lineage regulated myogenesis for dystrophin replacement: a novel therapeutic approach for treatment of muscular dystrophy," Hum Mol Genet 17, 2008, 2507-2517.
Konermann, S. et al., "Optical control of mammalian endogenous transcription and epigenetic states," Nature, 2013, 500(7463): p. 472-6.
Konieczny, P. et al., "Gene and cell-mediated therapies for muscular dystrophy," Muscle Nerve, 2013, 47:649-663.
Kubokawa, I. et al., "Molecular characterization of the 5'-UTR of retinal dystrophin reveals a cryptic intron that regulates translational activity," Molecular Vision, 2010, vol. 16, pp. 2590-2597.
Kyte et al., "A Simple Method for Displaying the Hydropathic Character of a Protein," J. Mol. Biol., 1982, 157:105-132.
Langmead, B. et al., "Ultrafast and memory-efficient alignment of short DNA sequences to the human genome," Genome biology 10, 2009, R25.
Larson, M. H. et al., "CRISPR interference (CRISPRi) for sequence-editing control of gene expression," Nat Protoc, 2013, 8(11): p. 2180-96.
Lattanzi, L. et al., "High efficiency myogenic conversion of human fibroblasts by adenoviral vector-mediated MyoD gene transfer. An alternative strategy for ex vivo gene therapy of primary myopathies," The Journal of clinical investigation 101, 1998, 2119-2128.
Lee, H. J. et al., "Targeted chromosomal deletions in human cells using zinc finger nucleases," Genome research 20, 2010, 81-89.
Li, D. et al., "Marginal level dystrophin expression improves clinical outcome in a strain of dystrophin/utrophin double knockout mice," PLoS One, 2010, 5:e15286.
Li, H. et al, "In vivo genome editing restores haemostasis in a mouse model of haemophilia," Nature 475, 2011, 217-221.
Li, T. et al., "Modularly assembled designer TAL effector nucleases for targeted gene knockout and gene replacement in eukaryotes," Nucleic Acids Research, 2011, vol. 39, No. 14, pp. 6315-6325.
Li, Y. et al., "Transcription activator-like effector hybrids for conditional control and rewiring of chromosomal transgene expression," Scientific reports 2, 2012, 897.
Liang, J.C. et al., "Engineering biological systems with synthetic RNA molecules," Mol Cell 43, 2011, 915-926.
Lohmueller, J.J. et al., "A tunable zinc finger-based framework for Boolean logic computation in mammalian cells," Nucleic Acids Res 40, 2012, 5180-5187.
Lovric, J. et al., "Terminal Differentiation of Cardiac and Skeletal Myocytes Induces Permissivity to AAV Transduction by Relieving Inhibition Imposed by DNA Damage Response Proteins," Molecular Therapy, 2012, 2087-2097.
Lu, Q. L. et al., "The status of exon skipping as a therapeutic approach to duchenne muscular dystrophy," Molecular Therapy 19, 2011, 9-15.
Maeder, M. L., "Targeted Dna demethylation and activation of endogenous genes using programmable TALE-TET 1 fusion proteins," Nat Biotechnol, 2013, 31(12): p. 1137-42.
Mali, P. et al., "Cas9 as a versatile tool for engineering biology," Nat Methods, 2013, 10(10): p. 957-63.
Mali, P. et al., "CAS9 transcriptional activators for target specificity screening and paired nickases for cooperative genome engineering," Nat Biotechnol, 2013, 31(9): p. 833-8.
Mali, P. et al., "RNA-Guided Human Genome Engineering via Cas9," Science 339, 2013, 823-826.
Mamchaoui, K. et al., "Immortalized pathological human myoblasts: towards a universal tool for the study of neuromuscular disorders," Skelet Muscle 1, 2011, 1-11.
Mendell, J. R. et al., "Dystrophin immunity in Duchenne's muscular dystrophy," New England Journal of Medicine 363, 2010, 1429-1437.
Mendenhall, E. M. et al., "Locus-specific editing of histone modification at endogenous enhancers," Nat Biotechnol, 2013, 31(12): p. 1133-6.
Mercer, A. C. et al., "Regulation of Endogenous Human Gene Expression by Ligand-Inducible TALE Transcription Factors," ACS Synth Biol, 2013.
Miller, J.C. et al., "A TALE nuclease architecture for efficient genome editing," Nat Biotechnol 29, 2011, 143-148.
Moscow, M. J. et al., "A simple cipher governs DNA recognition by TAL effectors," Science 326, 2009, 1501.
Murphy et al., "The in vitro transcription of the 7SK RNA gene by RNA polymerase III is dependable only on the presence of an upstream promoter," Cell, 1987, 51:81-87.
Mussolino, C. et al., "A novel TALE nuclease scaffold enables high genome editing activity in combination with low toxicity," Nucleic Acids Res 39, 2011, 9283-9293.
Myslinski et al., "An unusually compact external promoter for RNA polymerase III transcription of the human H1RNA gene," Nucleic Acids Res, 2001, 29:2502-2509.
Negroni, E. et al., "In Vivo Myogenic Potential of Human CD133+ Muscle-derived Stem Cells: A Quantitative Study," Molecular Therapy 17, 2009, 1771-1778.
Nishimasu, H. et al., Crystal structure of cas9 in complex with guide RNA and traget DNA Cell, 2014, 156(5): p. 935-49.
Ohshima et al., "Nucleotide sequence of mouse genomic loci including a gene or pseudogene for U6 (4.85) nuclear RNA," Nucleic Acids Res, 1981, 9:5145-5158.
Ousterout et al., "Reading frame correction by targeted genome editing restores dystrophin expression in cells from Duchenne muscular dystrophy patients," Mol Ther, 2013, 21:1718-1726.
Papayannakos, C. et al., "Understanding lentiviral vector chromatin targeting: working to reduce insertional mutagenic potential for gene therapy," Gene Ther, 2013, 20(6): p. 581-8.

(56) References Cited

OTHER PUBLICATIONS

Park, K.S. et al., "Phenotypic alteration of eukaryotic cells using randomized libraries of artificial transcription factors," Nat Biotechnol 21, 2003, 1208-1214.
Pattanayak, V. et al., "High-throughput profiling of off-target DNA cleavage reveals RNA-programmed Cas9 nuclease specificity," Nat Biotechnol, 2013, 31(9): p. 839-43.
Peault, B. et al., "Stem and progenitor cells in skeletal muscle development, maintenance, and therapy," Molecular Therapy 15, 2007, 867-877.
Perez, E. et al., "Establishment of Hiv-1 resistance in CD4+ T cells by genome editing using zinc-finger nucleases," Nature biotechnology 26, 2008, 808-816.
Perez-Pinera et al., "Gene targeting to the ROSA26 locus directed by engineered zinc finger nucleases," Nucleic Acids Research, 2012, 40:3741-3752.
Perez-Pinera et al., "RNA-guided gene activation by CRISPR-Cas9-based transcription factors," Nat Methods, 2013, 10:973-976.
Perez-Pinera, P. et al., "Advances in targeted genome editing," Current Opinion in Chemical Biology 16, 2012, 268-277.
Persons, D. A., "Lentiviral vector gene therapy: effective and safe?" Mol Ther, 2010, 18(5): p. 861-2.
Piacentino et al., "X-Linked Inhibitor of Apoptosis Protein-Mediated Attenuation of Apoptosis, Using a Novel Cardiac-Enhanced Adeno-Associated Viral Vector," Human Gene Therapy, 2012, 23:635-646.
Pichavant, C. et al., "Current status of pharmaceutical and genetic therapeutic approaches to treat DMD," Molecular Therapy 19, 2011, 830-840.
Polstein, L. R. and Gersbach, C. A., "Light-inducible spatiotemporal control of gene activation by customizable zinc finger transcription factors," J Am Chem Soc, 2012, 134(40): p. 16480-3.
Popplewell, L. et al., "Gene correction of a duchenne muscular dystrophy mutation by meganuclease-enhanced exon knock-in," Hum Gene Ther, 2013, 24:692-701.
Qi, L.S. et al., "Repurposing CRISPR as an RNA-guided platform for sequence-specific control of gene expression," Cell 152, 2013, 1173-1183.
Ran, F. A. et al., "Double nicking by RNA-guided CRISPR Cas9 for enhanced genome editing specificity," Cell, 2013, 154(6): p. 1380-9.
Rebar, E.J. et al., "Induction of angiogenesis in a mouse model using engineered transcription factors," Nat Med 8, 2002, 1427-1432.
Reyon, D. et al., "FLASH assembly of TALENs for high-throughput genome editing," Nat Biotechnol 30, 2012, 460-465.
Rousseau, J. et al., "Endonucleases: tools to correct the dystrophin gene" The Journal of Gene Medicine, 2011, vol. 13, pp. 522-537.
Salmon, P. and Trono, D., "Production and titration of lentiviral vectors," Curr Protoc Neurosci, 2006, Chapter 4: Unit 4 21.
Sambrook et al., Molecular Cloning and Laboratory manual, Second Ed., Cold Spring Harbor (1989), Book 1, pp. xi-xxi; Book 2, pp. xxii-xxxi; Book 3, pp. xxvi-xxxviii.
Schmid-Burgk, J. L. et al., "A ligation-independent cloning technique for high-throughput of transcription activator-like effector genes," Nat Biotechnol 31, 2012, 76-81.
Schultz, B. R. & Chamberlain, J. S., "Recombinant adeno-associated virus transduction and integration," Molecular Therapy 16, 2008, 1189-1199.
Sebastiano, V. et al., "In Situ Genetic Correction of the Sickle Cell Anemia Mutation in Human Induced Pluripotent Stem Cells Using Engineered Zinc Finger Nucleases," Stem Cells 29, 2011, 1717-1726.
Seto et al., "Gene Replacement Therapies for Duchenne Muscular Dystrophy Using Adeno-Associated Viral Vectors," Current Gene Therapy, 2012, 12:139-151.
Sharma, S. et al., "Efficiency of nonhomologous DNA and joining varies among somatic tissues, despite similarity in mechanism," Cellular and Molecular Life Science 68, 2011, 661-676.
Silva, G. et al., "Meganucleases and other tools for targeted genome engineering: perspective and challenges for gene therapy," Current gene therapy, 2011, 11:11-27.
Şöllü, C. et al., "Autonomous zinc-finger nuclease pairs for targeted chromosomal deletion," Nucleic acids research 38, 2010, 8269-8276.
Song, L. et al., "Dnase-seq: a high-resolution technique for mapping active gene regulatory elements across the genome from mammalian cells," Cold Spring Harbor protocols 2010, pdb prot5384.
Song, L. et al., "Open chromatin defined by DNaseI and FAIRE identifies regulatory elements that shape cell-type identify," Genome Res 21, 2011, 1757-1767.
Sun, N. et al., "Optimized Tal effector nucleases (TALENs) for use in treatment of sickle cell disease," Molecular bioSystems 8, 2012, 1255-1263.
Taniguchi-Ikeda, M. et al., "Pathogenic exon-trapping by SVA retrotransposon and rescue in Fukuyama muscular dystrophy," Nature 478, 2011, 127-131.
Tebas, P. et al., "Gene editing of CCR5 in autologous CD4 T cells of persons infected with HIV," N Engl J Med, 2014, 370:901-910.
Tedesco, F. S. et al., "Reparing skeletal muscle: regenerative potential of skeletal muscle stem cells," J Clin Invest, 2010, 120:11-19.
Tedesco, F. S. et al., "Stem Cell-Mediated Transfer of a Human Artificial Chromosome Ameliorates Musculat Dystrophy," Science Translational Medicine 3, 96ra78-96ra78, 2011.
Tedesco, F. S. et al., "Transplantation of Genetically Corrected Human iPSC-Derived Progenitors in Mice with Limb-Girdle Muscular Dystrophy," Science Translational Medicine 4, 140ra189, 2012.
Urnov, F. et al., "Highly efficient endogenous human gene correction using designed zinc-finger nucleases," Nature 435, 2005, 646-651.
Van Putten, M. et al., "Low dystrophin levels in heart can delay heart failure in mdx mice," J Mol Cell Cardiol, 2014, 69C:17-23.
Van Putten, M. et al., "Low dystrophin levels increase survival and improve muscle pathology and function in dystrophin/utrophin double-knockout mice," FASEB J, 2013, 27:2484-2495.
Vierbuchen, T. et al., "Direct conversion of fibroblasts to functional neurons by defined factors," Nature 463, 2010, 1035-1041.
Wang, H. et al., "One-Step Generation of Mice Carrying Mutations in Multiple Genes by CRISPR-Cas-Mediated Genome Engineering," Cell, 2013, 153(4): p. 910-8.
Wang et al., "Adeno-associated virus vector carrying human minidystrophin genes effectively ameliorates muscular dystrophy in mdx mouse model," Proc Natl Acad Sci US A. (2000) 97(25):13714-13719.
Wein, N. et al., "Efficient bypass of mutations in dysferlin deficient patient cells by antisense-induced exon skipping," Hum Mutat 31, 2010, 136-142.
Welch, E. M. et al., "PTC124 targets genetic disorders caused by nonsense mutations," Nature 447, 2007, 87-91.
Yang, L., "Optimization of scarless human stem cell genome editing," Nucleic Acids Res, 2013, 41:9049-9061.
Yusa, K. et al., "Targeted gene correction of α1-antitrypsin deficiency in induced pluripotent stem cells," Nature 478, 2011, 391-394.
Zhang, F. et al. "Efficient construction of sequence-specific TAL effectors for modulating mammalian transcription," Nat Biotechnol 29, 2011, 149-153.
Zhu, C. H. et al., "Cellular senescence in human telomerase reverse transcriptase and cyclin-dependent kinase 4: consequences in aging muscle and therapeutic strategies for muscular dystrophies," Aging cell 6, 2007, 515-523.
Zou, J. et al., "Site-specific gene correction of a point mutation in human iPS cells derived from an adult patient with sickle cell disease," Blood 118, 2011, 4599-4608.
International Search Report and Written Opinion for Application No. PCT/US14/41190 dated Dec. 17, 2014 (14 pages).
United States Patent Office Action for U.S. Appl. No. 14/397,420 dated Jun. 2, 2016 (7 pages).
Humbert et al., "Targeted gene therapies: tools, applications, optimization", Critical Reviews in Biochemistry and Molecular Biology, CRC Press, vol. 47, No. 3, Apr. 2012, pp. 264-281.

(56) References Cited

OTHER PUBLICATIONS

Kayali et al., "Site-directed gene repair of the dystrophin gene mediated by PNA-ssODNs," Human Molecular Genetics, vol. 19, No. 16, Aug. 15, 2010, pp. 3266-3281.
Hsu et al. (2012) "Dissecting Neural Function Using Targeted Genome Engineering Technologies", ACS Chem. Neurosci., pp. 603-610.
United States Patent Office Action for U.S. Appl. No. 14/397,420 dated Oct. 5, 2016 (10 pages).
United States Patent Office Action for U.S. Appl. No. 14/895,316 dated Dec. 15, 2016 (13 pages).

* cited by examiner

Figure 3

SEQUENCE LISTING

<160> NUMBER OF SEQ ID NOS: 98

<210> SEQ ID NO 1
<211> LENGTH: 17
<212> TYPE: DNA
<213> ORGANISM: Homo sapiens

<400> SEQUENCE: 1
gggctcctcc ttgtact                                                    17

<210> SEQ ID NO 2
<211> LENGTH: 17
<212> TYPE: DNA
<213> ORGANISM: Homo sapiens

<400> SEQUENCE: 2
ggcatcaagt cagccat                                                    17

<210> SEQ ID NO 3
<211> LENGTH: 18
<212> TYPE: DNA
<213> ORGANISM: Homo sapiens

<400> SEQUENCE: 3
agcctgagtc accctcct                                                   18

<210> SEQ ID NO 4
<211> LENGTH: 18
<212> TYPE: DNA
<213> ORGANISM: Homo sapiens

<400> SEQUENCE: 4
acgcagataa gaaccagt                                                   18

```
<210> SEQ ID NO 5
<211> LENGTH: 18
<212> TYPE: DNA
<213> ORGANISM: Homo sapiens

<400> SEQUENCE: 5
gtctggcttg ttcccaat                                                  18

<210> SEQ ID NO 6
<211> LENGTH: 20
<212> TYPE: DNA
<213> ORGANISM: Homo sapiens

<400> SEQUENCE: 6
cctaggtccc tcaaaagcat                                                20

<210> SEQ ID NO 7
<211> LENGTH: 17
<212> TYPE: DNA
<213> ORGANISM: Homo sapiens

<400> SEQUENCE: 7
ccagcctcca gcagcat                                                   17

<210> SEQ ID NO 8
<211> LENGTH: 16
<212> TYPE: DNA
<213> ORGANISM: Homo sapiens

<400> SEQUENCE: 8
agctctccct cccctt                                                    16

<210> SEQ ID NO 9
<211> LENGTH: 16
<212> TYPE: DNA
<213> ORGANISM: Homo sapiens

<400> SEQUENCE: 9
cccctagatg aagtct                                                    16

<210> SEQ ID NO 10
<211> LENGTH: 19
<212> TYPE: DNA
<213> ORGANISM: Homo sapiens

<400> SEQUENCE: 10
acccaccccc tgtttctgt                                                 19

<210> SEQ ID NO 11
<211> LENGTH: 16
<212> TYPE: DNA
<213> ORGANISM: Homo sapiens

<400> SEQUENCE: 11
cttggagtgc aaagga                                                    16

<210> SEQ ID NO 12
<211> LENGTH: 17
<212> TYPE: DNA
<213> ORGANISM: Homo sapiens

<400> SEQUENCE: 12
ctcacaatct cctgagt                                                   17
```

```
<210> SEQ ID NO 13
<211> LENGTH: 16
<212> TYPE: DNA
<213> ORGANISM: Homo sapiens

<400> SEQUENCE: 13
ctgtggacca caagat                                                   16

<210> SEQ ID NO 14
<211> LENGTH: 18
<212> TYPE: DNA
<213> ORGANISM: Homo sapiens

<400> SEQUENCE: 14
aaagaccaca cccatgac                                                 18

<210> SEQ ID NO 15
<211> LENGTH: 16
<212> TYPE: DNA
<213> ORGANISM: Homo sapiens

<400> SEQUENCE: 15
ctgaggaact gaaaat                                                   16

<210> SEQ ID NO 16
<211> LENGTH: 18
<212> TYPE: DNA
<213> ORGANISM: Homo sapiens

<400> SEQUENCE: 16
ccaccttgcc gaaaagat                                                 18

<210> SEQ ID NO 17
<211> LENGTH: 17
<212> TYPE: DNA
<213> ORGANISM: Homo sapiens

<400> SEQUENCE: 17
tgtcctccca ggggatg                                                  17

<210> SEQ ID NO 18
<211> LENGTH: 16
<212> TYPE: DNA
<213> ORGANISM: Homo sapiens

<400> SEQUENCE: 18
ctgtcacaaa ggaaaa                                                   16

<210> SEQ ID NO 19
<211> LENGTH: 19
<212> TYPE: DNA
<213> ORGANISM: Artificial sequence
<220> FEATURE:
<223> OTHER INFORMATION: Synthetic

<400> SEQUENCE: 19
gttgggcatc atcccacct                                                19

<210> SEQ ID NO 20
<211> LENGTH: 17
<212> TYPE: DNA
<213> ORGANISM: Artificial sequence
<220> FEATURE:
<223> OTHER INFORMATION: Synthetic
```

<400> SEQUENCE: 20
ccctccacca cagtcct                                                          17

<210> SEQ ID NO 21
<211> LENGTH: 16
<212> TYPE: DNA
<213> ORGANISM: Artificial sequence
<220> FEATURE:
<223> OTHER INFORMATION: Synthetic

<400> SEQUENCE: 21
ccggctggac ccggct                                                           16

<210> SEQ ID NO 22
<211> LENGTH: 17
<212> TYPE: DNA
<213> ORGANISM: Artificial sequence
<220> FEATURE:
<223> OTHER INFORMATION: Synthetic

<400> SEQUENCE: 22
cgcagcaccc cgcgccc                                                          17

<210> SEQ ID NO 23
<211> LENGTH: 18
<212> TYPE: DNA
<213> ORGANISM: Artificial sequence
<220> FEATURE:
<223> OTHER INFORMATION: Synthetic

<400> SEQUENCE: 23
cccacggggc cctttact                                                         18

<210> SEQ ID NO 24
<211> LENGTH: 17
<212> TYPE: DNA
<213> ORGANISM: Artificial sequence
<220> FEATURE:
<223> OTHER INFORMATION: Synthetic

<400> SEQUENCE: 24
cccctggttt ctccggt                                                          17

<210> SEQ ID NO 25
<211> LENGTH: 18
<212> TYPE: DNA
<213> ORGANISM: Artificial sequence
<220> FEATURE:
<223> OTHER INFORMATION: Synthetic

<400> SEQUENCE: 25
gccactccca gacttgtt                                                         18

<210> SEQ ID NO 26
<211> LENGTH: 17
<212> TYPE: DNA
<213> ORGANISM: Artificial sequence
<220> FEATURE:
<223> OTHER INFORMATION: Synthetic

<400> SEQUENCE: 26
ctgcatttag ggattct                                                          17

<210> SEQ ID NO 27

```
<211> LENGTH: 19
<212> TYPE: DNA
<213> ORGANISM: Artificial sequence
<220> FEATURE:
<223> OTHER INFORMATION: Synthetic

<400> SEQUENCE: 27
ccccaggaaa gtttaagat                                                  19

<210> SEQ ID NO 28
<211> LENGTH: 17
<212> TYPE: DNA
<213> ORGANISM: Artificial sequence
<220> FEATURE:
<223> OTHER INFORMATION: Synthetic

<400> SEQUENCE: 28
cgatgtgact gtctcct                                                    17

<210> SEQ ID NO 29
<211> LENGTH: 18
<212> TYPE: DNA
<213> ORGANISM: Artificial sequence
<220> FEATURE:
<223> OTHER INFORMATION: Synthetic

<400> SEQUENCE: 29
agccgcgagc acccaagt                                                   18

<210> SEQ ID NO 30
<211> LENGTH: 22
<212> TYPE: DNA
<213> ORGANISM: Artificial sequence
<220> FEATURE:
<223> OTHER INFORMATION: Synthetic

<400> SEQUENCE: 30
ttggtgggca ggtaggtgag tt                                              22

<210> SEQ ID NO 31
<211> LENGTH: 18
<212> TYPE: DNA
<213> ORGANISM: Artificial sequence
<220> FEATURE:
<223> OTHER INFORMATION: Synthetic

<400> SEQUENCE: 31
tccccacaga tggtgcat                                                   18

<210> SEQ ID NO 32
<211> LENGTH: 20
<212> TYPE: DNA
<213> ORGANISM: Artificial sequence
<220> FEATURE:
<223> OTHER INFORMATION: Synthetic

<400> SEQUENCE: 32
gaacggcgtg gattcaatag                                                 20

<210> SEQ ID NO 33
<211> LENGTH: 18
<212> TYPE: DNA
<213> ORGANISM: Artificial sequence
<220> FEATURE:
<223> OTHER INFORMATION: Synthetic

<400> SEQUENCE: 33
```
ctcgtggcag ggcagtct                           18

<210> SEQ ID NO 34
<211> LENGTH: 20
<212> TYPE: DNA
<213> ORGANISM: Artificial sequence
<220> FEATURE:
<223> OTHER INFORMATION: Synthetic

<400> SEQUENCE: 34
agctgtggct gacctgaaat                         20

<210> SEQ ID NO 35
<211> LENGTH: 20
<212> TYPE: DNA
<213> ORGANISM: Artificial sequence
<220> FEATURE:
<223> OTHER INFORMATION: Synthetic

<400> SEQUENCE: 35
gaccctctgg gagaaaatcc                         20

<210> SEQ ID NO 36
<211> LENGTH: 20
<212> TYPE: DNA
<213> ORGANISM: Artificial sequence
<220> FEATURE:
<223> OTHER INFORMATION: Synthetic

<400> SEQUENCE: 36
gtccttgcaa gtatccagca                         20

<210> SEQ ID NO 37
<211> LENGTH: 18
<212> TYPE: DNA
<213> ORGANISM: Artificial sequence
<220> FEATURE:
<223> OTHER INFORMATION: Synthetic

<400> SEQUENCE: 37
gcagcacctc ctggtcac                           18

<210> SEQ ID NO 38
<211> LENGTH: 20
<212> TYPE: DNA
<213> ORGANISM: Artificial sequence
<220> FEATURE:
<223> OTHER INFORMATION: Synthetic

<400> SEQUENCE: 38
atccgacaca tcctgattcc                         20

<210> SEQ ID NO 39
<211> LENGTH: 20
<212> TYPE: DNA
<213> ORGANISM: Artificial sequence
<220> FEATURE:
<223> OTHER INFORMATION: Synthetic

<400> SEQUENCE: 39
cctccccatg gcaagatact                         20

<210> SEQ ID NO 40
<211> LENGTH: 20
<212> TYPE: DNA

```
<213> ORGANISM: Artificial sequence
<220> FEATURE:
<223> OTHER INFORMATION: Synthetic

<400> SEQUENCE: 40
agcagttgtc tgcaacagga                                                  20

<210> SEQ ID NO 41
<211> LENGTH: 20
<212> TYPE: DNA
<213> ORGANISM: Artificial sequence
<220> FEATURE:
<223> OTHER INFORMATION: Synthetic

<400> SEQUENCE: 41
caatgacccc ttcattgacc                                                  20

<210> SEQ ID NO 42
<211> LENGTH: 20
<212> TYPE: DNA
<213> ORGANISM: Artificial sequence
<220> FEATURE:
<223> OTHER INFORMATION: Synthetic

<400> SEQUENCE: 42
ttgattttgg agggatctcg                                                  20

<210> SEQ ID NO 43
<211> LENGTH: 2634
<212> TYPE: DNA
<213> ORGANISM: Artificial sequence
<220> FEATURE:
<223> OTHER INFORMATION: Synthetic Oligonucleotide

<400> SEQUENCE: 43
atggactaca aagaccatga cggtgattat aaagatcatg acatcgatta caaggatgac     60
gatgacaaga tggccccccaa gaagaagagg aaggtgggcc gcggatctgt ggatctacgc    120
acgctcggct acagtcagca gcagcaagag aagatcaaac cgaaggtgcg ttcgacagtg    180
gcgcagcacc acgaggcact ggtgggccat gggtttacac acgcgcacat cgttgcgctc    240
agccaacacc cggcagcgtt agggaccgtc gctgtcacgt atcagcacat aatcacggcg    300
ttgccagagg cgacacacga agacatcgtt ggcgtcggca aacagtggtc cggcgcacgc    360
gccctggagg ccttgctcac ggatgcgggg gagttgagag gtccgccgtt acagttggac    420
acaggccaac ttgtgaagat tgcaaaacgt ggcggcgtga ccgcaatgga ggcagtgcat    480
gcatcgcgca atgcactgac gggtgccccc ctgaacctga ccccggacca agtggtggct    540
atcgccagca caatggcgg caagcaagcg ctcgaaacgg tgcagcggct gttgccggtg    600
ctgtgccagg accatggcct gaccccggac caagtggtgg ctatcgccag caacaatggc    660
ggcaagcaag cgctcgaaac ggtgcagcgg ctgttgccgg tgctgtgcca ggaccatggc    720
ctgaccccgg accaagtggt ggctatcgcc agcaacaatg gcggcaagca agcgctcgaa    780
acggtgcagc ggctgttgcc ggtgctgtgc caggaccatg gcctgacccc ggaccaagtg    840
gtggctatcg ccagccacga tggcggcaag caagcgctcg aaacggtgca gcggctgttg    900
ccggtgctgt gccaggacca tggcctgacc ccggaccaag tggtggctat cgccagcaac    960
ggtggcggca agcaagcgct cgaaacggtg cagcggctgt tgccggtgct gtgccaggac   1020
catggcctga ccccggacca agtggtggct atcgccagcc acgatggcgg caagcaagcg   1080
ctcgaaacgg tgcagcggct gttgccggtg ctgtgccagg accatggcct gaccccggac   1140
```

-continued

```
caagtggtgg ctatcgccag ccacgatggc ggcaagcaag cgctcgaaac ggtgcagcgg    1200
ctgttgccgg tgctgtgcca ggaccatggc ctgaccccgg accaagtggt ggctatcgcc    1260
agcaacggtg cggcaagca agcgctcgaa acggtgcagc ggctgttgcc ggtgctgtgc     1320
caggaccatg gcctgacccc ggaccaagtg gtggctatcg ccagccacga tggcggcaag    1380
caagcgctcg aaacggtgca gcggctgttg ccggtgctgt gccaggacca tggcctgacc    1440
ccggaccaag tggtggctat cgccagccac gatggcggca agcaagcgct cgaaacggtg    1500
cagcggctgt tgccggtgct gtgccaggac catggcctga ctccggacca agtggtggct    1560
atcgccagca cggtggcgg caagcaagcg ctcgaaacgg tgcagcggct gttgccggtg     1620
ctgtgccagg accatggcct gaccccggac caagtggtgg ctatcgccag caacggtggc    1680
ggcaagcaag cgctcgaaac ggtgcagcgg ctgttgccgg tgctgtgcca ggaccatggc    1740
ctgaccccgg accaagtggt ggctatcgcc agcaacaatg gcggcaagca agcgctcgaa    1800
acggtgcagc ggctgttgcc ggtgctgtgc caggaccatg gcctgacccc ggaccaagtg    1860
gtggctatcg ccagcaacgg tggcggcaag caagcgctcg aaacggtgca gcggctgttg    1920
ccggtgctgt gccaggacca tggcctgacc ccggaccaag tggtggctat cgccagcaac    1980
attggcggca agcaagcgct cgaaacggtg cagcggctgt tgccggtgct gtgccaggac    2040
catggcctga ccccggacca agtggtggct atcgccagcc acgatggcgg caagcaagcg    2100
ctcgaaacgg tgcagcggct gttgccggtg ctgtgccagg accatggcct gaccccggac    2160
caagtggtgg ctatcgccag caacggtggc ggcaagcaag cgctcgaaag cattgtggcc    2220
cagctgagcc ggcctgatcc ggcgttggcc gcgttgacca acgacgacca cctcgtcgcc    2280
ttggcctgcc tcggcggacg tcctgccatg gatgcagtga aaaagggatt gccgcacgcg    2340
ccggaattga tcagaagagt caatcgccgt attggcgaac gcacgtccca tcgcgttgcc    2400
ggatccaagg ctagcccgaa aaagaaacgc aaagttgggc gcgccgacgc gctggacgat    2460
ttcgatctcg acatgctggg ttctgatgcc ctcgatgact tgacctgga tatgttggga    2520 agcgacgcat ggatgacttt gatctggac atgctcggct ccgatgctct ggacgatttc     2580
gatctcgata tgttaattaa ctacccgtac gacgttccgg actacgcttc ttga          2634
```

<210> SEQ ID NO 44
<211> LENGTH: 877
<212> TYPE: PRT
<213> ORGANISM: Unknown
<220> FEATURE:
<223> OTHER INFORMATION: Synthetic peptide

<400> SEQUENCE: 44

```
Met Asp Tyr Lys Asp His Asp Gly Asp Tyr Lys Asp His Asp Ile Asp
1               5                   10                  15

Tyr Lys Asp Asp Asp Asp Lys Met Ala Pro Lys Lys Arg Lys Val
            20                  25                  30

Gly Arg Gly Ser Val Asp Leu Arg Thr Leu Gly Tyr Ser Gln Gln Gln
        35                  40                  45

Gln Glu Lys Ile Lys Pro Lys Val Arg Ser Thr Val Ala Gln His His
    50                  55                  60

Glu Ala Leu Val Gly His Gly Phe Thr His Ala His Ile Val Ala Leu
65                  70                  75                  80

Ser Gln His Pro Ala Ala Leu Gly Thr Val Ala Val Thr Tyr Gln His
                85                  90                  95
```

Ile Ile Thr Ala Leu Pro Glu Ala Thr His Glu Asp Ile Val Gly Val
            100                 105                 110

Gly Lys Gln Trp Ser Gly Ala Arg Ala Leu Glu Ala Leu Leu Thr Asp
            115                 120                 125

Ala Gly Glu Leu Arg Gly Pro Pro Leu Gln Leu Asp Thr Gly Gln Leu
        130                 135                 140

Val Lys Ile Ala Lys Arg Gly Gly Val Thr Ala Met Glu Ala Val His
145                 150                 155                 160

Ala Ser Arg Asn Ala Leu Thr Gly Ala Pro Leu Asn Leu Thr Pro Asp
                165                 170                 175

Gln Val Val Ala Ile Ala Ser Asn Asn Gly Gly Lys Gln Ala Leu Glu
            180                 185                 190

Thr Val Gln Arg Leu Leu Pro Val Leu Cys Gln Asp His Gly Leu Thr
        195                 200                 205

Pro Asp Gln Val Val Ala Ile Ala Ser Asn Asn Gly Gly Lys Gln Ala
        210                 215                 220

Leu Glu Thr Val Gln Arg Leu Leu Pro Val Leu Cys Gln Asp His Gly
225                 230                 235                 240

Leu Thr Pro Asp Gln Val Val Ala Ile Ala Ser Asn Asn Gly Gly Lys
                245                 250                 255

Gln Ala Leu Glu Thr Val Gln Arg Leu Leu Pro Val Leu Cys Gln Asp
            260                 265                 270

His Gly Leu Thr Pro Asp Gln Val Val Ala Ile Ala Ser His Asp Gly
        275                 280                 285

Gly Lys Gln Ala Leu Glu Thr Val Gln Arg Leu Leu Pro Val Leu Cys
        290                 295                 300

Gln Asp His Gly Leu Thr Pro Asp Gln Val Val Ala Ile Ala Ser Asn
305                 310                 315                 320

Gly Gly Gly Lys Gln Ala Leu Glu Thr Val Gln Arg Leu Leu Pro Val
                325                 330                 335

Leu Cys Gln Asp His Gly Leu Thr Pro Asp Gln Val Val Ala Ile Ala
            340                 345                 350

Ser His Asp Gly Gly Lys Gln Ala Leu Glu Thr Val Gln Arg Leu Leu
        355                 360                 365

Pro Val Leu Cys Gln Asp His Gly Leu Thr Pro Asp Gln Val Val Ala
        370                 375                 380

Ile Ala Ser His Asp Gly Gly Lys Gln Ala Leu Glu Thr Val Gln Arg
385                 390                 395                 400

Leu Leu Pro Val Leu Cys Gln Asp His Gly Leu Thr Pro Asp Gln Val
                405                 410                 415

Val Ala Ile Ala Ser Asn Gly Gly Gly Lys Gln Ala Leu Glu Thr Val
            420                 425                 430

Gln Arg Leu Leu Pro Val Leu Cys Gln Asp His Gly Leu Thr Pro Asp
        435                 440                 445

Gln Val Val Ala Ile Ala Ser His Asp Gly Gly Lys Gln Ala Leu Glu
        450                 455                 460

Thr Val Gln Arg Leu Leu Pro Val Leu Cys Gln Asp His Gly Leu Thr
465                 470                 475                 480

Pro Asp Gln Val Val Ala Ile Ala Ser His Asp Gly Gly Lys Gln Ala
                485                 490                 495

Leu Glu Thr Val Gln Arg Leu Leu Pro Val Leu Cys Gln Asp His Gly
            500                 505                 510

Leu Thr Pro Asp Gln Val Val Ala Ile Ala Ser Asn Gly Gly Gly Lys

```
            515                 520                 525
Gln Ala Leu Glu Thr Val Gln Arg Leu Leu Pro Val Leu Cys Gln Asp
    530                 535                 540

His Gly Leu Thr Pro Asp Gln Val Val Ala Ile Ala Ser Asn Gly Gly
545                 550                 555                 560

Gly Lys Gln Ala Leu Glu Thr Val Gln Arg Leu Leu Pro Val Leu Cys
                565                 570                 575

Gln Asp His Gly Leu Thr Pro Asp Gln Val Val Ala Ile Ala Ser Asn
            580                 585                 590

Asn Gly Gly Lys Gln Ala Leu Glu Thr Val Gln Arg Leu Leu Pro Val
        595                 600                 605

Leu Cys Gln Asp His Gly Leu Thr Pro Asp Gln Val Val Ala Ile Ala
    610                 615                 620

Ser Asn Gly Gly Gly Lys Gln Ala Leu Glu Thr Val Gln Arg Leu Leu
625                 630                 635                 640

Pro Val Leu Cys Gln Asp His Gly Leu Thr Pro Asp Gln Val Val Ala
                645                 650                 655

Ile Ala Ser Asn Ile Gly Gly Lys Gln Ala Leu Glu Thr Val Gln Arg
            660                 665                 670

Leu Leu Pro Val Leu Cys Gln Asp His Gly Leu Thr Pro Asp Gln Val
        675                 680                 685

Val Ala Ile Ala Ser His Asp Gly Gly Lys Gln Ala Leu Glu Thr Val
    690                 695                 700

Gln Arg Leu Leu Pro Val Leu Cys Gln Asp His Gly Leu Thr Pro Asp
705                 710                 715                 720

Gln Val Val Ala Ile Ala Ser Asn Gly Gly Gly Lys Gln Ala Leu Glu
                725                 730                 735

Ser Ile Val Ala Gln Leu Ser Arg Pro Asp Pro Ala Leu Ala Ala Leu
            740                 745                 750

Thr Asn Asp Asp His Leu Val Ala Leu Ala Cys Leu Gly Gly Arg Pro
        755                 760                 765

Ala Met Asp Ala Val Lys Lys Gly Leu Pro His Ala Pro Glu Leu Ile
    770                 775                 780

Arg Arg Val Asn Arg Arg Ile Gly Glu Arg Thr Ser His Arg Val Ala
785                 790                 795                 800

Gly Ser Lys Ala Ser Pro Lys Lys Arg Lys Val Gly Arg Ala Asp
                805                 810                 815

Ala Leu Asp Asp Phe Asp Leu Asp Met Leu Gly Ser Asp Ala Leu Asp
            820                 825                 830

Asp Phe Asp Leu Asp Met Leu Gly Ser Asp Ala Leu Asp Phe Asp
        835                 840                 845

Leu Asp Met Leu Gly Ser Asp Ala Leu Asp Asp Phe Asp Leu Asp Met
    850                 855                 860

Leu Ile Asn Tyr Pro Tyr Asp Val Pro Asp Tyr Ala Ser
865                 870                 875

<210> SEQ ID NO 45
<211> LENGTH: 2634
<212> TYPE: DNA
<213> ORGANISM: Artificial sequence
<220> FEATURE:
<223> OTHER INFORMATION: Synthetic oligonucleotide

<400> SEQUENCE: 45
atggactaca aagaccatga cggtgattat aaagatcatg acatcgatta caaggatgac    60
```

```
gatgacaaga tggcccccaa gaagaagagg aaggtgggcc gcggatctgt ggatctacgc      120
acgctcggct acagtcagca gcagcaagag aagatcaaac cgaaggtgcg ttcgacagtg      180
gcgcagcacc acgaggcact ggtgggccat gggtttacac acgcgcacat cgttgcgctc      240
agccaacacc cggcagcgtt agggaccgtc gctgtcacgt atcagcacat aatcacggcg      300
ttgccagagg cgacacacga agacatcgtt ggcgtcggca acagtggtc cggcgcacgc       360 gccctggagg ccttgctcac ggatgcgggg gagttgagag gtccgccgtt acagttggac      420
acaggccaac ttgtgaagat tgcaaaacgt ggcggcgtga ccgcaatgga ggcagtgcat      480
gcatcgcgca atgcactgac gggtgccccc ctgaacctga ccccggacca agtggtggct      540
atcgccagca acaatggcgg caagcaagcg ctcgaaacgg tgcagcggct gttgccggtg      600
ctgtgccagg accatggcct gaccccggac caagtggtgg ctatcgccag caacaatggc      660
ggcaagcaag cgctcgaaac ggtgcagcgg ctgttgccgg tgctgtgcca ggaccatggc      720
ctgaccccgg accaagtggt ggctatcgcc agccacgatg gcggcaagca agcgctcgaa      780
acggtgcagc ggctgttgcc ggtgctgtgc caggaccatg gcctgacccc ggaccaagtg      840
gtggctatcg ccagcaacat ggcggcaag caagcgctcg aaacggtgca gcggctgttg       900
ccggtgctgt gccaggacca tggcctgacc ccggaccaag tggtggctat cgccagcaac      960
ggtggcggca agcaagcgct cgaaacggtg cagcggctgt tgccggtgct gtgccaggac     1020
catggcctga ccccggacca gtggtggct atcgccagcc acgatggcgg caagcaagcg      1080
ctcgaaacgg tgcagcggct gttgccggtg ctgtgccagg accatggcct gaccccggac     1140
caagtggtgg ctatcgccag caacattggc ggcaagcaag cgctcgaaac ggtgcagcgg     1200
ctgttgccgg tgctgtgcca ggaccatggc ctgaccccgg accaagtggt ggctatcgcc     1260
agcaacattg gcggcaagca agcgctcgaa acggtgcagc ggctgttgcc ggtgctgtgc     1320
caggaccatg gcctgacccc ggaccaagtg gtggctatcg ccagcaacaa tggcggcaag     1380
caagcgctcg aaacggtgca gcggctgttg ccggtgctgt gccaggacca tggcctgacc     1440
ccggaccaag tggtggctat cgccagcaac ggtggcggca agcaagcgct cgaaacggtg     1500
cagcggctgt tgccggtgct gtgccaggac catggcctga ctccggacca agtggtggct     1560
atcgccagcc acgatggcgg caagcaagcg ctcgaaacgg tgcagcggct gttgccggtg     1620
ctgtgccagg accatggcct gaccccggac caagtggtgg ctatcgccag caacattggc     1680
ggcaagcaag cgctcgaaac ggtgcagcgg ctgttgccgg tgctgtgcca ggaccatggc     1740
ctgaccccgg accaagtggt ggctatcgcc agcaacaatg gcggcaagca agcgctcgaa     1800
acggtgcagc ggctgttgcc ggtgctgtgc caggaccatg gcctgacccc ggaccaagtg     1860
gtggctatcg ccagccacga tggcggcaag caagcgctcg aaacggtgca gcggctgttg     1920
ccggtgctgt gccaggacca tggcctgacc ccggaccaag tggtggctat cgccagccac     1980 gatgcggca agcaagcgct cgaaacggtg cagcggctgt tgccggtgct gtgccaggac      2040
catggcctga ccccggacca gtggtggct atcgccagca acattggcgg caagcaagcg      2100
ctcgaaacgg tgcagcggct gttgccggtg ctgtgccagg accatggcct gaccccggac     2160
caagtggtgg ctatcgccag caacggtggc ggcaagcaag cgctcgaaag cattgtggcc     2220
cagctgagcc ggcctgatcc ggcgttggcc gcgttgacca acgacgacca cctcgtcgcc     2280
ttggcctgcc tcgcggacg tcctgccatg gatgcagtga aaaagggatt gccgcacgcg      2340
ccggaattga tcagaagagt caatcgccgt attggcgaac gcacgtccca tcgcgttgcc     2400
```

-continued

```
ggatccaagg ctagcccgaa aaagaaacgc aaagttgggc gcgccgacgc gctggacgat    2460
ttcgatctcg acatgctggg ttctgatgcc ctcgatgact ttgacctgga tatgttggga    2520
agcgacgcat tggatgactt tgatctggac atgctcggct ccgatgctct ggacgatttc    2580
gatctcgata tgttaattaa ctacccgtac gacgttccgg actacgcttc ttga          2634
```

<210> SEQ ID NO 46
<211> LENGTH: 877
<212> TYPE: PRT
<213> ORGANISM: Unknown
<220> FEATURE:
<223> OTHER INFORMATION: Synthetic peptide

<400> SEQUENCE: 46

```
Met Asp Tyr Lys Asp His Asp Gly Asp Tyr Lys Asp His Asp Ile Asp
1               5                   10                  15

Tyr Lys Asp Asp Asp Lys Met Ala Pro Lys Lys Arg Lys Val
            20                  25                  30

Gly Arg Gly Ser Val Asp Leu Arg Thr Leu Gly Tyr Ser Gln Gln Gln
        35                  40                  45

Gln Glu Lys Ile Lys Pro Lys Val Arg Ser Thr Val Ala Gln His His
    50                  55                  60

Glu Ala Leu Val Gly His Gly Phe Thr His Ala His Ile Val Ala Leu
65                  70                  75                  80

Ser Gln His Pro Ala Ala Leu Gly Thr Val Ala Val Thr Tyr Gln His
                85                  90                  95

Ile Ile Thr Ala Leu Pro Glu Ala Thr His Glu Asp Ile Val Gly Val
            100                 105                 110

Gly Lys Gln Trp Ser Gly Ala Arg Ala Leu Glu Ala Leu Leu Thr Asp
        115                 120                 125

Ala Gly Glu Leu Arg Gly Pro Pro Leu Gln Leu Asp Thr Gly Gln Leu
    130                 135                 140

Val Lys Ile Ala Lys Arg Gly Gly Val Thr Ala Met Glu Ala Val His
145                 150                 155                 160

Ala Ser Arg Asn Ala Leu Thr Gly Ala Pro Leu Asn Leu Thr Pro Asp
                165                 170                 175

Gln Val Val Ala Ile Ala Ser Asn Asn Gly Gly Lys Gln Ala Leu Glu
            180                 185                 190

Thr Val Gln Arg Leu Leu Pro Val Leu Cys Gln Asp His Gly Leu Thr
        195                 200                 205

Pro Asp Gln Val Val Ala Ile Ala Ser Asn Asn Gly Gly Lys Gln Ala
    210                 215                 220

Leu Glu Thr Val Gln Arg Leu Leu Pro Val Leu Cys Gln Asp His Gly
225                 230                 235                 240

Leu Thr Pro Asp Gln Val Val Ala Ile Ala Ser His Asp Gly Gly Lys
                245                 250                 255

Gln Ala Leu Glu Thr Val Gln Arg Leu Leu Pro Val Leu Cys Gln Asp
            260                 265                 270

His Gly Leu Thr Pro Asp Gln Val Val Ala Ile Ala Ser Asn Ile Gly
        275                 280                 285

Gly Lys Gln Ala Leu Glu Thr Val Gln Arg Leu Leu Pro Val Leu Cys
    290                 295                 300

Gln Asp His Gly Leu Thr Pro Asp Gln Val Val Ala Ile Ala Ser Asn
305                 310                 315                 320

Gly Gly Gly Lys Gln Ala Leu Glu Thr Val Gln Arg Leu Leu Pro Val
```

```
                    325                 330                 335
Leu Cys Gln Asp His Gly Leu Thr Pro Asp Gln Val Val Ala Ile Ala
                340                 345                 350
Ser His Asp Gly Gly Lys Gln Ala Leu Glu Thr Val Gln Arg Leu Leu
                355                 360                 365
Pro Val Leu Cys Gln Asp His Gly Leu Thr Pro Asp Gln Val Val Ala
            370                 375                 380
Ile Ala Ser Asn Ile Gly Gly Lys Gln Ala Leu Glu Thr Val Gln Arg
385                 390                 395                 400
Leu Leu Pro Val Leu Cys Gln Asp His Gly Leu Thr Pro Asp Gln Val
                405                 410                 415
Val Ala Ile Ala Ser Asn Ile Gly Gly Lys Gln Ala Leu Glu Thr Val
                420                 425                 430
Gln Arg Leu Leu Pro Val Leu Cys Gln Asp His Gly Leu Thr Pro Asp
                435                 440                 445
Gln Val Val Ala Ile Ala Ser Asn Asn Gly Gly Lys Gln Ala Leu Glu
            450                 455                 460
Thr Val Gln Arg Leu Leu Pro Val Leu Cys Gln Asp His Gly Leu Thr
465                 470                 475                 480
Pro Asp Gln Val Val Ala Ile Ala Ser Asn Gly Gly Gly Lys Gln Ala
                485                 490                 495
Leu Glu Thr Val Gln Arg Leu Leu Pro Val Leu Cys Gln Asp His Gly
                500                 505                 510
Leu Thr Pro Asp Gln Val Val Ala Ile Ala Ser His Asp Gly Gly Lys
                515                 520                 525
Gln Ala Leu Glu Thr Val Gln Arg Leu Leu Pro Val Leu Cys Gln Asp
                530                 535                 540
His Gly Leu Thr Pro Asp Gln Val Val Ala Ile Ala Ser Asn Ile Gly
545                 550                 555                 560
Gly Lys Gln Ala Leu Glu Thr Val Gln Arg Leu Leu Pro Val Leu Cys
                565                 570                 575
Gln Asp His Gly Leu Thr Pro Asp Gln Val Val Ala Ile Ala Ser Asn
                580                 585                 590
Asn Gly Gly Lys Gln Ala Leu Glu Thr Val Gln Arg Leu Leu Pro Val
            595                 600                 605
Leu Cys Gln Asp His Gly Leu Thr Pro Asp Gln Val Val Ala Ile Ala
            610                 615                 620
Ser His Asp Gly Gly Lys Gln Ala Leu Glu Thr Val Gln Arg Leu Leu
625                 630                 635                 640
Pro Val Leu Cys Gln Asp His Gly Leu Thr Pro Asp Gln Val Val Ala
                645                 650                 655
Ile Ala Ser His Asp Gly Gly Lys Gln Ala Leu Glu Thr Val Gln Arg
            660                 665                 670
Leu Leu Pro Val Leu Cys Gln Asp His Gly Leu Thr Pro Asp Gln Val
                675                 680                 685
Val Ala Ile Ala Ser Asn Ile Gly Gly Lys Gln Ala Leu Glu Thr Val
            690                 695                 700
Gln Arg Leu Leu Pro Val Leu Cys Gln Asp His Gly Leu Thr Pro Asp
705                 710                 715                 720
Gln Val Val Ala Ile Ala Ser Asn Gly Gly Gly Lys Gln Ala Leu Glu
                725                 730                 735
Ser Ile Val Ala Gln Leu Ser Arg Pro Asp Pro Ala Leu Ala Ala Leu
            740                 745                 750
```

```
Thr Asn Asp Asp His Leu Val Ala Leu Ala Cys Leu Gly Gly Arg Pro
        755                 760                 765

Ala Met Asp Ala Val Lys Lys Gly Leu Pro His Ala Pro Glu Leu Ile
    770                 775                 780

Arg Arg Val Asn Arg Arg Ile Gly Glu Arg Thr Ser His Arg Val Ala
785                 790                 795                 800

Gly Ser Lys Ala Ser Pro Lys Lys Arg Lys Val Gly Arg Ala Asp
                805                 810                 815

Ala Leu Asp Asp Phe Asp Leu Asp Met Leu Gly Ser Asp Ala Leu Asp
                820                 825                 830

Asp Phe Asp Leu Asp Met Leu Gly Ser Asp Ala Leu Asp Phe Asp
            835                 840                 845

Leu Asp Met Leu Gly Ser Asp Ala Leu Asp Asp Phe Asp Leu Asp Met
    850                 855                 860

Leu Ile Asn Tyr Pro Tyr Asp Val Pro Asp Tyr Ala Ser
865                 870                 875
```

```
<210> SEQ ID NO 47
<211> LENGTH: 2736
<212> TYPE: DNA
<213> ORGANISM: Artificial sequence
<220> FEATURE:
<223> OTHER INFORMATION: Synthetic oligonucleotide

<400> SEQUENCE: 47
```

| | | | | |
|---|---|---|---|---|
| atggactaca | aagaccatga | cggtgattat | aaagatcatg | acatcgatta caaggatgac | 60 |
| gatgacaaga | tggcccccaa | gaagaagagg | aaggtgggcc | gcggatctgt ggatctacgc | 120 |
| acgctcggct | acagtcagca | gcagcaagag | aagatcaaac | cgaaggtgcg ttcgacagtg | 180 |
| gcgcagcacc | acgaggcact | ggtgggccat | gggtttacac | acgcgcacat cgttgcgctc | 240 |
| agccaacacc | cggcagcgtt | agggaccgtc | gctgtcacgt | atcagcacat aatcacggcg | 300 |
| ttgccagagg | cgacacacga | agacatcgtt | ggcgtcggca | acagtggtc cggcgcacgc | 360 |
| gccctggagg | ccttgctcac | ggatgcgggg | gagttgagag | gtccgccgtt acagttggac | 420 |
| acaggccaac | ttgtgaagat | tgcaaaacgt | ggcggcgtga | ccgcaatgga ggcagtgcat | 480 |
| gcatcgcgca | atgcactgac | gggtgccccc | ctgaacctga | ccccggacca agtggtggct | 540 |
| atcgccagca | acattggcgg | caagcaagcg | ctcgaaacgg | tgcagcggct gttgccggtg | 600 |
| ctgtgccagg | accatggcct | gaccccggac | caagtggtgg | ctatcgccag caacaatggc | 660 |
| ggcaagcaag | cgctcgaaac | ggtgcagcgg | ctgttgccgg | tgctgtgcca ggaccatggc | 720 |
| ctgaccccgg | accaagtggt | ggctatcgcc | agccacgatg | gcggcaagca agcgctcgaa | 780 |
| acggtgcagc | ggctgttgcc | ggtgctgtgc | caggaccatg | gcctgacccc ggaccaagtg | 840 |
| gtggctatcg | ccagccacga | tggcggcaag | caagcgctcg | aaacggtgca gcggctgttg | 900 |
| ccggtgctgt | gccaggacca | tggcctgacc | ccggaccaag | tggtggctat cgccagcaac | 960 |
| ggtggcggca | agcaagcgct | cgaaacggtg | cagcggctgt | gccggtgct gtgccaggac | 1020 |
| catggcctga | ccccggacca | agtggtggct | atcgccagca | acaatggcgg caagcaagcg | 1080 |
| ctcgaaacgg | tgcagcggct | gttgccggtg | ctgtgccagg | accatggcct gaccccggac | 1140 |
| caagtggtgg | ctatcgccag | caacattggc | ggcaagcaag | cgctcgaaac ggtgcagcgg | 1200 |
| ctgttgccgg | tgctgtgcca | ggaccatggc | ctgaccccgg | accaagtggt ggctatcgcc | 1260 |
| agcaacaatg | gcggcaagca | agcgctcgaa | acggtgcagc | ggctgttgcc ggtgctgtgc | 1320 |

```
caggaccatg gcctgacccc ggaccaagtg gtggctatcg ccagcaacgg tggcggcaag     1380
caagcgctcg aaacggtgca gcggctgttg ccggtgctgt gccaggacca tggcctgacc     1440
ccggaccaag tggtggctat cgccagccac gatggcggca agcaagcgct cgaaacggtg     1500
cagcggctgt tgccggtgct gtgccaggac catggcctga ccccggacca agtggtggct     1560
atcgccagca acattggcgg caagcaagcg ctcgaaacgg tgcagcggct gttgccggtg     1620
ctgtgccagg accatggcct gactccggac caagtggtgg ctatcgccag ccacgatggc     1680
ggcaagcaag cgctcgaaac ggtgcagcgg ctgttgccgg tgctgtgcca ggaccatggc     1740
ctgaccccgg accaagtggt ggctatcgcc agccacgatg cggcaagca agcgctcgaa     1800 acggtgcagc ggctgttgcc ggtgctgtgc caggaccatg gcctgacccc ggaccaagtg     1860
gtggctatcg ccagccacga tggcggcaag caagcgctcg aaacggtgca gcggctgttg     1920
ccggtgctgt gccaggacca tggcctgacc ccggaccaag tggtggctat cgccagcaac     1980
ggtggcggca agcaagcgct cgaaacggtg cagcggctgt tgccggtgct gtgccaggac     2040
catggcctga ccccggacca gtggtggct atcgccagcc acgatggcgg caagcaagcg     2100
ctcgaaacgg tgcagcggct gttgccggtg ctgtgccagg accatggcct gaccccggac     2160
caagtggtgg ctatcgccag ccacgatggc ggcaagcaag cgctcgaaac ggtgcagcgg     2220
ctgttgccgg tgctgtgcca ggaccatggc ctgaccccgg accaagtggt ggctatcgcc     2280
agcaacggtg gcggcaagca agcgctcgaa agcattgtgg cccagctgag ccggcctgat     2340
ccggcgttgg ccgcgttgac caacgacgac cacctcgtcg ccttggcctg cctcggcgga     2400
cgtcctgcca tggatgcagt gaaaaaggga ttgccgcacg cgccggaatt gatcagaaga     2460
gtcaatcgcc gtattggcga acgcacgtcc catcgcgttg ccggatccaa ggctagcccg     2520
aaaaagaaac gcaaagttgg gcgcgccgac gcgctggacg atttcgatct cgacatgctg     2580
ggttctgatg ccctcgatga ctttgacctg gatatgttgg aagcgacgc attggatgac     2640 tttgatctgg acatgctcgg ctccgatgct ctggacgatt cgatctcga tatgttaatt     2700 aactacccgt acgacgttcc ggactacgct tcttga                              2736
```

<210> SEQ ID NO 48
<211> LENGTH: 911
<212> TYPE: PRT
<213> ORGANISM: Unknown
<220> FEATURE:
<223> OTHER INFORMATION: Synthetic peptide

<400> SEQUENCE: 48

```
Met Asp Tyr Lys Asp His Asp Gly Asp Tyr Lys Asp His Asp Ile Asp
1               5                   10                  15

Tyr Lys Asp Asp Asp Asp Lys Met Ala Pro Lys Lys Arg Lys Val
            20                  25                  30

Gly Arg Gly Ser Val Asp Leu Arg Thr Leu Gly Tyr Ser Gln Gln Gln
        35                  40                  45

Gln Glu Lys Ile Lys Pro Lys Val Arg Ser Thr Val Ala Gln His His
    50                  55                  60

Glu Ala Leu Val Gly His Gly Phe Thr His Ala His Ile Val Ala Leu
65                  70                  75                  80

Ser Gln His Pro Ala Ala Leu Gly Thr Val Ala Val Thr Tyr Gln His
                85                  90                  95

Ile Ile Thr Ala Leu Pro Glu Ala Thr His Glu Asp Ile Val Gly Val
            100                 105                 110
```

Gly Lys Gln Trp Ser Gly Ala Arg Ala Leu Glu Ala Leu Leu Thr Asp
            115                 120                 125

Ala Gly Glu Leu Arg Gly Pro Pro Leu Gln Leu Asp Thr Gly Gln Leu
130                 135                 140

Val Lys Ile Ala Lys Arg Gly Gly Val Thr Ala Met Glu Ala Val His
145                 150                 155                 160

Ala Ser Arg Asn Ala Leu Thr Gly Ala Pro Leu Asn Leu Thr Pro Asp
                165                 170                 175

Gln Val Val Ala Ile Ala Ser Asn Ile Gly Gly Lys Gln Ala Leu Glu
            180                 185                 190

Thr Val Gln Arg Leu Leu Pro Val Leu Cys Gln Asp His Gly Leu Thr
        195                 200                 205

Pro Asp Gln Val Val Ala Ile Ala Ser Asn Asn Gly Gly Lys Gln Ala
    210                 215                 220

Leu Glu Thr Val Gln Arg Leu Leu Pro Val Leu Cys Gln Asp His Gly
225                 230                 235                 240

Leu Thr Pro Asp Gln Val Val Ala Ile Ala Ser His Asp Gly Gly Lys
                245                 250                 255

Gln Ala Leu Glu Thr Val Gln Arg Leu Leu Pro Val Leu Cys Gln Asp
            260                 265                 270

His Gly Leu Thr Pro Asp Gln Val Val Ala Ile Ala Ser His Asp Gly
        275                 280                 285

Gly Lys Gln Ala Leu Glu Thr Val Gln Arg Leu Leu Pro Val Leu Cys
    290                 295                 300

Gln Asp His Gly Leu Thr Pro Asp Gln Val Val Ala Ile Ala Ser Asn
305                 310                 315                 320

Gly Gly Gly Lys Gln Ala Leu Glu Thr Val Gln Arg Leu Leu Pro Val
                325                 330                 335

Leu Cys Gln Asp His Gly Leu Thr Pro Asp Gln Val Val Ala Ile Ala
            340                 345                 350

Ser Asn Asn Gly Gly Lys Gln Ala Leu Glu Thr Val Gln Arg Leu Leu
        355                 360                 365

Pro Val Leu Cys Gln Asp His Gly Leu Thr Pro Asp Gln Val Val Ala
    370                 375                 380

Ile Ala Ser Asn Ile Gly Gly Lys Gln Ala Leu Glu Thr Val Gln Arg
385                 390                 395                 400

Leu Leu Pro Val Leu Cys Gln Asp His Gly Leu Thr Pro Asp Gln Val
                405                 410                 415

Val Ala Ile Ala Ser Asn Asn Gly Gly Lys Gln Ala Leu Glu Thr Val
            420                 425                 430

Gln Arg Leu Leu Pro Val Leu Cys Gln Asp His Gly Leu Thr Pro Asp
        435                 440                 445

Gln Val Val Ala Ile Ala Ser Asn Gly Gly Gly Lys Gln Ala Leu Glu
    450                 455                 460

Thr Val Gln Arg Leu Leu Pro Val Leu Cys Gln Asp His Gly Leu Thr
465                 470                 475                 480

Pro Asp Gln Val Val Ala Ile Ala Ser His Asp Gly Gly Lys Gln Ala
                485                 490                 495

Leu Glu Thr Val Gln Arg Leu Leu Pro Val Leu Cys Gln Asp His Gly
            500                 505                 510

Leu Thr Pro Asp Gln Val Val Ala Ile Ala Ser Asn Ile Gly Gly Lys
        515                 520                 525

Gln Ala Leu Glu Thr Val Gln Arg Leu Leu Pro Val Leu Cys Gln Asp

His Gly Leu Thr Pro Asp Gln Val Val Ala Ile Ala Ser His Asp Gly
545                 550                 555                 560

Gly Lys Gln Ala Leu Glu Thr Val Gln Arg Leu Leu Pro Val Leu Cys
            565                 570                 575

Gln Asp His Gly Leu Thr Pro Asp Gln Val Val Ala Ile Ala Ser His
        580                 585                 590

Asp Gly Gly Lys Gln Ala Leu Glu Thr Val Gln Arg Leu Leu Pro Val
    595                 600                 605

Leu Cys Gln Asp His Gly Leu Thr Pro Asp Gln Val Val Ala Ile Ala
610                 615                 620

Ser His Asp Gly Gly Lys Gln Ala Leu Glu Thr Val Gln Arg Leu Leu
625                 630                 635                 640

Pro Val Leu Cys Gln Asp His Gly Leu Thr Pro Asp Gln Val Val Ala
                645                 650                 655

Ile Ala Ser Asn Gly Gly Gly Lys Gln Ala Leu Glu Thr Val Gln Arg
            660                 665                 670

Leu Leu Pro Val Leu Cys Gln Asp His Gly Leu Thr Pro Asp Gln Val
        675                 680                 685

Val Ala Ile Ala Ser His Asp Gly Gly Lys Gln Ala Leu Glu Thr Val
    690                 695                 700

Gln Arg Leu Leu Pro Val Leu Cys Gln Asp His Gly Leu Thr Pro Asp
705                 710                 715                 720

Gln Val Val Ala Ile Ala Ser His Asp Gly Gly Lys Gln Ala Leu Glu
                725                 730                 735

Thr Val Gln Arg Leu Leu Pro Val Leu Cys Gln Asp His Gly Leu Thr
            740                 745                 750

Pro Asp Gln Val Val Ala Ile Ala Ser Asn Gly Gly Gly Lys Gln Ala
        755                 760                 765

Leu Glu Ser Ile Val Ala Gln Leu Ser Arg Pro Asp Pro Ala Leu Ala
    770                 775                 780

Ala Leu Thr Asn Asp His Leu Val Ala Leu Ala Cys Leu Gly Gly
785                 790                 795                 800

Arg Pro Ala Met Asp Ala Val Lys Lys Gly Leu Pro His Ala Pro Glu
                805                 810                 815

Leu Ile Arg Arg Val Asn Arg Arg Ile Gly Glu Arg Thr Ser His Arg
            820                 825                 830

Val Ala Gly Ser Lys Ala Ser Pro Lys Lys Arg Lys Val Gly Arg
        835                 840                 845

Ala Asp Ala Leu Asp Asp Phe Asp Leu Asp Met Leu Gly Ser Asp Ala
    850                 855                 860

Leu Asp Asp Phe Asp Leu Asp Met Leu Gly Ser Asp Ala Leu Asp Asp
865                 870                 875                 880

Phe Asp Leu Asp Met Leu Gly Ser Asp Ala Leu Asp Asp Phe Asp Leu
                885                 890                 895

Asp Met Leu Ile Asn Tyr Pro Tyr Asp Val Pro Asp Tyr Ala Ser
            900                 905                 910

<210> SEQ ID NO 49
<211> LENGTH: 2736
<212> TYPE: DNA
<213> ORGANISM: Artificial sequence
<220> FEATURE:
<223> OTHER INFORMATION: Synthetic oligonucleotide

<400> SEQUENCE: 49

```
atggactaca aagaccatga cggtgattat aaagatcatg acatcgatta caaggatgac      60
gatgacaaga tggcccccaa gaagaagagg aaggtgggcc gcggatctgt ggatctacgc     120
acgctcggct acagtcagca gcagcaagag aagatcaaac cgaaggtgcg ttcgacagtg     180
gcgcagcacc acgaggcact ggtgggccat gggtttacac acgcgcacat cgttgcgctc     240
agccaacacc cggcagcgtt agggaccgtc gctgtcacgt atcagcacat aatcacggcg     300
ttgccagagg cgacacacga agacatcgtt ggcgtcggca acagtggtc cggcgcacgc      360
gccctggagg ccttgctcac ggatgcgggg gagttgagag gtccgccgtt acagttggac     420
acaggccaac ttgtgaagat tgcaaaacgt ggcggcgtga ccgcaatgga ggcagtgcat     480
gcatcgcgca atgcactgac gggtgccccc ctgaacctga ccccggacca agtggtggct     540
atcgccagca acattggcgg caagcaagcg ctcgaaacgg tgcagcggct gttgccggtg     600
ctgtgccagg accatggcct gaccccggac caagtggtgg ctatcgccag ccacgatggc     660
ggcaagcaag cgctcgaaac ggtgcagcgg ctgttgccgg tgctgtgcca ggaccatggc     720
ctgaccccgg accaagtggt ggctatcgcc agcaacaatg gcggcaagca agcgctcgaa     780
acggtgcagc ggctgttgcc ggtgctgtgc caggaccatg gcctgacccc ggaccaagtg     840
gtggctatcg ccagccacga tggcggcaag caagcgctcg aaacggtgca gcggctgttg     900
ccggtgctgt gccaggacca tggcctgacc ccggaccaag tggtggctat cgccagcaac     960
attggcggca agcaagcgct cgaaacggtg cagcggctgt tgccggtgct gtgccaggac    1020
catggcctga ccccggacca agtggtggct atcgccagca acaatggcgg caagcaagcg    1080
ctcgaaacgg tgcagcggct gttgccggtg ctgtgccagg accatggcct gaccccggac    1140
caagtggtgg ctatcgccag caacattggc ggcaagcaag cgctcgaaac ggtgcagcgg    1200
ctgttgccgg tgctgtgcca ggaccatggc ctgaccccgg accaagtggt ggctatcgcc    1260
agcaacggtg gcggcaagca agcgctcgaa acggtgcagc ggctgttgcc ggtgctgtgc    1320
caggaccatg gcctgacccc ggaccaagtg gtggctatcg ccagcaacat tggcggcaag    1380
caagcgctcg aaacggtgca gcggctgttg ccggtgctgt gccaggacca tggcctgacc    1440
ccggaccaag tggtggctat cgccagcaac attggcggca agcaagcgct cgaaacggtg    1500
cagcggctgt tgccggtgct gtgccaggac catggcctga ccccggacca gtggtggct     1560
atcgccagca acaatggcgg caagcaagcg ctcgaaacgg tgcagcggct gttgccggtg    1620
ctgtgccagg accatggcct gactccggac caagtggtgg ctatcgccag caacattggc    1680
ggcaagcaag cgctcgaaac ggtgcagcgg ctgttgccgg tgctgtgcca ggaccatggc    1740
ctgaccccgg accaagtggt ggctatcgcc agcaacattg gcggcaagca agcgctcgaa    1800
acggtgcagc ggctgttgcc ggtgctgtgc caggaccatg gcctgacccc ggaccaagtg    1860
gtggctatcg ccagccacga tggcggcaag caagcgctcg aaacggtgca gcggctgttg    1920
ccggtgctgt gccaggacca tggcctgacc ccggaccaag tggtggctat cgccagccac    1980
gatggcggca agcaagcgct cgaaacggtg cagcggctgt tgccggtgct gtgccaggac    2040
catggcctga ccccggacca gtggtggct atcgccagca cattggcgg caagcaagcg      2100
ctcgaaacgg tgcagcggct gttgccggtg ctgtgccagg accatggcct gaccccggac    2160
caagtggtgg ctatcgccag caacaatggc ggcaagcaag cgctcgaaac ggtgcagcgg    2220
ctgttgccgg tgctgtgcca ggaccatggc ctgaccccgg accaagtggt ggctatcgcc    2280
agcaacggtg gcggcaagca agcgctcgaa agcattgtgg cccagctgag ccggcctgat    2340
```

```
ccggcgttgg ccgcgttgac caacgacgac cacctcgtcg ccttggcctg cctcggcgga   2400
cgtcctgcca tggatgcagt gaaaaaggga ttgccgcacg cgccggaatt gatcagaaga   2460
gtcaatcgcc gtattggcga acgcacgtcc catcgcgttg ccggatccaa ggctagcccg   2520
aaaaagaaac gcaaagttgg gcgcgccgac gcgctggacg atttcgatct cgacatgctg   2580
ggttctgatg ccctcgatga ctttgacctg gatatgttgg gaagcgacgc attggatgac   2640
tttgatctgg acatgctcgg ctccgatgct ctggacgatt tcgatctcga tatgttaatt   2700
aactacccgt acgacgttcc ggactacgct tcttga                            2736
```

<210> SEQ ID NO 50
<211> LENGTH: 911
<212> TYPE: PRT
<213> ORGANISM: Unknown
<220> FEATURE:
<223> OTHER INFORMATION: Synthetic peptide

<400> SEQUENCE: 50

```
Met Asp Tyr Lys Asp His Asp Gly Asp Tyr Lys Asp His Asp Ile Asp
1               5                   10                  15

Tyr Lys Asp Asp Asp Lys Met Ala Pro Lys Lys Arg Lys Val
            20                  25                  30

Gly Arg Gly Ser Val Asp Leu Arg Thr Leu Gly Tyr Ser Gln Gln Gln
        35                  40                  45

Gln Glu Lys Ile Lys Pro Lys Val Arg Ser Thr Val Ala Gln His His
    50                  55                  60

Glu Ala Leu Val Gly His Gly Phe Thr His Ala His Ile Val Ala Leu
65                  70                  75                  80

Ser Gln His Pro Ala Ala Leu Gly Thr Val Ala Val Thr Tyr Gln His
                85                  90                  95

Ile Ile Thr Ala Leu Pro Glu Ala Thr His Glu Asp Ile Val Gly Val
            100                 105                 110

Gly Lys Gln Trp Ser Gly Ala Arg Ala Leu Glu Ala Leu Leu Thr Asp
        115                 120                 125

Ala Gly Glu Leu Arg Gly Pro Pro Leu Gln Leu Asp Thr Gly Gln Leu
    130                 135                 140

Val Lys Ile Ala Lys Arg Gly Gly Val Thr Ala Met Glu Ala Val His
145                 150                 155                 160

Ala Ser Arg Asn Ala Leu Thr Gly Ala Pro Leu Asn Leu Thr Pro Asp
                165                 170                 175

Gln Val Val Ala Ile Ala Ser Asn Ile Gly Gly Lys Gln Ala Leu Glu
            180                 185                 190

Thr Val Gln Arg Leu Leu Pro Val Leu Cys Gln Asp His Gly Leu Thr
        195                 200                 205

Pro Asp Gln Val Val Ala Ile Ala Ser His Asp Gly Gly Lys Gln Ala
    210                 215                 220

Leu Glu Thr Val Gln Arg Leu Leu Pro Val Leu Cys Gln Asp His Gly
225                 230                 235                 240

Leu Thr Pro Asp Gln Val Val Ala Ile Ala Ser Asn Asn Gly Gly Lys
                245                 250                 255

Gln Ala Leu Glu Thr Val Gln Arg Leu Leu Pro Val Leu Cys Gln Asp
            260                 265                 270

His Gly Leu Thr Pro Asp Gln Val Val Ala Ile Ala Ser His Asp Gly
        275                 280                 285
```

-continued

```
Gly Lys Gln Ala Leu Glu Thr Val Gln Arg Leu Leu Pro Val Leu Cys
    290                 295                 300

Gln Asp His Gly Leu Thr Pro Asp Gln Val Val Ala Ile Ala Ser Asn
305                 310                 315                 320

Ile Gly Gly Lys Gln Ala Leu Glu Thr Val Gln Arg Leu Leu Pro Val
                325                 330                 335

Leu Cys Gln Asp His Gly Leu Thr Pro Asp Gln Val Val Ala Ile Ala
            340                 345                 350

Ser Asn Asn Gly Gly Lys Gln Ala Leu Glu Thr Val Gln Arg Leu Leu
        355                 360                 365

Pro Val Leu Cys Gln Asp His Gly Leu Thr Pro Asp Gln Val Val Ala
370                 375                 380

Ile Ala Ser Asn Ile Gly Gly Lys Gln Ala Leu Glu Thr Val Gln Arg
385                 390                 395                 400

Leu Leu Pro Val Leu Cys Gln Asp His Gly Leu Thr Pro Asp Gln Val
                405                 410                 415

Val Ala Ile Ala Ser Asn Gly Gly Gly Lys Gln Ala Leu Glu Thr Val
            420                 425                 430

Gln Arg Leu Leu Pro Val Leu Cys Gln Asp His Gly Leu Thr Pro Asp
        435                 440                 445

Gln Val Val Ala Ile Ala Ser Asn Ile Gly Gly Lys Gln Ala Leu Glu
450                 455                 460

Thr Val Gln Arg Leu Leu Pro Val Leu Cys Gln Asp His Gly Leu Thr
465                 470                 475                 480

Pro Asp Gln Val Val Ala Ile Ala Ser Asn Ile Gly Gly Lys Gln Ala
                485                 490                 495

Leu Glu Thr Val Gln Arg Leu Leu Pro Val Leu Cys Gln Asp His Gly
            500                 505                 510

Leu Thr Pro Asp Gln Val Val Ala Ile Ala Ser Asn Asn Gly Gly Lys
        515                 520                 525

Gln Ala Leu Glu Thr Val Gln Arg Leu Leu Pro Val Leu Cys Gln Asp
530                 535                 540

His Gly Leu Thr Pro Asp Gln Val Val Ala Ile Ala Ser Asn Ile Gly
545                 550                 555                 560

Gly Lys Gln Ala Leu Glu Thr Val Gln Arg Leu Leu Pro Val Leu Cys
                565                 570                 575

Gln Asp His Gly Leu Thr Pro Asp Gln Val Val Ala Ile Ala Ser Asn
            580                 585                 590

Ile Gly Gly Lys Gln Ala Leu Glu Thr Val Gln Arg Leu Leu Pro Val
        595                 600                 605

Leu Cys Gln Asp His Gly Leu Thr Pro Asp Gln Val Val Ala Ile Ala
610                 615                 620

Ser His Asp Gly Gly Lys Gln Ala Leu Glu Thr Val Gln Arg Leu Leu
625                 630                 635                 640

Pro Val Leu Cys Gln Asp His Gly Leu Thr Pro Asp Gln Val Val Ala
                645                 650                 655

Ile Ala Ser His Asp Gly Gly Lys Gln Ala Leu Glu Thr Val Gln Arg
            660                 665                 670

Leu Leu Pro Val Leu Cys Gln Asp His Gly Leu Thr Pro Asp Gln Val
        675                 680                 685

Val Ala Ile Ala Ser Asn Ile Gly Gly Lys Gln Ala Leu Glu Thr Val
690                 695                 700

Gln Arg Leu Leu Pro Val Leu Cys Gln Asp His Gly Leu Thr Pro Asp
```

```
                   705                 710                 715                 720
Gln Val Val Ala Ile Ala Ser Asn Asn Gly Gly Lys Gln Ala Leu Glu
                725                 730                 735

Thr Val Gln Arg Leu Leu Pro Val Leu Cys Gln Asp His Gly Leu Thr
                740                 745                 750

Pro Asp Gln Val Val Ala Ile Ala Ser Asn Gly Gly Lys Gln Ala
                755                 760                 765

Leu Glu Ser Ile Val Ala Gln Leu Ser Arg Pro Asp Pro Ala Leu Ala
            770                 775                 780

Ala Leu Thr Asn Asp Asp His Leu Val Ala Leu Ala Cys Leu Gly Gly
785                 790                 795                 800

Arg Pro Ala Met Asp Ala Val Lys Lys Gly Leu Pro His Ala Pro Glu
                805                 810                 815

Leu Ile Arg Arg Val Asn Arg Arg Ile Gly Glu Arg Thr Ser His Arg
            820                 825                 830

Val Ala Gly Ser Lys Ala Ser Pro Lys Lys Lys Arg Lys Val Gly Arg
            835                 840                 845

Ala Asp Ala Leu Asp Asp Phe Asp Leu Asp Met Leu Gly Ser Asp Ala
850                 855                 860

Leu Asp Asp Phe Asp Leu Asp Met Leu Gly Ser Asp Ala Leu Asp Asp
865                 870                 875                 880

Phe Asp Leu Asp Met Leu Gly Ser Asp Ala Leu Asp Asp Phe Asp Leu
                885                 890                 895

Asp Met Leu Ile Asn Tyr Pro Tyr Asp Val Pro Asp Tyr Ala Ser
                900                 905                 910

<210> SEQ ID NO 51
<211> LENGTH: 2736
<212> TYPE: DNA
<213> ORGANISM: Artificial sequence
<220> FEATURE:
<223> OTHER INFORMATION: Synthetic oligonucleotide

<400> SEQUENCE: 51
atggactaca aagaccatga cggtgattat aaagatcatg acatcgatta caaggatgac      60
gatgacaaga tggcccccaa gaagaagagg aaggtgggcc gcggatctgt ggatctacgc     120
acgctcggct acagtcagca gcagcaagag aagatcaaac cgaaggtgcg ttcgacagtg     180
gcgcagcacc acgaggcact ggtgggccat gggtttacac acgcgcacat cgttgcgctc     240
agccaacacc cggcagcgtt agggaccgtc gctgtcacgt atcagcacat aatcacggcg     300
ttgccagagg cgacacacga agacatcgtt ggcgtcggca acagtggtc cggcgcacgc      360 gccctggagg ccttgctcac ggatgcgggg gagttgagag gtccgccgtt acagttggac     420
acaggccaac ttgtgaagat tgcaaaacgt ggcggcgtga ccgcaatgga ggcagtgcat     480
gcatcgcgca atgcactgac gggtgccccc ctgaacctga ccccggacca agtggtggct     540
atcgccagca caatggcgg caagcaagcg ctcgaaacgg tgcagcggct gttgccggtg      600
ctgtgccagg accatggcct gaccccggac caagtggtgg ctatcgccag caacggtggc     660
ggcaagcaag cgctcgaaac ggtgcagcgg ctgttgccgg tgctgtgcca ggaccatggc     720
ctgaccccgg accaagtggt ggctatcgcc agccacgatg gcggcaagca agcgctcgaa     780
acggtgcagc ggctgttgcc ggtgctgtgc caggaccatg gcctgacccc ggaccaagtg     840
gtggctatcg ccagcaacgg tggcggcaag caagcgctcg aaacggtgca gcggctgttg     900
ccggtgctgt gccaggacca tggcctgacc ccggaccaag tggtggctat cgccagcaac     960
```

| | |
|---|---|
| aatggcggca agcaagcgct cgaaacggtg cagcggctgt tgccggtgct gtgccaggac | 1020 |
| catggcctga ccccggacca agtggtggct atcgccagca acaatggcgg caagcaagcg | 1080 |
| ctcgaaacgg tgcagcggct gttgccggtg ctgtgccagg accatggcct gaccccggac | 1140 |
| caagtggtgg ctatcgccag ccacgatggc ggcaagcaag cgctcgaaac ggtgcagcgg | 1200 |
| ctgttgccgg tgctgtgcca ggaccatggc ctgaccccgg accaagtggt ggctatcgcc | 1260 |
| agcaacggtg gcggcaagca agcgctcgaa acggtgcagc ggctgttgcc ggtgctgtgc | 1320 |
| caggaccatg gcctgacccc ggaccaagtg gtggctatcg ccagcaacgg tggcggcaag | 1380 |
| caagcgctcg aaacggtgca gcggctgttg ccggtgctgt gccaggacca tggcctgacc | 1440 |
| ccggaccaag tggtggctat cgccagcaac aatggcggca agcaagcgct cgaaacggtg | 1500 |
| cagcggctgt tgccggtgct gtgccaggac catggcctga ccccggacca agtggtggct | 1560 |
| atcgccagca acgtggcgg caagcaagcg ctcgaaacgg tgcagcggct gttgccggtg | 1620 |
| ctgtgccagg accatggcct gactccggac caagtggtgg ctatcgccag caacggtggc | 1680 |
| ggcaagcaag cgctcgaaac ggtgcagcgg ctgttgccgg tgctgtgcca ggaccatggc | 1740 |
| ctgaccccgg accaagtggt ggctatcgcc agccacgatg gcggcaagca agcgctcgaa | 1800 |
| acggtgcagc ggctgttgcc ggtgctgtgc caggaccatg gcctgacccc ggaccaagtg | 1860 |
| gtggctatcg ccagccacga tggcggcaag caagcgctcg aaacggtgca gcggctgttg | 1920 |
| ccggtgctgt gccaggacca tggcctgacc ccggaccaag tggtggctat cgccagccac | 1980 |
| gatggcggca agcaagcgct cgaaacggtg cagcggctgt tgccggtgct gtgccaggac | 2040 |
| catggcctga ccccggacca agtggtggct atcgccagca cattggcgg caagcaagcg | 2100 |
| ctcgaaacgg tgcagcggct gttgccggtg ctgtgccagg accatggcct gaccccggac | 2160 |
| caagtggtgg ctatcgccag caacattggc ggcaagcaag cgctcgaaac ggtgcagcgg | 2220 |
| ctgttgccgg tgctgtgcca ggaccatggc ctgaccccgg accaagtggt ggctatcgcc | 2280 |
| agcaacggtg gcggcaagca agcgctcgaa agcattgtgg cccagctgag ccggcctgat | 2340 |
| ccggcgttgg ccgcgttgac caacgacgac cacctcgtcg ccttggcctg cctcggcgga | 2400 |
| cgtcctgcca tggatgcagt gaaaaaggga ttgccgcacg cgccggaatt gatcagaaga | 2460 |
| gtcaatcgcc gtattggcga acgcacgtcc catcgcgttg ccggatccaa ggctagcccg | 2520 |
| aaaaagaaac gcaaagttgg gcgcgccgac gcgctggacg atttcgatct cgacatgctg | 2580 |
| ggttctgatg ccctcgatga cttttgacctg gatatgttgg aagcgacgc attggatgac | 2640 |
| tttgatctgg acatgctcgg ctccgatgct ctggacgatt cgatctcga tatgttaatt | 2700 |
| aactacccgt acgacgttcc ggactacgct tcttga | 2736 |

<210> SEQ ID NO 52
<211> LENGTH: 911
<212> TYPE: PRT
<213> ORGANISM: Unknown
<220> FEATURE:
<223> OTHER INFORMATION: Synthetic peptide

<400> SEQUENCE: 52

Met Asp Tyr Lys Asp His Asp Gly Asp Tyr Lys Asp His Asp Ile Asp
1               5                   10                  15

Tyr Lys Asp Asp Asp Asp Lys Met Ala Pro Lys Lys Arg Lys Val
            20                  25                  30

Gly Arg Gly Ser Val Asp Leu Arg Thr Leu Gly Tyr Ser Gln Gln Gln
        35                  40                  45

```
Gln Glu Lys Ile Lys Pro Lys Val Arg Ser Thr Val Ala Gln His His
         50                  55                  60

Glu Ala Leu Val Gly His Gly Phe Thr His Ala His Ile Val Ala Leu
 65                  70                  75                  80

Ser Gln His Pro Ala Ala Leu Gly Thr Val Ala Val Thr Tyr Gln His
                 85                  90                  95

Ile Ile Thr Ala Leu Pro Glu Ala Thr His Glu Asp Ile Val Gly Val
                100                 105                 110

Gly Lys Gln Trp Ser Gly Ala Arg Ala Leu Glu Ala Leu Leu Thr Asp
            115                 120                 125

Ala Gly Glu Leu Arg Gly Pro Pro Leu Gln Leu Asp Thr Gly Gln Leu
130                 135                 140

Val Lys Ile Ala Lys Arg Gly Gly Val Thr Ala Met Glu Ala Val His
145                 150                 155                 160

Ala Ser Arg Asn Ala Leu Thr Gly Ala Pro Leu Asn Leu Thr Pro Asp
                165                 170                 175

Gln Val Val Ala Ile Ala Ser Asn Asn Gly Gly Lys Gln Ala Leu Glu
                180                 185                 190

Thr Val Gln Arg Leu Leu Pro Val Leu Cys Gln Asp His Gly Leu Thr
            195                 200                 205

Pro Asp Gln Val Val Ala Ile Ala Ser Asn Gly Gly Gly Lys Gln Ala
210                 215                 220

Leu Glu Thr Val Gln Arg Leu Leu Pro Val Leu Cys Gln Asp His Gly
225                 230                 235                 240

Leu Thr Pro Asp Gln Val Val Ala Ile Ala Ser His Asp Gly Gly Lys
                245                 250                 255

Gln Ala Leu Glu Thr Val Gln Arg Leu Leu Pro Val Leu Cys Gln Asp
                260                 265                 270

His Gly Leu Thr Pro Asp Gln Val Val Ala Ile Ala Ser Asn Gly Gly
            275                 280                 285

Gly Lys Gln Ala Leu Glu Thr Val Gln Arg Leu Leu Pro Val Leu Cys
290                 295                 300

Gln Asp His Gly Leu Thr Pro Asp Gln Val Val Ala Ile Ala Ser Asn
305                 310                 315                 320

Asn Gly Gly Lys Gln Ala Leu Glu Thr Val Gln Arg Leu Leu Pro Val
                325                 330                 335

Leu Cys Gln Asp His Gly Leu Thr Pro Asp Gln Val Val Ala Ile Ala
                340                 345                 350

Ser Asn Asn Gly Gly Lys Gln Ala Leu Glu Thr Val Gln Arg Leu Leu
            355                 360                 365

Pro Val Leu Cys Gln Asp His Gly Leu Thr Pro Asp Gln Val Val Ala
370                 375                 380

Ile Ala Ser His Asp Gly Gly Lys Gln Ala Leu Glu Thr Val Gln Arg
385                 390                 395                 400

Leu Leu Pro Val Leu Cys Gln Asp His Gly Leu Thr Pro Asp Gln Val
                405                 410                 415

Val Ala Ile Ala Ser Asn Gly Gly Gly Lys Gln Ala Leu Glu Thr Val
                420                 425                 430

Gln Arg Leu Leu Pro Val Leu Cys Gln Asp His Gly Leu Thr Pro Asp
            435                 440                 445

Gln Val Val Ala Ile Ala Ser Asn Gly Gly Gly Lys Gln Ala Leu Glu
450                 455                 460
```

```
Thr Val Gln Arg Leu Leu Pro Val Leu Cys Gln Asp His Gly Leu Thr
465                 470                 475                 480

Pro Asp Gln Val Val Ala Ile Ala Ser Asn Asn Gly Gly Lys Gln Ala
            485                 490                 495

Leu Glu Thr Val Gln Arg Leu Leu Pro Val Leu Cys Gln Asp His Gly
        500                 505                 510

Leu Thr Pro Asp Gln Val Val Ala Ile Ala Ser Asn Gly Gly Gly Lys
            515                 520                 525

Gln Ala Leu Glu Thr Val Gln Arg Leu Leu Pro Val Leu Cys Gln Asp
        530                 535                 540

His Gly Leu Thr Pro Asp Gln Val Val Ala Ile Ala Ser Asn Gly Gly
545                 550                 555                 560

Gly Lys Gln Ala Leu Glu Thr Val Gln Arg Leu Leu Pro Val Leu Cys
                565                 570                 575

Gln Asp His Gly Leu Thr Pro Asp Gln Val Val Ala Ile Ala Ser His
            580                 585                 590

Asp Gly Gly Lys Gln Ala Leu Glu Thr Val Gln Arg Leu Leu Pro Val
        595                 600                 605

Leu Cys Gln Asp His Gly Leu Thr Pro Asp Gln Val Val Ala Ile Ala
610                 615                 620

Ser His Asp Gly Gly Lys Gln Ala Leu Glu Thr Val Gln Arg Leu Leu
625                 630                 635                 640

Pro Val Leu Cys Gln Asp His Gly Leu Thr Pro Asp Gln Val Val Ala
                645                 650                 655

Ile Ala Ser His Asp Gly Gly Lys Gln Ala Leu Glu Thr Val Gln Arg
            660                 665                 670

Leu Leu Pro Val Leu Cys Gln Asp His Gly Leu Thr Pro Asp Gln Val
        675                 680                 685

Val Ala Ile Ala Ser Asn Ile Gly Gly Lys Gln Ala Leu Glu Thr Val
    690                 695                 700

Gln Arg Leu Leu Pro Val Leu Cys Gln Asp His Gly Leu Thr Pro Asp
705                 710                 715                 720

Gln Val Val Ala Ile Ala Ser Asn Ile Gly Gly Lys Gln Ala Leu Glu
                725                 730                 735

Thr Val Gln Arg Leu Leu Pro Val Leu Cys Gln Asp His Gly Leu Thr
            740                 745                 750

Pro Asp Gln Val Val Ala Ile Ala Ser Asn Gly Gly Lys Gln Ala
        755                 760                 765

Leu Glu Ser Ile Val Ala Gln Leu Ser Arg Pro Asp Pro Ala Leu Ala
        770                 775                 780

Ala Leu Thr Asn Asp His Leu Val Ala Leu Ala Cys Leu Gly Gly
785                 790                 795                 800

Arg Pro Ala Met Asp Ala Val Lys Lys Gly Leu Pro His Ala Pro Glu
            805                 810                 815

Leu Ile Arg Arg Val Asn Arg Arg Ile Gly Glu Arg Thr Ser His Arg
        820                 825                 830

Val Ala Gly Ser Lys Ala Ser Pro Lys Lys Arg Lys Val Gly Arg
        835                 840                 845

Ala Asp Ala Leu Asp Asp Phe Asp Leu Asp Met Leu Gly Ser Asp Ala
        850                 855                 860

Leu Asp Asp Phe Asp Leu Asp Met Leu Gly Ser Asp Ala Leu Asp Asp
865                 870                 875                 880

Phe Asp Leu Asp Met Leu Gly Ser Asp Ala Leu Asp Asp Phe Asp Leu
```

```
                885                 890                 895
Asp Met Leu Ile Asn Tyr Pro Tyr Asp Val Pro Asp Tyr Ala Ser
                    900                 905                 910

<210> SEQ ID NO 53
<211> LENGTH: 2940
<212> TYPE: DNA
<213> ORGANISM: Artificial sequence
<220> FEATURE:
<223> OTHER INFORMATION: Synthetic oligonucleotide

<400> SEQUENCE: 53
atggactaca aagaccatga cggtgattat aaagatcatg acatcgatta caaggatgac      60
gatgacaaga tggcccccaa gaagaagagg aaggtgggcc gcggatctgt ggatctacgc     120
acgctcggct acagtcagca gcagcaagag aagatcaaac cgaaggtgcg ttcgacagtg     180
gcgcagcacc acgaggcact ggtgggccat gggtttacac acgcgcacat cgttgcgctc     240
agccaacacc cggcagcgtt agggaccgtc gctgtcacgt atcagcacat aatcacggcg     300
ttgccagagg cgacacacga agacatcgtt ggcgtcggca acagtggtc cggcgcacgc      360 gccctggagg ccttgctcac ggatgcgggg gagttgagag gtccgccgtt acagttggac     420
acaggccaac ttgtgaagat tgcaaaacgt ggcggcgtga ccgcaatgga ggcagtgcat     480
gcatcgcgca atgcactgac gggtgccccc ctgaacctga ccccggacca agtggtggct     540
atcgccagcc acgatggcgg caagcaagcg ctcgaaacgg tgcagcggct gttgccggtg     600
ctgtgccagg accatggcct gaccccggac caagtggtgg ctatcgccag ccacgatggc     660
ggcaagcaag cgctcgaaac ggtgcagcgg ctgttgccgg tgctgtgcca ggaccatggc     720
ctgaccccgg accaagtggt ggctatcgcc agcaacggtg gcggcaagca agcgctcgaa     780
acggtgcagc ggctgttgcc ggtgctgtgc caggaccatg gcctgacccc ggaccaagtg     840
gtggctatcg ccagcaacat tggcggcaag caagcgctcg aaacggtgca gcggctgttg     900
ccggtgctgt gccaggacca tggcctgacc ccggaccaag tggtggctat cgccagcaac     960
aatggcggca agcaagcgct cgaaacggtg cagcggctgt tgccggtgct gtgccaggac    1020
catggcctga ccccggacca agtggtggct atcgccagca acaatggcgg caagcaagcg    1080
ctcgaaacgg tgcagcggct gttgccggtg ctgtgccagg accatggcct gaccccggac    1140
caagtggtgg ctatcgccag caacggtggc ggcaagcaag cgctcgaaac ggtgcagcgg    1200
ctgttgccgg tgctgtgcca ggaccatggc ctgaccccgg accaagtggt ggctatcgcc    1260
agccacgatg gcggcaagca agcgctcgaa acggtgcagc ggctgttgcc ggtgctgtgc    1320
caggaccatg gcctgacccc ggaccaagtg gtggctatcg ccagccacga tggcggcaag    1380
caagcgctcg aaacggtgca gcggctgttg ccggtgctgt gccaggacca tggcctgacc    1440
ccggaccaag tggtggctat cgccagccac gatggcggca agcaagcgct cgaaacggtg    1500
cagcggctgt tgccggtgct gtgccaggac atggcctga ccccggacca agtggtggct     1560
atcgccagca acggtggcgg caagcaagcg ctcgaaacgg tgcagcggct gttgccggtg    1620
ctgtgccagg accatggcct gaccccggac caagtggtgg ctatcgccag ccacgatggc    1680
ggcaagcaag cgctcgaaac ggtgcagcgg ctgttgccgg tgctgtgcca ggaccatggc    1740
ctgaccccgg accaagtggt ggctatcgcc agcaacattg gcggcaagca agcgctcgaa    1800
acggtgcagc ggctgttgcc ggtgctgtgc caggaccatg gcctgactcc ggaccaagtg    1860
gtggctatcg ccagcaacat tggcggcaag caagcgctcg aaacggtgca gcggctgttg    1920
```

```
ccggtgctgt gccaggacca tggcctgacc ccggaccaag tggtggctat cgccagcaac   1980
attggcggca agcaagcgct cgaaacggtg cagcggctgt tgccggtgct gtgccaggac   2040
catggcctga ccccggacca agtggtggct atcgccagca acattggcgg caagcaagcg   2100
ctcgaaacgg tgcagcggct gttgccggtg ctgtgccagg accatggcct gaccccggac   2160
caagtggtgg ctatcgccag caacaatggc ggcaagcaag cgctcgaaac ggtgcagcgg   2220
ctgttgccgg tgctgtgcca ggaccatggc ctgaccccgg accaagtggt ggctatcgcc   2280
agccacgatg gcggcaagca agcgctcgaa acggtgcagc ggctgttgcc ggtgctgtgc   2340
caggaccatg gcctgacccc ggaccaagtg gtggctatcg ccagcaacat tggcggcaag   2400
caagcgctcg aaacggtgca gcggctgttg ccggtgctgt gccaggacca tggcctgacc   2460
ccggaccaag tggtggctat cgccagcaac ggtggcggca agcaagcgct cgaaagcatt   2520
gtggcccagc tgagccggcc tgatccggcg ttggccgcgt tgaccaacga cgaccacctc   2580
gtcgccttgg cctgcctcgg cggacgtcct gccatggatg cagtgaaaaa gggattgccg   2640
cacgcgccgg aattgatcag aagagtcaat cgccgtattg cgaacgcac  gtcccatcgc   2700
gttgccggat ccaaggctag cccgaaaaag aaacgcaaag ttgggcgcgc cgacgcgctg   2760
gacgatttcg atctcgacat gctgggttct gatgccctcg atgactttga cctggatatg   2820
ttgggaagcg acgcattgga tgactttgat ctggacatgc tcggctccga tgctctggac   2880
gatttcgatc tcgatatgtt aattaactac ccgtacgacg ttccggacta cgcttcttga   2940
```

```
<210> SEQ ID NO 54
<211> LENGTH: 979
<212> TYPE: PRT
<213> ORGANISM: Unknown
<220> FEATURE:
<223> OTHER INFORMATION: Synthetic peptide

<400> SEQUENCE: 54

Met Asp Tyr Lys Asp His Asp Gly Asp Tyr Lys Asp His Asp Ile Asp
1               5                   10                  15

Tyr Lys Asp Asp Asp Asp Lys Met Ala Pro Lys Lys Arg Lys Val
            20                  25                  30

Gly Arg Gly Ser Val Asp Leu Arg Thr Leu Gly Tyr Ser Gln Gln Gln
        35                  40                  45

Gln Glu Lys Ile Lys Pro Lys Val Arg Ser Thr Val Ala Gln His His
    50                  55                  60

Glu Ala Leu Val Gly His Gly Phe Thr His Ala His Ile Val Ala Leu
65                  70                  75                  80

Ser Gln His Pro Ala Ala Leu Gly Thr Val Ala Val Thr Tyr Gln His
                85                  90                  95

Ile Ile Thr Ala Leu Pro Glu Ala Thr His Glu Asp Ile Val Gly Val
            100                 105                 110

Gly Lys Gln Trp Ser Gly Ala Arg Ala Leu Glu Ala Leu Leu Thr Asp
        115                 120                 125

Ala Gly Glu Leu Arg Gly Pro Pro Leu Gln Leu Asp Thr Gly Gln Leu
    130                 135                 140

Val Lys Ile Ala Lys Arg Gly Gly Val Thr Ala Met Glu Ala Val His
145                 150                 155                 160

Ala Ser Arg Asn Ala Leu Thr Gly Ala Pro Leu Asn Leu Thr Pro Asp
                165                 170                 175

Gln Val Val Ala Ile Ala Ser His Asp Gly Gly Lys Gln Ala Leu Glu
            180                 185                 190
```

-continued

```
Thr Val Gln Arg Leu Leu Pro Val Leu Cys Gln Asp His Gly Leu Thr
    195                 200                 205

Pro Asp Gln Val Val Ala Ile Ala Ser His Asp Gly Gly Lys Gln Ala
210                 215                 220

Leu Glu Thr Val Gln Arg Leu Leu Pro Val Leu Cys Gln Asp His Gly
225                 230                 235                 240

Leu Thr Pro Asp Gln Val Val Ala Ile Ala Ser Asn Gly Gly Gly Lys
                245                 250                 255

Gln Ala Leu Glu Thr Val Gln Arg Leu Leu Pro Val Leu Cys Gln Asp
            260                 265                 270

His Gly Leu Thr Pro Asp Gln Val Ala Ile Ala Ser Asn Ile Gly
            275                 280                 285

Gly Lys Gln Ala Leu Glu Thr Val Gln Arg Leu Leu Pro Val Leu Cys
        290                 295                 300

Gln Asp His Gly Leu Thr Pro Asp Gln Val Val Ala Ile Ala Ser Asn
305                 310                 315                 320

Asn Gly Gly Lys Gln Ala Leu Glu Thr Val Gln Arg Leu Leu Pro Val
                325                 330                 335

Leu Cys Gln Asp His Gly Leu Thr Pro Asp Gln Val Val Ala Ile Ala
            340                 345                 350

Ser Asn Asn Gly Gly Lys Gln Ala Leu Glu Thr Val Gln Arg Leu Leu
            355                 360                 365

Pro Val Leu Cys Gln Asp His Gly Leu Thr Pro Asp Gln Val Val Ala
        370                 375                 380

Ile Ala Ser Asn Gly Gly Gly Lys Gln Ala Leu Glu Thr Val Gln Arg
385                 390                 395                 400

Leu Leu Pro Val Leu Cys Gln Asp His Gly Leu Thr Pro Asp Gln Val
                405                 410                 415

Val Ala Ile Ala Ser His Asp Gly Gly Lys Gln Ala Leu Glu Thr Val
            420                 425                 430

Gln Arg Leu Leu Pro Val Leu Cys Gln Asp His Gly Leu Thr Pro Asp
            435                 440                 445

Gln Val Val Ala Ile Ala Ser His Asp Gly Gly Lys Gln Ala Leu Glu
        450                 455                 460

Thr Val Gln Arg Leu Leu Pro Val Leu Cys Gln Asp His Gly Leu Thr
465                 470                 475                 480

Pro Asp Gln Val Val Ala Ile Ala Ser His Asp Gly Gly Lys Gln Ala
                485                 490                 495

Leu Glu Thr Val Gln Arg Leu Leu Pro Val Leu Cys Gln Asp His Gly
            500                 505                 510

Leu Thr Pro Asp Gln Val Val Ala Ile Ala Ser Asn Gly Gly Gly Lys
            515                 520                 525

Gln Ala Leu Glu Thr Val Gln Arg Leu Leu Pro Val Leu Cys Gln Asp
        530                 535                 540

His Gly Leu Thr Pro Asp Gln Val Val Ala Ile Ala Ser His Asp Gly
545                 550                 555                 560

Gly Lys Gln Ala Leu Glu Thr Val Gln Arg Leu Leu Pro Val Leu Cys
                565                 570                 575

Gln Asp His Gly Leu Thr Pro Asp Gln Val Val Ala Ile Ala Ser Asn
            580                 585                 590

Ile Gly Gly Lys Gln Ala Leu Glu Thr Val Gln Arg Leu Leu Pro Val
            595                 600                 605
```

Leu Cys Gln Asp His Gly Leu Thr Pro Asp Gln Val Ala Ile Ala
610                 615                 620

Ser Asn Ile Gly Gly Lys Gln Ala Leu Glu Thr Val Gln Arg Leu Leu
625                 630                 635                 640

Pro Val Leu Cys Gln Asp His Gly Leu Thr Pro Asp Gln Val Ala
            645                 650                 655

Ile Ala Ser Asn Ile Gly Gly Lys Gln Ala Leu Glu Thr Val Gln Arg
            660                 665                 670

Leu Leu Pro Val Leu Cys Gln Asp His Gly Leu Thr Pro Asp Gln Val
            675                 680                 685

Val Ala Ile Ala Ser Asn Ile Gly Gly Lys Gln Ala Leu Glu Thr Val
690                 695                 700

Gln Arg Leu Leu Pro Val Leu Cys Gln Asp His Gly Leu Thr Pro Asp
705                 710                 715                 720

Gln Val Val Ala Ile Ala Ser Asn Asn Gly Gly Lys Gln Ala Leu Glu
            725                 730                 735

Thr Val Gln Arg Leu Leu Pro Val Leu Cys Gln Asp His Gly Leu Thr
            740                 745                 750

Pro Asp Gln Val Val Ala Ile Ala Ser His Asp Gly Gly Lys Gln Ala
            755                 760                 765

Leu Glu Thr Val Gln Arg Leu Leu Pro Val Leu Cys Gln Asp His Gly
770                 775                 780

Leu Thr Pro Asp Gln Val Val Ala Ile Ala Ser Asn Ile Gly Gly Lys
785                 790                 795                 800

Gln Ala Leu Glu Thr Val Gln Arg Leu Leu Pro Val Leu Cys Gln Asp
            805                 810                 815

His Gly Leu Thr Pro Asp Gln Val Val Ala Ile Ala Ser Asn Gly Gly
            820                 825                 830

Gly Lys Gln Ala Leu Glu Ser Ile Val Ala Gln Leu Ser Arg Pro Asp
835                 840                 845

Pro Ala Leu Ala Ala Leu Thr Asn Asp His Leu Val Ala Leu Ala
850                 855                 860

Cys Leu Gly Gly Arg Pro Ala Met Asp Ala Val Lys Lys Gly Leu Pro
865                 870                 875                 880

His Ala Pro Glu Leu Ile Arg Arg Val Asn Arg Arg Ile Gly Glu Arg
            885                 890                 895

Thr Ser His Arg Val Ala Gly Ser Lys Ala Ser Pro Lys Lys Lys Arg
            900                 905                 910

Lys Val Gly Arg Ala Asp Ala Leu Asp Asp Phe Asp Leu Asp Met Leu
            915                 920                 925

Gly Ser Asp Ala Leu Asp Asp Phe Asp Leu Asp Met Leu Gly Ser Asp
930                 935                 940

Ala Leu Asp Asp Phe Asp Leu Asp Met Leu Gly Ser Asp Ala Leu Asp
945                 950                 955                 960

Asp Phe Asp Leu Asp Met Leu Ile Asn Tyr Pro Tyr Asp Val Pro Asp
            965                 970                 975

Tyr Ala Ser

<210> SEQ ID NO 55
<211> LENGTH: 2634
<212> TYPE: DNA
<213> ORGANISM: Artificial sequence
<220> FEATURE:
<223> OTHER INFORMATION: Synthetic oligonucleotide

<400> SEQUENCE: 55

```
atggactaca aagaccatga cggtgattat aaagatcatg acatcgatta caaggatgac      60
gatgacaaga tggcccccaa gaagaagagg aaggtgggcc gcggatctgt ggatctacgc     120
acgctcggct acagtcagca gcagcaagag aagatcaaac cgaaggtgcg ttcgacagtg     180
gcgcagcacc acgaggcact ggtgggccat gggtttacac acgcgcacat cgttgcgctc     240
agccaacacc cggcagcgtt agggaccgtc gctgtcacgt atcagcacat aatcacggcg     300
ttgccagagg cgacacacga agacatcgtt ggcgtcggca acagtggtc cggcgcacgc      360
gccctggagg ccttgctcac ggatgcgggg gagttgagag gtccgccgtt acagttggac     420
acaggccaac ttgtgaagat tgcaaaacgt ggcggcgtga ccgcaatgga ggcagtgcat     480
gcatcgcgca atgcactgac gggtgccccc ctgaacctga ccccggacca agtggtggct     540
atcgccagcc acgatggcgg caagcaagcg ctcgaaacgg tgcagcggct gttgccggtg     600
ctgtgccagg accatggcct gaccccggac caagtggtgg ctatcgccag ccacgatggc     660
ggcaagcaag cgctcgaaac ggtgcagcgg ctgttgccgg tgctgtgcca ggaccatggc     720
ctgaccccgg accaagtggt ggctatcgcc agcaacattg gcggcaagca agcgctcgaa     780
acggtgcagc ggctgttgcc ggtgctgtgc caggaccatg gcctgacccc ggaccaagtg     840
gtggctatcg ccagcaacaa tggcggcaag caagcgctcg aaacggtgca gcggctgttg     900
ccggtgctgt gccaggacca tggcctgacc ccggaccaag tggtggctat cgccagccac     960
gatggcggca agcaagcgct cgaaacggtg cagcggctgt tgccggtgct gtgccaggac    1020
catggcctga ccccggacca agtggtggct atcgccagcc acgatggcgg caagcaagcg    1080
ctcgaaacgg tgcagcggct gttgccggtg ctgtgccagg accatggcct gaccccggac    1140
caagtggtgg ctatcgccag caacggtggc ggcaagcaag cgctcgaaac ggtgcagcgg    1200
ctgttgccgg tgctgtgcca ggaccatggc ctgaccccgg accaagtggt ggctatcgcc    1260
agccacgatg gcggcaagca agcgctcgaa acggtgcagc ggctgttgcc ggtgctgtgc    1320
caggaccatg gcctgacccc ggaccaagtg gtggctatcg ccagcaacga tggcggcaag    1380
caagcgctcg aaacggtgca gcggctgttg ccggtgctgt gccaggacca tggcctgacc    1440
ccggaccaag tggtggctat cgccagcaac attggcggca agcaagcgct cgaaacggtg    1500
cagcggctgt tgccggtgct gtgccaggac catggcctga ccccggacca gtggtggct     1560
atcgccagca caatggcgg caagcaagcg ctcgaaacgg tgcagcggct gttgccggtg     1620
ctgtgccagg accatggcct gaccccggac caagtggtgg ctatcgccag ccacgatggc    1680
ggcaagcaag cgctcgaaac ggtgcagcgg ctgttgccgg tgctgtgcca ggaccatggc    1740
ctgaccccgg accaagtggt ggctatcgcc agcaacattg gcggcaagca agcgctcgaa    1800
acggtgcagc ggctgttgcc ggtgctgtgc caggaccatg gcctgacccc ggaccaagtg    1860
gtggctatcg ccagcaacaa tggcggcaag caagcgctcg aaacggtgca gcggctgttg    1920
ccggtgctgt gccaggacca tggcctgacc ccggaccaag tggtggctat cgccagccac    1980
gatggcggca agcaagcgct cgaaacggtg cagcggctgt tgccggtgct gtgccaggac    2040
catggcctga ccccggacca gtggtggct atcgccagca acattggcgg caagcaagcg     2100
ctcgaaacgg tgcagcggct gttgccggtg ctgtgccagg accatggcct gaccccggac    2160
caagtggtgg ctatcgccag caacggtggc ggcaagcaag cgctcgaaag cattgtggcc    2220
cagctgagcc ggcctgatcc ggcgttggcc gcgttgacca cgacgacca cctcgtcgcc     2280
ttggcctgcc tcggcggacg tcctgccatg gatgcagtga aaaagggatt gccgcacgcg    2340
```

```
ccggaattga tcagaagagt caatcgccgt attggcgaac gcacgtccca tcgcgttgcc    2400
ggatccaagg ctagcccgaa aaagaaacgc aaagttgggc gcgccgacgc gctggacgat    2460
ttcgatctcg acatgctggg ttctgatgcc ctcgatgact ttgacctgga tatgttggga    2520
agcgacgcat ggatgacttt gatctggac atgctcggct ccgatgctct ggacgatttc    2580
gatctcgata tgttaattaa ctacccgtac gacgttccgg actacgcttc ttga          2634
```

<210> SEQ ID NO 56
<211> LENGTH: 877
<212> TYPE: PRT
<213> ORGANISM: Unknown
<220> FEATURE:
<223> OTHER INFORMATION: Synthetic peptide

<400> SEQUENCE: 56

```
Met Asp Tyr Lys Asp His Asp Gly Asp Tyr Lys Asp His Asp Ile Asp
1               5                   10                  15

Tyr Lys Asp Asp Asp Lys Met Ala Pro Lys Lys Arg Lys Val
            20                  25                  30

Gly Arg Gly Ser Val Asp Leu Arg Thr Leu Gly Tyr Ser Gln Gln Gln
        35                  40                  45

Gln Glu Lys Ile Lys Pro Lys Val Arg Ser Thr Val Ala Gln His His
    50                  55                  60

Glu Ala Leu Val Gly His Gly Phe Thr His Ala His Ile Val Ala Leu
65                  70                  75                  80

Ser Gln His Pro Ala Ala Leu Gly Thr Val Ala Val Thr Tyr Gln His
                85                  90                  95

Ile Ile Thr Ala Leu Pro Glu Ala Thr His Glu Asp Ile Val Gly Val
            100                 105                 110

Gly Lys Gln Trp Ser Gly Ala Arg Ala Leu Glu Ala Leu Leu Thr Asp
        115                 120                 125

Ala Gly Glu Leu Arg Gly Pro Pro Leu Gln Leu Asp Thr Gly Gln Leu
    130                 135                 140

Val Lys Ile Ala Lys Arg Gly Gly Val Thr Ala Met Glu Ala Val His
145                 150                 155                 160

Ala Ser Arg Asn Ala Leu Thr Gly Ala Pro Leu Asn Leu Thr Pro Asp
                165                 170                 175

Gln Val Val Ala Ile Ala Ser His Asp Gly Gly Lys Gln Ala Leu Glu
            180                 185                 190

Thr Val Gln Arg Leu Leu Pro Val Leu Cys Gln Asp His Gly Leu Thr
        195                 200                 205

Pro Asp Gln Val Val Ala Ile Ala Ser His Asp Gly Gly Lys Gln Ala
    210                 215                 220

Leu Glu Thr Val Gln Arg Leu Leu Pro Val Leu Cys Gln Asp His Gly
225                 230                 235                 240

Leu Thr Pro Asp Gln Val Val Ala Ile Ala Ser Asn Ile Gly Gly Lys
                245                 250                 255

Gln Ala Leu Glu Thr Val Gln Arg Leu Leu Pro Val Leu Cys Gln Asp
            260                 265                 270

His Gly Leu Thr Pro Asp Gln Val Val Ala Ile Ala Ser Asn Asn Gly
        275                 280                 285

Gly Lys Gln Ala Leu Glu Thr Val Gln Arg Leu Leu Pro Val Leu Cys
    290                 295                 300

Gln Asp His Gly Leu Thr Pro Asp Gln Val Val Ala Ile Ala Ser His
```

```
         305                 310                 315                 320
Asp Gly Gly Lys Gln Ala Leu Glu Thr Val Gln Arg Leu Leu Pro Val
                325                 330                 335
Leu Cys Gln Asp His Gly Leu Thr Pro Asp Gln Val Val Ala Ile Ala
                340                 345                 350
Ser His Asp Gly Gly Lys Gln Ala Leu Glu Thr Val Gln Arg Leu Leu
                355                 360                 365
Pro Val Leu Cys Gln Asp His Gly Leu Thr Pro Asp Gln Val Val Ala
        370                 375                 380
Ile Ala Ser Asn Gly Gly Lys Gln Ala Leu Glu Thr Val Gln Arg
385                 390                 395                 400
Leu Leu Pro Val Leu Cys Gln Asp His Gly Leu Thr Pro Asp Gln Val
                405                 410                 415
Val Ala Ile Ala Ser His Asp Gly Gly Lys Gln Ala Leu Glu Thr Val
            420                 425                 430
Gln Arg Leu Leu Pro Val Leu Cys Gln Asp His Gly Leu Thr Pro Asp
        435                 440                 445
Gln Val Val Ala Ile Ala Ser His Asp Gly Gly Lys Gln Ala Leu Glu
    450                 455                 460
Thr Val Gln Arg Leu Leu Pro Val Leu Cys Gln Asp His Gly Leu Thr
465                 470                 475                 480
Pro Asp Gln Val Val Ala Ile Ala Ser Asn Ile Gly Gly Lys Gln Ala
                485                 490                 495
Leu Glu Thr Val Gln Arg Leu Leu Pro Val Leu Cys Gln Asp His Gly
                500                 505                 510
Leu Thr Pro Asp Gln Val Val Ala Ile Ala Ser Asn Asn Gly Gly Lys
            515                 520                 525
Gln Ala Leu Glu Thr Val Gln Arg Leu Leu Pro Val Leu Cys Gln Asp
    530                 535                 540
His Gly Leu Thr Pro Asp Gln Val Val Ala Ile Ala Ser His Asp Gly
545                 550                 555                 560
Gly Lys Gln Ala Leu Glu Thr Val Gln Arg Leu Leu Pro Val Leu Cys
                565                 570                 575
Gln Asp His Gly Leu Thr Pro Asp Gln Val Val Ala Ile Ala Ser Asn
                580                 585                 590
Ile Gly Gly Lys Gln Ala Leu Glu Thr Val Gln Arg Leu Leu Pro Val
            595                 600                 605
Leu Cys Gln Asp His Gly Leu Thr Pro Asp Gln Val Val Ala Ile Ala
        610                 615                 620
Ser Asn Asn Gly Gly Lys Gln Ala Leu Glu Thr Val Gln Arg Leu Leu
625                 630                 635                 640
Pro Val Leu Cys Gln Asp His Gly Leu Thr Pro Asp Gln Val Val Ala
                645                 650                 655
Ile Ala Ser His Asp Gly Gly Lys Gln Ala Leu Glu Thr Val Gln Arg
                660                 665                 670
Leu Leu Pro Val Leu Cys Gln Asp His Gly Leu Thr Pro Asp Gln Val
            675                 680                 685
Val Ala Ile Ala Ser Asn Ile Gly Gly Lys Gln Ala Leu Glu Thr Val
        690                 695                 700
Gln Arg Leu Leu Pro Val Leu Cys Gln Asp His Gly Leu Thr Pro Asp
705                 710                 715                 720
Gln Val Val Ala Ile Ala Ser Asn Gly Gly Gly Lys Gln Ala Leu Glu
                725                 730                 735
```

```
Ser Ile Val Ala Gln Leu Ser Arg Pro Asp Pro Ala Leu Ala Ala Leu
                740                 745                 750

Thr Asn Asp Asp His Leu Val Ala Leu Ala Cys Leu Gly Gly Arg Pro
            755                 760                 765

Ala Met Asp Ala Val Lys Lys Gly Leu Pro His Ala Pro Glu Leu Ile
770                 775                 780

Arg Arg Val Asn Arg Arg Ile Gly Glu Arg Thr Ser His Arg Val Ala
785                 790                 795                 800

Gly Ser Lys Ala Ser Pro Lys Lys Arg Lys Val Gly Arg Ala Asp
                805                 810                 815

Ala Leu Asp Asp Phe Asp Leu Asp Met Leu Gly Ser Asp Ala Leu Asp
            820                 825                 830

Asp Phe Asp Leu Asp Met Leu Gly Ser Asp Ala Leu Asp Phe Asp
            835                 840                 845

Leu Asp Met Leu Gly Ser Asp Ala Leu Asp Asp Phe Asp Leu Asp Met
850                 855                 860

Leu Ile Asn Tyr Pro Tyr Asp Val Pro Asp Tyr Ala Ser
865                 870                 875
```

<210> SEQ ID NO 57
<211> LENGTH: 2532
<212> TYPE: DNA
<213> ORGANISM: Artificial sequence
<220> FEATURE:
<223> OTHER INFORMATION: Synthetic oligonucleotide

<400> SEQUENCE: 57

```
atggactaca aagaccatga cggtgattat aaagatcatg acatcgatta caaggatgac    60
gatgacaaga tggcccccaa gaagaagagg aaggtgggcc gcggatctgt ggatctacgc   120
acgctcggct acagtcagca gcagcaagag aagatcaaac cgaaggtgcg ttcgacagtg   180
gcgcagcacc acgaggcact ggtgggccat gggtttacac acgcgcacat cgttgcgctc   240
agccaacacc cggcagcgtt agggaccgtc gctgtcacgt atcagcacat aatcacggcg   300
ttgccagagg cgacacacga agacatcgtt ggcgtcggca aacagtggtc cggcgcacgc   360
gccctggagg ccttgctcac ggatgcgggg gagttgagag gtccgccgtt acagttggac   420
acaggccaac ttgtgaagat tgcaaaacgt ggcggcgtga ccgcaatgga ggcagtgcat   480
gcatcgcgca atgcactgac gggtgccccc ctgaacctga ccccggacca agtggtggct   540
atcgccagca cattggcgg caagcaagcg ctcgaaacgg tgcagcggct gttgccggtg   600
ctgtgccagg accatggcct gaccccggac caagtggtgg ctatcgccag caacaatggc   660
ggcaagcaag cgctcgaaac ggtgcagcgg ctgttgccgg tgctgtgcca ggaccatggc   720
ctgaccccgg accaagtggt ggctatcgcc agccacgatg gcggcaagca agcgctcgaa   780
acggtgcagc ggctgttgcc ggtgctgtgc caggaccatg gcctgacccc ggaccaagtg   840
gtggctatcg ccagcaacgg tggcggcaag caagcgctcg aaacggtgca gcggctgttg   900
ccggtgctgt gccaggacca tggcctgacc ccggaccaag tggtggctat cgccagccac   960
gatgccggca gcaagcgct cgaaacggtg cagcggctgt tgccggtgct gtgccaggac  1020
catggcctga ccccggacca agtggtggct atcgccagca cggtggcgg caagcaagcg  1080
ctcgaaacgg tgcagcggct gttgccggtg ctgtgccagg accatggcct gaccccggac  1140
caagtggtgg ctatcgccag ccacgatggc ggcaagcaag cgctcgaaac ggtgcagcgg  1200
ctgttgccgg tgctgtgcca ggaccatggc ctgaccccgg accaagtggt ggctatcgcc  1260
```

-continued

```
agccacgatg gcggcaagca agcgctcgaa acggtgcagc ggctgttgcc ggtgctgtgc   1320
caggaccatg gcctgacccc ggaccaagtg gtggctatcg ccagccacga tggcggcaag   1380
caagcgctcg aaacggtgca gcggctgttg ccggtgctgt gccaggacca tggcctgacc   1440
ccggaccaag tggtggctat cgccagcaac ggtggcggca agcaagcgct cgaaacggtg   1500
cagcggctgt tgccggtgct gtgccaggac catggcctga ccccggacca agtggtggct   1560
atcgccagcc acgatggcgg caagcaagcg ctcgaaacgg tgcagcggct gttgccggtg   1620
ctgtgccagg accatggcct gaccccggac caagtggtgg ctatcgccag ccacgatggc   1680
ggcaagcaag cgctcgaaac ggtgcagcgg ctgttgccgg tgctgtgcca ggaccatggc   1740
ctgaccccgg accaagtggt ggctatcgcc agccacgatg gcggcaagca agcgctcgaa   1800
acggtgcagc ggctgttgcc ggtgctgtgc caggaccatg gcctgacccc ggaccaagtg   1860
gtggctatcg ccagccacga tggcggcaag caagcgctcg aaacggtgca gcggctgttg   1920
ccggtgctgt gccaggacca tggcctgacc ccggaccaag tggtggctat cgccagcaac   1980
ggtggcggca agcaagcgct cgaaacggtg cagcggctgt tgccggtgct gtgccaggac   2040
catggcctga ccccggacca agtggtggct atcgccagca acggtggcgg caagcaagcg   2100
ctcgaaagca ttgtggccca gctgagccgg cctgatccgg cgttggccgc gttgaccaac   2160
gacgaccacc tcgtcgcctt ggcctgcctc ggcggacgtc ctgccatgga tgcagtgaaa   2220
aagggattgc cgcacgcgcc ggaattgatc agaagagtca atcgccgtat tggcgaacgc   2280
acgtcccatc gcgttgccgg atccaaggct agcccgaaaa agaaacgcaa agttgggcgc   2340
gccgacgcgc tggacgattt cgatctcgac atgctgggtt ctgatgccct cgatgacttt   2400
gacctggata tgtttgggaag cgacgcattg atgactttg atctggacat gctcggctcc   2460
gatgctctgg acgatttcga tctcgatatg ttaattaact acccgtacga cgttccggac   2520
tacgcttctt ga                                                       2532
```

<210> SEQ ID NO 58
<211> LENGTH: 843
<212> TYPE: PRT
<213> ORGANISM: Unknown
<220> FEATURE:
<223> OTHER INFORMATION: Synthetic peptide

<400> SEQUENCE: 58

```
Met Asp Tyr Lys Asp His Asp Gly Asp Tyr Lys Asp His Asp Ile Asp
1               5                   10                  15

Tyr Lys Asp Asp Asp Lys Met Ala Pro Lys Lys Arg Lys Val
            20                  25                  30

Gly Arg Gly Ser Val Asp Leu Arg Thr Leu Gly Tyr Ser Gln Gln Gln
        35                  40                  45

Gln Glu Lys Ile Lys Pro Lys Val Arg Ser Thr Val Ala Gln His His
    50                  55                  60

Glu Ala Leu Val Gly His Gly Phe Thr His Ala His Ile Val Ala Leu
65                  70                  75                  80

Ser Gln His Pro Ala Ala Leu Gly Thr Val Ala Val Thr Tyr Gln His
                85                  90                  95

Ile Ile Thr Ala Leu Pro Glu Ala Thr His Glu Asp Ile Val Gly Val
            100                 105                 110

Gly Lys Gln Trp Ser Gly Ala Arg Ala Leu Glu Ala Leu Leu Thr Asp
        115                 120                 125
```

```
Ala Gly Glu Leu Arg Gly Pro Pro Leu Gln Leu Asp Thr Gly Gln Leu
    130                 135                 140

Val Lys Ile Ala Lys Arg Gly Val Thr Ala Met Glu Ala Val His
145                 150                 155                 160

Ala Ser Arg Asn Ala Leu Thr Gly Ala Pro Leu Asn Leu Thr Pro Asp
                165                 170                 175

Gln Val Val Ala Ile Ala Ser Asn Ile Gly Gly Lys Gln Ala Leu Glu
                180                 185                 190

Thr Val Gln Arg Leu Leu Pro Val Leu Cys Gln Asp His Gly Leu Thr
            195                 200                 205

Pro Asp Gln Val Val Ala Ile Ala Ser Asn Asn Gly Gly Lys Gln Ala
210                 215                 220

Leu Glu Thr Val Gln Arg Leu Leu Pro Val Leu Cys Gln Asp His Gly
225                 230                 235                 240

Leu Thr Pro Asp Gln Val Val Ala Ile Ala Ser His Asp Gly Gly Lys
                245                 250                 255

Gln Ala Leu Glu Thr Val Gln Arg Leu Leu Pro Val Leu Cys Gln Asp
                260                 265                 270

His Gly Leu Thr Pro Asp Gln Val Val Ala Ile Ala Ser Asn Gly Gly
        275                 280                 285

Gly Lys Gln Ala Leu Glu Thr Val Gln Arg Leu Leu Pro Val Leu Cys
290                 295                 300

Gln Asp His Gly Leu Thr Pro Asp Gln Val Val Ala Ile Ala Ser His
305                 310                 315                 320

Asp Gly Gly Lys Gln Ala Leu Glu Thr Val Gln Arg Leu Leu Pro Val
                325                 330                 335

Leu Cys Gln Asp His Gly Leu Thr Pro Asp Gln Val Val Ala Ile Ala
                340                 345                 350

Ser Asn Gly Gly Gly Lys Gln Ala Leu Glu Thr Val Gln Arg Leu Leu
            355                 360                 365

Pro Val Leu Cys Gln Asp His Gly Leu Thr Pro Asp Gln Val Val Ala
370                 375                 380

Ile Ala Ser His Asp Gly Gly Lys Gln Ala Leu Glu Thr Val Gln Arg
385                 390                 395                 400

Leu Leu Pro Val Leu Cys Gln Asp His Gly Leu Thr Pro Asp Gln Val
                405                 410                 415

Val Ala Ile Ala Ser His Asp Gly Gly Lys Gln Ala Leu Glu Thr Val
                420                 425                 430

Gln Arg Leu Leu Pro Val Leu Cys Gln Asp His Gly Leu Thr Pro Asp
            435                 440                 445

Gln Val Val Ala Ile Ala Ser His Asp Gly Gly Lys Gln Ala Leu Glu
        450                 455                 460

Thr Val Gln Arg Leu Leu Pro Val Leu Cys Gln Asp His Gly Leu Thr
465                 470                 475                 480

Pro Asp Gln Val Val Ala Ile Ala Ser Asn Gly Gly Gly Lys Gln Ala
                485                 490                 495

Leu Glu Thr Val Gln Arg Leu Leu Pro Val Leu Cys Gln Asp His Gly
                500                 505                 510

Leu Thr Pro Asp Gln Val Val Ala Ile Ala Ser His Asp Gly Gly Lys
            515                 520                 525

Gln Ala Leu Glu Thr Val Gln Arg Leu Leu Pro Val Leu Cys Gln Asp
        530                 535                 540

His Gly Leu Thr Pro Asp Gln Val Val Ala Ile Ala Ser His Asp Gly
```

Gly Lys Gln Ala Leu Glu Thr Val Gln Arg Leu Leu Pro Val Leu Cys
545                 550                 555                 560

Gln Asp His Gly Leu Thr Pro Asp Gln Val Val Ala Ile Ala Ser His
        565                 570                 575

Asp Gly Gly Lys Gln Ala Leu Glu Thr Val Gln Arg Leu Leu Pro Val
            580                 585                 590

Leu Cys Gln Asp His Gly Leu Thr Pro Asp Gln Val Val Ala Ile Ala
    595                 600                 605

Ser His Asp Gly Gly Lys Gln Ala Leu Glu Thr Val Gln Arg Leu Leu
610                 615                 620

Pro Val Leu Cys Gln Asp His Gly Leu Thr Pro Asp Gln Val Val Ala
625                 630                 635                 640

Ile Ala Ser Asn Gly Gly Gly Lys Gln Ala Leu Glu Thr Val Gln Arg
        645                 650                 655

Leu Leu Pro Val Leu Cys Gln Asp His Gly Leu Thr Pro Asp Gln Val
            660                 665                 670

Val Ala Ile Ala Ser Asn Gly Gly Gly Lys Gln Ala Leu Glu Ser Ile
    675                 680                 685

Val Ala Gln Leu Ser Arg Pro Asp Pro Ala Leu Ala Ala Leu Thr Asn
690                 695                 700

Asp Asp His Leu Val Ala Leu Ala Cys Leu Gly Gly Arg Pro Ala Met
705                 710                 715                 720

Asp Ala Val Lys Lys Gly Leu Pro His Ala Pro Glu Leu Ile Arg Arg
        725                 730                 735

Val Asn Arg Arg Ile Gly Glu Arg Thr Ser His Arg Val Ala Gly Ser
            740                 745                 750

Lys Ala Ser Pro Lys Lys Lys Arg Lys Val Gly Arg Ala Asp Ala Leu
    755                 760                 765

Asp Asp Phe Asp Leu Asp Met Leu Gly Ser Asp Ala Leu Asp Asp Phe
770                 775                 780

Asp Leu Asp Met Leu Gly Ser Asp Ala Leu Asp Asp Phe Asp Leu Asp
785                 790                 795                 800

Met Leu Gly Ser Asp Ala Leu Asp Asp Phe Asp Leu Asp Met Leu Ile
        805                 810                 815

Asn Tyr Pro Tyr Asp Val Pro Asp Tyr Ala Ser
            820                 825                 830

<210> SEQ ID NO 59
<211> LENGTH: 2532
<212> TYPE: DNA
<213> ORGANISM: Artificial sequence
<220> FEATURE:
<223> OTHER INFORMATION: Synthetic oligonucleotide

<400> SEQUENCE: 59
atggactaca aagaccatga cggtgattat aaagatcatg acatcgatta caaggatgac      60
gatgacaaga tggccccccaa gaagaagagg aaggtgggcc gcggatctgt ggatctacgc    120
acgctcggct acagtcagca gcagcaagag aagatcaaac cgaaggtgcg ttcgacagtg    180
gcgcagcacc acgaggcact ggtgggccat gggtttacac acgcgcacat cgttgcgctc    240
agccaacacc cggcagcgtt agggaccgtc gctgtcacgt atcagcacat aatcacggcg    300
ttgccagagg cgacacacga agacatcgtt ggcgtcggca aacagtggtc cggcgcacgc    360
gccctggagg ccttgctcac ggatgcgggg gagttgagag gtccgccgtt acagttggac    420

```
acaggccaac ttgtgaagat tgcaaaacgt ggcggcgtga ccgcaatgga ggcagtgcat      480
gcatcgcgca atgcactgac gggtgccccc ctgaacctga ccccggacca agtggtggct      540
atcgccagcc acgatggcgg caagcaagcg ctcgaaacgg tgcagcggct gttgccggtg      600
ctgtgccagg accatggcct gaccccggac caagtggtgg ctatcgccag ccacgatggc      660
ggcaagcaag cgctcgaaac ggtgcagcgg ctgttgccgg tgctgtgcca ggaccatggc      720
ctgaccccgg accaagtggt ggctatcgcc agccacgatg gcggcaagca agcgctcgaa      780
acggtgcagc ggctgttgcc ggtgctgtgc caggaccatg gcctgacccc ggaccaagtg      840
gtggctatcg ccagccacga tggcggcaag caagcgctcg aaacggtgca gcggctgttg      900
ccggtgctgt gccaggacca tggcctgacc ccggaccaag tggtggctat cgccagcaac      960
ggtggcggca agcaagcgct cgaaacggtg cagcggctgt tgccggtgct gtgccaggac     1020
catggcctga ccccggacca agtggtggct atcgccagca cattggcgg caagcaagcg     1080 ctcgaaacgg tgcagcggct gttgccggtg ctgtgccagg accatggcct gaccccggac     1140
caagtggtgg ctatcgccag caacaatggc ggcaagcaag cgctcgaaac ggtgcagcgg     1200
ctgttgccgg tgctgtgcca ggaccatggc ctgaccccgg accaagtggt ggctatcgcc     1260
agcaacattg gcggcaagca agcgctcgaa acggtgcagc ggctgttgcc ggtgctgtgc     1320
caggaccatg gcctgacccc ggaccaagtg gtggctatcg ccagcaacgg tggcggcaag     1380
caagcgctcg aaacggtgca gcggctgttg ccggtgctgt gccaggacca tggcctgacc     1440
ccggaccaag tggtggctat cgccagcaac aatggcggca agcaagcgct cgaaacggtg     1500
cagcggctgt tgccggtgct gtgccaggac catggcctga ccccggacca agtggtggct     1560
atcgccagca cattggcgg caagcaagcg ctcgaaacgg tgcagcggct gttgccggtg     1620
ctgtgccagg accatggcct gaccccggac caagtggtgg ctatcgccag caacattggc     1680
ggcaagcaag cgctcgaaac ggtgcagcgg ctgttgccgg tgctgtgcca ggaccatggc     1740
ctgaccccgg accaagtggt ggctatcgcc agcaacaatg gcggcaagca agcgctcgaa     1800
acggtgcagc ggctgttgcc ggtgctgtgc caggaccatg gcctgacccc ggaccaagtg     1860
gtggctatcg ccagcaacgg tggcggcaag caagcgctcg aaacggtgca gcggctgttg     1920
ccggtgctgt gccaggacca tggcctgacc ccggaccaag tggtggctat cgccagccac     1980
gatggcggca agcaagcgct cgaaacggtg cagcggctgt tgccggtgct gtgccaggac     2040
catggcctga ccccggacca agtggtggct atcgccagca cggtggcgg caagcaagcg     2100 ctcgaaagca ttgtgcccca gctgagccgg cctgatccgg cgttggccgc gttgaccaac     2160
gacgaccacc tcgtcgcctt ggcctgcctc ggcggacgtc ctgccatgga tgcagtgaaa     2220
aagggattgc cgcacgcgcc ggaattgatc agaagagtca atcgccgtat tggcgaacgc     2280
acgtcccatc gcgttgccgg atccaaggct agcccgaaaa agaaacgcaa agttgggcgc     2340
gccgacgcgc tggacgattt cgatctcgac atgctgggtt ctgatgccct cgatgacttt     2400
gacctggata tgttgggaag cgacgcattg gatgactttg atctggacat gctcggctcc     2460
gatgctctgg acgatttcga tctcgatatg ttaattaact acccgtacga cgttccggac     2520
tacgcttctt ga                                                        2532
```

<210> SEQ ID NO 60
<211> LENGTH: 843
<212> TYPE: PRT
<213> ORGANISM: Unknown
<220> FEATURE:

<223> OTHER INFORMATION: Synthetic peptide

<400> SEQUENCE: 60

```
Met Asp Tyr Lys Asp His Asp Gly Asp Tyr Lys Asp His Asp Ile Asp
1               5                   10                  15
Tyr Lys Asp Asp Asp Asp Lys Met Ala Pro Lys Lys Lys Arg Lys Val
            20                  25                  30
Gly Arg Gly Ser Val Asp Leu Arg Thr Leu Gly Tyr Ser Gln Gln Gln
        35                  40                  45
Gln Glu Lys Ile Lys Pro Lys Val Arg Ser Thr Val Ala Gln His His
    50                  55                  60
Glu Ala Leu Val Gly His Gly Phe Thr His Ala His Ile Val Ala Leu
65                  70                  75                  80
Ser Gln His Pro Ala Ala Leu Gly Thr Val Ala Val Thr Tyr Gln His
                85                  90                  95
Ile Ile Thr Ala Leu Pro Glu Ala Thr His Glu Asp Ile Val Gly Val
            100                 105                 110
Gly Lys Gln Trp Ser Gly Ala Arg Ala Leu Glu Ala Leu Leu Thr Asp
        115                 120                 125
Ala Gly Glu Leu Arg Gly Pro Pro Leu Gln Leu Asp Thr Gly Gln Leu
    130                 135                 140
Val Lys Ile Ala Lys Arg Gly Gly Val Thr Ala Met Glu Ala Val His
145                 150                 155                 160
Ala Ser Arg Asn Ala Leu Thr Gly Ala Pro Leu Asn Leu Thr Pro Asp
                165                 170                 175
Gln Val Val Ala Ile Ala Ser His Asp Gly Gly Lys Gln Ala Leu Glu
            180                 185                 190
Thr Val Gln Arg Leu Leu Pro Val Leu Cys Gln Asp His Gly Leu Thr
        195                 200                 205
Pro Asp Gln Val Val Ala Ile Ala Ser His Asp Gly Gly Lys Gln Ala
    210                 215                 220
Leu Glu Thr Val Gln Arg Leu Leu Pro Val Leu Cys Gln Asp His Gly
225                 230                 235                 240
Leu Thr Pro Asp Gln Val Val Ala Ile Ala Ser His Asp Gly Gly Lys
                245                 250                 255
Gln Ala Leu Glu Thr Val Gln Arg Leu Leu Pro Val Leu Cys Gln Asp
            260                 265                 270
His Gly Leu Thr Pro Asp Gln Val Val Ala Ile Ala Ser His Asp Gly
        275                 280                 285
Gly Lys Gln Ala Leu Glu Thr Val Gln Arg Leu Leu Pro Val Leu Cys
    290                 295                 300
Gln Asp His Gly Leu Thr Pro Asp Gln Val Val Ala Ile Ala Ser Asn
305                 310                 315                 320
Gly Gly Gly Lys Gln Ala Leu Glu Thr Val Gln Arg Leu Leu Pro Val
                325                 330                 335
Leu Cys Gln Asp His Gly Leu Thr Pro Asp Gln Val Val Ala Ile Ala
            340                 345                 350
Ser Asn Ile Gly Gly Lys Gln Ala Leu Glu Thr Val Gln Arg Leu Leu
        355                 360                 365
Pro Val Leu Cys Gln Asp His Gly Leu Thr Pro Asp Gln Val Val Ala
    370                 375                 380
Ile Ala Ser Asn Asn Gly Gly Lys Gln Ala Leu Glu Thr Val Gln Arg
385                 390                 395                 400
```

```
Leu Leu Pro Val Leu Cys Gln Asp His Gly Leu Thr Pro Asp Gln Val
                405                 410                 415
Val Ala Ile Ala Ser Asn Ile Gly Gly Lys Gln Ala Leu Glu Thr Val
            420                 425                 430
Gln Arg Leu Leu Pro Val Leu Cys Gln Asp His Gly Leu Thr Pro Asp
        435                 440                 445
Gln Val Val Ala Ile Ala Ser Asn Gly Gly Lys Gln Ala Leu Glu
    450                 455                 460
Thr Val Gln Arg Leu Leu Pro Val Leu Cys Gln Asp His Gly Leu Thr
465                 470                 475                 480
Pro Asp Gln Val Val Ala Ile Ala Ser Asn Asn Gly Gly Lys Gln Ala
                485                 490                 495
Leu Glu Thr Val Gln Arg Leu Leu Pro Val Leu Cys Gln Asp His Gly
            500                 505                 510
Leu Thr Pro Asp Gln Val Val Ala Ile Ala Ser Asn Ile Gly Gly Lys
        515                 520                 525
Gln Ala Leu Glu Thr Val Gln Arg Leu Leu Pro Val Leu Cys Gln Asp
    530                 535                 540
His Gly Leu Thr Pro Asp Gln Val Val Ala Ile Ala Ser Asn Ile Gly
545                 550                 555                 560
Gly Lys Gln Ala Leu Glu Thr Val Gln Arg Leu Leu Pro Val Leu Cys
                565                 570                 575
Gln Asp His Gly Leu Thr Pro Asp Gln Val Val Ala Ile Ala Ser Asn
            580                 585                 590
Asn Gly Gly Lys Gln Ala Leu Glu Thr Val Gln Arg Leu Leu Pro Val
        595                 600                 605
Leu Cys Gln Asp His Gly Leu Thr Pro Asp Gln Val Val Ala Ile Ala
    610                 615                 620
Ser Asn Gly Gly Lys Gln Ala Leu Glu Thr Val Gln Arg Leu Leu
625                 630                 635                 640
Pro Val Leu Cys Gln Asp His Gly Leu Thr Pro Asp Gln Val Val Ala
                645                 650                 655
Ile Ala Ser His Asp Gly Gly Lys Gln Ala Leu Glu Thr Val Gln Arg
            660                 665                 670
Leu Leu Pro Val Leu Cys Gln Asp His Gly Leu Thr Pro Asp Gln Val
        675                 680                 685
Val Ala Ile Ala Ser Asn Gly Gly Gly Lys Gln Ala Leu Glu Ser Ile
    690                 695                 700
Val Ala Gln Leu Ser Arg Pro Asp Pro Ala Leu Ala Ala Leu Thr Asn
705                 710                 715                 720
Asp Asp His Leu Val Ala Leu Ala Cys Leu Gly Gly Arg Pro Ala Met
                725                 730                 735
Asp Ala Val Lys Lys Gly Leu Pro His Ala Pro Glu Leu Ile Arg Arg
            740                 745                 750
Val Asn Arg Arg Ile Gly Glu Arg Thr Ser His Arg Val Ala Gly Ser
        755                 760                 765
Lys Ala Ser Pro Lys Lys Arg Lys Val Gly Arg Ala Asp Ala Leu
    770                 775                 780
Asp Asp Phe Asp Leu Asp Met Leu Gly Ser Asp Ala Leu Asp Asp Phe
785                 790                 795                 800
Asp Leu Asp Met Leu Gly Ser Asp Ala Leu Asp Asp Phe Asp Leu Asp
                805                 810                 815
Met Leu Gly Ser Asp Ala Leu Asp Asp Phe Asp Leu Asp Met Leu Ile
```

```
                   820               825               830
Asn Tyr Pro Tyr Asp Val Pro Asp Tyr Ala Ser
        835                 840

<210> SEQ ID NO 61
<211> LENGTH: 2838
<212> TYPE: DNA
<213> ORGANISM: Artificial sequence
<220> FEATURE:
<223> OTHER INFORMATION: Synthetic oligonucleotide

<400> SEQUENCE: 61
atggactaca aagaccatga cggtgattat aaagatcatg acatcgatta caaggatgac      60
gatgacaaga tggcccccaa gaagaagagg aaggtgggcc gcggatctgt ggatctacgc     120
acgctcggct acagtcagca gcagcaagag aagatcaaac cgaaggtgcg ttcgacagtg     180
gcgcagcacc acgaggcact ggtgggccat gggtttacac acgcgcacat cgttgcgctc     240
agccaacacc cggcagcgtt agggaccgtc gctgtcacgt atcagcacat aatcacggcg     300
ttgccagagg cgacacacga agacatcgtt ggcgtcggca acagtggtc cggcgcacgc      360 gccctggagg ccttgctcac ggatgcgggg gagttgagag gtccgccgtt acagttggac     420
acaggccaac ttgtgaagat tgcaaaacgt ggcggcgtga ccgcaatgga ggcagtgcat     480
gcatcgcgca atgcactgac gggtgccccc ctgaacctga ccccggacca agtggtggct     540
atcgccagca acattggcgg caagcaagcg ctcgaaacgg tgcagcggct gttgccggtg     600
ctgtgccagg accatggcct gaccccggac caagtggtgg ctatcgccag ccacgatggc     660
ggcaagcaag cgctcgaaac ggtgcagcgg ctgttgccgg tgctgtgcca ggaccatggc     720
ctgaccccgg accaagtggt ggctatcgcc agccacgatg gcggcaagca agcgctcgaa     780
acggtgcagc ggctgttgcc ggtgctgtgc caggaccatg gcctgacccc ggaccaagtg     840
gtggctatcg ccagccacga tggcggcaag caagcgctcg aaacggtgca gcggctgttg     900
ccggtgctgt gccaggacca tggcctgacc ccggaccaag tggtggctat cgccagcaac     960
attggcggca agcaagcgct cgaaacggtg cagcggctgt tgccggtgct gtgccaggac    1020
catggcctga ccccggacca agtggtggct atcgccagcc acgatggcgg caagcaagcg    1080
ctcgaaacgg tgcagcggct gttgccggtg ctgtgccagg accatggcct gaccccggac    1140
caagtggtgg ctatcgccag ccacgatggc ggcaagcaag cgctcgaaac ggtgcagcgg    1200
ctgttgccgg tgctgtgcca ggaccatggc ctgaccccgg accaagtggt ggctatcgcc    1260
agccacgatg gcggcaagca agcgctcgaa acggtgcagc ggctgttgcc ggtgctgtgc    1320
caggaccatg gcctgacccc ggaccaagtg gtggctatcg ccagccacga tggcggcaag    1380
caagcgctcg aaacggtgca gcggctgttg ccggtgctgt gccaggacca tggcctgacc    1440
ccggaccaag tggtggctat cgccagccac gatggcggca agcaagcgct cgaaacggtg    1500
cagcggctgt tgccggtgct gtgccaggac atggcctga ccccggacca agtggtggct     1560
atcgccagca acggtggcgg caagcaagcg ctcgaaacgg tgcagcggct gttgccggtg    1620
ctgtgccagg accatggcct gaccccggac caagtggtgg ctatcgccag caacaatggc    1680
ggcaagcaag cgctcgaaac ggtgcagcgg ctgttgccgg tgctgtgcca ggaccatggc    1740
ctgaccccgg accaagtggt ggctatcgcc agcaacggtg gcggcaagca agcgctcgaa    1800
acggtgcagc ggctgttgcc ggtgctgtgc caggaccatg gcctgacccc ggaccaagtg    1860
gtggctatcg ccagcaacgg tggcggcaag caagcgctcg aaacggtgca gcggctgttg    1920
```

-continued

```
ccggtgctgt gccaggacca tggcctgacc ccggaccaag tggtggctat cgccagcaac    1980
ggtggcggca agcaagcgct cgaaacggtg cagcggctgt tgccggtgct gtgccaggac    2040
catggcctga ccccggacca agtggtggct atcgccagcc acgatggcgg caagcaagcg    2100
ctcgaaacgg tgcagcggct gttgccggtg ctgtgccagg accatggcct gaccccggac    2160
caagtggtgg ctatcgccag caacggtggc ggcaagcaag cgctcgaaac ggtgcagcgg    2220
ctgttgccgg tgctgtgcca ggaccatggc ctgaccccgg accaagtggt ggctatcgcc    2280
agcaacaatg gcggcaagca agcgctcgaa acggtgcagc ggctgttgcc ggtgctgtgc    2340
caggaccatg gcctgacccc ggaccaagtg gtggctatcg ccagcaacgg tggcggcaag    2400
caagcgctcg aaagcattgt ggcccagctg agccggcctg atccggcgtt ggccgcgttg    2460
accaacgacg accacctcgt cgccttggcc tgcctcggcg acgtcctgc catggatgca     2520 gtgaaaaagg gattgccgca cgcgccggaa ttgatcagaa gagtcaatcg ccgtattggc    2580
gaacgcacgt cccatcgcgt tgccggatcc aaggctagcc cgaaaaagaa acgcaaagtt    2640
gggcgcgccg acgcgctgga cgatttcgat ctcgacatgc tgggttctga tgccctcgat    2700
gactttgacc tggatatgtt gggaagcgac gcattggatg actttgatct ggacatgctc    2760
ggctccgatg ctctggacga tttcgatctc gatatgttaa ttaactaccc gtacgacgtt    2820
ccggactacg cttcttga                                                  2838
```

<210> SEQ ID NO 62
<211> LENGTH: 945
<212> TYPE: PRT
<213> ORGANISM: Unknown
<220> FEATURE:
<223> OTHER INFORMATION: Synthetic peptide

<400> SEQUENCE: 62

```
Met Asp Tyr Lys Asp His Asp Gly Asp Tyr Lys Asp His Asp Ile Asp
1               5                   10                  15

Tyr Lys Asp Asp Asp Asp Lys Met Ala Pro Lys Lys Arg Lys Val
            20                  25                  30

Gly Arg Gly Ser Val Asp Leu Arg Thr Leu Gly Tyr Ser Gln Gln Gln
        35                  40                  45

Gln Glu Lys Ile Lys Pro Lys Val Arg Ser Thr Val Ala Gln His His
    50                  55                  60

Glu Ala Leu Val Gly His Gly Phe Thr His Ala His Ile Val Ala Leu
65                  70                  75                  80

Ser Gln His Pro Ala Ala Leu Gly Thr Val Ala Val Thr Tyr Gln His
                85                  90                  95

Ile Ile Thr Ala Leu Pro Glu Ala Thr His Glu Asp Ile Val Gly Val
            100                 105                 110

Gly Lys Gln Trp Ser Gly Ala Arg Ala Leu Glu Ala Leu Leu Thr Asp
        115                 120                 125

Ala Gly Glu Leu Arg Gly Pro Pro Leu Gln Leu Asp Thr Gly Gln Leu
    130                 135                 140

Val Lys Ile Ala Lys Arg Gly Gly Val Thr Ala Met Glu Ala Val His
145                 150                 155                 160

Ala Ser Arg Asn Ala Leu Thr Gly Ala Pro Leu Asn Leu Thr Pro Asp
                165                 170                 175

Gln Val Val Ala Ile Ala Ser Asn Ile Gly Gly Lys Gln Ala Leu Glu
            180                 185                 190

Thr Val Gln Arg Leu Leu Pro Val Leu Cys Gln Asp His Gly Leu Thr
```

```
                195                 200                 205
Pro Asp Gln Val Val Ala Ile Ala Ser His Asp Gly Lys Gln Ala
210                 215                 220

Leu Glu Thr Val Gln Arg Leu Leu Pro Val Leu Cys Gln Asp His Gly
225                 230                 235                 240

Leu Thr Pro Asp Gln Val Val Ala Ile Ala Ser His Asp Gly Gly Lys
                245                 250                 255

Gln Ala Leu Glu Thr Val Gln Arg Leu Leu Pro Val Leu Cys Gln Asp
                260                 265                 270

His Gly Leu Thr Pro Asp Gln Val Val Ala Ile Ala Ser His Asp Gly
            275                 280                 285

Gly Lys Gln Ala Leu Glu Thr Val Gln Arg Leu Leu Pro Val Leu Cys
290                 295                 300

Gln Asp His Gly Leu Thr Pro Asp Gln Val Val Ala Ile Ala Ser Asn
305                 310                 315                 320

Ile Gly Gly Lys Gln Ala Leu Glu Thr Val Gln Arg Leu Leu Pro Val
                325                 330                 335

Leu Cys Gln Asp His Gly Leu Thr Pro Asp Gln Val Val Ala Ile Ala
                340                 345                 350

Ser His Asp Gly Gly Lys Gln Ala Leu Glu Thr Val Gln Arg Leu Leu
            355                 360                 365

Pro Val Leu Cys Gln Asp His Gly Leu Thr Pro Asp Gln Val Val Ala
370                 375                 380

Ile Ala Ser His Asp Gly Gly Lys Gln Ala Leu Glu Thr Val Gln Arg
385                 390                 395                 400

Leu Leu Pro Val Leu Cys Gln Asp His Gly Leu Thr Pro Asp Gln Val
                405                 410                 415

Val Ala Ile Ala Ser His Asp Gly Gly Lys Gln Ala Leu Glu Thr Val
                420                 425                 430

Gln Arg Leu Leu Pro Val Leu Cys Gln Asp His Gly Leu Thr Pro Asp
            435                 440                 445

Gln Val Val Ala Ile Ala Ser His Asp Gly Gly Lys Gln Ala Leu Glu
450                 455                 460

Thr Val Gln Arg Leu Leu Pro Val Leu Cys Gln Asp His Gly Leu Thr
465                 470                 475                 480

Pro Asp Gln Val Val Ala Ile Ala Ser His Asp Gly Gly Lys Gln Ala
                485                 490                 495

Leu Glu Thr Val Gln Arg Leu Leu Pro Val Leu Cys Gln Asp His Gly
                500                 505                 510

Leu Thr Pro Asp Gln Val Val Ala Ile Ala Ser Asn Gly Gly Lys
            515                 520                 525

Gln Ala Leu Glu Thr Val Gln Arg Leu Leu Pro Val Leu Cys Gln Asp
530                 535                 540

His Gly Leu Thr Pro Asp Gln Val Val Ala Ile Ala Ser Asn Asn Gly
545                 550                 555                 560

Gly Lys Gln Ala Leu Glu Thr Val Gln Arg Leu Leu Pro Val Leu Cys
                565                 570                 575

Gln Asp His Gly Leu Thr Pro Asp Gln Val Val Ala Ile Ala Ser Asn
                580                 585                 590

Gly Gly Gly Lys Gln Ala Leu Glu Thr Val Gln Arg Leu Leu Pro Val
            595                 600                 605

Leu Cys Gln Asp His Gly Leu Thr Pro Asp Gln Val Val Ala Ile Ala
610                 615                 620
```

Ser Asn Gly Gly Gly Lys Gln Ala Leu Glu Thr Val Gln Arg Leu Leu
625                 630                 635                 640

Pro Val Leu Cys Gln Asp His Gly Leu Thr Pro Asp Gln Val Val Ala
            645                 650                 655

Ile Ala Ser Asn Gly Gly Gly Lys Gln Ala Leu Glu Thr Val Gln Arg
        660                 665                 670

Leu Leu Pro Val Leu Cys Gln Asp His Gly Leu Thr Pro Asp Gln Val
    675                 680                 685

Val Ala Ile Ala Ser His Asp Gly Gly Lys Gln Ala Leu Glu Thr Val
690                 695                 700

Gln Arg Leu Leu Pro Val Leu Cys Gln Asp His Gly Leu Thr Pro Asp
705                 710                 715                 720

Gln Val Val Ala Ile Ala Ser Asn Gly Gly Gly Lys Gln Ala Leu Glu
            725                 730                 735

Thr Val Gln Arg Leu Leu Pro Val Leu Cys Gln Asp His Gly Leu Thr
        740                 745                 750

Pro Asp Gln Val Val Ala Ile Ala Ser Asn Asn Gly Gly Lys Gln Ala
    755                 760                 765

Leu Glu Thr Val Gln Arg Leu Leu Pro Val Leu Cys Gln Asp His Gly
770                 775                 780

Leu Thr Pro Asp Gln Val Val Ala Ile Ala Ser Asn Gly Gly Gly Lys
785                 790                 795                 800

Gln Ala Leu Glu Ser Ile Val Ala Gln Leu Ser Arg Pro Asp Pro Ala
            805                 810                 815

Leu Ala Ala Leu Thr Asn Asp His Leu Val Ala Leu Ala Cys Leu
        820                 825                 830

Gly Gly Arg Pro Ala Met Asp Ala Val Lys Lys Gly Leu Pro His Ala
    835                 840                 845

Pro Glu Leu Ile Arg Arg Val Asn Arg Arg Ile Gly Glu Arg Thr Ser
850                 855                 860

His Arg Val Ala Gly Ser Lys Ala Ser Pro Lys Lys Arg Lys Val
865                 870                 875                 880

Gly Arg Ala Asp Ala Leu Asp Asp Phe Asp Leu Asp Met Leu Gly Ser
            885                 890                 895

Asp Ala Leu Asp Asp Phe Asp Leu Asp Met Leu Gly Ser Asp Ala Leu
        900                 905                 910

Asp Asp Phe Asp Leu Asp Met Leu Gly Ser Asp Ala Leu Asp Phe
    915                 920                 925

Asp Leu Asp Met Leu Ile Asn Tyr Pro Tyr Asp Val Pro Asp Tyr Ala
930                 935                 940

Ser
945

<210> SEQ ID NO 63
<211> LENGTH: 2532
<212> TYPE: DNA
<213> ORGANISM: Artificial sequence
<220> FEATURE:
<223> OTHER INFORMATION: Synthetic oligonucleotide

<400> SEQUENCE: 63
atggactaca aagaccatga cggtgattat aaagatcatg acatcgatta caaggatgac      60
gatgacaaga tggcccccaa gaagaagagg aaggtgggcc gcggatctgt ggatctacgc     120
acgctcggct acagtcagca gcagcaagag aagatcaaac cgaaggtgcg ttcgacagtg     180

```
gcgcagcacc acgaggcact ggtgggccat gggtttacac acgcgcacat cgttgcgctc      240
agccaacacc cggcagcgtt agggaccgtc gctgtcacgt atcagcacat aatcacggcg      300
ttgccagagg cgacacacga agacatcgtt ggcgtcggca acagtggtc cggcgcacgc       360 gccctggagg ccttgctcac ggatgcgggg gagttgagag gtccgccgtt acagttggac      420
acaggccaac ttgtgaagat tgcaaaacgt ggcggcgtga ccgcaatgga ggcagtgcat      480
gcatcgcgca atgcactgac gggtgccccc ctgaacctga ccccggacca agtggtggct     540
atcgccagcc acgatggcgg caagcaagcg ctcgaaacgg tgcagcggct gttgccggtg      600
ctgtgccagg accatggcct gaccccggac caagtggtgg ctatcgccag caacggtggc      660
ggcaagcaag cgctcgaaac ggtgcagcgg ctgttgccgg tgctgtgcca ggaccatggc      720
ctgaccccgg accaagtggt ggctatcgcc agcaacggtg gcggcaagca agcgctcgaa      780
acggtgcagc ggctgttgcc ggtgctgtgc caggaccatg gcctgacccc ggaccaagtg      840
gtggctatcg ccagcaacaa tggcggcaag caagcgctcg aaacggtgca gcggctgttg      900
ccggtgctgt gccaggacca tggcctgacc ccggaccaag tggtggctat cgccagcaac      960
aatggcggca agcaagcgct cgaaacggtg cagcggctgt tgccggtgct gtgccaggac     1020
catggcctga ccccggacca agtggtggct atcgccagca cattggcgg caagcaagcg     1080 ctcgaaacgg tgcagcggct gttgccggtg ctgtgccagg accatggcct gaccccggac     1140
caagtggtgg ctatcgccag caacaatggc ggcaagcaag cgctcgaaac ggtgcagcgg     1200
ctgttgccgg tgctgtgcca ggaccatggc ctgaccccgg accaagtggt ggctatcgcc     1260
agcaacggtg gcggcaagca agcgctcgaa acggtgcagc ggctgttgcc ggtgctgtgc     1320
caggaccatg gcctgacccc ggaccaagtg gtggctatcg ccagcaacaa tggcggcaag     1380
caagcgctcg aaacggtgca gcggctgttg ccggtgctgt gccaggacca tggcctgacc     1440
ccggaccaag tggtggctat cgccagccac gatggcggca agcaagcgct cgaaacggtg     1500
cagcggctgt tgccggtgct gtgccaggac catggcctga ccccggacca agtggtggct     1560
atcgccagca cattggcgg caagcaagcg ctcgaaacgg tgcagcggct gttgccggtg      1620
ctgtgccagg accatggcct gaccccggac caagtggtgg ctatcgccag caacattggc     1680
ggcaagcaag cgctcgaaac ggtgcagcgg ctgttgccgg tgctgtgcca ggaccatggc      1740
ctgaccccgg accaagtggt ggctatcgcc agcaacattg gcggcaagca agcgctcgaa      1800
acggtgcagc ggctgttgcc ggtgctgtgc caggaccatg gcctgacccc ggaccaagtg      1860
gtggctatcg ccagcaacaa tggcggcaag caagcgctcg aaacggtgca gcggctgttg     1920
ccggtgctgt gccaggacca tggcctgacc ccggaccaag tggtggctat cgccagcaac     1980
aatggcggca agcaagcgct cgaaacggtg cagcggctgt tgccggtgct gtgccaggac     2040
catggcctga ccccggacca agtggtggct atcgccagca cattggcgg caagcaagcg     2100 ctcgaaagca ttgtgggccca gctgagccgg cctgatccgg cgttggccgc gttgaccaac    2160
gacgaccacc tcgtcgcctt ggcctgcctc ggcggacgtc ctgccatgga tgcagtgaaa     2220
aagggattgc cgcacgcgcc ggaattgatc agaagagtca atcgccgtat tggcgaacgc     2280
acgtcccatc gcgttgccgg atccaaggct agcccgaaaa agaaacgcaa agttgggcgc     2340
gccgacgcgc tggacgattt cgatctcgac atgctgggtt ctgatgccct cgatgacttt     2400
gacctggata tgttgggaag cgacgcattg gatgactttg atctggacat gctcggctcc     2460
gatgctctgg acgatttcga tctcgatatg ttaattaact acccgtacga cgttccggac     2520
```
tacgcttctt ga                                                2532

<210> SEQ ID NO 64
<211> LENGTH: 843
<212> TYPE: PRT
<213> ORGANISM: Unknown
<220> FEATURE:
<223> OTHER INFORMATION: Synthetic peptide

<400> SEQUENCE: 64

Met Asp Tyr Lys Asp His Asp Gly Asp Tyr Lys Asp His Asp Ile Asp
1               5                   10                  15

Tyr Lys Asp Asp Asp Asp Lys Met Ala Pro Lys Lys Arg Lys Val
            20                  25                  30

Gly Arg Gly Ser Val Asp Leu Arg Thr Leu Gly Tyr Ser Gln Gln Gln
        35                  40                  45

Gln Glu Lys Ile Lys Pro Lys Val Arg Ser Thr Val Ala Gln His His
    50                  55                  60

Glu Ala Leu Val Gly His Gly Phe Thr His Ala His Ile Val Ala Leu
65              70                  75                  80

Ser Gln His Pro Ala Ala Leu Gly Thr Val Ala Val Thr Tyr Gln His
                85                  90                  95

Ile Ile Thr Ala Leu Pro Glu Ala Thr His Glu Asp Ile Val Gly Val
            100                 105                 110

Gly Lys Gln Trp Ser Gly Ala Arg Ala Leu Glu Ala Leu Leu Thr Asp
        115                 120                 125

Ala Gly Glu Leu Arg Gly Pro Pro Leu Gln Leu Asp Thr Gly Gln Leu
    130                 135                 140

Val Lys Ile Ala Lys Arg Gly Gly Val Thr Ala Met Glu Ala Val His
145                 150                 155                 160

Ala Ser Arg Asn Ala Leu Thr Gly Ala Pro Leu Asn Leu Thr Pro Asp
                165                 170                 175

Gln Val Val Ala Ile Ala Ser His Asp Gly Gly Lys Gln Ala Leu Glu
            180                 185                 190

Thr Val Gln Arg Leu Leu Pro Val Leu Cys Gln Asp His Gly Leu Thr
        195                 200                 205

Pro Asp Gln Val Val Ala Ile Ala Ser Asn Gly Gly Gly Lys Gln Ala
    210                 215                 220

Leu Glu Thr Val Gln Arg Leu Leu Pro Val Leu Cys Gln Asp His Gly
225                 230                 235                 240

Leu Thr Pro Asp Gln Val Val Ala Ile Ala Ser Asn Gly Gly Gly Lys
                245                 250                 255

Gln Ala Leu Glu Thr Val Gln Arg Leu Leu Pro Val Leu Cys Gln Asp
            260                 265                 270

His Gly Leu Thr Pro Asp Gln Val Val Ala Ile Ala Ser Asn Asn Gly
        275                 280                 285

Gly Lys Gln Ala Leu Glu Thr Val Gln Arg Leu Leu Pro Val Leu Cys
    290                 295                 300

Gln Asp His Gly Leu Thr Pro Asp Gln Val Val Ala Ile Ala Ser Asn
305                 310                 315                 320

Asn Gly Gly Lys Gln Ala Leu Glu Thr Val Gln Arg Leu Leu Pro Val
                325                 330                 335

Leu Cys Gln Asp His Gly Leu Thr Pro Asp Gln Val Val Ala Ile Ala
            340                 345                 350

Ser Asn Ile Gly Gly Lys Gln Ala Leu Glu Thr Val Gln Arg Leu Leu

```
                355                 360                 365
Pro Val Leu Cys Gln Asp His Gly Leu Thr Pro Asp Gln Val Val Ala
370                 375                 380
Ile Ala Ser Asn Asn Gly Gly Lys Gln Ala Leu Glu Thr Val Gln Arg
385                 390                 395                 400
Leu Leu Pro Val Leu Cys Gln Asp His Gly Leu Thr Pro Asp Gln Val
                405                 410                 415
Val Ala Ile Ala Ser Asn Gly Gly Lys Gln Ala Leu Glu Thr Val
            420                 425                 430
Gln Arg Leu Leu Pro Val Leu Cys Gln Asp His Gly Leu Thr Pro Asp
                435                 440                 445
Gln Val Val Ala Ile Ala Ser Asn Asn Gly Gly Lys Gln Ala Leu Glu
450                 455                 460
Thr Val Gln Arg Leu Leu Pro Val Leu Cys Gln Asp His Gly Leu Thr
465                 470                 475                 480
Pro Asp Gln Val Val Ala Ile Ala Ser His Asp Gly Gly Lys Gln Ala
                485                 490                 495
Leu Glu Thr Val Gln Arg Leu Leu Pro Val Leu Cys Gln Asp His Gly
            500                 505                 510
Leu Thr Pro Asp Gln Val Val Ala Ile Ala Ser Asn Ile Gly Gly Lys
                515                 520                 525
Gln Ala Leu Glu Thr Val Gln Arg Leu Leu Pro Val Leu Cys Gln Asp
530                 535                 540
His Gly Leu Thr Pro Asp Gln Val Val Ala Ile Ala Ser Asn Ile Gly
545                 550                 555                 560
Gly Lys Gln Ala Leu Glu Thr Val Gln Arg Leu Leu Pro Val Leu Cys
                565                 570                 575
Gln Asp His Gly Leu Thr Pro Asp Gln Val Val Ala Ile Ala Ser Asn
            580                 585                 590
Ile Gly Gly Lys Gln Ala Leu Glu Thr Val Gln Arg Leu Leu Pro Val
                595                 600                 605
Leu Cys Gln Asp His Gly Leu Thr Pro Asp Gln Val Val Ala Ile Ala
610                 615                 620
Ser Asn Asn Gly Gly Lys Gln Ala Leu Glu Thr Val Gln Arg Leu Leu
625                 630                 635                 640
Pro Val Leu Cys Gln Asp His Gly Leu Thr Pro Asp Gln Val Val Ala
                645                 650                 655
Ile Ala Ser Asn Asn Gly Gly Lys Gln Ala Leu Glu Thr Val Gln Arg
            660                 665                 670
Leu Leu Pro Val Leu Cys Gln Asp His Gly Leu Thr Pro Asp Gln Val
                675                 680                 685
Val Ala Ile Ala Ser Asn Ile Gly Gly Lys Gln Ala Leu Glu Ser Ile
690                 695                 700
Val Ala Gln Leu Ser Arg Pro Asp Pro Ala Leu Ala Ala Leu Thr Asn
705                 710                 715                 720
Asp Asp His Leu Val Ala Leu Ala Cys Leu Gly Gly Arg Pro Ala Met
                725                 730                 735
Asp Ala Val Lys Lys Gly Leu Pro His Ala Pro Glu Leu Ile Arg Arg
            740                 745                 750
Val Asn Arg Arg Ile Gly Glu Arg Thr Ser His Arg Val Ala Gly Ser
                755                 760                 765
Lys Ala Ser Pro Lys Lys Arg Lys Val Gly Arg Ala Asp Ala Leu
770                 775                 780
```

| Asp<br>785 | Phe | Asp | Leu | Asp<br>790 | Met | Leu | Gly | Ser<br>795 | Asp | Ala | Leu | Asp | Phe<br>800 |
| Asp | Leu | Asp | Met<br>805 | Leu | Gly | Ser | Asp<br>810 | Ala | Leu | Asp | Phe | Asp<br>815 | Leu |
| Asp | Met | Leu<br>820 | Gly | Ser | Asp | Ala<br>825 | Leu | Asp | Phe | Asp<br>830 | Leu | Met | Leu Ile |
| Asn | Tyr | Pro<br>835 | Tyr | Asp | Val | Pro<br>840 | Asp | Tyr | Ala | Ser |

<210> SEQ ID NO 65
<211> LENGTH: 2532
<212> TYPE: DNA
<213> ORGANISM: Artificial sequence
<220> FEATURE:
<223> OTHER INFORMATION: Synthetic oligonucleotide

<400> SEQUENCE: 65

```
atggactaca aagaccatga cggtgattat aaagatcatg acatcgatta caaggatgac      60
gatgacaaga tggcccccaa gaagaagagg aaggtgggcc gcggatctgt ggatctacgc     120
acgctcggct acagtcagca gcagcaagag aagatcaaac cgaaggtgcg ttcgacagtg     180
gcgcagcacc acgaggcact ggtgggccat gggtttacac acgcgcacat cgttgcgctc     240
agccaacacc cggcagcgtt agggaccgtc gctgtcacgt atcagcacat aatcacggcg     300
ttgccagagg cgacacacga agacatcgtt ggcgtcggca acagtggtc cggcgcacgc      360
gccctggagc ccttgctcac ggatgcgggg gagttgagag gtccgccgtt acagttggac     420
acaggccaac ttgtgaagat tgcaaaacgt ggcggcgtga ccgcaatgga ggcagtgcat     480
gcatcgcgca atgcactgac gggtgccccc ctgaacctga ccccggacca agtggtggct     540
atcgccagcc acgatggcgg caagcaagcg ctcgaaacgg tgcagcggct gttgccggtg     600
ctgtgccagg accatggcct gaccccggac caagtggtgg ctatcgccag caacggtggc     660
ggcaagcaag cgctcgaaac ggtgcagcgg ctgttgccgg tgctgtgcca ggaccatggc     720
ctgaccccgg accaagtggt ggctatcgcc agcaacggtg gcggcaagca agcgctcgaa     780
acggtgcagc ggctgttgcc ggtgctgtgc caggaccatg gcctgacccc ggaccaagtg     840
gtggctatcg ccagcaacaa tggcggcaag caagcgctcg aaacggtgca gcggctgttg     900
ccggtgctgt gccaggacca tggcctgacc ccggaccaag tggtggctat cgccagcaac     960
aatggcggca agcaagcgct cgaaacggtg cagcggctgt tgccggtgct gtgccaggac    1020
catggcctga ccccggacca agtggtggct atcgccagca acattggcgg caagcaagcg    1080
ctcgaaacgg tgcagcggct gttgccggtg ctgtgccagg accatggcct gaccccggac    1140
caagtggtgg ctatcgccag caacaatggc ggcaagcaag cgctcgaaac ggtgcagcgg    1200
ctgttgccgg tgctgtgcca ggaccatggc ctgaccccgg accaagtggt ggctatcgcc    1260
agcaacggtg gcggcaagca agcgctcgaa acggtgcagc ggctgttgcc ggtgctgtgc    1320
caggaccatg gcctgacccc ggaccaagtg gtggctatcg ccagcaacaa tggcggcaag    1380
caagcgctcg aaacggtgca gcggctgttg ccggtgctgt gccaggacca tggcctgacc    1440
ccggaccaag tggtggctat cgccagccac gatggcggca agcaagcgct cgaaacggtg    1500
cagcggctgt tgccggtgct gtgccaggac catggcctga ccccggacca agtggtggct    1560
atcgccagca acattggcgg caagcaagcg ctcgaaacgg tgcagcggct gttgccggtg    1620
ctgtgccagg accatggcct gaccccggac caagtggtgg ctatcgccag caacattggc    1680
```

-continued

```
ggcaagcaag cgctcgaaac ggtgcagcgg ctgttgccgg tgctgtgcca ggaccatggc    1740
ctgaccccgg accaagtggt ggctatcgcc agcaacattg gcggcaagca agcgctcgaa    1800
acggtgcagc ggctgttgcc ggtgctgtgc caggaccatg gcctgacccc ggaccaagtg    1860
gtggctatcg ccagcaacaa tggcggcaag caagcgctcg aaacggtgca gcggctgttg    1920
ccggtgctgt gccaggacca tggcctgacc ccggaccaag tggtggctat cgccagcaac    1980
aatggcggca agcaagcgct cgaaacggtg cagcggctgt tgccggtgct gtgccaggac    2040
catggcctga ccccggacca agtggtggct atcgccagca acggtggcgg caagcaagcg    2100
ctcgaaagca ttgtgggccca gctgagccgg cctgatccgg cgttggccgc gttgaccaac    2160
gacgaccacc tcgtcgcctt ggcctgcctc ggcggacgtc ctgccatgga tgcagtgaaa    2220
aagggattgc cgcacgcgcc ggaattgatc agaagagtca atcgccgtat ggcgaacgc    2280 acgtcccatc gcgttgccgg atccaaggct agcccgaaaa agaaacgcaa agttgggcgc    2340
gccgacgcgc tggacgattt cgatctcgac atgctgggtt ctgatgccct cgatgacttt    2400
gacctggata tgttgggaag cgacgcattg gatgactttg atctggacat gctcggctcc    2460
gatgctctgg acgatttcga tctcgatatg ttaattaact acccgtacga cgttccggac    2520
tacgcttctt ga                                                        2532
```

<210> SEQ ID NO 66
<211> LENGTH: 843
<212> TYPE: PRT
<213> ORGANISM: Unknown
<220> FEATURE:
<223> OTHER INFORMATION: Synthetic peptide

<400> SEQUENCE: 66

```
Met Asp Tyr Lys Asp His Asp Gly Asp Tyr Lys Asp His Asp Ile Asp
1               5                   10                  15

Tyr Lys Asp Asp Asp Asp Lys Met Ala Pro Lys Lys Arg Lys Val
            20                  25                  30

Gly Arg Gly Ser Val Asp Leu Arg Thr Leu Gly Tyr Ser Gln Gln Gln
        35                  40                  45

Gln Glu Lys Ile Lys Pro Lys Val Arg Ser Thr Val Ala Gln His His
    50                  55                  60

Glu Ala Leu Val Gly His Gly Phe Thr His Ala His Ile Val Ala Leu
65                  70                  75                  80

Ser Gln His Pro Ala Ala Leu Gly Thr Val Ala Val Thr Tyr Gln His
                85                  90                  95

Ile Ile Thr Ala Leu Pro Glu Ala Thr His Glu Asp Ile Val Gly Val
            100                 105                 110

Gly Lys Gln Trp Ser Gly Ala Arg Ala Leu Glu Ala Leu Leu Thr Asp
        115                 120                 125

Ala Gly Glu Leu Arg Gly Pro Pro Leu Gln Leu Asp Thr Gly Gln Leu
    130                 135                 140

Val Lys Ile Ala Lys Arg Gly Gly Val Thr Ala Met Glu Ala Val His
145                 150                 155                 160

Ala Ser Arg Asn Ala Leu Thr Gly Ala Pro Leu Asn Leu Thr Pro Asp
                165                 170                 175

Gln Val Val Ala Ile Ala Ser His Asp Gly Gly Lys Gln Ala Leu Glu
            180                 185                 190

Thr Val Gln Arg Leu Leu Pro Val Leu Cys Gln Asp His Gly Leu Thr
        195                 200                 205
```

```
Pro Asp Gln Val Val Ala Ile Ala Ser Asn Gly Gly Gly Lys Gln Ala
    210                 215                 220

Leu Glu Thr Val Gln Arg Leu Leu Pro Val Leu Cys Gln Asp His Gly
225                 230                 235                 240

Leu Thr Pro Asp Gln Val Val Ala Ile Ala Ser Asn Gly Gly Gly Lys
                    245                 250                 255

Gln Ala Leu Glu Thr Val Gln Arg Leu Leu Pro Val Leu Cys Gln Asp
        260                 265                 270

His Gly Leu Thr Pro Asp Gln Val Val Ala Ile Ala Ser Asn Asn Gly
            275                 280                 285

Gly Lys Gln Ala Leu Glu Thr Val Gln Arg Leu Leu Pro Val Leu Cys
290                 295                 300

Gln Asp His Gly Leu Thr Pro Asp Gln Val Val Ala Ile Ala Ser Asn
305                 310                 315                 320

Asn Gly Gly Lys Gln Ala Leu Glu Thr Val Gln Arg Leu Leu Pro Val
                325                 330                 335

Leu Cys Gln Asp His Gly Leu Thr Pro Asp Gln Val Val Ala Ile Ala
                340                 345                 350

Ser Asn Ile Gly Gly Lys Gln Ala Leu Glu Thr Val Gln Arg Leu Leu
        355                 360                 365

Pro Val Leu Cys Gln Asp His Gly Leu Thr Pro Asp Gln Val Val Ala
        370                 375                 380

Ile Ala Ser Asn Asn Gly Gly Lys Gln Ala Leu Glu Thr Val Gln Arg
385                 390                 395                 400

Leu Leu Pro Val Leu Cys Gln Asp His Gly Leu Thr Pro Asp Gln Val
                405                 410                 415

Val Ala Ile Ala Ser Asn Gly Gly Gly Lys Gln Ala Leu Glu Thr Val
            420                 425                 430

Gln Arg Leu Leu Pro Val Leu Cys Gln Asp His Gly Leu Thr Pro Asp
        435                 440                 445

Gln Val Val Ala Ile Ala Ser Asn Asn Gly Gly Lys Gln Ala Leu Glu
    450                 455                 460

Thr Val Gln Arg Leu Leu Pro Val Leu Cys Gln Asp His Gly Leu Thr
465                 470                 475                 480

Pro Asp Gln Val Val Ala Ile Ala Ser His Asp Gly Gly Lys Gln Ala
                485                 490                 495

Leu Glu Thr Val Gln Arg Leu Leu Pro Val Leu Cys Gln Asp His Gly
                500                 505                 510

Leu Thr Pro Asp Gln Val Val Ala Ile Ala Ser Asn Ile Gly Gly Lys
            515                 520                 525

Gln Ala Leu Glu Thr Val Gln Arg Leu Leu Pro Val Leu Cys Gln Asp
        530                 535                 540

His Gly Leu Thr Pro Asp Gln Val Val Ala Ile Ala Ser Asn Ile Gly
545                 550                 555                 560

Gly Lys Gln Ala Leu Glu Thr Val Gln Arg Leu Leu Pro Val Leu Cys
                565                 570                 575

Gln Asp His Gly Leu Thr Pro Asp Gln Val Val Ala Ile Ala Ser Asn
            580                 585                 590

Ile Gly Gly Lys Gln Ala Leu Glu Thr Val Gln Arg Leu Leu Pro Val
        595                 600                 605

Leu Cys Gln Asp His Gly Leu Thr Pro Asp Gln Val Val Ala Ile Ala
        610                 615                 620

Ser Asn Asn Gly Gly Lys Gln Ala Leu Glu Thr Val Gln Arg Leu Leu
```

```
                625                 630                 635                 640
        Pro Val Leu Cys Gln Asp His Gly Leu Thr Pro Asp Gln Val Ala
                            645                 650                 655
        Ile Ala Ser Asn Asn Gly Gly Lys Gln Ala Leu Glu Thr Val Gln Arg
                        660                 665                 670
        Leu Leu Pro Val Leu Cys Gln Asp His Gly Leu Thr Pro Asp Gln Val
                    675                 680                 685
        Val Ala Ile Ala Ser Asn Gly Gly Lys Gln Ala Leu Glu Ser Ile
                690                 695                 700
        Val Ala Gln Leu Ser Arg Pro Asp Pro Ala Leu Ala Ala Leu Thr Asn
        705                 710                 715                 720
        Asp Asp His Leu Val Ala Leu Ala Cys Leu Gly Gly Arg Pro Ala Met
                            725                 730                 735
        Asp Ala Val Lys Lys Gly Leu Pro His Ala Pro Glu Leu Ile Arg Arg
                        740                 745                 750
        Val Asn Arg Arg Ile Gly Glu Arg Thr Ser His Arg Val Ala Gly Ser
                    755                 760                 765
        Lys Ala Ser Pro Lys Lys Lys Arg Lys Val Gly Arg Ala Asp Ala Leu
                770                 775                 780
        Asp Asp Phe Asp Leu Asp Met Leu Gly Ser Asp Ala Leu Asp Asp Phe
        785                 790                 795                 800
        Asp Leu Asp Met Leu Gly Ser Asp Ala Leu Asp Asp Phe Asp Leu Asp
                            805                 810                 815
        Met Leu Gly Ser Asp Ala Leu Asp Asp Phe Asp Leu Asp Met Leu Ile
                        820                 825                 830
        Asn Tyr Pro Tyr Asp Val Pro Asp Tyr Ala Ser
                    835                 840

<210> SEQ ID NO 67
<211> LENGTH: 2532
<212> TYPE: DNA
<213> ORGANISM: Artificial sequence
<220> FEATURE:
<223> OTHER INFORMATION: Synthetic oligonucleotide

<400> SEQUENCE: 67
atggactaca aagaccatga cggtgattat aaagatcatg acatcgatta caaggatgac      60
gatgacaaga tggccccaa gaagaagagg aaggtgggcc gcggatctgt ggatctacgc     120
acgctcggct acagtcagca gcagcaagag aagatcaaac cgaaggtgcg ttcgacagtg     180
gcgcagcacc acgaggcact ggtgggccat gggtttacac acgcgcacat cgttgcgctc     240
agccaacacc cggcagcgtt agggaccgtc gctgtcacgt atcagcacat aatcacggcg     300
ttgccagagg cgacacacga agacatcgtt ggcgtcggca acagtggtc cggcgcacgc     360
gccctggagg ccttgctcac ggatgcgggg gagttgagag gtccgccgtt acagttggac     420
acaggccaac ttgtgaagat tgcaaaacgt ggcggcgtga ccgcaatgga ggcagtgcat     480
gcatcgcgca atgcactgac gggtgccccc ctgaacctga ccccggacca agtggtggct     540
atcgccagcc acgatggcgg caagcaagcg ctcgaaacgg tgcagcggct gttgccggtg     600
ctgtgccagg accatggcct gaccccggac caagtggtgg ctatcgccag caacggtggc     660
ggcaagcaag cgctcgaaac ggtgcagcgg ctgttgccgg tgctgtgcca ggaccatggc     720
ctgaccccgg accaagtggt ggctatcgcc agcaacaatg gcggcaagca agcgctcgaa     780
acggtgcagc ggctgttgcc ggtgctgtgc caggaccatg gcctgacccc ggaccaagtg     840
```

-continued

```
gtggctatcg ccagcaacgg tggcggcaag caagcgctcg aaacggtgca gcggctgttg     900
ccggtgctgt gccaggacca tggcctgacc ccggaccaag tggtggctat cgccagcaac     960
aatggcggca agcaagcgct cgaaacggtg cagcggctgt tgccggtgct gtgccaggac    1020
catggcctga ccccggacca agtggtggct atcgccagca acaatggcgg caagcaagcg    1080
ctcgaaacgg tgcagcggct gttgccggtg ctgtgccagg accatggcct gaccccggac    1140
caagtggtgg ctatcgccag caacattggc ggcaagcaag cgctcgaaac ggtgcagcgg    1200
ctgttgccgg tgctgtgcca ggaccatggc ctgaccccgg accaagtggt ggctatcgcc    1260
agccacgatg gcggcaagca agcgctcgaa acggtgcagc ggctgttgcc ggtgctgtgc    1320
caggaccatg gcctgacccc ggaccaagtg gtggctatcg ccagccacga tggcggcaag    1380
caagcgctcg aaacggtgca gcggctgttg ccggtgctgt gccaggacca tggcctgacc    1440
ccggaccaag tggtggctat cgccagcaac attggcggca agcaagcgct cgaaacggtg    1500
cagcggctgt tgccggtgct gtgccaggac catggcctga ccccggacca agtggtggct    1560
atcgccagcc acgatggcgg caagcaagcg ctcgaaacgg tgcagcggct gttgccggtg    1620
ctgtgccagg accatggcct gaccccggac caagtggtgg ctatcgccag caacattggc    1680
ggcaagcaag cgctcgaaac ggtgcagcgg ctgttgccgg tgctgtgcca ggaccatggc    1740
ctgaccccgg accaagtggt ggctatcgcc agcaacattg gcggcaagca agcgctcgaa    1800
acggtgcagc ggctgttgcc ggtgctgtgc caggaccatg gcctgacccc ggaccaagtg    1860
gtggctatcg ccagcaacaa tggcggcaag caagcgctcg aaacggtgca gcggctgttg    1920
ccggtgctgt gccaggacca tggcctgacc ccggaccaag tggtggctat cgccagcaac    1980
attggcggca agcaagcgct cgaaacggtg cagcggctgt tgccggtgct gtgccaggac    2040
catggcctga ccccggacca gtggtggct atcgccagca acggtggcgg caagcaagcg    2100
ctcgaaagca ttgtggccca gctgagccgg cctgatccgg cgttggccgc gttgaccaac    2160
gacgaccacc tcgtcgcctt ggcctgcctc ggcggacgtc ctgccatgga tgcagtgaaa    2220
aagggattgc cgcacgcgcc ggaattgatc agaagagtca atcgccgtat ggcgaacgc     2280
acgtcccatc gcgttgccgg atccaaggct agcccgaaaa agaaacgcaa agttgggcgc    2340
gccgacgcgc tggacgattt cgatctcgac atgctgggtt ctgatgccct cgatgacttt    2400
gacctggata tgttgggaag cgacgcattg atgactttg atctggacat gctcggctcc     2460
gatgctctgg acgatttcga tctcgatatg ttaattaact acccgtacga cgttccggac    2520
tacgcttctt ga                                                        2532
```

<210> SEQ ID NO 68
<211> LENGTH: 843
<212> TYPE: PRT
<213> ORGANISM: Unknown
<220> FEATURE:
<223> OTHER INFORMATION: Synthetic peptide

<400> SEQUENCE: 68

Met Asp Tyr Lys Asp His Asp Gly Asp Tyr Lys Asp His Asp Ile Asp
1               5                   10                  15

Tyr Lys Asp Asp Asp Lys Met Ala Pro Lys Lys Arg Lys Val
            20                  25                  30

Gly Arg Gly Ser Val Asp Leu Arg Thr Leu Gly Tyr Ser Gln Gln Gln
        35                  40                  45

Gln Glu Lys Ile Lys Pro Lys Val Arg Ser Thr Val Ala Gln His His
    50                  55                  60

```
Glu Ala Leu Val Gly His Gly Phe Thr His Ala His Ile Val Ala Leu
 65                  70                  75                  80

Ser Gln His Pro Ala Ala Leu Gly Thr Val Ala Val Thr Tyr Gln His
             85                  90                  95

Ile Ile Thr Ala Leu Pro Glu Ala Thr His Glu Asp Ile Val Gly Val
        100                 105                 110

Gly Lys Gln Trp Ser Gly Ala Arg Ala Leu Glu Ala Leu Leu Thr Asp
            115                 120                 125

Ala Gly Glu Leu Arg Gly Pro Pro Leu Gln Leu Asp Thr Gly Gln Leu
130                 135                 140

Val Lys Ile Ala Lys Arg Gly Gly Val Thr Ala Met Glu Ala Val His
145                 150                 155                 160

Ala Ser Arg Asn Ala Leu Thr Gly Ala Pro Leu Asn Leu Thr Pro Asp
                165                 170                 175

Gln Val Val Ala Ile Ala Ser His Asp Gly Gly Lys Gln Ala Leu Glu
            180                 185                 190

Thr Val Gln Arg Leu Leu Pro Val Leu Cys Gln Asp His Gly Leu Thr
        195                 200                 205

Pro Asp Gln Val Val Ala Ile Ala Ser Asn Gly Gly Lys Gln Ala
210                 215                 220

Leu Glu Thr Val Gln Arg Leu Leu Pro Val Leu Cys Gln Asp His Gly
225                 230                 235                 240

Leu Thr Pro Asp Gln Val Val Ala Ile Ala Ser Asn Asn Gly Gly Lys
                245                 250                 255

Gln Ala Leu Glu Thr Val Gln Arg Leu Leu Pro Val Leu Cys Gln Asp
            260                 265                 270

His Gly Leu Thr Pro Asp Gln Val Val Ala Ile Ala Ser Asn Gly Gly
        275                 280                 285

Gly Lys Gln Ala Leu Glu Thr Val Gln Arg Leu Leu Pro Val Leu Cys
290                 295                 300

Gln Asp His Gly Leu Thr Pro Asp Gln Val Val Ala Ile Ala Ser Asn
305                 310                 315                 320

Asn Gly Gly Lys Gln Ala Leu Glu Thr Val Gln Arg Leu Leu Pro Val
                325                 330                 335

Leu Cys Gln Asp His Gly Leu Thr Pro Asp Gln Val Val Ala Ile Ala
            340                 345                 350

Ser Asn Asn Gly Gly Lys Gln Ala Leu Glu Thr Val Gln Arg Leu Leu
        355                 360                 365

Pro Val Leu Cys Gln Asp His Gly Leu Thr Pro Asp Gln Val Val Ala
370                 375                 380

Ile Ala Ser Asn Ile Gly Gly Lys Gln Ala Leu Glu Thr Val Gln Arg
385                 390                 395                 400

Leu Leu Pro Val Leu Cys Gln Asp His Gly Leu Thr Pro Asp Gln Val
                405                 410                 415

Val Ala Ile Ala Ser His Asp Gly Gly Lys Gln Ala Leu Glu Thr Val
            420                 425                 430

Gln Arg Leu Leu Pro Val Leu Cys Gln Asp His Gly Leu Thr Pro Asp
        435                 440                 445

Gln Val Val Ala Ile Ala Ser His Asp Gly Gly Lys Gln Ala Leu Glu
450                 455                 460

Thr Val Gln Arg Leu Leu Pro Val Leu Cys Gln Asp His Gly Leu Thr
465                 470                 475                 480
```

```
Pro Asp Gln Val Val Ala Ile Ala Ser Asn Ile Gly Gly Lys Gln Ala
            485                 490                 495

Leu Glu Thr Val Gln Arg Leu Leu Pro Val Leu Cys Gln Asp His Gly
        500                 505                 510

Leu Thr Pro Asp Gln Val Val Ala Ile Ala Ser His Asp Gly Gly Lys
        515                 520                 525

Gln Ala Leu Glu Thr Val Gln Arg Leu Leu Pro Val Leu Cys Gln Asp
    530                 535                 540

His Gly Leu Thr Pro Asp Gln Val Val Ala Ile Ala Ser Asn Ile Gly
545                 550                 555                 560

Gly Lys Gln Ala Leu Glu Thr Val Gln Arg Leu Leu Pro Val Leu Cys
                565                 570                 575

Gln Asp His Gly Leu Thr Pro Asp Gln Val Val Ala Ile Ala Ser Asn
            580                 585                 590

Ile Gly Gly Lys Gln Ala Leu Glu Thr Val Gln Arg Leu Leu Pro Val
        595                 600                 605

Leu Cys Gln Asp His Gly Leu Thr Pro Asp Gln Val Val Ala Ile Ala
        610                 615                 620

Ser Asn Asn Gly Gly Lys Gln Ala Leu Glu Thr Val Gln Arg Leu Leu
625                 630                 635                 640

Pro Val Leu Cys Gln Asp His Gly Leu Thr Pro Asp Gln Val Val Ala
                645                 650                 655

Ile Ala Ser Asn Ile Gly Gly Lys Gln Ala Leu Glu Thr Val Gln Arg
            660                 665                 670

Leu Leu Pro Val Leu Cys Gln Asp His Gly Leu Thr Pro Asp Gln Val
        675                 680                 685

Val Ala Ile Ala Ser Asn Gly Gly Lys Gln Ala Leu Glu Ser Ile
        690                 695                 700

Val Ala Gln Leu Ser Arg Pro Asp Pro Ala Leu Ala Ala Leu Thr Asn
705                 710                 715                 720

Asp Asp His Leu Val Ala Leu Ala Cys Leu Gly Gly Arg Pro Ala Met
                725                 730                 735

Asp Ala Val Lys Lys Gly Leu Pro His Ala Pro Glu Leu Ile Arg Arg
            740                 745                 750

Val Asn Arg Arg Ile Gly Glu Arg Thr Ser His Arg Val Ala Gly Ser
        755                 760                 765

Lys Ala Ser Pro Lys Lys Arg Lys Val Gly Arg Ala Asp Ala Leu
        770                 775                 780

Asp Asp Phe Asp Leu Asp Met Leu Gly Ser Asp Ala Leu Asp Asp Phe
785                 790                 795                 800

Asp Leu Asp Met Leu Gly Ser Asp Ala Leu Asp Asp Phe Asp Leu Asp
                805                 810                 815

Met Leu Gly Ser Asp Ala Leu Asp Asp Phe Asp Leu Asp Met Leu Ile
            820                 825                 830

Asn Tyr Pro Tyr Asp Val Pro Asp Tyr Ala Ser
        835                 840

<210> SEQ ID NO 69
<211> LENGTH: 2736
<212> TYPE: DNA
<213> ORGANISM: Artificial sequence
<220> FEATURE:
<223> OTHER INFORMATION: Synthetic oligonucleotide

<400> SEQUENCE: 69
```

-continued

| | |
|---|---|
| atggactaca aagaccatga cggtgattat aaagatcatg acatcgatta caaggatgac | 60 |
| gatgacaaga tggcccccaa gaagaagagg aaggtgggcc gcggatctgt ggatctacgc | 120 |
| acgctcggct acagtcagca gcagcaagag aagatcaaac cgaaggtgcg ttcgacagtg | 180 |
| gcgcagcacc acgaggcact ggtgggccat gggtttacac acgcgcacat cgttgcgctc | 240 |
| agccaacacc cggcagcgtt agggaccgtc gctgtcacgt atcagcacat aatcacggcg | 300 |
| ttgccagagg cgacacacga agacatcgtt ggcgtcggca acagtggtc cggcgcacgc | 360 |
| gccctggagg ccttgctcac ggatgcgggg gagttgagag gtccgccgtt acagttggac | 420 |
| acaggccaac ttgtgaagat tgcaaaacgt ggcggcgtga ccgcaatgga ggcagtgcat | 480 |
| gcatcgcgca atgcactgac gggtgccccc ctgaacctga ccccggacca agtggtggct | 540 |
| atcgccagca acattggcgg caagcaagcg ctcgaaacgg tgcagcggct gttgccggtg | 600 |
| ctgtgccagg accatggcct gaccccggac caagtggtgg ctatcgccag caacattggc | 660 |
| ggcaagcaag cgctcgaaac ggtgcagcgg ctgttgccgg tgctgtgcca ggaccatggc | 720 |
| ctgaccccgg accaagtggt ggctatcgcc agcaacattg gcggcaagca agcgctcgaa | 780 |
| acggtgcagc ggctgttgcc ggtgctgtgc caggaccatg gcctgacccc ggaccaagtg | 840 |
| gtggctatcg ccagcaacaa tggcggcaag caagcgctcg aaacggtgca gcggctgttg | 900 |
| ccggtgctgt gccaggacca tggcctgacc ccggaccaag tggtggctat cgccagcaac | 960 |
| attggcggca agcaagcgct cgaaacggtg cagcggctgt tgccggtgct gtgccaggac | 1020 |
| catggcctga ccccggacca agtggtggct atcgccagcc acgatggcgg caagcaagcg | 1080 |
| ctcgaaacgg tgcagcggct gttgccggtg ctgtgccagg accatggcct gaccccggac | 1140 |
| caagtggtgg ctatcgccag ccacgatggc ggcaagcaag cgctcgaaac ggtgcagcgg | 1200 |
| ctgttgccgg tgctgtgcca ggaccatggc ctgaccccgg accaagtggt ggctatcgcc | 1260 |
| agcaacattg gcggcaagca agcgctcgaa acggtgcagc ggctgttgcc ggtgctgtgc | 1320 |
| caggaccatg gcctgacccc ggaccaagtg gtggctatcg ccagccacga tggcggcaag | 1380 |
| caagcgctcg aaacggtgca gcggctgttg ccggtgctgt gccaggacca tggcctgacc | 1440 |
| ccggaccaag tggtggctat cgccagcaac attggcggca agcaagcgct cgaaacggtg | 1500 |
| cagcggctgt tgccggtgct gtgccaggac catggcctga ccccggacca agtggtggct | 1560 |
| atcgccagcc acgatggcgg caagcaagcg ctcgaaacgg tgcagcggct gttgccggtg | 1620 |
| ctgtgccagg accatggcct gaccccggac caagtggtgg ctatcgccag ccacgatggc | 1680 |
| ggcaagcaag cgctcgaaac ggtgcagcgg ctgttgccgg tgctgtgcca ggaccatggc | 1740 |
| ctgaccccgg accaagtggt ggctatcgcc agccacgatg cggcaagca agcgctcgaa | 1800 |
| acggtgcagc ggctgttgcc ggtgctgtgc caggaccatg gcctgacccc ggaccaagtg | 1860 |
| gtggctatcg ccagcaacat tggcggcaag caagcgctcg aaacggtgca gcggctgttg | 1920 |
| ccggtgctgt gccaggacca tggcctgacc ccggaccaag tggtggctat cgccagcaac | 1980 |
| ggtggcggca agcaagcgct cgaaacggtg cagcggctgt tgccggtgct gtgccaggac | 2040 |
| catggcctga ccccggacca agtggtggct atcgccagca acaatggcgg caagcaagcg | 2100 |
| ctcgaaacgg tgcagcggct gttgccggtg ctgtgccagg accatggcct gaccccggac | 2160 |
| caagtggtgg ctatcgccag caacattggc ggcaagcaag cgctcgaaac ggtgcagcgg | 2220 |
| ctgttgccgg tgctgtgcca ggaccatggc ctgaccccgg accaagtggt ggctatcgcc | 2280 |
| agccacgatg cggcaagca agcgctcgaa agcattgtgg cccagctgag ccggcctgat | 2340 |
| ccggcgttgg ccgcgttgac caacgacgac cacctcgtcg ccttggcctg cctcggcgga | 2400 |

```
cgtcctgcca tggatgcagt gaaaaaggga ttgccgcacg cgccggaatt gatcagaaga   2460
gtcaatcgcc gtattggcga acgcacgtcc catcgcgttg ccggatccaa ggctagcccg   2520
aaaaagaaac gcaaagttgg gcgcgccgac gcgctggacg atttcgatct cgacatgctg   2580
ggttctgatg ccctcgatga ctttgacctg gatatgttgg gaagcgacgc attggatgac   2640
tttgatctgg acatgctcgg ctccgatgct ctggacgatt tcgatctcga tatgttaatt   2700
aactacccgt acgacgttcc ggactacgct tcttga                            2736
```

<210> SEQ ID NO 70
<211> LENGTH: 911
<212> TYPE: PRT
<213> ORGANISM: Unknown
<220> FEATURE:
<223> OTHER INFORMATION: Synthetic peptide

<400> SEQUENCE: 70

Met Asp Tyr Lys Asp His Asp Gly Asp Tyr Lys Asp His Asp Ile Asp
1               5                   10                  15

Tyr Lys Asp Asp Asp Asp Lys Met Ala Pro Lys Lys Arg Lys Val
            20                  25                  30

Gly Arg Gly Ser Val Asp Leu Arg Thr Leu Gly Tyr Ser Gln Gln Gln
        35                  40                  45

Gln Glu Lys Ile Lys Pro Lys Val Arg Ser Thr Val Ala Gln His His
    50                  55                  60

Glu Ala Leu Val Gly His Gly Phe Thr His Ala His Ile Val Ala Leu
65                  70                  75                  80

Ser Gln His Pro Ala Ala Leu Gly Thr Val Ala Val Thr Tyr Gln His
                85                  90                  95

Ile Ile Thr Ala Leu Pro Glu Ala Thr His Glu Asp Ile Val Gly Val
            100                 105                 110

Gly Lys Gln Trp Ser Gly Ala Arg Ala Leu Glu Ala Leu Leu Thr Asp
        115                 120                 125

Ala Gly Glu Leu Arg Gly Pro Pro Leu Gln Leu Asp Thr Gly Gln Leu
    130                 135                 140

Val Lys Ile Ala Lys Arg Gly Gly Val Thr Ala Met Glu Ala Val His
145                 150                 155                 160

Ala Ser Arg Asn Ala Leu Thr Gly Ala Pro Leu Asn Leu Thr Pro Asp
                165                 170                 175

Gln Val Val Ala Ile Ala Ser Asn Ile Gly Gly Lys Gln Ala Leu Glu
            180                 185                 190

Thr Val Gln Arg Leu Leu Pro Val Leu Cys Gln Asp His Gly Leu Thr
        195                 200                 205

Pro Asp Gln Val Val Ala Ile Ala Ser Asn Ile Gly Gly Lys Gln Ala
    210                 215                 220

Leu Glu Thr Val Gln Arg Leu Leu Pro Val Leu Cys Gln Asp His Gly
225                 230                 235                 240

Leu Thr Pro Asp Gln Val Val Ala Ile Ala Ser Asn Ile Gly Gly Lys
                245                 250                 255

Gln Ala Leu Glu Thr Val Gln Arg Leu Leu Pro Val Leu Cys Gln Asp
            260                 265                 270

His Gly Leu Thr Pro Asp Gln Val Val Ala Ile Ala Ser Asn Asn Gly
        275                 280                 285

Gly Lys Gln Ala Leu Glu Thr Val Gln Arg Leu Leu Pro Val Leu Cys
    290                 295                 300

```
Gln Asp His Gly Leu Thr Pro Asp Gln Val Val Ala Ile Ala Ser Asn
305                 310                 315                 320

Ile Gly Gly Lys Gln Ala Leu Glu Thr Val Gln Arg Leu Leu Pro Val
            325                 330                 335

Leu Cys Gln Asp His Gly Leu Thr Pro Asp Gln Val Val Ala Ile Ala
                340                 345                 350

Ser His Asp Gly Gly Lys Gln Ala Leu Glu Thr Val Gln Arg Leu Leu
            355                 360                 365

Pro Val Leu Cys Gln Asp His Gly Leu Thr Pro Asp Gln Val Val Ala
370                 375                 380

Ile Ala Ser His Asp Gly Gly Lys Gln Ala Leu Glu Thr Val Gln Arg
385                 390                 395                 400

Leu Leu Pro Val Leu Cys Gln Asp His Gly Leu Thr Pro Asp Gln Val
                405                 410                 415

Val Ala Ile Ala Ser Asn Ile Gly Gly Lys Gln Ala Leu Glu Thr Val
            420                 425                 430

Gln Arg Leu Leu Pro Val Leu Cys Gln Asp His Gly Leu Thr Pro Asp
            435                 440                 445

Gln Val Val Ala Ile Ala Ser His Asp Gly Gly Lys Gln Ala Leu Glu
450                 455                 460

Thr Val Gln Arg Leu Leu Pro Val Leu Cys Gln Asp His Gly Leu Thr
465                 470                 475                 480

Pro Asp Gln Val Val Ala Ile Ala Ser Asn Ile Gly Gly Lys Gln Ala
                485                 490                 495

Leu Glu Thr Val Gln Arg Leu Leu Pro Val Leu Cys Gln Asp His Gly
            500                 505                 510

Leu Thr Pro Asp Gln Val Val Ala Ile Ala Ser His Asp Gly Gly Lys
            515                 520                 525

Gln Ala Leu Glu Thr Val Gln Arg Leu Leu Pro Val Leu Cys Gln Asp
530                 535                 540

His Gly Leu Thr Pro Asp Gln Val Val Ala Ile Ala Ser His Asp Gly
545                 550                 555                 560

Gly Lys Gln Ala Leu Glu Thr Val Gln Arg Leu Leu Pro Val Leu Cys
                565                 570                 575

Gln Asp His Gly Leu Thr Pro Asp Gln Val Val Ala Ile Ala Ser His
            580                 585                 590

Asp Gly Gly Lys Gln Ala Leu Glu Thr Val Gln Arg Leu Leu Pro Val
            595                 600                 605

Leu Cys Gln Asp His Gly Leu Thr Pro Asp Gln Val Val Ala Ile Ala
610                 615                 620

Ser Asn Ile Gly Gly Lys Gln Ala Leu Glu Thr Val Gln Arg Leu Leu
625                 630                 635                 640

Pro Val Leu Cys Gln Asp His Gly Leu Thr Pro Asp Gln Val Val Ala
                645                 650                 655

Ile Ala Ser Asn Gly Gly Lys Gln Ala Leu Glu Thr Val Gln Arg
            660                 665                 670

Leu Leu Pro Val Leu Cys Gln Asp His Gly Leu Thr Pro Asp Gln Val
            675                 680                 685

Val Ala Ile Ala Ser Asn Asn Gly Gly Lys Gln Ala Leu Glu Thr Val
690                 695                 700

Gln Arg Leu Leu Pro Val Leu Cys Gln Asp His Gly Leu Thr Pro Asp
705                 710                 715                 720
```

```
Gln Val Val Ala Ile Ala Ser Asn Ile Gly Gly Lys Gln Ala Leu Glu
            725                 730                 735

Thr Val Gln Arg Leu Leu Pro Val Leu Cys Gln Asp His Gly Leu Thr
        740                 745                 750

Pro Asp Gln Val Val Ala Ile Ala Ser His Asp Gly Gly Lys Gln Ala
            755                 760                 765

Leu Glu Ser Ile Val Ala Gln Leu Ser Arg Pro Asp Pro Ala Leu Ala
        770                 775                 780

Ala Leu Thr Asn Asp His Leu Val Ala Leu Ala Cys Leu Gly Gly
785                 790                 795                 800

Arg Pro Ala Met Asp Ala Val Lys Lys Gly Leu Pro His Ala Pro Glu
                805                 810                 815

Leu Ile Arg Arg Val Asn Arg Arg Ile Gly Glu Arg Thr Ser His Arg
            820                 825                 830

Val Ala Gly Ser Lys Ala Ser Pro Lys Lys Arg Lys Val Gly Arg
        835                 840                 845

Ala Asp Ala Leu Asp Asp Phe Asp Leu Asp Met Leu Gly Ser Asp Ala
    850                 855                 860

Leu Asp Asp Phe Asp Leu Asp Met Leu Gly Ser Asp Ala Leu Asp Asp
865                 870                 875                 880

Phe Asp Leu Asp Met Leu Gly Ser Asp Ala Leu Asp Asp Phe Asp Leu
                885                 890                 895

Asp Met Leu Ile Asn Tyr Pro Tyr Asp Val Pro Asp Tyr Ala Ser
            900                 905                 910

<210> SEQ ID NO 71
<211> LENGTH: 2532
<212> TYPE: DNA
<213> ORGANISM: Artificial sequence
<220> FEATURE:
<223> OTHER INFORMATION: Synthetic oligonucleotide

<400> SEQUENCE: 71
atggactaca aagaccatga cggtgattat aaagatcatg acatcgatta caaggatgac      60
gatgacaaga tggcccccaa gaagaagagg aaggtgggcc gcggatctgt ggatctacgc     120
acgctcggct acagtcagca gcagcaagag aagatcaaac cgaaggtgcg ttcgacagtg     180
gcgcagcacc acgaggcact ggtgggccat gggtttacac acgcgcacat cgttgcgctc     240
agccaacacc cggcagcgtt agggaccgtc gctgtcacgt atcagcacat aatcacggcg     300
ttgccagagg cgacacacga agacatcgtt ggcgtcggca aacagtggtc cggcgcacgc     360
gccctggagg ccttgctcac ggatgcgggg gagttgagag gtccgccgtt acagttggac     420
acaggccaac ttgtgaagat tgcaaaacgt ggcggcgtga ccgcaatgga ggcagtgcat     480
gcatcgcgca atgcactgac gggtgccccc ctgaacctga ccccggacca agtggtggct     540
atcgccagcc acgatggcgg caagcaagcg ctcgaaacgg tgcagcggct gttgccggtg     600
ctgtgccagg accatggcct gaccccggac caagtggtgg ctatcgccag caacggtggc     660
ggcaagcaag cgctcgaaac ggtgcagcgg ctgttgccgg tgctgtgcca ggaccatggc     720
ctgaccccgg accaagtggt ggctatcgcc agcaacaatg gcggcaagca agcgctcgaa     780
acggtgcagc ggctgttgcc ggtgctgtgc caggaccatg gcctgacccc ggaccaagtg     840
gtggctatcg ccagcaacat tggcggcaag caagcgctcg aaacggtgca gcggctgttg     900
ccggtgctgt gccaggacca tggcctgacc ccggaccaag tggtggctat cgccagcaac     960
aatggcggca agcaagcgct cgaaacggtg cagcggctgt gccggtgct gtgccaggac    1020
```

```
catggcctga ccccggacca agtggtggct atcgccagca acaatggcgg caagcaagcg   1080
ctcgaaacgg tgcagcggct gttgccggtg ctgtgccagg accatggcct gaccccggac   1140
caagtggtgg ctatcgccag caacattggc ggcaagcaag cgctcgaaac ggtgcagcgg   1200
ctgttgccgg tgctgtgcca ggaccatggc ctgaccccgg accaagtggt ggctatcgcc   1260
agcaacattg gcggcaagca agcgctcgaa acggtgcagc ggctgttgcc ggtgctgtgc   1320
caggaccatg gcctgacccc ggaccaagtg gtggctatcg ccagccacga tggcggcaag   1380
caagcgctcg aaacggtgca gcggctgttg ccggtgctgt gccaggacca tggcctgacc   1440
ccggaccaag tggtggctat cgccagcaac ggtggcggca agcaagcgct cgaaacggtg   1500
cagcggctgt tgccggtgct gtgccaggac catggcctga ccccggacca agtggtggct   1560
atcgccagca acaatggcgg caagcaagcg ctcgaaacgg tgcagcggct gttgccggtg   1620
ctgtgccagg accatggcct gaccccggac caagtggtgg ctatcgccag caacattggc   1680
ggcaagcaag cgctcgaaac ggtgcagcgg ctgttgccgg tgctgtgcca ggaccatggc   1740
ctgaccccgg accaagtggt ggctatcgcc agcaacattg gcggcaagca agcgctcgaa   1800
acggtgcagc ggctgttgcc ggtgctgtgc caggaccatg gcctgacccc ggaccaagtg   1860
gtggctatcg ccagcaacat tggcggcaag caagcgctcg aaacggtgca gcggctgttg   1920
ccggtgctgt gccaggacca tggcctgacc ccggaccaag tggtggctat cgccagcaac   1980
attggcggca agcaagcgct cgaaacggtg cagcggctgt tgccggtgct gtgccaggac   2040
catggcctga ccccggacca agtggtggct atcgccagca acggtggcgg caagcaagcg   2100
ctcgaaagca ttgtggccca gctgagccgg cctgatccgg cgttggccgc gttgaccaac   2160
gacgaccacc tcgtcgcctt ggcctgcctc ggcggacgtc ctgccatgga tgcagtgaaa   2220
aagggattgc cgcacgcgcc ggaattgatc agaagagtca atcgccgtat tggcgaacgc   2280
acgtcccatc gcgttgccgg atccaaggct agcccgaaaa agaaacgcaa agttgggcgc   2340
gccgacgcgc tggacgattt cgatctcgac atgctgggtt ctgatgccct cgatgacttt   2400
gacctggata tgttgggaag cgacgcattg gatgactttg atctggacat gctcggctcc   2460
gatgctctgg acgatttcga tctcgatatg ttaattaact acccgtacga cgttccggac   2520
tacgcttctt ga                                                       2532
```

<210> SEQ ID NO 72
<211> LENGTH: 843
<212> TYPE: PRT
<213> ORGANISM: Unknown
<220> FEATURE:
<223> OTHER INFORMATION: Synthetic peptide

<400> SEQUENCE: 72

Met Asp Tyr Lys Asp His Asp Gly Asp Tyr Lys Asp His Asp Ile Asp
1               5                   10                  15

Tyr Lys Asp Asp Asp Asp Lys Met Ala Pro Lys Lys Arg Lys Val
            20                  25                  30

Gly Arg Gly Ser Val Asp Leu Arg Thr Leu Gly Tyr Ser Gln Gln Gln
        35                  40                  45

Gln Glu Lys Ile Lys Pro Lys Val Arg Ser Thr Val Ala Gln His His
    50                  55                  60

Glu Ala Leu Val Gly His Gly Phe Thr His Ala His Ile Val Ala Leu
65                  70                  75                  80

Ser Gln His Pro Ala Ala Leu Gly Thr Val Ala Val Thr Tyr Gln His

```
                    85                  90                  95
Ile Ile Thr Ala Leu Pro Glu Ala Thr His Glu Asp Ile Val Gly Val
                100                 105                 110

Gly Lys Gln Trp Ser Gly Ala Arg Ala Leu Glu Ala Leu Leu Thr Asp
            115                 120                 125

Ala Gly Glu Leu Arg Gly Pro Pro Leu Gln Leu Asp Thr Gly Gln Leu
        130                 135                 140

Val Lys Ile Ala Lys Arg Gly Gly Val Thr Ala Met Glu Ala Val His
145                 150                 155                 160

Ala Ser Arg Asn Ala Leu Thr Gly Ala Pro Leu Asn Leu Thr Pro Asp
                165                 170                 175

Gln Val Val Ala Ile Ala Ser His Asp Gly Gly Lys Gln Ala Leu Glu
            180                 185                 190

Thr Val Gln Arg Leu Leu Pro Val Leu Cys Gln Asp His Gly Leu Thr
        195                 200                 205

Pro Asp Gln Val Val Ala Ile Ala Ser Asn Gly Gly Lys Gln Ala
    210                 215                 220

Leu Glu Thr Val Gln Arg Leu Leu Pro Val Leu Cys Gln Asp His Gly
225                 230                 235                 240

Leu Thr Pro Asp Gln Val Val Ala Ile Ala Ser Asn Gly Gly Lys
                245                 250                 255

Gln Ala Leu Glu Thr Val Gln Arg Leu Leu Pro Val Leu Cys Gln Asp
            260                 265                 270

His Gly Leu Thr Pro Asp Gln Val Val Ala Ile Ala Ser Asn Ile Gly
        275                 280                 285

Gly Lys Gln Ala Leu Glu Thr Val Gln Arg Leu Leu Pro Val Leu Cys
    290                 295                 300

Gln Asp His Gly Leu Thr Pro Asp Gln Val Val Ala Ile Ala Ser Asn
305                 310                 315                 320

Asn Gly Gly Lys Gln Ala Leu Glu Thr Val Gln Arg Leu Leu Pro Val
                325                 330                 335

Leu Cys Gln Asp His Gly Leu Thr Pro Asp Gln Val Val Ala Ile Ala
            340                 345                 350

Ser Asn Asn Gly Gly Lys Gln Ala Leu Glu Thr Val Gln Arg Leu Leu
        355                 360                 365

Pro Val Leu Cys Gln Asp His Gly Leu Thr Pro Asp Gln Val Val Ala
    370                 375                 380

Ile Ala Ser Asn Ile Gly Gly Lys Gln Ala Leu Glu Thr Val Gln Arg
385                 390                 395                 400

Leu Leu Pro Val Leu Cys Gln Asp His Gly Leu Thr Pro Asp Gln Val
                405                 410                 415

Val Ala Ile Ala Ser Asn Ile Gly Gly Lys Gln Ala Leu Glu Thr Val
            420                 425                 430

Gln Arg Leu Leu Pro Val Leu Cys Gln Asp His Gly Leu Thr Pro Asp
        435                 440                 445

Gln Val Val Ala Ile Ala Ser His Asp Gly Gly Lys Gln Ala Leu Glu
    450                 455                 460

Thr Val Gln Arg Leu Leu Pro Val Leu Cys Gln Asp His Gly Leu Thr
465                 470                 475                 480

Pro Asp Gln Val Val Ala Ile Ala Ser Asn Gly Gly Lys Gln Ala
                485                 490                 495

Leu Glu Thr Val Gln Arg Leu Leu Pro Val Leu Cys Gln Asp His Gly
            500                 505                 510
```

Leu Thr Pro Asp Gln Val Val Ala Ile Ala Ser Asn Asn Gly Gly Lys
            515                 520                 525

Gln Ala Leu Glu Thr Val Gln Arg Leu Leu Pro Val Leu Cys Gln Asp
        530                 535                 540

His Gly Leu Thr Pro Asp Gln Val Val Ala Ile Ala Ser Asn Ile Gly
545                 550                 555                 560

Gly Lys Gln Ala Leu Glu Thr Val Gln Arg Leu Leu Pro Val Leu Cys
                565                 570                 575

Gln Asp His Gly Leu Thr Pro Asp Gln Val Val Ala Ile Ala Ser Asn
            580                 585                 590

Ile Gly Gly Lys Gln Ala Leu Glu Thr Val Gln Arg Leu Leu Pro Val
        595                 600                 605

Leu Cys Gln Asp His Gly Leu Thr Pro Asp Gln Val Val Ala Ile Ala
    610                 615                 620

Ser Asn Ile Gly Gly Lys Gln Ala Leu Glu Thr Val Gln Arg Leu Leu
625                 630                 635                 640

Pro Val Leu Cys Gln Asp His Gly Leu Thr Pro Asp Gln Val Val Ala
                645                 650                 655

Ile Ala Ser Asn Ile Gly Gly Lys Gln Ala Leu Glu Thr Val Gln Arg
            660                 665                 670

Leu Leu Pro Val Leu Cys Gln Asp His Gly Leu Thr Pro Asp Gln Val
        675                 680                 685

Val Ala Ile Ala Ser Asn Gly Gly Lys Gln Ala Leu Glu Ser Ile
    690                 695                 700

Val Ala Gln Leu Ser Arg Pro Asp Pro Ala Leu Ala Ala Leu Thr Asn
705                 710                 715                 720

Asp Asp His Leu Val Ala Leu Ala Cys Leu Gly Gly Arg Pro Ala Met
                725                 730                 735

Asp Ala Val Lys Lys Gly Leu Pro His Ala Pro Glu Leu Ile Arg Arg
            740                 745                 750

Val Asn Arg Arg Ile Gly Glu Arg Thr Ser His Arg Val Ala Gly Ser
        755                 760                 765

Lys Ala Ser Pro Lys Lys Arg Lys Val Gly Arg Ala Asp Ala Leu
    770                 775                 780

Asp Asp Phe Asp Leu Asp Met Leu Gly Ser Asp Ala Leu Asp Asp Phe
785                 790                 795                 800

Asp Leu Asp Met Leu Gly Ser Asp Ala Leu Asp Asp Phe Asp Leu Asp
                805                 810                 815

Met Leu Gly Ser Asp Ala Leu Asp Asp Phe Asp Leu Asp Met Leu Ile
            820                 825                 830

Asn Tyr Pro Tyr Asp Val Pro Asp Tyr Ala Ser
        835                 840

<210> SEQ ID NO 73
<211> LENGTH: 2838
<212> TYPE: DNA
<213> ORGANISM: Artificial sequence
<220> FEATURE:
<223> OTHER INFORMATION: Synthetic oligonucleotide

<400> SEQUENCE: 73
atggactaca aagaccatga cggtgattat aaagatcatg acatcgatta caaggatgac     60
gatgacaaga tggccccaa gaagaagagg aaggtgggcc gcggatctgt ggatctacgc    120
acgctcggct acagtcagca gcagcaagag aagatcaaac cgaaggtgcg ttcgacagtg    180

```
gcgcagcacc acgaggcact ggtgggccat gggtttacac acgcgcacat cgttgcgctc    240
agccaacacc cggcagcgtt agggaccgtc gctgtcacgt atcagcacat aatcacggcg    300
ttgccagagg cgacacacga agacatcgtt ggcgtcggca acagtggtc cggcgcacgc    360 gccctggagg ccttgctcac ggatgcgggg gagttgagag gtccgccgtt acagttggac    420
acaggccaac ttgtgaagat tgcaaaacgt ggcggcgtga ccgcaatgga ggcagtgcat    480
gcatcgcgca atgcactgac gggtgccccc ctgaacctga ccccggacca agtggtggct    540
atcgccagcc acgatggcgg caagcaagcg ctcgaaacgg tgcagcggct gttgccggtg    600
ctgtgccagg accatggcct gaccccggac caagtggtgg ctatcgccag ccacgatggc    660
ggcaagcaag cgctcgaaac ggtgcagcgg ctgttgccgg tgctgtgcca ggaccatggc    720
ctgaccccgg accaagtggt ggctatcgcc agcaacattg gcggcaagca agcgctcgaa    780
acggtgcagc ggctgttgcc ggtgctgtgc caggaccatg gcctgacccc ggaccaagtg    840
gtggctatcg ccagccacga tgcggcaag caagcgctcg aaacggtgca gcggctgttg    900
ccggtgctgt gccaggacca tggcctgacc ccggaccaag tggtggctat cgccagccac    960
gatggcggca agcaagcgct cgaaacggtg cagcggctgt tgccggtgct gtgccaggac   1020
catggcctga ccccggacca agtggtggct atcgccagca cggtggcgg caagcaagcg   1080 ctcgaaacgg tgcagcggct gttgccggtg ctgtgccagg accatggcct gaccccggac   1140
caagtggtgg ctatcgccag caacggtggc ggcaagcaag cgctcgaaac ggtgcagcgg   1200
ctgttgccgg tgctgtgcca ggaccatggc ctgaccccgg accaagtggt ggctatcgcc   1260
agcaacaatg gcggcaagca agcgctcgaa acggtgcagc ggctgttgcc ggtgctgtgc   1320
caggaccatg gcctgacccc ggaccaagtg gtggctatcg ccagccacga tgcggcaag   1380 caagcgctcg aaacggtgca gcggctgttg ccggtgctgt gccaggacca tggcctgacc   1440
ccggaccaag tggtggctat cgccagccac gatggcggca agcaagcgct cgaaacggtg   1500
cagcggctgt gccggtgct gtgccaggac catggcctga ccccggacca agtggtggct   1560
atcgccagca acaatggcgg caagcaagcg ctcgaaacgg tgcagcggct gttgccggtg   1620
ctgtgccagg accatggcct gaccccggac caagtggtgg ctatcgccag caacattggc   1680
ggcaagcaag cgctcgaaac ggtgcagcgg ctgttgccgg tgctgtgcca ggaccatggc   1740
ctgaccccgg accaagtggt ggctatcgcc agcaacattg gcggcaagca agcgctcgaa   1800
acggtgcagc ggctgttgcc ggtgctgtgc caggaccatg gcctgacccc ggaccaagtg   1860
gtggctatcg ccagcaacat tggcggcaag caagcgctcg aaacggtgca gcggctgttg   1920
ccggtgctgt gccaggacca tggcctgacc ccggaccaag tggtggctat cgccagcaac   1980
attggcggca agcaagcgct cgaaacggtg cagcggctgt tgccggtgct gtgccaggac   2040
catggcctga ccccggacca agtggtggct atcgccagca acattggcgg caagcaagcg   2100
ctcgaaacgg tgcagcggct gttgccggtg ctgtgccagg accatggcct gaccccggac   2160
caagtggtgg ctatcgccag caacaatggc ggcaagcaag cgctcgaaac ggtgcagcgg   2220
ctgttgccgg tgctgtgcca ggaccatggc ctgaccccgg accaagtggt ggctatcgcc   2280
agcaacattg gcggcaagca agcgctcgaa acggtgcagc ggctgttgcc ggtgctgtgc   2340
caggaccatg gcctgacccc ggaccaagtg gtggctatcg ccagcaacgg tggcggcaag   2400
caagcgctcg aaagcattgt ggcccagctg agcggcctg atccggcgtt ggccgcgttg   2460
accaacgacg accacctcgt cgccttggcc tgcctcggcg gacgtcctgc catggatgca   2520
```

-continued

```
gtgaaaaagg gattgccgca cgcgccggaa ttgatcagaa gagtcaatcg ccgtattggc    2580
gaacgcacgt cccatcgcgt tgccggatcc aaggctagcc cgaaaaagaa acgcaaagtt    2640
gggcgcgccg acgcgctgga cgatttcgat ctcgacatgc tgggttctga tgccctcgat    2700
gactttgacc tggatatgtt gggaagcgac gcattggatg actttgatct ggacatgctc    2760
ggctccgatg ctctggacga tttcgatctc gatatgttaa ttaactaccc gtacgacgtt    2820
ccggactacg cttcttga                                                   2838
```

<210> SEQ ID NO 74
<211> LENGTH: 945
<212> TYPE: PRT
<213> ORGANISM: Unknown
<220> FEATURE:
<223> OTHER INFORMATION: Synthetic peptide

<400> SEQUENCE: 74

Met Asp Tyr Lys Asp His Asp Gly Asp Tyr Lys Asp His Asp Ile Asp
1               5                   10                  15

Tyr Lys Asp Asp Asp Lys Met Ala Pro Lys Lys Arg Lys Val
            20                  25                  30

Gly Arg Gly Ser Val Asp Leu Arg Thr Leu Gly Tyr Ser Gln Gln Gln
        35                  40                  45

Gln Glu Lys Ile Lys Pro Lys Val Arg Ser Thr Val Ala Gln His His
    50                  55                  60

Glu Ala Leu Val Gly His Gly Phe Thr His Ala His Ile Val Ala Leu
65                  70                  75                  80

Ser Gln His Pro Ala Ala Leu Gly Thr Val Ala Val Thr Tyr Gln His
                85                  90                  95

Ile Ile Thr Ala Leu Pro Glu Ala Thr His Glu Asp Ile Val Gly Val
            100                 105                 110

Gly Lys Gln Trp Ser Gly Ala Arg Ala Leu Glu Ala Leu Leu Thr Asp
        115                 120                 125

Ala Gly Glu Leu Arg Gly Pro Pro Leu Gln Leu Asp Thr Gly Gln Leu
    130                 135                 140

Val Lys Ile Ala Lys Arg Gly Gly Val Thr Ala Met Glu Ala Val His
145                 150                 155                 160

Ala Ser Arg Asn Ala Leu Thr Gly Ala Pro Leu Asn Leu Thr Pro Asp
                165                 170                 175

Gln Val Val Ala Ile Ala Ser His Asp Gly Gly Lys Gln Ala Leu Glu
            180                 185                 190

Thr Val Gln Arg Leu Leu Pro Val Leu Cys Gln Asp His Gly Leu Thr
        195                 200                 205

Pro Asp Gln Val Val Ala Ile Ala Ser His Asp Gly Gly Lys Gln Ala
    210                 215                 220

Leu Glu Thr Val Gln Arg Leu Leu Pro Val Leu Cys Gln Asp His Gly
225                 230                 235                 240

Leu Thr Pro Asp Gln Val Val Ala Ile Ala Ser Asn Ile Gly Gly Lys
                245                 250                 255

Gln Ala Leu Glu Thr Val Gln Arg Leu Leu Pro Val Leu Cys Gln Asp
            260                 265                 270

His Gly Leu Thr Pro Asp Gln Val Val Ala Ile Ala Ser His Asp Gly
        275                 280                 285

Gly Lys Gln Ala Leu Glu Thr Val Gln Arg Leu Leu Pro Val Leu Cys
    290                 295                 300

-continued

```
Gln Asp His Gly Leu Thr Pro Asp Gln Val Val Ala Ile Ala Ser His
305                 310                 315                 320

Asp Gly Gly Lys Gln Ala Leu Glu Thr Val Gln Arg Leu Leu Pro Val
            325                 330                 335

Leu Cys Gln Asp His Gly Leu Thr Pro Asp Gln Val Val Ala Ile Ala
                340                 345                 350

Ser Asn Gly Gly Gly Lys Gln Ala Leu Glu Thr Val Gln Arg Leu Leu
        355                 360                 365

Pro Val Leu Cys Gln Asp His Gly Leu Thr Pro Asp Gln Val Val Ala
370                 375                 380

Ile Ala Ser Asn Gly Gly Gly Lys Gln Ala Leu Glu Thr Val Gln Arg
385                 390                 395                 400

Leu Leu Pro Val Leu Cys Gln Asp His Gly Leu Thr Pro Asp Gln Val
                405                 410                 415

Val Ala Ile Ala Ser Asn Asn Gly Gly Lys Gln Ala Leu Glu Thr Val
            420                 425                 430

Gln Arg Leu Leu Pro Val Leu Cys Gln Asp His Gly Leu Thr Pro Asp
        435                 440                 445

Gln Val Val Ala Ile Ala Ser His Asp Gly Gly Lys Gln Ala Leu Glu
450                 455                 460

Thr Val Gln Arg Leu Leu Pro Val Leu Cys Gln Asp His Gly Leu Thr
465                 470                 475                 480

Pro Asp Gln Val Val Ala Ile Ala Ser His Asp Gly Gly Lys Gln Ala
                485                 490                 495

Leu Glu Thr Val Gln Arg Leu Leu Pro Val Leu Cys Gln Asp His Gly
            500                 505                 510

Leu Thr Pro Asp Gln Val Val Ala Ile Ala Ser Asn Asn Gly Gly Lys
        515                 520                 525

Gln Ala Leu Glu Thr Val Gln Arg Leu Leu Pro Val Leu Cys Gln Asp
530                 535                 540

His Gly Leu Thr Pro Asp Gln Val Val Ala Ile Ala Ser Asn Ile Gly
545                 550                 555                 560

Gly Lys Gln Ala Leu Glu Thr Val Gln Arg Leu Leu Pro Val Leu Cys
                565                 570                 575

Gln Asp His Gly Leu Thr Pro Asp Gln Val Val Ala Ile Ala Ser Asn
            580                 585                 590

Ile Gly Gly Lys Gln Ala Leu Glu Thr Val Gln Arg Leu Leu Pro Val
        595                 600                 605

Leu Cys Gln Asp His Gly Leu Thr Pro Asp Gln Val Val Ala Ile Ala
610                 615                 620

Ser Asn Ile Gly Gly Lys Gln Ala Leu Glu Thr Val Gln Arg Leu Leu
625                 630                 635                 640

Pro Val Leu Cys Gln Asp His Gly Leu Thr Pro Asp Gln Val Val Ala
                645                 650                 655

Ile Ala Ser Asn Ile Gly Gly Lys Gln Ala Leu Glu Thr Val Gln Arg
            660                 665                 670

Leu Leu Pro Val Leu Cys Gln Asp His Gly Leu Thr Pro Asp Gln Val
        675                 680                 685

Val Ala Ile Ala Ser Asn Ile Gly Gly Lys Gln Ala Leu Glu Thr Val
690                 695                 700

Gln Arg Leu Leu Pro Val Leu Cys Gln Asp His Gly Leu Thr Pro Asp
705                 710                 715                 720

Gln Val Val Ala Ile Ala Ser Asn Asn Gly Gly Lys Gln Ala Leu Glu
```

```
                    725                 730                 735
Thr Val Gln Arg Leu Leu Pro Val Leu Cys Gln Asp His Gly Leu Thr
                740                 745                 750
Pro Asp Gln Val Val Ala Ile Ala Ser Asn Ile Gly Gly Lys Gln Ala
                755                 760                 765
Leu Glu Thr Val Gln Arg Leu Leu Pro Val Leu Cys Gln Asp His Gly
            770                 775                 780
Leu Thr Pro Asp Gln Val Val Ala Ile Ala Ser Asn Gly Gly Lys
785                 790                 795                 800
Gln Ala Leu Glu Ser Ile Val Ala Gln Leu Ser Arg Pro Asp Pro Ala
                805                 810                 815
Leu Ala Ala Leu Thr Asn Asp His Leu Val Ala Leu Ala Cys Leu
                820                 825                 830
Gly Gly Arg Pro Ala Met Asp Ala Val Lys Lys Gly Leu Pro His Ala
                835                 840                 845
Pro Glu Leu Ile Arg Arg Val Asn Arg Arg Ile Gly Glu Arg Thr Ser
850                 855                 860
His Arg Val Ala Gly Ser Lys Ala Ser Pro Lys Lys Arg Lys Val
865                 870                 875                 880
Gly Arg Ala Asp Ala Leu Asp Asp Phe Asp Leu Asp Met Leu Gly Ser
                            885                 890                 895
Asp Ala Leu Asp Asp Phe Asp Leu Asp Met Leu Gly Ser Asp Ala Leu
                900                 905                 910
Asp Asp Phe Asp Leu Asp Met Leu Gly Ser Asp Ala Leu Asp Asp Phe
                915                 920                 925
Asp Leu Asp Met Leu Ile Asn Tyr Pro Tyr Asp Val Pro Asp Tyr Ala
            930                 935                 940
Ser
945

<210> SEQ ID NO 75
<211> LENGTH: 2532
<212> TYPE: DNA
<213> ORGANISM: Artificial sequence
<220> FEATURE:
<223> OTHER INFORMATION: Synthetic oligonucleotide

<400> SEQUENCE: 75
atggactaca aagaccatga cggtgattat aaagatcatg acatcgatta caaggatgac    60
gatgacaaga tggcccccaa gaagaagagg aaggtgggcc gcggatctgt ggatctacgc   120
acgctcggct acagtcagca gcagcaagag aagatcaaac cgaaggtgcg ttcgacagtg   180
gcgcagcacc acgaggcact ggtgggccat gggtttacac acgcgcacat cgttgcgctc   240
agccaacacc cggcagcgtt agggaccgtc gctgtcacgt atcagcacat aatcacggcg   300
ttgccagagg cgacacacga agacatcgtt ggcgtcggca acagtggtc cggcgcacgc   360 gccctggagg ccttgctcac ggatgcgggg gagttgagag tccgccgtt acagttggac   420 acaggccaac ttgtgaagat tgcaaaacgt ggcggcgtga ccgcaatgga ggcagtgcat   480
gcatcgcgca atgcactgac gggtgccccc ctgaacctga ccccggacca agtggtggct   540
atcgccagca acggtggcgg caagcaagcg ctcgaaacgg tgcagcggct gttgccggtg   600
ctgtgccagg accatggcct gaccccggac caagtggtgg ctatcgccag caacaatggc   660
ggcaagcaag cgctcgaaac ggtgcagcgg ctgttgccgg tgctgtgcca ggaccatggc   720
ctgaccccgg accaagtggt ggctatcgcc agccacgatg gcggcaagca agcgctcgaa   780
```

```
acggtgcagc ggctgttgcc ggtgctgtgc caggaccatg gcctgacccc ggaccaagtg    840
gtggctatcg ccagccacga tggcggcaag caagcgctcg aaacggtgca gcggctgttg    900
ccggtgctgt gccaggacca tggcctgacc ccggaccaag tggtggctat cgccagcaac    960
ggtggcggca agcaagcgct cgaaacggtg cagcggctgt tgccggtgct gtgccaggac   1020
catggcctga ccccggacca agtggtggct atcgccagcc acgatggcgg caagcaagcg   1080
ctcgaaacgg tgcagcggct gttgccggtg ctgtgccagg accatggcct gaccccggac   1140
caagtggtgg ctatcgccag ccacgatggc ggcaagcaag cgctcgaaac ggtgcagcgg   1200
ctgttgccgg tgctgtgcca ggaccatggc ctgaccccgg accaagtggt ggctatcgcc   1260
agccacgatg gcggcaagca agcgctcgaa acggtgcagc ggctgttgcc ggtgctgtgc   1320
caggaccatg gcctgacccc ggaccaagtg gtggctatcg ccagcaacat ggcggcaag   1380 caagcgctcg aaacggtgca gcggctgttg ccggtgctgt gccaggacca tggcctgacc   1440
ccggaccaag tggtggctat cgccagcaac aatggcggca agcaagcgct cgaaacggtg   1500
cagcggctgt tgccggtgct gtgccaggac catggcctga ccccggacca agtggtggct   1560
atcgccagca acaatggcgg caagcaagcg ctcgaaacgg tgcagcggct gttgccggtg   1620
ctgtgccagg accatggcct gaccccggac caagtggtgg ctatcgccag caacaatggc   1680
ggcaagcaag cgctcgaaac ggtgcagcgg ctgttgccgg tgctgtgcca ggaccatggc   1740
ctgaccccgg accaagtggt ggctatcgcc agcaacaatg gcggcaagca agcgctcgaa   1800
acggtgcagc ggctgttgcc ggtgctgtgc caggaccatg gcctgacccc ggaccaagtg   1860
gtggctatcg ccagcaacat ggcggcaag caagcgctcg aaacggtgca gcggctgttg   1920
ccggtgctgt gccaggacca tggcctgacc ccggaccaag tggtggctat cgccagcaac   1980
ggtggcggca agcaagcgct cgaaacggtg cagcggctgt tgccggtgct gtgccaggac   2040
catggcctga ccccggacca agtggtggct atcgccagca cggtggcgg caagcaagcg   2100 ctcgaaagca ttgtggccca gctgagccgg cctgatccgg cgttggccgc gttgaccaac   2160
gacgaccacc tcgtcgcctt ggcctgcctc ggcggacgtc ctgccatgga tgcagtgaaa   2220
aagggattgc cgcacgcgcc ggaattgatc agaagagtca atcgccgtat tggcgaacgc   2280
acgtcccatc gcgttgccgg atccaaggct agcccgaaaa agaaacgcaa agttgggcgc   2340
gccgacgcgc tggacgattt cgatctcgac atgctgggtt ctgatgccct cgatgacttt   2400
gacctggata tgttgggaag cgacgcattg gatgactttg atctggacat gctcggctcc   2460
gatgctctgg acgatttcga tctcgatatg ttaattaact accccgtacga cgttccggac   2520 tacgcttctt ga                                                      2532
```

<210> SEQ ID NO 76
<211> LENGTH: 843
<212> TYPE: PRT
<213> ORGANISM: Unknown
<220> FEATURE:
<223> OTHER INFORMATION: Synthetic peptide

<400> SEQUENCE: 76

Met Asp Tyr Lys Asp His Asp Gly Asp Tyr Lys Asp His Asp Ile Asp
1               5                   10                  15

Tyr Lys Asp Asp Asp Asp Lys Met Ala Pro Lys Lys Arg Lys Val
            20                  25                  30

Gly Arg Gly Ser Val Asp Leu Arg Thr Leu Gly Tyr Ser Gln Gln Gln
        35                  40                  45

```
Gln Glu Lys Ile Lys Pro Lys Val Arg Ser Thr Val Ala Gln His His
    50                  55                  60

Glu Ala Leu Val Gly His Gly Phe Thr His Ala His Ile Val Ala Leu
65                  70                  75                  80

Ser Gln His Pro Ala Ala Leu Gly Thr Val Ala Val Thr Tyr Gln His
                85                  90                  95

Ile Ile Thr Ala Leu Pro Glu Ala Thr His Glu Asp Ile Val Gly Val
            100                 105                 110

Gly Lys Gln Trp Ser Gly Ala Arg Ala Leu Glu Ala Leu Leu Thr Asp
            115                 120                 125

Ala Gly Glu Leu Arg Gly Pro Pro Leu Gln Leu Asp Thr Gly Gln Leu
        130                 135                 140

Val Lys Ile Ala Lys Arg Gly Gly Val Thr Ala Met Glu Ala Val His
145                 150                 155                 160

Ala Ser Arg Asn Ala Leu Thr Gly Ala Pro Leu Asn Leu Thr Pro Asp
                165                 170                 175

Gln Val Val Ala Ile Ala Ser Asn Gly Gly Lys Gln Ala Leu Glu
                180                 185                 190

Thr Val Gln Arg Leu Leu Pro Val Leu Cys Gln Asp His Gly Leu Thr
        195                 200                 205

Pro Asp Gln Val Val Ala Ile Ala Ser Asn Asn Gly Gly Lys Gln Ala
210                 215                 220

Leu Glu Thr Val Gln Arg Leu Leu Pro Val Leu Cys Gln Asp His Gly
225                 230                 235                 240

Leu Thr Pro Asp Gln Val Val Ala Ile Ala Ser His Asp Gly Gly Lys
                245                 250                 255

Gln Ala Leu Glu Thr Val Gln Arg Leu Leu Pro Val Leu Cys Gln Asp
            260                 265                 270

His Gly Leu Thr Pro Asp Gln Val Val Ala Ile Ala Ser His Asp Gly
        275                 280                 285

Gly Lys Gln Ala Leu Glu Thr Val Gln Arg Leu Leu Pro Val Leu Cys
        290                 295                 300

Gln Asp His Gly Leu Thr Pro Asp Gln Val Val Ala Ile Ala Ser Asn
305                 310                 315                 320

Gly Gly Gly Lys Gln Ala Leu Glu Thr Val Gln Arg Leu Leu Pro Val
                325                 330                 335

Leu Cys Gln Asp His Gly Leu Thr Pro Asp Gln Val Val Ala Ile Ala
            340                 345                 350

Ser His Asp Gly Gly Lys Gln Ala Leu Glu Thr Val Gln Arg Leu Leu
        355                 360                 365

Pro Val Leu Cys Gln Asp His Gly Leu Thr Pro Asp Gln Val Val Ala
        370                 375                 380

Ile Ala Ser His Asp Gly Gly Lys Gln Ala Leu Glu Thr Val Gln Arg
385                 390                 395                 400

Leu Leu Pro Val Leu Cys Gln Asp His Gly Leu Thr Pro Asp Gln Val
                405                 410                 415

Val Ala Ile Ala Ser His Asp Gly Gly Lys Gln Ala Leu Glu Thr Val
            420                 425                 430

Gln Arg Leu Leu Pro Val Leu Cys Gln Asp His Gly Leu Thr Pro Asp
        435                 440                 445

Gln Val Val Ala Ile Ala Ser Asn Ile Gly Gly Lys Gln Ala Leu Glu
        450                 455                 460
```

Thr Val Gln Arg Leu Leu Pro Val Leu Cys Gln Asp His Gly Leu Thr
465                 470                 475                 480

Pro Asp Gln Val Val Ala Ile Ala Ser Asn Asn Gly Gly Lys Gln Ala
            485                 490                 495

Leu Glu Thr Val Gln Arg Leu Leu Pro Val Leu Cys Gln Asp His Gly
        500                 505                 510

Leu Thr Pro Asp Gln Val Val Ala Ile Ala Ser Asn Asn Gly Gly Lys
    515                 520                 525

Gln Ala Leu Glu Thr Val Gln Arg Leu Leu Pro Val Leu Cys Gln Asp
530                 535                 540

His Gly Leu Thr Pro Asp Gln Val Val Ala Ile Ala Ser Asn Asn Gly
545                 550                 555                 560

Gly Lys Gln Ala Leu Glu Thr Val Gln Arg Leu Leu Pro Val Leu Cys
            565                 570                 575

Gln Asp His Gly Leu Thr Pro Asp Gln Val Val Ala Ile Ala Ser Asn
        580                 585                 590

Asn Gly Gly Lys Gln Ala Leu Glu Thr Val Gln Arg Leu Leu Pro Val
    595                 600                 605

Leu Cys Gln Asp His Gly Leu Thr Pro Asp Gln Val Val Ala Ile Ala
610                 615                 620

Ser Asn Ile Gly Gly Lys Gln Ala Leu Glu Thr Val Gln Arg Leu Leu
625                 630                 635                 640

Pro Val Leu Cys Gln Asp His Gly Leu Thr Pro Asp Gln Val Val Ala
            645                 650                 655

Ile Ala Ser Asn Gly Gly Gly Lys Gln Ala Leu Glu Thr Val Gln Arg
        660                 665                 670

Leu Leu Pro Val Leu Cys Gln Asp His Gly Leu Thr Pro Asp Gln Val
    675                 680                 685

Val Ala Ile Ala Ser Asn Gly Gly Lys Gln Ala Leu Glu Ser Ile
690                 695                 700

Val Ala Gln Leu Ser Arg Pro Asp Pro Ala Leu Ala Ala Leu Thr Asn
705                 710                 715                 720

Asp Asp His Leu Val Ala Leu Ala Cys Leu Gly Gly Arg Pro Ala Met
            725                 730                 735

Asp Ala Val Lys Lys Gly Leu Pro His Ala Pro Glu Leu Ile Arg Arg
        740                 745                 750

Val Asn Arg Arg Ile Gly Glu Arg Thr Ser His Arg Val Ala Gly Ser
    755                 760                 765

Lys Ala Ser Pro Lys Lys Arg Lys Val Gly Arg Ala Asp Ala Leu
770                 775                 780

Asp Asp Phe Asp Leu Asp Met Leu Gly Ser Asp Ala Leu Asp Asp Phe
785                 790                 795                 800

Asp Leu Asp Met Leu Gly Ser Asp Ala Leu Asp Asp Phe Asp Leu Asp
            805                 810                 815

Met Leu Gly Ser Asp Ala Leu Asp Asp Phe Asp Leu Asp Met Leu Ile
        820                 825                 830

Asn Tyr Pro Tyr Asp Val Pro Asp Tyr Ala Ser
    835                 840

<210> SEQ ID NO 77
<211> LENGTH: 2532
<212> TYPE: DNA
<213> ORGANISM: Artificial sequence
<220> FEATURE:
<223> OTHER INFORMATION: Synthetic oligonucleotide

<400> SEQUENCE: 77

```
atggactaca aagaccatga cggtgattat aaagatcatg acatcgatta caaggatgac    60
gatgacaaga tggcccccaa gaagaagagg aaggtgggcc gcggatctgt ggatctacgc   120
acgctcggct acagtcagca gcagcaagag aagatcaaac cgaaggtgcg ttcgacagtg   180
gcgcagcacc acgaggcact ggtgggccat gggtttacac acgcgcacat cgttgcgctc   240
agccaacacc cggcagcgtt agggaccgtc gctgtcacgt atcagcacat aatcacggcg   300
ttgccagagg cgacacacga agacatcgtt ggcgtcggca acagtggtc cggcgcacgc    360
gccctggagg ccttgctcac ggatgcgggg gagttgagag gtccgccgtt acagttggac   420
acaggccaac ttgtgaagat tgcaaaacgt ggcggcgtga ccgcaatgga ggcagtgcat   480
gcatcgcgca atgcactgac gggtgccccc ctgaacctga ccccggacca agtggtggct   540
atcgccagcc acgatggcgg caagcaagcg ctcgaaacgg tgcagcggct gttgccggtg   600
ctgtgccagg accatggcct gaccccggac caagtggtgg ctatcgccag caacggtggc   660
ggcaagcaag cgctcgaaac ggtgcagcgg ctgttgccgg tgctgtgcca ggaccatggc   720
ctgaccccgg accaagtggt ggctatcgcc agcaacaatg gcggcaagca agcgctcgaa   780
acggtgcagc ggctgttgcc ggtgctgtgc caggaccatg gcctgacccc ggaccaagtg   840
gtggctatcg ccagcaacgg tggcggcaag caagcgctcg aaacggtgca gcggctgttg   900
ccggtgctgt gccaggacca tggcctgacc ccggaccaag tggtggctat cgccagccac   960
gatggcggca agcaagcgct cgaaacggtg cagcggctgt tgccggtgct gtgccaggac  1020
catggcctga ccccggacca agtggtggct atcgccagca cattggcgg caagcaagcg   1080
ctcgaaacgg tgcagcggct gttgccggtg ctgtgccagg accatggcct gaccccggac  1140
caagtggtgg ctatcgccag ccacgatggc ggcaagcaag cgctcgaaac ggtgcagcgg  1200
ctgttgccgg tgctgtgcca ggaccatggc ctgaccccgg accaagtggt ggctatcgcc  1260
agcaacattg gcggcaagca agcgctcgaa acggtgcagc ggctgttgcc ggtgctgtgc  1320
caggaccatg gcctgacccc ggaccaagtg gtggctatcg ccagcaacat tggcggcaag  1380
caagcgctcg aaacggtgca gcggctgttg ccggtgctgt gccaggacca tggcctgacc  1440
ccggaccaag tggtggctat cgccagcaac attggcggca agcaagcgct cgaaacggtg  1500
cagcggctgt tgccggtgct gtgccaggac catggcctga ccccggacca agtggtggct  1560
atcgccagca caatggcgg caagcaagcg ctcgaaacgg tgcagcggct gttgccggtg   1620
ctgtgccagg accatggcct gaccccggac caagtggtgg ctatcgccag caacaatggc  1680
ggcaagcaag cgctcgaaac ggtgcagcgg ctgttgccgg tgctgtgcca ggaccatggc  1740
ctgaccccgg accaagtggt ggctatcgcc agcaacattg gcggcaagca agcgctcgaa  1800
acggtgcagc ggctgttgcc ggtgctgtgc caggaccatg gcctgacccc ggaccaagtg  1860
gtggctatcg ccagcaacat tggcggcaag caagcgctcg aaacggtgca gcggctgttg  1920
ccggtgctgt gccaggacca tggcctgacc ccggaccaag tggtggctat cgccagcaac  1980
attggcggca agcaagcgct cgaaacggtg cagcggctgt tgccggtgct gtgccaggac  2040
catggcctga ccccggacca agtggtggct atcgccagca cattggcgg caagcaagcg   2100
ctcgaaagca ttgtggccca gctgagccgg cctgatccgg cgttggccgc gttgaccaac  2160
gacgaccacc tcgtcgcctt ggcctgcctc ggcggacgtc ctgccatgga tgcagtgaaa  2220
aagggattgc cgcacgcgcc ggaattgatc agaagagtca atcgccgtat tggcgaacgc  2280
```

-continued

```
acgtcccatc gcgttgccgg atccaaggct agcccgaaaa agaaacgcaa agttgggcgc    2340
gccgacgcgc tggacgattt cgatctcgac atgctgggtt ctgatgccct cgatgacttt    2400
gacctggata tgttgggaag cgacgcattg gatgactttg atctggacat gctcggctcc    2460
gatgctctgg acgatttcga tctcgatatg ttaattaact acccgtacga cgttccggac    2520
tacgcttctt ga                                                        2532
```

<210> SEQ ID NO 78
<211> LENGTH: 843
<212> TYPE: PRT
<213> ORGANISM: Unknown
<220> FEATURE:
<223> OTHER INFORMATION: Synthetic peptide

<400> SEQUENCE: 78

```
Met Asp Tyr Lys Asp His Asp Gly Asp Tyr Lys Asp His Asp Ile Asp
1               5                   10                  15

Tyr Lys Asp Asp Asp Asp Lys Met Ala Pro Lys Lys Arg Lys Val
                20                  25                  30

Gly Arg Gly Ser Val Asp Leu Arg Thr Leu Gly Tyr Ser Gln Gln Gln
            35                  40                  45

Gln Glu Lys Ile Lys Pro Lys Val Arg Ser Thr Val Ala Gln His His
    50                  55                  60

Glu Ala Leu Val Gly His Gly Phe Thr His Ala His Ile Val Ala Leu
65                  70                  75                  80

Ser Gln His Pro Ala Ala Leu Gly Thr Val Ala Val Thr Tyr Gln His
                85                  90                  95

Ile Ile Thr Ala Leu Pro Glu Ala Thr His Glu Asp Ile Val Gly Val
            100                 105                 110

Gly Lys Gln Trp Ser Gly Ala Arg Ala Leu Glu Ala Leu Leu Thr Asp
        115                 120                 125

Ala Gly Glu Leu Arg Gly Pro Pro Leu Gln Leu Asp Thr Gly Gln Leu
    130                 135                 140

Val Lys Ile Ala Lys Arg Gly Gly Val Thr Ala Met Glu Ala Val His
145                 150                 155                 160

Ala Ser Arg Asn Ala Leu Thr Gly Ala Pro Leu Asn Leu Thr Pro Asp
                165                 170                 175

Gln Val Val Ala Ile Ala Ser His Asp Gly Gly Lys Gln Ala Leu Glu
            180                 185                 190

Thr Val Gln Arg Leu Leu Pro Val Leu Cys Gln Asp His Gly Leu Thr
        195                 200                 205

Pro Asp Gln Val Val Ala Ile Ala Ser Asn Gly Gly Lys Gln Ala
    210                 215                 220

Leu Glu Thr Val Gln Arg Leu Leu Pro Val Leu Cys Gln Asp His Gly
225                 230                 235                 240

Leu Thr Pro Asp Gln Val Val Ala Ile Ala Ser Asn Gly Gly Lys
                245                 250                 255

Gln Ala Leu Glu Thr Val Gln Arg Leu Leu Pro Val Leu Cys Gln Asp
            260                 265                 270

His Gly Leu Thr Pro Asp Gln Val Val Ala Ile Ala Ser Asn Gly Gly
        275                 280                 285

Gly Lys Gln Ala Leu Glu Thr Val Gln Arg Leu Leu Pro Val Leu Cys
    290                 295                 300

Gln Asp His Gly Leu Thr Pro Asp Gln Val Val Ala Ile Ala Ser His
305                 310                 315                 320
```

```
Asp Gly Gly Lys Gln Ala Leu Glu Thr Val Gln Arg Leu Leu Pro Val
            325                 330                 335

Leu Cys Gln Asp His Gly Leu Thr Pro Asp Gln Val Val Ala Ile Ala
            340                 345                 350

Ser Asn Ile Gly Gly Lys Gln Ala Leu Glu Thr Val Gln Arg Leu Leu
            355                 360                 365

Pro Val Leu Cys Gln Asp His Gly Leu Thr Pro Asp Gln Val Val Ala
        370                 375                 380

Ile Ala Ser His Asp Gly Gly Lys Gln Ala Leu Glu Thr Val Gln Arg
385                 390                 395                 400

Leu Leu Pro Val Leu Cys Gln Asp His Gly Leu Thr Pro Asp Gln Val
                405                 410                 415

Val Ala Ile Ala Ser Asn Ile Gly Gly Lys Gln Ala Leu Glu Thr Val
                420                 425                 430

Gln Arg Leu Leu Pro Val Leu Cys Gln Asp His Gly Leu Thr Pro Asp
            435                 440                 445

Gln Val Val Ala Ile Ala Ser Asn Ile Gly Gly Lys Gln Ala Leu Glu
            450                 455                 460

Thr Val Gln Arg Leu Leu Pro Val Leu Cys Gln Asp His Gly Leu Thr
465                 470                 475                 480

Pro Asp Gln Val Val Ala Ile Ala Ser Asn Ile Gly Gly Lys Gln Ala
                485                 490                 495

Leu Glu Thr Val Gln Arg Leu Leu Pro Val Leu Cys Gln Asp His Gly
                500                 505                 510

Leu Thr Pro Asp Gln Val Val Ala Ile Ala Ser Asn Asn Gly Gly Lys
            515                 520                 525

Gln Ala Leu Glu Thr Val Gln Arg Leu Leu Pro Val Leu Cys Gln Asp
            530                 535                 540

His Gly Leu Thr Pro Asp Gln Val Val Ala Ile Ala Ser Asn Asn Gly
545                 550                 555                 560

Gly Lys Gln Ala Leu Glu Thr Val Gln Arg Leu Leu Pro Val Leu Cys
                565                 570                 575

Gln Asp His Gly Leu Thr Pro Asp Gln Val Val Ala Ile Ala Ser Asn
                580                 585                 590

Ile Gly Gly Lys Gln Ala Leu Glu Thr Val Gln Arg Leu Leu Pro Val
            595                 600                 605

Leu Cys Gln Asp His Gly Leu Thr Pro Asp Gln Val Val Ala Ile Ala
            610                 615                 620

Ser Asn Ile Gly Gly Lys Gln Ala Leu Glu Thr Val Gln Arg Leu Leu
625                 630                 635                 640

Pro Val Leu Cys Gln Asp His Gly Leu Thr Pro Asp Gln Val Val Ala
                645                 650                 655

Ile Ala Ser Asn Ile Gly Gly Lys Gln Ala Leu Glu Thr Val Gln Arg
                660                 665                 670

Leu Leu Pro Val Leu Cys Gln Asp His Gly Leu Thr Pro Asp Gln Val
            675                 680                 685

Val Ala Ile Ala Ser Asn Ile Gly Gly Lys Gln Ala Leu Glu Ser Ile
            690                 695                 700

Val Ala Gln Leu Ser Arg Pro Asp Pro Ala Leu Ala Ala Leu Thr Asn
705                 710                 715                 720

Asp Asp His Leu Val Ala Leu Ala Cys Leu Gly Gly Arg Pro Ala Met
                725                 730                 735
```

```
Asp Ala Val Lys Lys Gly Leu Pro His Ala Pro Glu Leu Ile Arg Arg
                740                 745                 750

Val Asn Arg Arg Ile Gly Glu Arg Thr Ser His Arg Val Ala Gly Ser
        755                 760                 765

Lys Ala Ser Pro Lys Lys Arg Lys Val Gly Arg Ala Asp Ala Leu
        770                 775                 780

Asp Asp Phe Asp Leu Asp Met Leu Gly Ser Asp Ala Leu Asp Phe
785                 790                 795                 800

Asp Leu Asp Met Leu Gly Ser Asp Ala Leu Asp Phe Asp Leu Asp
                805                 810                 815

Met Leu Gly Ser Asp Ala Leu Asp Phe Asp Leu Asp Met Leu Ile
            820                 825                 830

Asn Tyr Pro Tyr Asp Val Pro Asp Tyr Ala Ser
        835                 840
```

<210> SEQ ID NO 79
<211> LENGTH: 2838
<212> TYPE: DNA
<213> ORGANISM: Artificial sequence
<220> FEATURE:
<223> OTHER INFORMATION: Synthetic oligonucleotide

<400> SEQUENCE: 79

```
atggactaca aagaccatga cggtgattat aaagatcatg acatcgatta caaggatgac    60
gatgacaaga tggcccccaa gaagaagagg aaggtgggcc gcggatctgt ggatctacgc   120
acgctcggct acagtcagca gcagcaagag aagatcaaac cgaaggtgcg ttcgacagtg   180
gcgcagcacc acgaggcact ggtgggccat gggtttacac acgcgcacat cgttgcgctc   240
agccaacacc cggcagcgtt agggaccgtc gctgtcacgt atcagcacat aatcacggcg   300
ttgccagagg cgacacacga agacatcgtt ggcgtcggca acagtggtc cggcgcacgc    360
gccctggagg ccttgctcac ggatgcgggg gagttgagag gtccgccgtt acagttggac   420
acaggccaac ttgtgaagat tgcaaaacgt ggcggcgtga ccgcaatgga ggcagtgcat   480
gcatcgcgca atgcactgac gggtgccccc ctgaacctga ccccggacca agtggtggct   540
atcgccagca acaatggcgg caagcaagcg ctcgaaacgg tgcagcggct gttgccggtg   600
ctgtgccagg accatggcct gaccccggac caagtggtgg ctatcgccag caacggtggc   660
ggcaagcaag cgctcgaaac ggtgcagcgg ctgttgccgg tgctgtgcca ggaccatggc   720
ctgaccccgg accaagtggt ggctatcgcc agcaacggtg gcggcaagca agcgctcgaa   780
acggtgcagc ggctgttgcc ggtgctgtgc caggaccatg gcctgacccc ggaccaagtg   840
gtggctatcg ccagcaacaa tggcggcaag caagcgctcg aaacggtgca gcggctgttg   900
ccggtgctgt gccaggacca tggcctgacc ccggaccaag tggtggctat cgccagcaac   960
aatggcggca agcaagcgct cgaaacggtg cagcggctgt tgccggtgct gtgccaggac  1020
catggcctga ccccggacca agtggtggct atcgccagca acaatggcgg caagcaagcg  1080
ctcgaaacgg tgcagcggct gttgccggtg ctgtgccagg accatggcct gaccccggac  1140
caagtggtgg ctatcgccag ccacgatggc ggcaagcaag cgctcgaaac ggtgcagcgg  1200
ctgttgccgg tgctgtgcca ggaccatggc ctgaccccgg accaagtggt ggctatcgcc  1260
agcaacattg cggcaagca agcgctcgaa acggtgcagc ggctgttgcc ggtgctgtgc   1320
caggaccatg gcctgacccc ggaccaagtg gtggctatcg ccagcaacgg tggcggcaag  1380
caagcgctcg aaacggtgca gcggctgttg ccggtgctgt gccaggacca tggcctgacc  1440
```

```
ccggaccaag tggtggctat cgccagccac gatggcggca agcaagcgct cgaaacggtg    1500
cagcggctgt tgccggtgct gtgccaggac catggcctga ccccggacca agtggtggct    1560
atcgccagca acattggcgg caagcaagcg ctcgaaacgg tgcagcggct gttgccggtg    1620
ctgtgccagg accatggcct gaccccggac caagtggtgg ctatcgccag caacggtggc    1680
ggcaagcaag cgctcgaaac ggtgcagcgg ctgttgccgg tgctgtgcca ggaccatggc    1740
ctgaccccgg accaagtggt ggctatcgcc agccacgatg gcggcaagca agcgctcgaa    1800
acggtgcagc ggctgttgcc ggtgctgtgc caggaccatg gcctgacccc ggaccaagtg    1860
gtggctatcg ccagccacga tggcggcaag caagcgctcg aaacggtgca gcggctgttg    1920
ccggtgctgt gccaggacca tggcctgacc ccggaccaag tggtggctat cgccagccac    1980
gatggcggca agcaagcgct cgaaacggtg cagcggctgt tgccggtgct gtgccaggac    2040
catggcctga ccccggacca agtggtggct atcgccagca acattggcgg caagcaagcg    2100
ctcgaaacgg tgcagcggct gttgccggtg ctgtgccagg accatggcct gaccccggac    2160
caagtggtgg ctatcgccag ccacgatggc ggcaagcaag cgctcgaaac ggtgcagcgg    2220
ctgttgccgg tgctgtgcca ggaccatggc ctgaccccgg accaagtggt ggctatcgcc    2280
agccacgatg gcggcaagca agcgctcgaa acggtgcagc ggctgttgcc ggtgctgtgc    2340
caggaccatg gcctgacccc ggaccaagtg gtggctatcg ccagcaacgg tggcggcaag    2400
caagcgctcg aaagcattgt ggcccagctg agccggcctg atccggcgtt ggccgcgttg    2460
accaacgacg accacctcgt cgccttggcc tgcctcggcg acgtcctgc atggatgca     2520 gtgaaaaagg gattgccgca cgcgccggaa ttgatcagaa gagtcaatcg ccgtattggc    2580
gaacgcacgt cccatcgcgt tgccggatcc aaggctagcc cgaaaaagaa acgcaaagtt    2640
gggcgcgccg acgcgctgga cgatttcgat ctcgacatgc tgggttctga tgccctcgat    2700
gactttgacc tggatatgtt gggaagcgac gcattggatg actttgatct ggacatgctc    2760
ggctccgatg ctctggacga tttcgatctc gatatgttaa ttaactaccc gtacgacgtt    2820
ccggactacg cttcttga                                                 2838
```

<210> SEQ ID NO 80
<211> LENGTH: 945
<212> TYPE: PRT
<213> ORGANISM: Unknown
<220> FEATURE:
<223> OTHER INFORMATION: Synthetic peptide

<400> SEQUENCE: 80

```
Met Asp Tyr Lys Asp His Asp Gly Asp Tyr Lys Asp His Asp Ile Asp
1               5                   10                  15

Tyr Lys Asp Asp Asp Asp Lys Met Ala Pro Lys Lys Arg Lys Val
            20                  25                  30

Gly Arg Gly Ser Val Asp Leu Arg Thr Leu Gly Tyr Ser Gln Gln Gln
        35                  40                  45

Gln Glu Lys Ile Lys Pro Lys Val Arg Ser Thr Val Ala Gln His His
    50                  55                  60

Glu Ala Leu Val Gly His Gly Phe Thr His Ala His Ile Val Ala Leu
65                  70                  75                  80

Ser Gln His Pro Ala Ala Leu Gly Thr Val Ala Val Thr Tyr Gln His
                85                  90                  95

Ile Ile Thr Ala Leu Pro Glu Ala Thr His Glu Asp Ile Val Gly Val
            100                 105                 110
```

-continued

```
Gly Lys Gln Trp Ser Gly Ala Arg Ala Leu Glu Ala Leu Leu Thr Asp
        115                 120                 125

Ala Gly Glu Leu Arg Gly Pro Pro Leu Gln Leu Asp Thr Gly Gln Leu
130                 135                 140

Val Lys Ile Ala Lys Arg Gly Gly Val Thr Ala Met Glu Ala Val His
145                 150                 155                 160

Ala Ser Arg Asn Ala Leu Thr Gly Ala Pro Leu Asn Leu Thr Pro Asp
                165                 170                 175

Gln Val Val Ala Ile Ala Ser Asn Asn Gly Gly Lys Gln Ala Leu Glu
            180                 185                 190

Thr Val Gln Arg Leu Leu Pro Val Leu Cys Gln Asp His Gly Leu Thr
        195                 200                 205

Pro Asp Gln Val Val Ala Ile Ala Ser Asn Gly Gly Gly Lys Gln Ala
    210                 215                 220

Leu Glu Thr Val Gln Arg Leu Leu Pro Val Leu Cys Gln Asp His Gly
225                 230                 235                 240

Leu Thr Pro Asp Gln Val Val Ala Ile Ala Ser Asn Gly Gly Gly Lys
                245                 250                 255

Gln Ala Leu Glu Thr Val Gln Arg Leu Leu Pro Val Leu Cys Gln Asp
            260                 265                 270

His Gly Leu Thr Pro Asp Gln Val Val Ala Ile Ala Ser Asn Asn Gly
        275                 280                 285

Gly Lys Gln Ala Leu Glu Thr Val Gln Arg Leu Leu Pro Val Leu Cys
    290                 295                 300

Gln Asp His Gly Leu Thr Pro Asp Gln Val Val Ala Ile Ala Ser Asn
305                 310                 315                 320

Asn Gly Gly Lys Gln Ala Leu Glu Thr Val Gln Arg Leu Leu Pro Val
                325                 330                 335

Leu Cys Gln Asp His Gly Leu Thr Pro Asp Gln Val Val Ala Ile Ala
            340                 345                 350

Ser Asn Asn Gly Gly Lys Gln Ala Leu Glu Thr Val Gln Arg Leu Leu
        355                 360                 365

Pro Val Leu Cys Gln Asp His Gly Leu Thr Pro Asp Gln Val Val Ala
    370                 375                 380

Ile Ala Ser His Asp Gly Gly Lys Gln Ala Leu Glu Thr Val Gln Arg
385                 390                 395                 400

Leu Leu Pro Val Leu Cys Gln Asp His Gly Leu Thr Pro Asp Gln Val
                405                 410                 415

Val Ala Ile Ala Ser Asn Ile Gly Gly Lys Gln Ala Leu Glu Thr Val
            420                 425                 430

Gln Arg Leu Leu Pro Val Leu Cys Gln Asp His Gly Leu Thr Pro Asp
        435                 440                 445

Gln Val Val Ala Ile Ala Ser Asn Gly Gly Gly Lys Gln Ala Leu Glu
    450                 455                 460

Thr Val Gln Arg Leu Leu Pro Val Leu Cys Gln Asp His Gly Leu Thr
465                 470                 475                 480

Pro Asp Gln Val Val Ala Ile Ala Ser His Asp Gly Gly Lys Gln Ala
                485                 490                 495

Leu Glu Thr Val Gln Arg Leu Leu Pro Val Leu Cys Gln Asp His Gly
            500                 505                 510

Leu Thr Pro Asp Gln Val Val Ala Ile Ala Ser Asn Ile Gly Gly Lys
        515                 520                 525

Gln Ala Leu Glu Thr Val Gln Arg Leu Leu Pro Val Leu Cys Gln Asp
```

-continued

```
            530                 535                 540
His Gly Leu Thr Pro Asp Gln Val Val Ala Ile Ala Ser Asn Gly Gly
545                 550                 555                 560

Gly Lys Gln Ala Leu Glu Thr Val Gln Arg Leu Leu Pro Val Leu Cys
                    565                 570                 575

Gln Asp His Gly Leu Thr Pro Asp Gln Val Val Ala Ile Ala Ser His
                580                 585                 590

Asp Gly Gly Lys Gln Ala Leu Glu Thr Val Gln Arg Leu Leu Pro Val
                595                 600                 605

Leu Cys Gln Asp His Gly Leu Thr Pro Asp Gln Val Val Ala Ile Ala
            610                 615                 620

Ser His Asp Gly Gly Lys Gln Ala Leu Glu Thr Val Gln Arg Leu Leu
625                 630                 635                 640

Pro Val Leu Cys Gln Asp His Gly Leu Thr Pro Asp Gln Val Val Ala
                645                 650                 655

Ile Ala Ser His Asp Gly Gly Lys Gln Ala Leu Glu Thr Val Gln Arg
                660                 665                 670

Leu Leu Pro Val Leu Cys Gln Asp His Gly Leu Thr Pro Asp Gln Val
            675                 680                 685

Val Ala Ile Ala Ser Asn Ile Gly Gly Lys Gln Ala Leu Glu Thr Val
            690                 695                 700

Gln Arg Leu Leu Pro Val Leu Cys Gln Asp His Gly Leu Thr Pro Asp
705                 710                 715                 720

Gln Val Val Ala Ile Ala Ser His Asp Gly Gly Lys Gln Ala Leu Glu
                725                 730                 735

Thr Val Gln Arg Leu Leu Pro Val Leu Cys Gln Asp His Gly Leu Thr
                740                 745                 750

Pro Asp Gln Val Val Ala Ile Ala Ser His Asp Gly Gly Lys Gln Ala
            755                 760                 765

Leu Glu Thr Val Gln Arg Leu Leu Pro Val Leu Cys Gln Asp His Gly
770                 775                 780

Leu Thr Pro Asp Gln Val Val Ala Ile Ala Ser Asn Gly Gly Lys
785                 790                 795                 800

Gln Ala Leu Glu Ser Ile Val Ala Gln Leu Ser Arg Pro Asp Pro Ala
                805                 810                 815

Leu Ala Ala Leu Thr Asn Asp His Leu Val Ala Leu Ala Cys Leu
                820                 825                 830

Gly Gly Arg Pro Ala Met Asp Ala Val Lys Lys Gly Leu Pro His Ala
                835                 840                 845

Pro Glu Leu Ile Arg Arg Val Asn Arg Arg Ile Gly Glu Arg Thr Ser
850                 855                 860

His Arg Val Ala Gly Ser Lys Ala Ser Pro Lys Lys Arg Lys Val
865                 870                 875                 880

Gly Arg Ala Asp Ala Leu Asp Asp Phe Asp Leu Asp Met Leu Gly Ser
                885                 890                 895

Asp Ala Leu Asp Asp Phe Asp Leu Asp Met Leu Gly Ser Asp Ala Leu
                900                 905                 910

Asp Asp Phe Asp Leu Asp Met Leu Gly Ser Asp Ala Leu Asp Asp Phe
            915                 920                 925

Asp Leu Asp Met Leu Ile Asn Tyr Pro Tyr Asp Val Pro Asp Tyr Ala
            930                 935                 940

Ser
945
```

<210> SEQ ID NO 81
<211> LENGTH: 2634
<212> TYPE: DNA
<213> ORGANISM: Artificial sequence
<220> FEATURE:
<223> OTHER INFORMATION: Synthetic oligonucleotide

<400> SEQUENCE: 81

| | | | | | |
|---|---|---|---|---|---|
| atggactaca | aagaccatga | cggtgattat | aaagatcatg | acatcgatta | caaggatgac | 60 |
| gatgacaaga | tggcccccaa | gaagaagagg | aaggtgggcc | gcggatctgt | ggatctacgc | 120 |
| acgctcggct | acagtcagca | gcagcaagag | aagatcaaac | cgaaggtgcg | ttcgacagtg | 180 |
| gcgcagcacc | acgaggcact | ggtgggccat | gggtttacac | acgcgcacat | cgttgcgctc | 240 |
| agccaacacc | cggcagcgtt | agggaccgtc | gctgtcacgt | atcagcacat | aatcacggcg | 300 |
| ttgccagagg | cgacacacga | agacatcgtt | ggcgtcggca | acagtggtc | cggcgcacgc | 360 |
| gccctggagg | ccttgctcac | ggatgcgggg | gagttgagag | gtccgccgtt | acagttggac | 420 |
| acaggccaac | ttgtgaagat | tgcaaaacgt | ggcggcgtga | ccgcaatgga | ggcagtgcat | 480 |
| gcatcgcgca | atgcactgac | gggtgccccc | ctgaacctga | ccccggacca | agtggtggct | 540 |
| atcgccagcc | acgatggcgg | caagcaagcg | ctcgaaacgg | tgcagcggct | gttgccggtg | 600 |
| ctgtgccagg | accatggcct | gaccccggac | caagtggtgg | ctatcgccag | ccacgatggc | 660 |
| ggcaagcaag | cgctcgaaac | ggtgcagcgg | ctgttgccgg | tgctgtgcca | ggaccatggc | 720 |
| ctgaccccgg | accaagtggt | ggctatcgcc | agccacgatg | gcggcaagca | agcgctcgaa | 780 |
| acggtgcagc | ggctgttgcc | ggtgctgtgc | caggaccatg | gcctgacccc | ggaccaagtg | 840 |
| gtggctatcg | ccagcaacgg | tggcggcaag | caagcgctcg | aaacggtgca | gcggctgttg | 900 |
| ccggtgctgt | gccaggacca | tggcctgacc | ccggaccaag | tggtggctat | cgccagccac | 960 |
| gatggcggca | agcaagcgct | cgaaacggtg | cagcggctgt | tgccggtgct | gtgccaggac | 1020 |
| catggcctga | ccccggacca | agtggtggct | atcgccagcc | acgatggcgg | caagcaagcg | 1080 |
| ctcgaaacgg | tgcagcggct | gttgccggtg | ctgtgccagg | accatggcct | gaccccggac | 1140 |
| caagtggtgg | ctatcgccag | caacattggc | ggcaagcaag | cgctcgaaac | ggtgcagcgg | 1200 |
| ctgttgccgg | tgctgtgcca | ggaccatggc | ctgaccccgg | accaagtggt | ggctatcgcc | 1260 |
| agccacgatg | gcggcaagca | agcgctcgaa | acggtgcagc | ggctgttgcc | ggtgctgtgc | 1320 |
| caggaccatg | gcctgacccc | ggaccaagtg | gtggctatcg | ccagccacga | tggcggcaag | 1380 |
| caagcgctcg | aaacggtgca | gcggctgttg | ccggtgctgt | gccaggacca | tggcctgacc | 1440 |
| ccggaccaag | tggtggctat | cgccagcaac | attggcggca | agcaagcgct | cgaaacggtg | 1500 |
| cagcggctgt | tgccggtgct | gtgccaggac | catggcctga | ccccggacca | agtggtggct | 1560 |
| atcgccagcc | acgatggcgg | caagcaagcg | ctcgaaacgg | tgcagcggct | gttgccggtg | 1620 |
| ctgtgccagg | accatggcct | gaccccggac | caagtggtgg | ctatcgccag | caacattggc | 1680 |
| ggcaagcaag | cgctcgaaac | ggtgcagcgg | ctgttgccgg | tgctgtgcca | ggaccatggc | 1740 |
| ctgaccccgg | accaagtggt | ggctatcgcc | agcaacaatg | gcggcaagca | agcgctcgaa | 1800 |
| acggtgcagc | ggctgttgcc | ggtgctgtgc | caggaccatg | gcctgacccc | ggaccaagtg | 1860 |
| gtggctatcg | ccagcaacgg | tggcggcaag | caagcgctcg | aaacggtgca | gcggctgttg | 1920 |
| ccggtgctgt | gccaggacca | tggcctgacc | ccggaccaag | tggtggctat | cgccagccac | 1980 |
| gatggcggca | agcaagcgct | cgaaacggtg | cagcggctgt | tgccggtgct | gtgccaggac | 2040 |

```
catggcctga ccccggacca agtggtggct atcgccagcc acgatggcgg caagcaagcg    2100
ctcgaaacgg tgcagcggct gttgccggtg ctgtgccagg accatggcct gaccccggac    2160
caagtggtgg ctatcgccag caacggtggc ggcaagcaag cgctcgaaag cattgtggcc    2220
cagctgagcc ggcctgatcc ggcgttggcc gcgttgacca acgacgacca cctcgtcgcc    2280
ttggcctgcc tcggcggacg tcctgccatg gatgcagtga aaaagggatt gccgcacgcg    2340
ccggaattga tcagaagagt caatcgccgt attggcgaac gcacgtccca tcgcgttgcc    2400
ggatccaagg ctagcccgaa aagaaacgc aaagttgggc gcgccgacgc gctggacgat    2460
ttcgatctcg acatgctggg ttctgatgcc ctcgatgact ttgacctgga tatgttggga    2520
agcgacgcat tggatgactt tgatctggac atgctcggct ccgatgctct ggacgatttc    2580
gatctcgata tgttaattaa ctacccgtac gacgttccgg actacgcttc ttga         2634
```

<210> SEQ ID NO 82
<211> LENGTH: 877
<212> TYPE: PRT
<213> ORGANISM: Unknown
<220> FEATURE:
<223> OTHER INFORMATION: Synthetic peptide

<400> SEQUENCE: 82

```
Met Asp Tyr Lys Asp His Asp Gly Asp Tyr Lys Asp His Asp Ile Asp
1               5                   10                  15

Tyr Lys Asp Asp Asp Lys Met Ala Pro Lys Lys Arg Lys Val
            20                  25                  30

Gly Arg Gly Ser Val Asp Leu Arg Thr Leu Gly Tyr Ser Gln Gln Gln
        35                  40                  45

Gln Glu Lys Ile Lys Pro Lys Val Arg Ser Thr Val Ala Gln His His
    50                  55                  60

Glu Ala Leu Val Gly His Gly Phe Thr His Ala His Ile Val Ala Leu
65                  70                  75                  80

Ser Gln His Pro Ala Ala Leu Gly Thr Val Ala Val Thr Tyr Gln His
                85                  90                  95

Ile Ile Thr Ala Leu Pro Glu Ala Thr His Glu Asp Ile Val Gly Val
            100                 105                 110

Gly Lys Gln Trp Ser Gly Ala Arg Ala Leu Glu Ala Leu Leu Thr Asp
        115                 120                 125

Ala Gly Glu Leu Arg Gly Pro Pro Leu Gln Leu Asp Thr Gly Gln Leu
    130                 135                 140

Val Lys Ile Ala Lys Arg Gly Gly Val Thr Ala Met Glu Ala Val His
145                 150                 155                 160

Ala Ser Arg Asn Ala Leu Thr Gly Ala Pro Leu Asn Leu Thr Pro Asp
                165                 170                 175

Gln Val Val Ala Ile Ala Ser His Asp Gly Gly Lys Gln Ala Leu Glu
            180                 185                 190

Thr Val Gln Arg Leu Leu Pro Val Leu Cys Gln Asp His Gly Leu Thr
        195                 200                 205

Pro Asp Gln Val Val Ala Ile Ala Ser His Asp Gly Gly Lys Gln Ala
    210                 215                 220

Leu Glu Thr Val Gln Arg Leu Leu Pro Val Leu Cys Gln Asp His Gly
225                 230                 235                 240

Leu Thr Pro Asp Gln Val Val Ala Ile Ala Ser His Asp Gly Gly Lys
                245                 250                 255

Gln Ala Leu Glu Thr Val Gln Arg Leu Leu Pro Val Leu Cys Gln Asp
```

-continued

```
                260                 265                 270
His Gly Leu Thr Pro Asp Gln Val Val Ala Ile Ala Ser Asn Gly Gly
            275                 280                 285

Gly Lys Gln Ala Leu Glu Thr Val Gln Arg Leu Leu Pro Val Leu Cys
            290                 295                 300

Gln Asp His Gly Leu Thr Pro Asp Gln Val Val Ala Ile Ala Ser His
305                 310                 315                 320

Asp Gly Gly Lys Gln Ala Leu Glu Thr Val Gln Arg Leu Leu Pro Val
                325                 330                 335

Leu Cys Gln Asp His Gly Leu Thr Pro Asp Gln Val Val Ala Ile Ala
            340                 345                 350

Ser His Asp Gly Gly Lys Gln Ala Leu Glu Thr Val Gln Arg Leu Leu
            355                 360                 365

Pro Val Leu Cys Gln Asp His Gly Leu Thr Pro Asp Gln Val Val Ala
            370                 375                 380

Ile Ala Ser Asn Ile Gly Gly Lys Gln Ala Leu Glu Thr Val Gln Arg
385                 390                 395                 400

Leu Leu Pro Val Leu Cys Gln Asp His Gly Leu Thr Pro Asp Gln Val
                405                 410                 415

Val Ala Ile Ala Ser His Asp Gly Gly Lys Gln Ala Leu Glu Thr Val
            420                 425                 430

Gln Arg Leu Leu Pro Val Leu Cys Gln Asp His Gly Leu Thr Pro Asp
            435                 440                 445

Gln Val Val Ala Ile Ala Ser His Asp Gly Gly Lys Gln Ala Leu Glu
            450                 455                 460

Thr Val Gln Arg Leu Leu Pro Val Leu Cys Gln Asp His Gly Leu Thr
465                 470                 475                 480

Pro Asp Gln Val Val Ala Ile Ala Ser Asn Ile Gly Gly Lys Gln Ala
                485                 490                 495

Leu Glu Thr Val Gln Arg Leu Leu Pro Val Leu Cys Gln Asp His Gly
            500                 505                 510

Leu Thr Pro Asp Gln Val Val Ala Ile Ala Ser His Asp Gly Gly Lys
            515                 520                 525

Gln Ala Leu Glu Thr Val Gln Arg Leu Leu Pro Val Leu Cys Gln Asp
            530                 535                 540

His Gly Leu Thr Pro Asp Gln Val Val Ala Ile Ala Ser Asn Ile Gly
545                 550                 555                 560

Gly Lys Gln Ala Leu Glu Thr Val Gln Arg Leu Leu Pro Val Leu Cys
                565                 570                 575

Gln Asp His Gly Leu Thr Pro Asp Gln Val Val Ala Ile Ala Ser Asn
            580                 585                 590

Asn Gly Gly Lys Gln Ala Leu Glu Thr Val Gln Arg Leu Leu Pro Val
            595                 600                 605

Leu Cys Gln Asp His Gly Leu Thr Pro Asp Gln Val Val Ala Ile Ala
            610                 615                 620

Ser Asn Gly Gly Gly Lys Gln Ala Leu Glu Thr Val Gln Arg Leu Leu
625                 630                 635                 640

Pro Val Leu Cys Gln Asp His Gly Leu Thr Pro Asp Gln Val Val Ala
                645                 650                 655

Ile Ala Ser His Asp Gly Gly Lys Gln Ala Leu Glu Thr Val Gln Arg
            660                 665                 670

Leu Leu Pro Val Leu Cys Gln Asp His Gly Leu Thr Pro Asp Gln Val
            675                 680                 685
```

```
Val Ala Ile Ala Ser His Asp Gly Gly Lys Gln Ala Leu Glu Thr Val
        690                 695                 700

Gln Arg Leu Leu Pro Val Leu Cys Gln Asp His Gly Leu Thr Pro Asp
705                 710                 715                 720

Gln Val Val Ala Ile Ala Ser Asn Gly Gly Lys Gln Ala Leu Glu
            725                 730                 735

Ser Ile Val Ala Gln Leu Ser Arg Pro Asp Pro Ala Leu Ala Ala Leu
            740                 745                 750

Thr Asn Asp His Leu Val Ala Leu Ala Cys Leu Gly Gly Arg Pro
            755                 760                 765

Ala Met Asp Ala Val Lys Lys Gly Leu Pro His Ala Pro Glu Leu Ile
        770                 775                 780

Arg Arg Val Asn Arg Arg Ile Gly Glu Arg Thr Ser His Arg Val Ala
785                 790                 795                 800

Gly Ser Lys Ala Ser Pro Lys Lys Arg Lys Val Gly Arg Ala Asp
            805                 810                 815

Ala Leu Asp Asp Phe Asp Leu Asp Met Leu Gly Ser Asp Ala Leu Asp
                820                 825                 830

Asp Phe Asp Leu Asp Met Leu Gly Ser Asp Ala Leu Asp Phe Asp
        835                 840                 845

Leu Asp Met Leu Gly Ser Asp Ala Leu Asp Asp Phe Asp Leu Asp Met
850                 855                 860

Leu Ile Asn Tyr Pro Tyr Asp Val Pro Asp Tyr Ala Ser
865                 870                 875

<210> SEQ ID NO 83
<211> LENGTH: 2532
<212> TYPE: DNA
<213> ORGANISM: Artificial sequence
<220> FEATURE:
<223> OTHER INFORMATION: Synthetic oligonucleotide

<400> SEQUENCE: 83
atggactaca aagaccatga cggtgattat aaagatcatg acatcgatta caaggatgac    60
gatgacaaga tggcccccaa gaagaagagg aaggtgggcc gcggatctgt ggatctacgc   120
acgctcggct acagtcagca gcagcaagag aagatcaaac cgaaggtgcg ttcgacagtg   180
gcgcagcacc acgaggcact ggtgggccat gggtttacac acgcgcacat cgttgcgctc   240
agccaacacc cggcagcgtt agggaccgtc gctgtcacgt atcagcacat aatcacggcg   300
ttgccagagg cgacacacga agacatcgtt ggcgtcggca acagtggtc cggcgcacgc    360 gccctggagg ccttgctcac ggatgcgggg gagttgagag gtccgccgtt acagttggac    420
acaggccaac ttgtgaagat tgcaaaacgt ggcggcgtga ccgcaatgga ggcagtgcat    480
gcatcgcgca atgcactgac gggtgccccc ctgaacctga ccccggacca agtggtggct    540
atcgccagcc acgatggcgg caagcaagcg ctcgaaacgg tgcagcggct gttgccggtg    600
ctgtgccagg accatggcct gaccccggac caagtggtgg ctatcgccag ccacgatggc   660
ggcaagcaag cgctcgaaac ggtgcagcgg ctgttgccgg tgctgtgcca ggaccatggc    720
ctgaccccgg accaagtggt ggctatcgcc agcaacaatg gcggcaagca agcgctcgaa    780
acggtgcagc ggctgttgcc ggtgctgtgc caggaccatg gcctgacccc ggaccaagtg    840
gtggctatcg ccagcaacaa tggcggcaag caagcgctcg aaacggtgca gcggctgttg    900
ccggtgctgt gccaggacca tggcctgacc ccggaccaag tggtggctat cgccagccac    960
```

```
gatggcggca agcaagcgct cgaaacggtg cagcggctgt tgccggtgct gtgccaggac   1020
catggcctga ccccggacca agtggtggct atcgccagca acggtggcgg caagcaagcg   1080
ctcgaaacgg tgcagcggct gttgccggtg ctgtgccagg accatggcct gaccccggac   1140
caagtggtgg ctatcgccag caacaatggc ggcaagcaag cgctcgaaac ggtgcagcgg   1200
ctgttgccgg tgctgtgcca ggaccatggc ctgaccccgg accaagtggt ggctatcgcc   1260
agcaacaatg gcggcaagca agcgctcgaa acggtgcagc ggctgttgcc ggtgctgtgc   1320
caggaccatg gcctgacccc ggaccaagtg gtggctatcg ccagcaacat ggcggcaag   1380 caagcgctcg aaacggtgca gcggctgttg ccggtgctgt gccaggacca tggcctgacc   1440
ccggaccaag tggtggctat cgccagccac gatggcggca agcaagcgct cgaaacggtg   1500
cagcggctgt tgccggtgct gtgccaggac catggcctga ccccggacca agtggtggct   1560
atcgccagcc acgatggcgg caagcaagcg ctcgaaacgg tgcagcggct gttgccggtg   1620
ctgtgccagg accatggcct gaccccggac caagtggtgg ctatcgccag ccacgatggc   1680
ggcaagcaag cgctcgaaac ggtgcagcgg ctgttgccgg tgctgtgcca ggaccatggc   1740
ctgaccccgg accaagtggt ggctatcgcc agcaacaatg gcggcaagca agcgctcgaa   1800
acggtgcagc ggctgttgcc ggtgctgtgc caggaccatg gcctgacccc ggaccaagtg   1860
gtggctatcg ccagcaacaa tggcggcaag caagcgctcg aaacggtgca gcggctgttg   1920
ccggtgctgt gccaggacca tggcctgacc ccggaccaag tggtggctat cgccagccac   1980
gatggcggca agcaagcgct cgaaacggtg cagcggctgt tgccggtgct gtgccaggac   2040
catggcctga ccccggacca agtggtggct atcgccagca acggtggcgg caagcaagcg   2100
ctcgaaagca ttgtggccca gctgagccgg cctgatccgg cgttggccgc gttgaccaac   2160
gacgaccacc tcgtcgcctt ggcctgcctc ggcggacgtc ctgccatgga tgcagtgaaa   2220
aagggattgc cgcacgcgcc ggaattgatc agaagagtca atcgccgtat ggcgaacgc   2280 acgtcccatc gcgttgccgg atccaaggct agcccgaaaa agaaacgcaa agttgggcgc   2340
gccgacgcgc tggacgattt cgatctcgac atgctgggtt ctgatgccct cgatgacttt   2400
gacctggata tgttgggaag cgacgcattg gatgactttg atctggacat gctcggctcc   2460
gatgctctgg acgatttcga tctcgatatg ttaattaact acccgtacga cgttccggac   2520
tacgcttctt ga                                                       2532
```

<210> SEQ ID NO 84
<211> LENGTH: 843
<212> TYPE: PRT
<213> ORGANISM: Unknown
<220> FEATURE:
<223> OTHER INFORMATION: Synthetic peptide

<400> SEQUENCE: 84

```
Met Asp Tyr Lys Asp His Asp Gly Asp Tyr Lys Asp His Asp Ile Asp
1               5                   10                  15

Tyr Lys Asp Asp Asp Lys Met Ala Pro Lys Lys Arg Lys Val
            20                  25                  30

Gly Arg Gly Ser Val Asp Leu Arg Thr Leu Gly Tyr Ser Gln Gln Gln
        35                  40                  45

Gln Glu Lys Ile Lys Pro Lys Val Arg Ser Thr Val Ala Gln His His
    50                  55                  60

Glu Ala Leu Val Gly His Gly Phe Thr His Ala His Ile Val Ala Leu
65                  70                  75                  80
```

-continued

```
Ser Gln His Pro Ala Leu Gly Thr Val Ala Val Thr Tyr Gln His
                85                  90                  95

Ile Ile Thr Ala Leu Pro Glu Ala Thr His Glu Asp Ile Val Gly Val
            100                 105                 110

Gly Lys Gln Trp Ser Gly Ala Arg Ala Leu Glu Ala Leu Leu Thr Asp
            115                 120                 125

Ala Gly Glu Leu Arg Gly Pro Pro Leu Gln Leu Asp Thr Gly Gln Leu
130                 135                 140

Val Lys Ile Ala Lys Arg Gly Gly Val Thr Ala Met Glu Ala Val His
145                 150                 155                 160

Ala Ser Arg Asn Ala Leu Thr Gly Ala Pro Leu Asn Leu Thr Pro Asp
                165                 170                 175

Gln Val Val Ala Ile Ala Ser His Asp Gly Gly Lys Gln Ala Leu Glu
            180                 185                 190

Thr Val Gln Arg Leu Leu Pro Val Leu Cys Gln Asp His Gly Leu Thr
            195                 200                 205

Pro Asp Gln Val Val Ala Ile Ala Ser His Asp Gly Gly Lys Gln Ala
210                 215                 220

Leu Glu Thr Val Gln Arg Leu Leu Pro Val Leu Cys Gln Asp His Gly
225                 230                 235                 240

Leu Thr Pro Asp Gln Val Val Ala Ile Ala Ser Asn Asn Gly Gly Lys
                245                 250                 255

Gln Ala Leu Glu Thr Val Gln Arg Leu Leu Pro Val Leu Cys Gln Asp
            260                 265                 270

His Gly Leu Thr Pro Asp Gln Val Val Ala Ile Ala Ser Asn Asn Gly
            275                 280                 285

Gly Lys Gln Ala Leu Glu Thr Val Gln Arg Leu Leu Pro Val Leu Cys
290                 295                 300

Gln Asp His Gly Leu Thr Pro Asp Gln Val Val Ala Ile Ala Ser His
305                 310                 315                 320

Asp Gly Gly Lys Gln Ala Leu Glu Thr Val Gln Arg Leu Leu Pro Val
                325                 330                 335

Leu Cys Gln Asp His Gly Leu Thr Pro Asp Gln Val Val Ala Ile Ala
            340                 345                 350

Ser Asn Gly Gly Gly Lys Gln Ala Leu Glu Thr Val Gln Arg Leu Leu
            355                 360                 365

Pro Val Leu Cys Gln Asp His Gly Leu Thr Pro Asp Gln Val Val Ala
370                 375                 380

Ile Ala Ser Asn Asn Gly Gly Lys Gln Ala Leu Glu Thr Val Gln Arg
385                 390                 395                 400

Leu Leu Pro Val Leu Cys Gln Asp His Gly Leu Thr Pro Asp Gln Val
                405                 410                 415

Val Ala Ile Ala Ser Asn Asn Gly Gly Lys Gln Ala Leu Glu Thr Val
            420                 425                 430

Gln Arg Leu Leu Pro Val Leu Cys Gln Asp His Gly Leu Thr Pro Asp
            435                 440                 445

Gln Val Val Ala Ile Ala Ser Asn Ile Gly Gly Lys Gln Ala Leu Glu
450                 455                 460

Thr Val Gln Arg Leu Leu Pro Val Leu Cys Gln Asp His Gly Leu Thr
465                 470                 475                 480

Pro Asp Gln Val Val Ala Ile Ala Ser His Asp Gly Gly Lys Gln Ala
                485                 490                 495

Leu Glu Thr Val Gln Arg Leu Leu Pro Val Leu Cys Gln Asp His Gly
```

```
                    500                 505                 510
Leu Thr Pro Asp Gln Val Val Ala Ile Ala Ser His Asp Gly Gly Lys
        515                 520                 525

Gln Ala Leu Glu Thr Val Gln Arg Leu Leu Pro Val Leu Cys Gln Asp
        530                 535                 540

His Gly Leu Thr Pro Asp Gln Val Val Ala Ile Ala Ser His Asp Gly
545                 550                 555                 560

Gly Lys Gln Ala Leu Glu Thr Val Gln Arg Leu Leu Pro Val Leu Cys
                565                 570                 575

Gln Asp His Gly Leu Thr Pro Asp Gln Val Val Ala Ile Ala Ser Asn
            580                 585                 590

Asn Gly Gly Lys Gln Ala Leu Glu Thr Val Gln Arg Leu Leu Pro Val
        595                 600                 605

Leu Cys Gln Asp His Gly Leu Thr Pro Asp Gln Val Val Ala Ile Ala
        610                 615                 620

Ser Asn Asn Gly Gly Lys Gln Ala Leu Glu Thr Val Gln Arg Leu Leu
625                 630                 635                 640

Pro Val Leu Cys Gln Asp His Gly Leu Thr Pro Asp Gln Val Val Ala
                645                 650                 655

Ile Ala Ser His Asp Gly Gly Lys Gln Ala Leu Glu Thr Val Gln Arg
            660                 665                 670

Leu Leu Pro Val Leu Cys Gln Asp His Gly Leu Thr Pro Asp Gln Val
        675                 680                 685

Val Ala Ile Ala Ser Asn Gly Gly Lys Gln Ala Leu Glu Ser Ile
        690                 695                 700

Val Ala Gln Leu Ser Arg Pro Asp Pro Ala Leu Ala Ala Leu Thr Asn
705                 710                 715                 720

Asp His Leu Val Ala Leu Ala Cys Leu Gly Gly Arg Pro Ala Met
                725                 730                 735

Asp Ala Val Lys Lys Gly Leu Pro His Ala Pro Glu Leu Ile Arg Arg
            740                 745                 750

Val Asn Arg Arg Ile Gly Glu Arg Thr Ser His Arg Val Ala Gly Ser
        755                 760                 765

Lys Ala Ser Pro Lys Lys Arg Lys Val Gly Arg Ala Asp Ala Leu
        770                 775                 780

Asp Asp Phe Asp Leu Asp Met Leu Gly Ser Asp Ala Leu Asp Asp Phe
785                 790                 795                 800

Asp Leu Asp Met Leu Gly Ser Asp Ala Leu Asp Asp Phe Asp Leu Asp
                805                 810                 815

Met Leu Gly Ser Asp Ala Leu Asp Asp Phe Asp Leu Asp Met Leu Ile
            820                 825                 830

Asn Tyr Pro Tyr Asp Val Pro Asp Tyr Ala Ser
        835                 840

<210> SEQ ID NO 85
<211> LENGTH: 2634
<212> TYPE: DNA
<213> ORGANISM: Artificial sequence
<220> FEATURE:
<223> OTHER INFORMATION: Synthetic oligonucleotide

<400> SEQUENCE: 85
atggactaca aagaccatga cggtgattat aaagatcatg acatcgatta caaggatgac      60
gatgacaaga tggcccccaa gaagaagagg aaggtgggcc gcggatctgt ggatctacgc     120
```

```
acgctcggct acagtcagca gcagcaagag aagatcaaac cgaaggtgcg ttcgacagtg      180
gcgcagcacc acgaggcact ggtgggccat gggtttacac acgcgcacat cgttgcgctc      240
agccaacacc cggcagcgtt agggaccgtc gctgtcacgt atcagcacat aatcacggcg      300
ttgccagagg cgacacacga agacatcgtt ggcgtcggca aacagtggtc cggcgcacgc      360
gccctggagg ccttgctcac ggatgcgggg gagttgagag gtccgccgtt acagttggac      420
acaggccaac ttgtgaagat tgcaaaacgt ggcggcgtga ccgcaatgga ggcagtgcat      480
gcatcgcgca atgcactgac gggtgccccc ctgaacctga ccccggacca agtggtggct      540
atcgccagcc acgatggcgg caagcaagcg ctcgaaacgg tgcagcggct gttgccggtg      600
ctgtgccagg accatggcct gaccccggac caagtggtgg ctatcgccag caacaatggc      660
ggcaagcaag cgctcgaaac ggtgcagcgg ctgttgccgg tgctgtgcca ggaccatggc      720
ctgaccccgg accaagtggt ggctatcgcc agccacgatg gcggcaagca agcgctcgaa      780
acggtgcagc ggctgttgcc ggtgctgtgc caggaccatg gcctgacccc ggaccaagtg      840
gtggctatcg ccagcaacat tggcggcaag caagcgctcg aaacggtgca gcggctgttg      900
ccggtgctgt gccaggacca tggcctgacc ccggaccaag tggtggctat cgccagcaac      960
aatggcggca agcaagcgct cgaaacggtg cagcggctgt tgccggtgct gtgccaggac     1020
catggcctga ccccggacca agtggtggct atcgccagcc acgatggcgg caagcaagcg     1080
ctcgaaacgg tgcagcggct gttgccggtg ctgtgccagg accatggcct gaccccggac     1140
caagtggtgg ctatcgccag caacattggc ggcaagcaag cgctcgaaac ggtgcagcgg     1200
ctgttgccgg tgctgtgcca ggaccatggc ctgaccccgg accaagtggt ggctatcgcc     1260
agccacgatg gcggcaagca agcgctcgaa acggtgcagc ggctgttgcc ggtgctgtgc     1320
caggaccatg gcctgacccc ggaccaagtg gtggctatcg ccagccacga tggcggcaag     1380
caagcgctcg aaacggtgca gcggctgttg ccggtgctgt gccaggacca tggcctgacc     1440
ccggaccaag tggtggctat cgccagccac gatggcggca agcaagcgct cgaaacggtg     1500
cagcggctgt tgccggtgct gtgccaggac catggcctga ccccggacca agtggtggct     1560
atcgccagcc acgatggcgg caagcaagcg ctcgaaacgg tgcagcggct gttgccggtg     1620
ctgtgccagg accatggcct gaccccggac caagtggtgg ctatcgccag caacaatggc     1680
ggcaagcaag cgctcgaaac ggtgcagcgg ctgttgccgg tgctgtgcca ggaccatggc     1740
ctgaccccgg accaagtggt ggctatcgcc agccacgatg gcggcaagca agcgctcgaa     1800
acggtgcagc ggctgttgcc ggtgctgtgc caggaccatg gcctgacccc ggaccaagtg     1860
gtggctatcg ccagcaacaa tggcggcaag caagcgctcg aaacggtgca gcggctgttg     1920
ccggtgctgt gccaggacca tggcctgacc ccggaccaag tggtggctat cgccagccac     1980
gatggcggca agcaagcgct cgaaacggtg cagcggctgt tgccggtgct gtgccaggac     2040
catggcctga ccccggacca agtggtggct atcgccagcc acgatggcgg caagcaagcg     2100
ctcgaaacgg tgcagcggct gttgccggtg ctgtgccagg accatggcct gaccccggac     2160
caagtggtgg ctatcgccag ccacgatggc ggcaagcaag cgctcgaaag cattgtggcc     2220
cagctgagcc ggcctgatcc ggcgttggcc gcgttgacca acgacgacca cctcgtcgcc     2280
ttggcctgcc tcggcggacg tcctgccatg gatgcagtga aaaagggatt gccgcacgcg     2340
ccggaattga tcagaagagt caatcgccgt attggcgaac gcacgtccca tcgcgttgcc     2400
ggatccaagc ctagcccgaa aaagaaacgc aaagttgggc gcgccgacgc gctggacgat     2460
ttcgatctcg acatgctggg ttctgatgcc ctcgatgact ttgacctgga tatgttggga     2520
```

```
agcgacgcat tggatgactt tgatctggac atgctcggct ccgatgctct ggacgatttc  2580
gatctcgata tgttaattaa ctacccgtac gacgttccgg actacgcttc ttga        2634
```

<210> SEQ ID NO 86
<211> LENGTH: 877
<212> TYPE: PRT
<213> ORGANISM: Unknown
<220> FEATURE:
<223> OTHER INFORMATION: Synthetic peptide

<400> SEQUENCE: 86

```
Met Asp Tyr Lys Asp His Asp Gly Asp Tyr Lys Asp His Asp Ile Asp
1               5                   10                  15

Tyr Lys Asp Asp Asp Asp Lys Met Ala Pro Lys Lys Arg Lys Val
            20                  25                  30

Gly Arg Gly Ser Val Asp Leu Arg Thr Leu Gly Tyr Ser Gln Gln Gln
        35                  40                  45

Gln Glu Lys Ile Lys Pro Lys Val Arg Ser Thr Val Ala Gln His His
    50                  55                  60

Glu Ala Leu Val Gly His Gly Phe Thr His Ala His Ile Val Ala Leu
65                  70                  75                  80

Ser Gln His Pro Ala Ala Leu Gly Thr Val Ala Val Thr Tyr Gln His
                85                  90                  95

Ile Ile Thr Ala Leu Pro Glu Ala Thr His Glu Asp Ile Val Gly Val
            100                 105                 110

Gly Lys Gln Trp Ser Gly Ala Arg Ala Leu Glu Ala Leu Leu Thr Asp
        115                 120                 125

Ala Gly Glu Leu Arg Gly Pro Pro Leu Gln Leu Asp Thr Gly Gln Leu
    130                 135                 140

Val Lys Ile Ala Lys Arg Gly Gly Val Thr Ala Met Glu Ala Val His
145                 150                 155                 160

Ala Ser Arg Asn Ala Leu Thr Gly Ala Pro Leu Asn Leu Thr Pro Asp
                165                 170                 175

Gln Val Val Ala Ile Ala Ser His Asp Gly Gly Lys Gln Ala Leu Glu
            180                 185                 190

Thr Val Gln Arg Leu Leu Pro Val Leu Cys Gln Asp His Gly Leu Thr
        195                 200                 205

Pro Asp Gln Val Val Ala Ile Ala Ser Asn Asn Gly Gly Lys Gln Ala
    210                 215                 220

Leu Glu Thr Val Gln Arg Leu Leu Pro Val Leu Cys Gln Asp His Gly
225                 230                 235                 240

Leu Thr Pro Asp Gln Val Val Ala Ile Ala Ser His Asp Gly Gly Lys
                245                 250                 255

Gln Ala Leu Glu Thr Val Gln Arg Leu Leu Pro Val Leu Cys Gln Asp
            260                 265                 270

His Gly Leu Thr Pro Asp Gln Val Val Ala Ile Ala Ser Asn Ile Gly
        275                 280                 285

Gly Lys Gln Ala Leu Glu Thr Val Gln Arg Leu Leu Pro Val Leu Cys
    290                 295                 300

Gln Asp His Gly Leu Thr Pro Asp Gln Val Val Ala Ile Ala Ser Asn
305                 310                 315                 320

Asn Gly Gly Lys Gln Ala Leu Glu Thr Val Gln Arg Leu Leu Pro Val
                325                 330                 335

Leu Cys Gln Asp His Gly Leu Thr Pro Asp Gln Val Val Ala Ile Ala
```

```
            340                 345                 350
Ser His Asp Gly Gly Lys Gln Ala Leu Glu Thr Val Gln Arg Leu Leu
            355                 360                 365

Pro Val Leu Cys Gln Asp His Gly Leu Thr Pro Asp Gln Val Val Ala
            370                 375                 380

Ile Ala Ser Asn Ile Gly Gly Lys Gln Ala Leu Glu Thr Val Gln Arg
385                 390                 395                 400

Leu Leu Pro Val Leu Cys Gln Asp His Gly Leu Thr Pro Asp Gln Val
                    405                 410                 415

Val Ala Ile Ala Ser His Asp Gly Gly Lys Gln Ala Leu Glu Thr Val
            420                 425                 430

Gln Arg Leu Leu Pro Val Leu Cys Gln Asp His Gly Leu Thr Pro Asp
            435                 440                 445

Gln Val Val Ala Ile Ala Ser His Asp Gly Gly Lys Gln Ala Leu Glu
            450                 455                 460

Thr Val Gln Arg Leu Leu Pro Val Leu Cys Gln Asp His Gly Leu Thr
465                 470                 475                 480

Pro Asp Gln Val Val Ala Ile Ala Ser His Asp Gly Gly Lys Gln Ala
                    485                 490                 495

Leu Glu Thr Val Gln Arg Leu Leu Pro Val Leu Cys Gln Asp His Gly
            500                 505                 510

Leu Thr Pro Asp Gln Val Val Ala Ile Ala Ser His Asp Gly Gly Lys
            515                 520                 525

Gln Ala Leu Glu Thr Val Gln Arg Leu Leu Pro Val Leu Cys Gln Asp
            530                 535                 540

His Gly Leu Thr Pro Asp Gln Val Val Ala Ile Ala Ser Asn Asn Gly
545                 550                 555                 560

Gly Lys Gln Ala Leu Glu Thr Val Gln Arg Leu Leu Pro Val Leu Cys
                    565                 570                 575

Gln Asp His Gly Leu Thr Pro Asp Gln Val Val Ala Ile Ala Ser His
            580                 585                 590

Asp Gly Gly Lys Gln Ala Leu Glu Thr Val Gln Arg Leu Leu Pro Val
            595                 600                 605

Leu Cys Gln Asp His Gly Leu Thr Pro Asp Gln Val Val Ala Ile Ala
            610                 615                 620

Ser Asn Asn Gly Gly Lys Gln Ala Leu Glu Thr Val Gln Arg Leu Leu
625                 630                 635                 640

Pro Val Leu Cys Gln Asp His Gly Leu Thr Pro Asp Gln Val Val Ala
                    645                 650                 655

Ile Ala Ser His Asp Gly Gly Lys Gln Ala Leu Glu Thr Val Gln Arg
            660                 665                 670

Leu Leu Pro Val Leu Cys Gln Asp His Gly Leu Thr Pro Asp Gln Val
            675                 680                 685

Val Ala Ile Ala Ser His Asp Gly Gly Lys Gln Ala Leu Glu Thr Val
            690                 695                 700

Gln Arg Leu Leu Pro Val Leu Cys Gln Asp His Gly Leu Thr Pro Asp
705                 710                 715                 720

Gln Val Val Ala Ile Ala Ser His Asp Gly Gly Lys Gln Ala Leu Glu
                    725                 730                 735

Ser Ile Val Ala Gln Leu Ser Arg Pro Asp Pro Ala Leu Ala Ala Leu
            740                 745                 750

Thr Asn Asp His Leu Val Ala Leu Ala Cys Leu Gly Gly Arg Pro
            755                 760                 765
```

```
Ala Met Asp Ala Val Lys Lys Gly Leu Pro His Ala Pro Glu Leu Ile
        770                 775                 780
Arg Arg Val Asn Arg Arg Ile Gly Glu Arg Thr Ser His Arg Val Ala
785                 790                 795                 800
Gly Ser Lys Ala Ser Pro Lys Lys Lys Arg Lys Val Gly Arg Ala Asp
                805                 810                 815
Ala Leu Asp Asp Phe Asp Leu Asp Met Leu Gly Ser Asp Ala Leu Asp
                820                 825                 830
Asp Phe Asp Leu Asp Met Leu Gly Ser Asp Ala Leu Asp Asp Phe Asp
            835                 840                 845
Leu Asp Met Leu Gly Ser Asp Ala Leu Asp Asp Phe Asp Leu Asp Met
    850                 855                 860
Leu Ile Asn Tyr Pro Tyr Asp Val Pro Asp Tyr Ala Ser
865                 870                 875

<210> SEQ ID NO 87
<211> LENGTH: 2736
<212> TYPE: DNA
<213> ORGANISM: Artificial sequence
<220> FEATURE:
<223> OTHER INFORMATION: Synthetic oligonucleotide

<400> SEQUENCE: 87
atggactaca aagaccatga cggtgattat aaagatcatg acatcgatta caaggatgac     60
gatgacaaga tggcccccaa gaagaagagg aaggtgggcc gcggatctgt ggatctacgc    120
acgctcggct acagtcagca gcagcaagag aagatcaaac cgaaggtgcg ttcgacagtg    180
gcgcagcacc acgaggcact ggtgggccat gggtttacac acgcgcacat cgttgcgctc    240
agccaacacc cggcagcgtt agggaccgtc gctgtcacgt atcagcacat aatcacggcg    300
ttgccagagg cgacacacga agacatcgtt ggcgtcggca acagtggtc cggcgcacgc     360
gccctggagg ccttgctcac ggatgcgggg agttgagag gtccgccgtt acagttggac     420
acaggccaac ttgtgaagat tgcaaaacgt ggcggcgtga ccgcaatgga ggcagtgcat    480
gcatcgcgca atgcactgac gggtgccccc ctgaacctga ccccggacca agtggtggct    540
atcgccagcc acgatggcgg caagcaagcg ctcgaaacgg tgcagcggct gttgccggtg    600
ctgtgccagg accatggcct gaccccggac caagtggtgg ctatcgccag ccacgatggc    660
ggcaagcaag cgctcgaaac ggtgcagcgg ctgttgccgg tgctgtgcca ggaccatggc    720
ctgaccccgg accaagtggt ggctatcgcc agccacgatg gcggcaagca agcgctcgaa    780
acggtgcagc ggctgttgcc ggtgctgtgc caggaccatg gcctgacccc ggaccaagtg    840
gtggctatcg ccagcaacat tggcggcaag caagcgctcg aaacggtgca gcggctgttg    900
ccggtgctgt gccaggacca tggcctgacc ccggaccaag tggtggctat cgccagccac    960
gatggcggca agcaagcgct cgaaacggtg cagcggctgt tgccggtgct gtgccaggac   1020
catggcctga ccccggacca agtggtggct atcgccagca caatggcgg caagcaagcg    1080
ctcgaaacgg tgcagcggct gttgccggtg ctgtgccagg accatggcct gaccccggac   1140
caagtggtgg ctatcgccag caacaatggc ggcaagcaag cgctcgaaac ggtgcagcgg   1200
ctgttgccgg tgctgtgcca ggaccatggc ctgaccccgg accaagtggt ggctatcgcc   1260
agcaacaatg gcggcaagca agcgctcgaa acggtgcagc ggctgttgcc ggtgctgtgc   1320
caggaccatg gcctgacccc ggaccaagtg gtggctatcg ccagcaacaa tggcggcaag   1380
caagcgctcg aaacggtgca gcggctgttg ccggtgctgt gccaggacca tggcctgacc   1440
```

-continued

```
ccggaccaag tggtggctat cgccagccac gatggcggca agcaagcgct cgaaacggtg    1500
cagcggctgt tgccggtgct gtgccaggac catggcctga ccccggacca agtggtggct    1560
atcgccagcc acgatggcgg caagcaagcg ctcgaaacgg tgcagcggct gttgccggtg    1620
ctgtgccagg accatggcct gaccccggac caagtggtgg ctatcgccag ccacgatggc    1680
ggcaagcaag cgctcgaaac ggtgcagcgg ctgttgccgg tgctgtgcca ggaccatggc    1740
ctgaccccgg accaagtggt ggctatcgcc agcaacggtg gcggcaagca agcgctcgaa    1800
acggtgcagc ggctgttgcc ggtgctgtgc caggaccatg gcctgacccc ggaccaagtg    1860
gtggctatcg ccagcaacgg tggcggcaag caagcgctcg aaacggtgca gcggctgttg    1920
ccggtgctgt gccaggacca tggcctgacc ccggaccaag tggtggctat cgccagcaac    1980
ggtggcggca agcaagcgct cgaaacggtg cagcggctgt tgccggtgct gtgccaggac    2040
catggcctga ccccggacca agtggtggct atcgccagca cattggcgg caagcaagcg    2100
ctcgaaacgg tgcagcggct gttgccggtg ctgtgccagg accatggcct gaccccggac    2160
caagtggtgg ctatcgccag ccacgatggc ggcaagcaag cgctcgaaac ggtgcagcgg    2220
ctgttgccgg tgctgtgcca ggaccatggc ctgaccccgg accaagtggt ggctatcgcc    2280
agcaacggtg gcggcaagca agcgctcgaa agcattgtgg cccagctgag ccggcctgat    2340
ccggcgttgg ccgcgttgac caacgacgac cacctcgtcg ccttggcctg cctcggcgga    2400
cgtcctgcca tggatgcagt gaaaaaggga ttgccgcacg cgccggaatt gatcagaaga    2460
gtcaatcgcc gtattggcga acgcacgtcc catcgcgttg ccggatccaa ggctagcccg    2520
aaaaagaaac gcaaagttgg gcgcgccgac gcgctggacg atttcgatct cgacatgctg    2580
ggttctgatg ccctcgatga ctttgacctg gatatgttgg gaagcgacgc attggatgac    2640
tttgatctgg acatgctcgg ctccgatgct ctggacgatt cgatctcga tatgttaatt    2700
aactacccgt acgacgttcc ggactacgct tcttga                              2736
```

<210> SEQ ID NO 88
<211> LENGTH: 911
<212> TYPE: PRT
<213> ORGANISM: Unknown
<220> FEATURE:
<223> OTHER INFORMATION: Synthetic peptide

<400> SEQUENCE: 88

```
Met Asp Tyr Lys Asp His Asp Gly Asp Tyr Lys Asp His Asp Ile Asp
1               5                   10                  15

Tyr Lys Asp Asp Asp Lys Met Ala Pro Lys Lys Arg Lys Val
            20                  25                  30

Gly Arg Gly Ser Val Asp Leu Arg Thr Leu Gly Tyr Ser Gln Gln Gln
        35                  40                  45

Gln Glu Lys Ile Lys Pro Lys Val Arg Ser Thr Val Ala Gln His His
    50                  55                  60

Glu Ala Leu Val Gly His Gly Phe Thr His Ala His Ile Val Ala Leu
65                  70                  75                  80

Ser Gln His Pro Ala Ala Leu Gly Thr Val Ala Val Thr Tyr Gln His
                85                  90                  95

Ile Ile Thr Ala Leu Pro Glu Ala Thr His Glu Asp Ile Val Gly Val
            100                 105                 110

Gly Lys Gln Trp Ser Gly Ala Arg Ala Leu Glu Ala Leu Leu Thr Asp
        115                 120                 125
```

```
Ala Gly Glu Leu Arg Gly Pro Pro Leu Gln Leu Asp Thr Gly Gln Leu
    130                 135                 140

Val Lys Ile Ala Lys Arg Gly Val Thr Ala Met Glu Ala Val His
145                 150                 155                 160

Ala Ser Arg Asn Ala Leu Thr Gly Ala Pro Leu Asn Leu Thr Pro Asp
                165                 170                 175

Gln Val Val Ala Ile Ala Ser His Asp Gly Lys Gln Ala Leu Glu
                180                 185                 190

Thr Val Gln Arg Leu Leu Pro Val Leu Cys Gln Asp His Gly Leu Thr
                195                 200                 205

Pro Asp Gln Val Val Ala Ile Ala Ser His Asp Gly Gly Lys Gln Ala
    210                 215                 220

Leu Glu Thr Val Gln Arg Leu Leu Pro Val Leu Cys Gln Asp His Gly
225                 230                 235                 240

Leu Thr Pro Asp Gln Val Val Ala Ile Ala Ser His Asp Gly Gly Lys
                245                 250                 255

Gln Ala Leu Glu Thr Val Gln Arg Leu Leu Pro Val Leu Cys Gln Asp
                260                 265                 270

His Gly Leu Thr Pro Asp Gln Val Val Ala Ile Ala Ser Asn Ile Gly
                275                 280                 285

Gly Lys Gln Ala Leu Glu Thr Val Gln Arg Leu Leu Pro Val Leu Cys
    290                 295                 300

Gln Asp His Gly Leu Thr Pro Asp Gln Val Val Ala Ile Ala Ser His
305                 310                 315                 320

Asp Gly Gly Lys Gln Ala Leu Glu Thr Val Gln Arg Leu Leu Pro Val
                325                 330                 335

Leu Cys Gln Asp His Gly Leu Thr Pro Asp Gln Val Val Ala Ile Ala
                340                 345                 350

Ser Asn Asn Gly Gly Lys Gln Ala Leu Glu Thr Val Gln Arg Leu Leu
            355                 360                 365

Pro Val Leu Cys Gln Asp His Gly Leu Thr Pro Asp Gln Val Val Ala
    370                 375                 380

Ile Ala Ser Asn Asn Gly Gly Lys Gln Ala Leu Glu Thr Val Gln Arg
385                 390                 395                 400

Leu Leu Pro Val Leu Cys Gln Asp His Gly Leu Thr Pro Asp Gln Val
                405                 410                 415

Val Ala Ile Ala Ser Asn Asn Gly Gly Lys Gln Ala Leu Glu Thr Val
                420                 425                 430

Gln Arg Leu Leu Pro Val Leu Cys Gln Asp His Gly Leu Thr Pro Asp
                435                 440                 445

Gln Val Val Ala Ile Ala Ser Asn Asn Gly Gly Lys Gln Ala Leu Glu
    450                 455                 460

Thr Val Gln Arg Leu Leu Pro Val Leu Cys Gln Asp His Gly Leu Thr
465                 470                 475                 480

Pro Asp Gln Val Val Ala Ile Ala Ser His Asp Gly Gly Lys Gln Ala
                485                 490                 495

Leu Glu Thr Val Gln Arg Leu Leu Pro Val Leu Cys Gln Asp His Gly
                500                 505                 510

Leu Thr Pro Asp Gln Val Val Ala Ile Ala Ser His Asp Gly Gly Lys
                515                 520                 525

Gln Ala Leu Glu Thr Val Gln Arg Leu Leu Pro Val Leu Cys Gln Asp
    530                 535                 540

His Gly Leu Thr Pro Asp Gln Val Val Ala Ile Ala Ser His Asp Gly
```

```
                545                 550                 555                 560
        Gly Lys Gln Ala Leu Glu Thr Val Gln Arg Leu Leu Pro Val Leu Cys
                        565                 570                 575

Gln Asp His Gly Leu Thr Pro Asp Gln Val Val Ala Ile Ala Ser Asn
                        580                 585                 590

Gly Gly Gly Lys Gln Ala Leu Glu Thr Val Gln Arg Leu Leu Pro Val
                        595                 600                 605

Leu Cys Gln Asp His Gly Leu Thr Pro Asp Gln Val Val Ala Ile Ala
                        610                 615                 620

Ser Asn Gly Gly Gly Lys Gln Ala Leu Glu Thr Val Gln Arg Leu Leu
        625                 630                 635                 640

Pro Val Leu Cys Gln Asp His Gly Leu Thr Pro Asp Gln Val Val Ala
                        645                 650                 655

Ile Ala Ser Asn Gly Gly Gly Lys Gln Ala Leu Glu Thr Val Gln Arg
                        660                 665                 670

Leu Leu Pro Val Leu Cys Gln Asp His Gly Leu Thr Pro Asp Gln Val
                        675                 680                 685

Val Ala Ile Ala Ser Asn Ile Gly Gly Lys Gln Ala Leu Glu Thr Val
                        690                 695                 700

Gln Arg Leu Leu Pro Val Leu Cys Gln Asp His Gly Leu Thr Pro Asp
        705                 710                 715                 720

Gln Val Val Ala Ile Ala Ser His Asp Gly Gly Lys Gln Ala Leu Glu
                        725                 730                 735

Thr Val Gln Arg Leu Leu Pro Val Leu Cys Gln Asp His Gly Leu Thr
                        740                 745                 750

Pro Asp Gln Val Val Ala Ile Ala Ser Asn Gly Gly Gly Lys Gln Ala
                        755                 760                 765

Leu Glu Ser Ile Val Ala Gln Leu Ser Arg Pro Asp Pro Ala Leu Ala
                        770                 775                 780

Ala Leu Thr Asn Asp His Leu Val Ala Leu Ala Cys Leu Gly Gly
        785                 790                 795                 800

Arg Pro Ala Met Asp Ala Val Lys Lys Gly Leu Pro His Ala Pro Glu
                        805                 810                 815

Leu Ile Arg Arg Val Asn Arg Arg Ile Gly Glu Arg Thr Ser His Arg
                        820                 825                 830

Val Ala Gly Ser Lys Ala Ser Pro Lys Lys Arg Lys Val Gly Arg
                        835                 840                 845

Ala Asp Ala Leu Asp Asp Phe Asp Leu Asp Met Leu Gly Ser Asp Ala
        850                 855                 860

Leu Asp Asp Phe Asp Leu Asp Met Leu Gly Ser Asp Ala Leu Asp Asp
        865                 870                 875                 880

Phe Asp Leu Asp Met Leu Gly Ser Asp Ala Leu Asp Asp Phe Asp Leu
                        885                 890                 895

Asp Met Leu Ile Asn Tyr Pro Tyr Asp Val Pro Asp Tyr Ala Ser
                        900                 905                 910

<210> SEQ ID NO 89
<211> LENGTH: 2634
<212> TYPE: DNA
<213> ORGANISM: Artificial sequence
<220> FEATURE:
<223> OTHER INFORMATION: Synthetic oligonucleotide

<400> SEQUENCE: 89
atggactaca aagaccatga cggtgattat aaagatcatg acatcgatta caaggatgac      60
```

```
gatgacaaga tggcccccaa gaagaagagg aaggtgggcc gcggatctgt ggatctacgc    120
acgctcggct acagtcagca gcagcaagag aagatcaaac cgaaggtgcg ttcgacagtg    180
gcgcagcacc acgaggcact ggtgggccat gggtttacac acgcgcacat cgttgcgctc    240
agccaacacc cggcagcgtt agggaccgtc gctgtcacgt atcagcacat aatcacggcg    300
ttgccagagg cgacacacga agacatcgtt ggcgtcggca acagtggtc cggcgcacgc    360 gccctggagg ccttgctcac ggatgcgggg gagttgagag gtccgccgtt acagttggac    420
acaggccaac ttgtgaagat tgcaaaacgt ggcggcgtga ccgcaatgga ggcagtgcat    480
gcatcgcgca atgcactgac gggtgccccc ctgaacctga ccccggacca agtggtggct    540
atcgccagcc acgatggcgg caagcaagcg ctcgaaacgg tgcagcggct gttgccggtg    600
ctgtgccagg accatggcct gaccccggac caagtggtgg ctatcgccag ccacgatggc    660
ggcaagcaag cgctcgaaac ggtgcagcgg ctgttgccgg tgctgtgcca ggaccatggc    720
ctgaccccgg accaagtggt ggctatcgcc agccacgatg gcggcaagca agcgctcgaa    780
acggtgcagc ggctgttgcc ggtgctgtgc caggaccatg gcctgacccc ggaccaagtg    840
gtggctatcg ccagccacga tggcggcaag caagcgctcg aaacggtgca gcggctgttg    900
ccggtgctgt gccaggacca tggcctgacc ccggaccaag tggtggctat cgccagcaac    960
ggtggcggca agcaagcgct cgaaacggtg cagcggctgt tgccggtgct gtgccaggac   1020
catggcctga ccccggacca gtggtggct atcgccagca caatggcgg caagcaagcg   1080 ctcgaaacgg tgcagcggct gttgccggtg ctgtgccagg accatggcct gaccccggac   1140
caagtggtgg ctatcgccag caacaatggc ggcaagcaag cgctcgaaac ggtgcagcgg   1200
ctgttgccgg tgctgtgcca ggaccatggc ctgaccccgg accaagtggt ggctatcgcc   1260
agcaacggtg gcggcaagca agcgctcgaa acggtgcagc ggctgttgcc ggtgctgtgc   1320
caggaccatg gcctgacccc ggaccaagtg gtggctatcg ccagcaacgg tggcggcaag   1380
caagcgctcg aaacggtgca gcggctgttg ccggtgctgt gccaggacca tggcctgacc   1440
ccggaccaag tggtggctat cgccagcaac ggtggcggca agcaagcgct cgaaacggtg   1500
cagcggctgt tgccggtgct gtgccaggac catggcctga ccccggacca gtggtggct   1560 atcgccagcc acgatggcgg caagcaagcg ctcgaaacgg tgcagcggct gttgccggtg   1620
ctgtgccagg accatggcct gaccccggac caagtggtgg ctatcgccag caacggtggc   1680
ggcaagcaag cgctcgaaac ggtgcagcgg ctgttgccgg tgctgtgcca ggaccatggc   1740
ctgaccccgg accaagtggt ggctatcgcc agccacgatg gcggcaagca agcgctcgaa   1800
acggtgcagc ggctgttgcc ggtgctgtgc caggaccatg gcctgacccc ggaccaagtg   1860
gtggctatcg ccagccacga tggcggcaag caagcgctcg aaacggtgca gcggctgttg   1920
ccggtgctgt gccaggacca tggcctgacc ccggaccaag tggtggctat cgccagcaac   1980
aatggcggca agcaagcgct cgaaacggtg cagcggctgt tgccggtgct gtgccaggac   2040
catggcctga ccccggacca gtggtggct atcgccagca caatggcgg caagcaagcg   2100 ctcgaaacgg tgcagcggct gttgccggtg ctgtgccagg accatggcct gaccccggac   2160
caagtggtgg ctatcgccag caacggtggc ggcaagcaag cgctcgaaag cattgtggcc   2220
cagctgagcc ggcctgatcc ggcgttggcc gcgttgacca acgacgacca cctcgtcgcc   2280
ttggcctgcc tcgcggacg tcctgccatg gatgcagtga aaaagggatt gccgcacgcg   2340
ccggaattga tcagaagagt caatcgccgt attggcgaac gcacgtccca tcgcgttgcc   2400
```

-continued

```
ggatccaagg ctagcccgaa aaagaaacgc aaagttgggc gcgccgacgc gctggacgat    2460
ttcgatctcg acatgctggg ttctgatgcc ctcgatgact ttgacctgga tatgttggga    2520
agcgacgcat tggatgactt tgatctggac atgctcggct ccgatgctct ggacgatttc    2580
gatctcgata tgttaattaa ctacccgtac gacgttccgg actacgcttc ttga          2634
```

<210> SEQ ID NO 90
<211> LENGTH: 877
<212> TYPE: PRT
<213> ORGANISM: Unknown
<220> FEATURE:
<223> OTHER INFORMATION: Synthetic peptide

<400> SEQUENCE: 90

```
Met Asp Tyr Lys Asp His Asp Gly Asp Tyr Lys Asp His Asp Ile Asp
1               5                   10                  15

Tyr Lys Asp Asp Asp Lys Met Ala Pro Lys Lys Arg Lys Val
            20                  25                  30

Gly Arg Gly Ser Val Asp Leu Arg Thr Leu Gly Tyr Ser Gln Gln Gln
        35                  40                  45

Gln Glu Lys Ile Lys Pro Lys Val Arg Ser Thr Val Ala Gln His His
    50                  55                  60

Glu Ala Leu Val Gly His Gly Phe Thr His Ala His Ile Val Ala Leu
65                  70                  75                  80

Ser Gln His Pro Ala Ala Leu Gly Thr Val Ala Val Thr Tyr Gln His
                85                  90                  95

Ile Ile Thr Ala Leu Pro Glu Ala Thr His Glu Asp Ile Val Gly Val
            100                 105                 110

Gly Lys Gln Trp Ser Gly Ala Arg Ala Leu Glu Ala Leu Leu Thr Asp
        115                 120                 125

Ala Gly Glu Leu Arg Gly Pro Pro Leu Gln Leu Asp Thr Gly Gln Leu
    130                 135                 140

Val Lys Ile Ala Lys Arg Gly Gly Val Thr Ala Met Glu Ala Val His
145                 150                 155                 160

Ala Ser Arg Asn Ala Leu Thr Gly Ala Pro Leu Asn Leu Thr Pro Asp
                165                 170                 175

Gln Val Val Ala Ile Ala Ser His Asp Gly Gly Lys Gln Ala Leu Glu
            180                 185                 190

Thr Val Gln Arg Leu Leu Pro Val Leu Cys Gln Asp His Gly Leu Thr
        195                 200                 205

Pro Asp Gln Val Val Ala Ile Ala Ser His Asp Gly Gly Lys Gln Ala
    210                 215                 220

Leu Glu Thr Val Gln Arg Leu Leu Pro Val Leu Cys Gln Asp His Gly
225                 230                 235                 240

Leu Thr Pro Asp Gln Val Val Ala Ile Ala Ser His Asp Gly Gly Lys
                245                 250                 255

Gln Ala Leu Glu Thr Val Gln Arg Leu Leu Pro Val Leu Cys Gln Asp
            260                 265                 270

His Gly Leu Thr Pro Asp Gln Val Val Ala Ile Ala Ser His Asp Gly
        275                 280                 285

Gly Lys Gln Ala Leu Glu Thr Val Gln Arg Leu Leu Pro Val Leu Cys
    290                 295                 300

Gln Asp His Gly Leu Thr Pro Asp Gln Val Val Ala Ile Ala Ser Asn
305                 310                 315                 320

Gly Gly Gly Lys Gln Ala Leu Glu Thr Val Gln Arg Leu Leu Pro Val
```

```
                325                 330                 335
Leu Cys Gln Asp His Gly Leu Thr Pro Asp Gln Val Val Ala Ile Ala
            340                 345                 350
Ser Asn Asn Gly Gly Lys Gln Ala Leu Glu Thr Val Gln Arg Leu Leu
            355                 360                 365
Pro Val Leu Cys Gln Asp His Gly Leu Thr Pro Asp Gln Val Val Ala
            370                 375                 380
Ile Ala Ser Asn Asn Gly Gly Lys Gln Ala Leu Glu Thr Val Gln Arg
385                 390                 395                 400
Leu Leu Pro Val Leu Cys Gln Asp His Gly Leu Thr Pro Asp Gln Val
                405                 410                 415
Val Ala Ile Ala Ser Asn Gly Gly Lys Gln Ala Leu Glu Thr Val
                420                 425                 430
Gln Arg Leu Leu Pro Val Leu Cys Gln Asp His Gly Leu Thr Pro Asp
                435                 440                 445
Gln Val Val Ala Ile Ala Ser Asn Gly Gly Lys Gln Ala Leu Glu
                450                 455                 460
Thr Val Gln Arg Leu Leu Pro Val Leu Cys Gln Asp His Gly Leu Thr
465                 470                 475                 480
Pro Asp Gln Val Val Ala Ile Ala Ser Asn Gly Gly Lys Gln Ala
                485                 490                 495
Leu Glu Thr Val Gln Arg Leu Leu Pro Val Leu Cys Gln Asp His Gly
                500                 505                 510
Leu Thr Pro Asp Gln Val Val Ala Ile Ala Ser His Asp Gly Gly Lys
                515                 520                 525
Gln Ala Leu Glu Thr Val Gln Arg Leu Leu Pro Val Leu Cys Gln Asp
                530                 535                 540
His Gly Leu Thr Pro Asp Gln Val Val Ala Ile Ala Ser Asn Gly Gly
545                 550                 555                 560
Gly Lys Gln Ala Leu Glu Thr Val Gln Arg Leu Leu Pro Val Leu Cys
                565                 570                 575
Gln Asp His Gly Leu Thr Pro Asp Gln Val Val Ala Ile Ala Ser His
                580                 585                 590
Asp Gly Gly Lys Gln Ala Leu Glu Thr Val Gln Arg Leu Leu Pro Val
                595                 600                 605
Leu Cys Gln Asp His Gly Leu Thr Pro Asp Gln Val Val Ala Ile Ala
                610                 615                 620
Ser His Asp Gly Gly Lys Gln Ala Leu Glu Thr Val Gln Arg Leu Leu
625                 630                 635                 640
Pro Val Leu Cys Gln Asp His Gly Leu Thr Pro Asp Gln Val Val Ala
                645                 650                 655
Ile Ala Ser Asn Asn Gly Gly Lys Gln Ala Leu Glu Thr Val Gln Arg
                660                 665                 670
Leu Leu Pro Val Leu Cys Gln Asp His Gly Leu Thr Pro Asp Gln Val
                675                 680                 685
Val Ala Ile Ala Ser Asn Asn Gly Gly Lys Gln Ala Leu Glu Thr Val
                690                 695                 700
Gln Arg Leu Leu Pro Val Leu Cys Gln Asp His Gly Leu Thr Pro Asp
705                 710                 715                 720
Gln Val Val Ala Ile Ala Ser Asn Gly Gly Gly Lys Gln Ala Leu Glu
                725                 730                 735
Ser Ile Val Ala Gln Leu Ser Arg Pro Asp Pro Ala Leu Ala Ala Leu
                740                 745                 750
```

-continued

```
Thr Asn Asp Asp His Leu Val Ala Leu Ala Cys Leu Gly Gly Arg Pro
        755                 760                 765
Ala Met Asp Ala Val Lys Lys Gly Leu Pro His Ala Pro Glu Leu Ile
    770                 775                 780
Arg Arg Val Asn Arg Arg Ile Gly Glu Arg Thr Ser His Arg Val Ala
785                 790                 795                 800
Gly Ser Lys Ala Ser Pro Lys Lys Arg Lys Val Gly Arg Ala Asp
                805                 810                 815
Ala Leu Asp Asp Phe Asp Leu Asp Met Leu Gly Ser Asp Ala Leu Asp
                820                 825                 830
Asp Phe Asp Leu Asp Met Leu Gly Ser Asp Ala Leu Asp Asp Phe Asp
            835                 840                 845
Leu Asp Met Leu Gly Ser Asp Ala Leu Asp Asp Phe Asp Leu Asp Met
    850                 855                 860
Leu Ile Asn Tyr Pro Tyr Asp Val Pro Asp Tyr Ala Ser
865                 870                 875
```

<210> SEQ ID NO 91
<211> LENGTH: 2634
<212> TYPE: DNA
<213> ORGANISM: Artificial sequence
<220> FEATURE:
<223> OTHER INFORMATION: Synthetic oligonucleotide

<400> SEQUENCE: 91

```
atggactaca aagaccatga cggtgattat aaagatcatg acatcgatta caaggatgac      60
gatgacaaga tggcccccaa gaagaagagg aaggtgggcc gcggatctgt ggatctacgc     120
acgctcggct acagtcagca gcagcaagag aagatcaaac cgaaggtgcg ttcgacagtg     180
gcgcagcacc acgaggcact ggtgggccat gggtttacac acgcgcacat cgttgcgctc     240
agccaacacc cggcagcgtt agggaccgtc gctgtcacgt atcagcacat aatcacggcg     300
ttgccagagg cgacacacga agacatcgtt ggcgtcggca acagtggtc cggcgcacgc     360
gccctggagg ccttgctcac ggatgcgggg gagttgagag gtccgccgtt acagttggac     420
acaggccaac ttgtgaagat tgcaaaacgt ggcggcgtga ccgcaatgga ggcagtgcat     480
gcatcgcgca atgcactgac gggtgccccc ctgaacctga ccccggacca agtggtggct     540
atcgccagca caatggcgg caagcaagcg ctcgaaacgg tgcagcggct gttgccggtg     600
ctgtgccagg accatggcct gaccccggac caagtggtgg ctatcgccag ccacgatggc     660
ggcaagcaag cgctcgaaac ggtgcagcgg ctgttgccgg tgctgtgcca ggaccatggc     720
ctgaccccgg accaagtggt ggctatcgcc agccacgatg cggcaagca agcgctcgaa     780
acggtgcagc ggctgttgcc ggtgctgtgc caggaccatg gcctgacccc ggaccaagtg     840
gtggctatcg ccagcaacat tggcggcaag caagcgctcg aaacggtgca gcggctgttg     900
ccggtgctgt gccaggacca tggcctgacc ccggaccaag tggtggctat cgccagccac     960
gatggcggca agcaagcgct cgaaacggtg cagcggctgt tgccggtgct gtgccaggac    1020
catggcctga ccccggacca agtggtggct atcgccagca acgtggcgg caagcaagcg    1080
ctcgaaacgg tgcagcggct gttgccggtg ctgtgccagg accatggcct gaccccggac    1140
caagtggtgg ctatcgccag ccacgatggc ggcaagcaag cgctcgaaac ggtgcagcgg    1200
ctgttgccgg tgctgtgcca ggaccatggc ctgaccccgg accaagtggt ggctatcgcc    1260
agccacgatg cggcaagca agcgctcgaa acggtgcagc ggctgttgcc ggtgctgtgc    1320
```

```
caggaccatg gcctgacccc ggaccaagtg gtggctatcg ccagccacga tggcggcaag    1380
caagcgctcg aaacggtgca gcggctgttg ccggtgctgt gccaggacca tggcctgacc    1440
ccggaccaag tggtggctat cgccagcaac attggcggca agcaagcgct cgaaacggtg    1500
cagcggctgt tgccggtgct gtgccaggac catggcctga ccccggacca agtggtggct    1560
atcgccagca acaatggcgg caagcaagcg ctcgaaacgg tgcagcggct gttgccggtg    1620
ctgtgccagg accatggcct gaccccggac caagtggtgg ctatcgccag caacattggc    1680
ggcaagcaag cgctcgaaac ggtgcagcgg ctgttgccgg tgctgtgcca ggaccatggc    1740
ctgaccccgg accaagtggt ggctatcgcc agccacgatg gcggcaagca agcgctcgaa    1800
acggtgcagc ggctgttgcc ggtgctgtgc caggaccatg gcctgacccc ggaccaagtg    1860
gtggctatcg ccagcaacgg tggcggcaag caagcgctcg aaacggtgca gcggctgttg    1920
ccggtgctgt gccaggacca tggcctgacc ccggaccaag tggtggctat cgccagcaac    1980
ggtggcggca agcaagcgct cgaaacggtg cagcggctgt tgccggtgct gtgccaggac    2040
catggcctga ccccggacca agtggtggct atcgccagca acaatggcgg caagcaagcg    2100
ctcgaaacgg tgcagcggct gttgccggtg ctgtgccagg accatggcct gaccccggac    2160
caagtggtgg ctatcgccag caacggtggc ggcaagcaag cgctcgaaag cattgtggcc    2220
cagctgagcc ggcctgatcc ggcgttggcc gcgttgacca acgacgacca cctcgtcgcc    2280
ttggcctgcc tcggcggacg tcctgccatg gatgcagtga aaaagggatt gccgcacgcg    2340
ccggaattga tcagaagagt caatcgccgt attggcgaac gcacgtccca tcgcgttgcc    2400
ggatccaagc tagcccgaa aaagaaacgc aaagttgggc gcgccgacgc gctggacgat    2460
ttcgatctcg acatgctggg ttctgatgcc ctcgatgact ttgacctgga tatgttggga    2520
agcgacgcat ggatgacttt gatctggac atgctcggct ccgatgctct ggacgatttc    2580
gatctcgata tgttaattaa ctacccgtac gacgttccgg actacgcttc ttga          2634
```

<210> SEQ ID NO 92
<211> LENGTH: 877
<212> TYPE: PRT
<213> ORGANISM: Unknown
<220> FEATURE:
<223> OTHER INFORMATION: Synthetic peptide

<400> SEQUENCE: 92

```
Met Asp Tyr Lys Asp His Asp Gly Asp Tyr Lys Asp His Asp Ile Asp
1               5                   10                  15

Tyr Lys Asp Asp Asp Lys Met Ala Pro Lys Lys Arg Lys Val
            20                  25                  30

Gly Arg Gly Ser Val Asp Leu Arg Thr Leu Gly Tyr Ser Gln Gln Gln
        35                  40                  45

Gln Glu Lys Ile Lys Pro Lys Val Arg Ser Thr Val Ala Gln His His
    50                  55                  60

Glu Ala Leu Val Gly His Gly Phe Thr His Ala His Ile Val Ala Leu
65                  70                  75                  80

Ser Gln His Pro Ala Ala Leu Gly Thr Val Ala Val Thr Tyr Gln His
                85                  90                  95

Ile Ile Thr Ala Leu Pro Glu Ala His Glu Asp Ile Val Gly Val
                100                 105                 110

Gly Lys Gln Trp Ser Gly Ala Arg Ala Leu Glu Ala Leu Leu Thr Asp
            115                 120                 125

Ala Gly Glu Leu Arg Gly Pro Pro Leu Gln Leu Asp Thr Gly Gln Leu
```

```
                    130                 135                 140
Val Lys Ile Ala Lys Arg Gly Val Thr Ala Met Glu Ala Val His
145                 150                 155                 160

Ala Ser Arg Asn Ala Leu Thr Gly Ala Pro Leu Asn Leu Thr Pro Asp
                165                 170                 175

Gln Val Val Ala Ile Ala Ser Asn Asn Gly Gly Lys Gln Ala Leu Glu
                180                 185                 190

Thr Val Gln Arg Leu Leu Pro Val Leu Cys Gln Asp His Gly Leu Thr
                195                 200                 205

Pro Asp Gln Val Val Ala Ile Ala Ser His Asp Gly Gly Lys Gln Ala
            210                 215                 220

Leu Glu Thr Val Gln Arg Leu Leu Pro Val Leu Cys Gln Asp His Gly
225                 230                 235                 240

Leu Thr Pro Asp Gln Val Val Ala Ile Ala Ser His Asp Gly Gly Lys
                245                 250                 255

Gln Ala Leu Glu Thr Val Gln Arg Leu Leu Pro Val Leu Cys Gln Asp
                260                 265                 270

His Gly Leu Thr Pro Asp Gln Val Val Ala Ile Ala Ser Asn Ile Gly
            275                 280                 285

Gly Lys Gln Ala Leu Glu Thr Val Gln Arg Leu Leu Pro Val Leu Cys
        290                 295                 300

Gln Asp His Gly Leu Thr Pro Asp Gln Val Val Ala Ile Ala Ser His
305                 310                 315                 320

Asp Gly Gly Lys Gln Ala Leu Glu Thr Val Gln Arg Leu Leu Pro Val
                325                 330                 335

Leu Cys Gln Asp His Gly Leu Thr Pro Asp Gln Val Val Ala Ile Ala
                340                 345                 350

Ser Asn Gly Gly Gly Lys Gln Ala Leu Glu Thr Val Gln Arg Leu Leu
                355                 360                 365

Pro Val Leu Cys Gln Asp His Gly Leu Thr Pro Asp Gln Val Val Ala
            370                 375                 380

Ile Ala Ser His Asp Gly Gly Lys Gln Ala Leu Glu Thr Val Gln Arg
385                 390                 395                 400

Leu Leu Pro Val Leu Cys Gln Asp His Gly Leu Thr Pro Asp Gln Val
                405                 410                 415

Val Ala Ile Ala Ser His Asp Gly Gly Lys Gln Ala Leu Glu Thr Val
            420                 425                 430

Gln Arg Leu Leu Pro Val Leu Cys Gln Asp His Gly Leu Thr Pro Asp
            435                 440                 445

Gln Val Val Ala Ile Ala Ser His Asp Gly Gly Lys Gln Ala Leu Glu
        450                 455                 460

Thr Val Gln Arg Leu Leu Pro Val Leu Cys Gln Asp His Gly Leu Thr
465                 470                 475                 480

Pro Asp Gln Val Val Ala Ile Ala Ser Asn Ile Gly Gly Lys Gln Ala
                485                 490                 495

Leu Glu Thr Val Gln Arg Leu Leu Pro Val Leu Cys Gln Asp His Gly
            500                 505                 510

Leu Thr Pro Asp Gln Val Val Ala Ile Ala Ser Asn Asn Gly Gly Lys
            515                 520                 525

Gln Ala Leu Glu Thr Val Gln Arg Leu Leu Pro Val Leu Cys Gln Asp
        530                 535                 540

His Gly Leu Thr Pro Asp Gln Val Val Ala Ile Ala Ser Asn Ile Gly
545                 550                 555                 560
```

```
Gly Lys Gln Ala Leu Glu Thr Val Gln Arg Leu Leu Pro Val Leu Cys
                565                 570                 575
Gln Asp His Gly Leu Thr Pro Asp Gln Val Val Ala Ile Ala Ser His
            580                 585                 590
Asp Gly Gly Lys Gln Ala Leu Glu Thr Val Gln Arg Leu Leu Pro Val
        595                 600                 605
Leu Cys Gln Asp His Gly Leu Thr Pro Asp Gln Val Val Ala Ile Ala
    610                 615                 620
Ser Asn Gly Gly Lys Gln Ala Leu Glu Thr Val Gln Arg Leu Leu
625                 630                 635                 640
Pro Val Leu Cys Gln Asp His Gly Leu Thr Pro Asp Gln Val Val Ala
                645                 650                 655
Ile Ala Ser Asn Gly Gly Lys Gln Ala Leu Glu Thr Val Gln Arg
            660                 665                 670
Leu Leu Pro Val Leu Cys Gln Asp His Gly Leu Thr Pro Asp Gln Val
        675                 680                 685
Val Ala Ile Ala Ser Asn Asn Gly Gly Lys Gln Ala Leu Glu Thr Val
    690                 695                 700
Gln Arg Leu Leu Pro Val Leu Cys Gln Asp His Gly Leu Thr Pro Asp
705                 710                 715                 720
Gln Val Val Ala Ile Ala Ser Asn Gly Gly Gly Lys Gln Ala Leu Glu
                725                 730                 735
Ser Ile Val Ala Gln Leu Ser Arg Pro Asp Pro Ala Leu Ala Ala Leu
            740                 745                 750
Thr Asn Asp Asp His Leu Val Ala Leu Ala Cys Leu Gly Gly Arg Pro
        755                 760                 765
Ala Met Asp Ala Val Lys Lys Gly Leu Pro His Ala Pro Glu Leu Ile
    770                 775                 780
Arg Arg Val Asn Arg Arg Ile Gly Glu Arg Thr Ser His Arg Val Ala
785                 790                 795                 800
Gly Ser Lys Ala Ser Pro Lys Lys Arg Lys Val Gly Arg Ala Asp
                805                 810                 815
Ala Leu Asp Asp Phe Asp Leu Asp Met Leu Gly Ser Asp Ala Leu Asp
            820                 825                 830
Asp Phe Asp Leu Asp Met Leu Gly Ser Asp Ala Leu Asp Phe Asp
        835                 840                 845
Leu Asp Met Leu Gly Ser Asp Ala Leu Asp Asp Phe Asp Leu Asp Met
    850                 855                 860
Leu Ile Asn Tyr Pro Tyr Asp Val Pro Asp Tyr Ala Ser
865                 870                 875

<210> SEQ ID NO 93
<211> LENGTH: 2634
<212> TYPE: DNA
<213> ORGANISM: Artificial sequence
<220> FEATURE:
<223> OTHER INFORMATION: Synthetic oligonucleotide

<400> SEQUENCE: 93
atggactaca aagaccatga cggtgattat aaagatcatg acatcgatta caaggatgac    60
gatgacaaga tggcccccaa gaagaagagg aaggtgggcc gcggatctgt ggatctacgc   120
acgctcggct acagtcagca gcagcaagag aagatcaaac cgaaggtgcg ttcgacagtg   180
gcgcagcacc acgaggcact ggtgggccat gggtttacac acgcgcacat cgttgcgctc   240
```

```
agccaacacc cggcagcgtt agggaccgtc gctgtcacgt atcagcacat aatcacggcg    300
ttgccagagg cgacacacga agacatcgtt ggcgtcggca aacagtggtc cggcgcacgc    360
gccctggagg ccttgctcac ggatgcgggg gagttgagag gtccgccgtt acagttggac    420
acaggccaac ttgtgaagat tgcaaaacgt ggcggcgtga ccgcaatgga ggcagtgcat    480
gcatcgcgca atgcactgac gggtgccccc ctgaacctga ccccggacca agtggtggct    540
atcgccagcc acgatggcgg caagcaagcg ctcgaaacgg tgcagcggct gttgccggtg    600
ctgtgccagg accatggcct gaccccggac caagtggtgg ctatcgccag caacggtggc    660
ggcaagcaag cgctcgaaac ggtgcagcgg ctgttgccgg tgctgtgcca ggaccatggc    720
ctgaccccgg accaagtggt ggctatcgcc agcaacaatg gcggcaagca agcgctcgaa    780
acggtgcagc ggctgttgcc ggtgctgtgc caggaccatg gcctgacccc ggaccaagtg    840
gtggctatcg ccagccacga tggcggcaag caagcgctcg aaacggtgca gcggctgttg    900
ccggtgctgt gccaggacca tggcctgacc ccggaccaag tggtggctat cgccagcaac    960
attggcggca agcaagcgct cgaaacggtg cagcggctgt tgccggtgct gtgccaggac   1020
catggcctga ccccggacca agtggtggct atcgccagca acggtggcgg caagcaagcg   1080
ctcgaaacgg tgcagcggct gttgccggtg ctgtgccagg accatggcct gaccccggac   1140
caagtggtgg ctatcgccag caacggtggc ggcaagcaag cgctcgaaac ggtgcagcgg   1200
ctgttgccgg tgctgtgcca ggaccatggc ctgaccccgg accaagtggt ggctatcgcc   1260
agcaacggtg gcggcaagca agcgctcgaa acggtgcagc ggctgttgcc ggtgctgtgc   1320
caggaccatg gcctgacccc ggaccaagtg gtggctatcg ccagcaacat tggcggcaag   1380
caagcgctcg aaacggtgca gcggctgttg ccggtgctgt gccaggacca tggcctgacc   1440
ccggaccaag tggtggctat cgccagcaac aatggcggca agcaagcgct cgaaacggtg   1500
cagcggctgt tgccggtgct gtgccaggac catggcctga ccccggacca agtggtggct   1560
atcgccagca caatggcgg caagcaagcg ctcgaaacgg tgcagcggct gttgccggtg   1620
ctgtgccagg accatggcct gaccccggac caagtggtgg ctatcgccag caacaatggc   1680
ggcaagcaag cgctcgaaac ggtgcagcgg ctgttgccgg tgctgtgcca ggaccatggc   1740
ctgaccccgg accaagtggt ggctatcgcc agcaacattg gcggcaagca agcgctcgaa   1800
acggtgcagc ggctgttgcc ggtgctgtgc caggaccatg gcctgacccc ggaccaagtg   1860
gtggctatcg ccagcaacgg tggcggcaag caagcgctcg aaacggtgca gcggctgttg   1920
ccggtgctgt gccaggacca tggcctgacc ccggaccaag tggtggctat cgccagcaac   1980
ggtggcggca agcaagcgct cgaaacggtg cagcggctgt tgccggtgct gtgccaggac   2040
catggcctga ccccggacca agtggtggct atcgccagcc acgatggcgg caagcaagcg   2100
ctcgaaacgg tgcagcggct gttgccggtg ctgtgccagg accatggcct gaccccggac   2160
caagtggtgg ctatcgccag caacggtggc ggcaagcaag cgctcgaaag cattgtggcc   2220
cagctgagcc ggcctgatcc ggcgttggcc gcgttgacca acgacgacca cctcgtcgcc   2280
ttggcctgcc tcggcggacg tcctgccatg gatgcagtga aaaagggatt gccgcacgcg   2340
ccggaattga tcagaagagt caatcgccgt attggcgaac gcacgtccca tcgcgttgcc   2400
ggatccaagg ctagcccgaa aaagaaacgc aaagttgggc gcgccgacgc gctggacgat   2460
ttcgatctcg acatgctggg ttctgatgcc ctcgatgact tgacctggat tatgttggga   2520
agcgacgcat ggatgacttt gatctggac atgctcggct ccgatgctct ggacgatttc   2580
gatctcgata tgttaattaa ctacccgtac gacgttccgg actacgcttc ttga         2634
```

<210> SEQ ID NO 94
<211> LENGTH: 877
<212> TYPE: PRT
<213> ORGANISM: Unknown
<220> FEATURE:
<223> OTHER INFORMATION: Synthetic peptide

<400> SEQUENCE: 94

Met Asp Tyr Lys Asp His Asp Gly Asp Tyr Lys Asp His Asp Ile Asp
1               5                   10                  15

Tyr Lys Asp Asp Asp Asp Lys Met Ala Pro Lys Lys Arg Lys Val
            20                  25                  30

Gly Arg Gly Ser Val Asp Leu Arg Thr Leu Gly Tyr Ser Gln Gln Gln
        35                  40                  45

Gln Glu Lys Ile Lys Pro Lys Val Arg Ser Thr Val Ala Gln His His
    50                  55                  60

Glu Ala Leu Val Gly His Gly Phe Thr His Ala His Ile Val Ala Leu
65                  70                  75                  80

Ser Gln His Pro Ala Ala Leu Gly Thr Val Ala Val Thr Tyr Gln His
                85                  90                  95

Ile Ile Thr Ala Leu Pro Glu Ala Thr His Glu Asp Ile Val Gly Val
            100                 105                 110

Gly Lys Gln Trp Ser Gly Ala Arg Ala Leu Glu Ala Leu Leu Thr Asp
        115                 120                 125

Ala Gly Glu Leu Arg Gly Pro Pro Leu Gln Leu Asp Thr Gly Gln Leu
    130                 135                 140

Val Lys Ile Ala Lys Arg Gly Gly Val Thr Ala Met Glu Ala Val His
145                 150                 155                 160

Ala Ser Arg Asn Ala Leu Thr Gly Ala Pro Leu Asn Leu Thr Pro Asp
                165                 170                 175

Gln Val Val Ala Ile Ala Ser His Asp Gly Gly Lys Gln Ala Leu Glu
            180                 185                 190

Thr Val Gln Arg Leu Leu Pro Val Leu Cys Gln Asp His Gly Leu Thr
        195                 200                 205

Pro Asp Gln Val Val Ala Ile Ala Ser Asn Gly Gly Gly Lys Gln Ala
    210                 215                 220

Leu Glu Thr Val Gln Arg Leu Leu Pro Val Leu Cys Gln Asp His Gly
225                 230                 235                 240

Leu Thr Pro Asp Gln Val Val Ala Ile Ala Ser Asn Asn Gly Gly Lys
                245                 250                 255

Gln Ala Leu Glu Thr Val Gln Arg Leu Leu Pro Val Leu Cys Gln Asp
            260                 265                 270

His Gly Leu Thr Pro Asp Gln Val Val Ala Ile Ala Ser His Asp Gly
        275                 280                 285

Gly Lys Gln Ala Leu Glu Thr Val Gln Arg Leu Leu Pro Val Leu Cys
    290                 295                 300

Gln Asp His Gly Leu Thr Pro Asp Gln Val Val Ala Ile Ala Ser Asn
305                 310                 315                 320

Ile Gly Gly Lys Gln Ala Leu Glu Thr Val Gln Arg Leu Leu Pro Val
                325                 330                 335

Leu Cys Gln Asp His Gly Leu Thr Pro Asp Gln Val Val Ala Ile Ala
            340                 345                 350

Ser Asn Gly Gly Gly Lys Gln Ala Leu Glu Thr Val Gln Arg Leu Leu
        355                 360                 365

-continued

```
Pro Val Leu Cys Gln Asp His Gly Leu Thr Pro Asp Gln Val Val Ala
    370                 375                 380
Ile Ala Ser Asn Gly Gly Gly Lys Gln Ala Leu Glu Thr Val Gln Arg
385                 390                 395                 400
Leu Leu Pro Val Leu Cys Gln Asp His Gly Leu Thr Pro Asp Gln Val
                405                 410                 415
Val Ala Ile Ala Ser Asn Gly Gly Gly Lys Gln Ala Leu Glu Thr Val
            420                 425                 430
Gln Arg Leu Leu Pro Val Leu Cys Gln Asp His Gly Leu Thr Pro Asp
        435                 440                 445
Gln Val Val Ala Ile Ala Ser Asn Ile Gly Gly Lys Gln Ala Leu Glu
    450                 455                 460
Thr Val Gln Arg Leu Leu Pro Val Leu Cys Gln Asp His Gly Leu Thr
465                 470                 475                 480
Pro Asp Gln Val Val Ala Ile Ala Ser Asn Asn Gly Gly Lys Gln Ala
                485                 490                 495
Leu Glu Thr Val Gln Arg Leu Leu Pro Val Leu Cys Gln Asp His Gly
            500                 505                 510
Leu Thr Pro Asp Gln Val Val Ala Ile Ala Ser Asn Asn Gly Gly Lys
        515                 520                 525
Gln Ala Leu Glu Thr Val Gln Arg Leu Leu Pro Val Leu Cys Gln Asp
    530                 535                 540
His Gly Leu Thr Pro Asp Gln Val Val Ala Ile Ala Ser Asn Asn Gly
545                 550                 555                 560
Gly Lys Gln Ala Leu Glu Thr Val Gln Arg Leu Leu Pro Val Leu Cys
                565                 570                 575
Gln Asp His Gly Leu Thr Pro Asp Gln Val Val Ala Ile Ala Ser Asn
            580                 585                 590
Ile Gly Gly Lys Gln Ala Leu Glu Thr Val Gln Arg Leu Leu Pro Val
        595                 600                 605
Leu Cys Gln Asp His Gly Leu Thr Pro Asp Gln Val Val Ala Ile Ala
    610                 615                 620
Ser Asn Gly Gly Gly Lys Gln Ala Leu Glu Thr Val Gln Arg Leu Leu
625                 630                 635                 640
Pro Val Leu Cys Gln Asp His Gly Leu Thr Pro Asp Gln Val Val Ala
                645                 650                 655
Ile Ala Ser Asn Gly Gly Gly Lys Gln Ala Leu Glu Thr Val Gln Arg
            660                 665                 670
Leu Leu Pro Val Leu Cys Gln Asp His Gly Leu Thr Pro Asp Gln Val
        675                 680                 685
Val Ala Ile Ala Ser His Asp Gly Gly Lys Gln Ala Leu Glu Thr Val
    690                 695                 700
Gln Arg Leu Leu Pro Val Leu Cys Gln Asp His Gly Leu Thr Pro Asp
705                 710                 715                 720
Gln Val Val Ala Ile Ala Ser Asn Gly Gly Lys Gln Ala Leu Glu
                725                 730                 735
Ser Ile Val Ala Gln Leu Ser Arg Pro Asp Pro Ala Leu Ala Ala Leu
            740                 745                 750
Thr Asn Asp His Leu Val Ala Leu Ala Cys Leu Gly Gly Arg Pro
        755                 760                 765
Ala Met Asp Ala Val Lys Lys Gly Leu Pro His Ala Pro Glu Leu Ile
    770                 775                 780
```

```
Arg Arg Val Asn Arg Arg Ile Gly Glu Arg Thr Ser His Arg Val Ala
785                 790                 795                 800

Gly Ser Lys Ala Ser Pro Lys Lys Lys Arg Lys Val Gly Arg Ala Asp
            805                 810                 815

Ala Leu Asp Asp Phe Asp Leu Asp Met Leu Gly Ser Asp Ala Leu Asp
            820                 825                 830

Asp Phe Asp Leu Asp Met Leu Gly Ser Asp Ala Leu Asp Asp Phe Asp
        835                 840                 845

Leu Asp Met Leu Gly Ser Asp Ala Leu Asp Asp Phe Asp Leu Asp Met
    850                 855                 860

Leu Ile Asn Tyr Pro Tyr Asp Val Pro Asp Tyr Ala Ser
865                 870                 875

<210> SEQ ID NO 95
<211> LENGTH: 2838
<212> TYPE: DNA
<213> ORGANISM: Artificial sequence
<220> FEATURE:
<223> OTHER INFORMATION: Synthetic oligonucleotide

<400> SEQUENCE: 95
```

| | | | | | |
|---|---|---|---|---|---|
| atggactaca | aagaccatga | cggtgattat | aaagatcatg | acatcgatta | caaggatgac | 60 |
| gatgacaaga | tggcccccaa | gaagaagagg | aaggtgggcc | gcggatctgt | ggatctacgc | 120 |
| acgctcggct | acagtcagca | gcagcaagag | aagatcaaac | cgaaggtgcg | ttcgacagtg | 180 |
| gcgcagcacc | acgaggcact | ggtgggccat | gggtttacac | acgcgcacat | cgttgcgctc | 240 |
| agccaacacc | cggcagcgtt | agggaccgtc | gctgtcacgt | atcagcacat | aatcacggcg | 300 |
| ttgccagagg | cgacacacga | agacatcgtt | ggcgtcggca | acagtggtc | cggcgcacgc | 360 |
| gccctggagg | ccttgctcac | ggatgcgggg | gagttgagag | gtccgccgtt | acagttggac | 420 |
| acaggccaac | ttgtgaagat | tgcaaaacgt | ggcggcgtga | ccgcaatgga | ggcagtgcat | 480 |
| gcatcgcgca | atgcactgac | gggtgccccc | ctgaacctga | ccccggacca | agtggtggct | 540 |
| atcgccagcc | acgatggcgg | caagcaagcg | ctcgaaacgg | tgcagcggct | gttgccggtg | 600 |
| ctgtgccagg | accatggcct | gacccccgac | caagtggtgg | ctatcgccag | ccacgatggc | 660 |
| ggcaagcaag | cgctcgaaac | ggtgcagcgg | ctgttgccgg | tgctgtgcca | ggaccatggc | 720 |
| ctgacccccg | accaagtggt | ggctatcgcc | agccacgatg | gcggcaagca | agcgctcgaa | 780 |
| acggtgcagc | ggctgttgcc | ggtgctgtgc | caggaccatg | gcctgacccc | ggaccaagtg | 840 |
| gtggctatcg | ccagccacga | tggcggcaag | caagcgctcg | aaacggtgca | gcggctgttg | 900 |
| ccggtgctgt | gccaggacca | tggcctgacc | ccggaccaag | tggtggctat | cgccagcaac | 960 |
| attgcggca | agcaagcgct | cgaaacggtg | cagcggctgt | tgccggtgct | gtgccaggac | 1020 |
| catggcctga | ccccggacca | agtggtggct | atcgccagca | caatggcgg | caagcaagcg | 1080 |
| ctcgaaacgg | tgcagcggct | gttgccggtg | ctgtgccagg | accatggcct | gaccccggac | 1140 |
| caagtggtgg | ctatcgccag | caacaatggc | ggcaagcaag | cgctcgaaac | ggtgcagcgg | 1200 |
| ctgttgccgg | tgctgtgcca | ggaccatggc | ctgacccggg | accaagtggt | ggctatcgcc | 1260 |
| agcaacattg | cggcaagca | agcgctcgaa | acggtgcagc | ggctgttgcc | ggtgctgtgc | 1320 |
| caggaccatg | gcctgacccc | ggaccaagtg | gtggctatcg | ccagcaacat | ggcggcaag | 1380 |
| caagcgctcg | aaacggtgca | gcggctgttg | ccggtgctgt | gccaggacca | tggcctgacc | 1440 |
| ccggaccaag | tggtggctat | cgccagcaac | attgcggca | agcaagcgct | cgaaacggtg | 1500 |
| cagcggctgt | tgccggtgct | gtgccaggac | catggcctga | ccccggacca | agtggtggct | 1560 |

```
atcgccagca acaatggcgg caagcaagcg ctcgaaacgg tgcagcggct gttgccggtg    1620
ctgtgccagg accatggcct gaccccggac caagtggtgg ctatcgccag caacggtggc    1680
ggcaagcaag cgctcgaaac ggtgcagcgg ctgttgccgg tgctgtgcca ggaccatggc    1740
ctgaccccgg accaagtggt ggctatcgcc agcaacggtg gcggcaagca agcgctcgaa    1800
acggtgcagc ggctgttgcc ggtgctgtgc caggaccatg gcctgacccc ggaccaagtg    1860
gtggctatcg ccagcaacgg tggcggcaag caagcgctcg aaacggtgca gcggctgttg    1920
ccggtgctgt gccaggacca tggcctgacc ccggaccaag tggtggctat cgccagcaac    1980
attggcggca agcaagcgct cgaaacggtg cagcggctgt gccggtgct gtgccaggac    2040 catggcctga ccccggacca agtggtggct atcgccagca acattggcgg caagcaagcg    2100
ctcgaaacgg tgcagcggct gttgccggtg ctgtgccagg accatggcct gaccccggac    2160
caagtggtgg ctatcgccag caacaatggc ggcaagcaag cgctcgaaac ggtgcagcgg    2220
ctgttgccgg tgctgtgcca ggaccatggc ctgaccccgg accaagtggt ggctatcgcc    2280
agcaacattg gcggcaagca agcgctcgaa acggtgcagc ggctgttgcc ggtgctgtgc    2340
caggaccatg gcctgacccc ggaccaagtg gtggctatcg ccagcaacgg tggcggcaag    2400
caagcgctcg aaagcattgt ggcccagctg agccggcctg atccggcgtt ggccgcgttg    2460
accaacgacg accacctcgt cgccttggcc tgcctcggcg acgtcctgc catggatgca    2520 gtgaaaaagg gattgccgca cgcgccggaa ttgatcagaa gagtcaatcg ccgtattggc    2580
gaacgcacgt cccatcgcgt tgccggatcc aaggctagcc cgaaaaagaa acgcaaagtt    2640
gggcgcgccg acgcgctgga cgatttcgat ctcgacatgc tgggttctga tgccctcgat    2700
gactttgacc tggatatgtt gggaagcgac gcattggatg actttgatct ggacatgctc    2760
ggctccgatg ctctggacga tttcgatctc gatatgttaa ttaactaccc gtacgacgtt    2820
ccggactacg cttcttga                                                 2838
```

<210> SEQ ID NO 96
<211> LENGTH: 945
<212> TYPE: PRT
<213> ORGANISM: Unknown
<220> FEATURE:
<223> OTHER INFORMATION: Synthetic peptide

<400> SEQUENCE: 96

```
Met Asp Tyr Lys Asp His Asp Gly Asp Tyr Lys Asp His Asp Ile Asp
1               5                   10                  15

Tyr Lys Asp Asp Asp Lys Met Ala Pro Lys Lys Arg Lys Val
            20                  25                  30

Gly Arg Gly Ser Val Asp Leu Arg Thr Leu Gly Tyr Ser Gln Gln Gln
        35                  40                  45

Gln Glu Lys Ile Lys Pro Lys Val Arg Ser Thr Val Ala Gln His His
    50                  55                  60

Glu Ala Leu Val Gly His Gly Phe Thr His Ala His Ile Val Ala Leu
65                  70                  75                  80

Ser Gln His Pro Ala Ala Leu Gly Thr Val Ala Val Thr Tyr Gln His
                85                  90                  95

Ile Ile Thr Ala Leu Pro Glu Ala Thr His Glu Asp Ile Val Gly Val
            100                 105                 110

Gly Lys Gln Trp Ser Gly Ala Arg Ala Leu Glu Ala Leu Leu Thr Asp
        115                 120                 125
```

```
Ala Gly Glu Leu Arg Gly Pro Pro Leu Gln Leu Asp Thr Gly Gln Leu
130                 135                 140

Val Lys Ile Ala Lys Arg Gly Val Thr Ala Met Glu Ala Val His
145                 150                 155                 160

Ala Ser Arg Asn Ala Leu Thr Gly Ala Pro Leu Asn Leu Thr Pro Asp
            165                 170                 175

Gln Val Val Ala Ile Ala Ser His Asp Gly Lys Gln Ala Leu Glu
        180                 185                 190

Thr Val Gln Arg Leu Leu Pro Val Leu Cys Gln Asp His Gly Leu Thr
        195                 200                 205

Pro Asp Gln Val Val Ala Ile Ala Ser His Asp Gly Gly Lys Gln Ala
210                 215                 220

Leu Glu Thr Val Gln Arg Leu Leu Pro Val Leu Cys Gln Asp His Gly
225                 230                 235                 240

Leu Thr Pro Asp Gln Val Val Ala Ile Ala Ser His Asp Gly Gly Lys
            245                 250                 255

Gln Ala Leu Glu Thr Val Gln Arg Leu Leu Pro Val Leu Cys Gln Asp
        260                 265                 270

His Gly Leu Thr Pro Asp Gln Val Val Ala Ile Ala Ser His Asp Gly
275                 280                 285

Gly Lys Gln Ala Leu Glu Thr Val Gln Arg Leu Leu Pro Val Leu Cys
290                 295                 300

Gln Asp His Gly Leu Thr Pro Asp Gln Val Val Ala Ile Ala Ser Asn
305                 310                 315                 320

Ile Gly Gly Lys Gln Ala Leu Glu Thr Val Gln Arg Leu Leu Pro Val
            325                 330                 335

Leu Cys Gln Asp His Gly Leu Thr Pro Asp Gln Val Val Ala Ile Ala
        340                 345                 350

Ser Asn Asn Gly Gly Lys Gln Ala Leu Glu Thr Val Gln Arg Leu Leu
        355                 360                 365

Pro Val Leu Cys Gln Asp His Gly Leu Thr Pro Asp Gln Val Val Ala
370                 375                 380

Ile Ala Ser Asn Asn Gly Gly Lys Gln Ala Leu Glu Thr Val Gln Arg
385                 390                 395                 400

Leu Leu Pro Val Leu Cys Gln Asp His Gly Leu Thr Pro Asp Gln Val
            405                 410                 415

Val Ala Ile Ala Ser Asn Ile Gly Gly Lys Gln Ala Leu Glu Thr Val
        420                 425                 430

Gln Arg Leu Leu Pro Val Leu Cys Gln Asp His Gly Leu Thr Pro Asp
        435                 440                 445

Gln Val Val Ala Ile Ala Ser Asn Ile Gly Gly Lys Gln Ala Leu Glu
        450                 455                 460

Thr Val Gln Arg Leu Leu Pro Val Leu Cys Gln Asp His Gly Leu Thr
465                 470                 475                 480

Pro Asp Gln Val Val Ala Ile Ala Ser Asn Ile Gly Gly Lys Gln Ala
            485                 490                 495

Leu Glu Thr Val Gln Arg Leu Leu Pro Val Leu Cys Gln Asp His Gly
        500                 505                 510

Leu Thr Pro Asp Gln Val Val Ala Ile Ala Ser Asn Asn Gly Gly Lys
        515                 520                 525

Gln Ala Leu Glu Thr Val Gln Arg Leu Leu Pro Val Leu Cys Gln Asp
530                 535                 540
```

-continued

His Gly Leu Thr Pro Asp Gln Val Val Ala Ile Ala Ser Asn Gly Gly
545                 550                 555                 560

Gly Lys Gln Ala Leu Glu Thr Val Gln Arg Leu Leu Pro Val Leu Cys
            565                 570                 575

Gln Asp His Gly Leu Thr Pro Asp Gln Val Val Ala Ile Ala Ser Asn
        580                 585                 590

Gly Gly Gly Lys Gln Ala Leu Glu Thr Val Gln Arg Leu Leu Pro Val
    595                 600                 605

Leu Cys Gln Asp His Gly Leu Thr Pro Asp Gln Val Val Ala Ile Ala
610                 615                 620

Ser Asn Gly Gly Gly Lys Gln Ala Leu Glu Thr Val Gln Arg Leu Leu
625                 630                 635                 640

Pro Val Leu Cys Gln Asp His Gly Leu Thr Pro Asp Gln Val Val Ala
            645                 650                 655

Ile Ala Ser Asn Ile Gly Gly Lys Gln Ala Leu Glu Thr Val Gln Arg
        660                 665                 670

Leu Leu Pro Val Leu Cys Gln Asp His Gly Leu Thr Pro Asp Gln Val
    675                 680                 685

Val Ala Ile Ala Ser Asn Ile Gly Gly Lys Gln Ala Leu Glu Thr Val
690                 695                 700

Gln Arg Leu Leu Pro Val Leu Cys Gln Asp His Gly Leu Thr Pro Asp
705                 710                 715                 720

Gln Val Val Ala Ile Ala Ser Asn Asn Gly Gly Lys Gln Ala Leu Glu
            725                 730                 735

Thr Val Gln Arg Leu Leu Pro Val Leu Cys Gln Asp His Gly Leu Thr
        740                 745                 750

Pro Asp Gln Val Val Ala Ile Ala Ser Asn Ile Gly Gly Lys Gln Ala
    755                 760                 765

Leu Glu Thr Val Gln Arg Leu Leu Pro Val Leu Cys Gln Asp His Gly
770                 775                 780

Leu Thr Pro Asp Gln Val Val Ala Ile Ala Ser Asn Gly Gly Gly Lys
785                 790                 795                 800

Gln Ala Leu Glu Ser Ile Val Ala Gln Leu Ser Arg Pro Asp Pro Ala
            805                 810                 815

Leu Ala Ala Leu Thr Asn Asp His Leu Val Ala Leu Ala Cys Leu
        820                 825                 830

Gly Gly Arg Pro Ala Met Asp Ala Val Lys Lys Gly Leu Pro His Ala
    835                 840                 845

Pro Glu Leu Ile Arg Arg Val Asn Arg Arg Ile Gly Glu Arg Thr Ser
850                 855                 860

His Arg Val Ala Gly Ser Lys Ala Ser Pro Lys Lys Arg Lys Val
865                 870                 875                 880

Gly Arg Ala Asp Ala Leu Asp Asp Phe Asp Leu Asp Met Leu Gly Ser
            885                 890                 895

Asp Ala Leu Asp Asp Phe Asp Leu Asp Met Leu Gly Ser Asp Ala Leu
        900                 905                 910

Asp Asp Phe Asp Leu Asp Met Leu Gly Ser Asp Ala Leu Asp Asp Phe
    915                 920                 925

Asp Leu Asp Met Leu Ile Asn Tyr Pro Tyr Asp Val Pro Asp Tyr Ala
930                 935                 940

Ser
945

<210> SEQ ID NO 97
<211> LENGTH: 2634
<212> TYPE: DNA
<213> ORGANISM: Artificial sequence
<220> FEATURE:
<223> OTHER INFORMATION: Synthetic oligonucleotide

<400> SEQUENCE: 97

```
atggactaca aagaccatga cggtgattat aaagatcatg acatcgatta caaggatgac      60
gatgacaaga tggccccccaa gaagaagagg aaggtgggcc gcggatctgt ggatctacgc    120
acgctcggct acagtcagca gcagcaagag aagatcaaac cgaaggtgcg ttcgacagtg    180
gcgcagcacc acgaggcact ggtgggccat gggtttacac acgcgcacat cgttgcgctc    240
agccaacacc cggcagcgtt agggaccgtc gctgtcacgt atcagcacat aatcacggcg    300
ttgccagagg cgacacacga agacatcgtt ggcgtcggca acagtggtc cggcgcacgc    360
gccctggagg ccttgctcac ggatgcgggg gagttgagag gtccgccgtt acagttggac    420
acaggccaac ttgtgaagat tgcaaaacgt ggcggcgtga ccgcaatgga ggcagtgcat    480
gcatcgcgca atgcactgac gggtgccccc ctgaacctga ccccggacca agtggtggct    540
atcgccagcc acgatggcgg caagcaagcg ctcgaaacgg tgcagcggct gttgccggtg    600
ctgtgccagg accatggcct gaccccggac caagtggtgg ctatcgccag caacaatggc    660
ggcaagcaag cgctcgaaac ggtgcagcgg ctgttgccgg tgctgtgcca ggaccatggc    720
ctgaccccgg accaagtggt ggctatcgcc agcaacattg gcggcaagca agcgctcgaa    780
acggtgcagc ggctgttgcc ggtgctgtgc caggaccatg gcctgacccc ggaccaagtg    840
gtggctatcg ccagcaacgg tggcggcaag caagcgctcg aaacggtgca gcggctgttg    900
ccggtgctgt gccaggacca tggcctgacc ccggaccaag tggtggctat cgccagcaac    960
aatggcggca agcaagcgct cgaaacggtg cagcggctgt tgccggtgct gtgccaggac   1020
catggcctga ccccggacca agtggtggct atcgccagca acggtggcgg caagcaagcg   1080
ctcgaaacgg tgcagcggct gttgccggtg ctgtgccagg accatggcct gaccccggac   1140
caagtggtgg ctatcgccag caacaatggc ggcaagcaag cgctcgaaac ggtgcagcgg   1200
ctgttgccgg tgctgtgcca ggaccatggc ctgaccccgg accaagtggt ggctatcgcc   1260
agcaacattg gcggcaagca agcgctcgaa acggtgcagc ggctgttgcc ggtgctgtgc   1320
caggaccatg gcctgacccc ggaccaagtg gtggctatcg ccagccacga tggcggcaag   1380
caagcgctcg aaacggtgca gcggctgttg ccggtgctgt gccaggacca tggcctgacc   1440
ccggaccaag tggtggctat cgccagcaac ggtggcggca agcaagcgct cgaaacggtg   1500
cagcggctgt tgccggtgct gtgccaggac catggcctga ccccggacca agtggtggct   1560
atcgccagca acaatggcgg caagcaagcg ctcgaaacgg tgcagcggct gttgccggtg   1620
ctgtgccagg accatggcct gaccccggac caagtggtgg ctatcgccag caacggtggc   1680
ggcaagcaag cgctcgaaac ggtgcagcgg ctgttgccgg tgctgtgcca ggaccatggc   1740
ctgaccccgg accaagtggt ggctatcgcc agccacgatg gcggcaagca agcgctcgaa   1800
acggtgcagc ggctgttgcc ggtgctgtgc caggaccatg gcctgacccc ggaccaagtg   1860
gtggctatcg ccagcaacgg tggcggcaag caagcgctcg aaacggtgca gcggctgttg   1920
ccggtgctgt gccaggacca tggcctgacc ccggaccaag tggtggctat cgccagccac   1980
gatggcggca agcaagcgct cgaaacggtg cagcggctgt tgccggtgct gtgccaggac   2040
catggcctga ccccggacca agtggtggct atcgccagcc acgatggcgg caagcaagcg   2100
```

```
ctcgaaacgg tgcagcggct gttgccggtg ctgtgccagg accatggcct gaccccggac    2160
caagtggtgg ctatcgccag caacggtggc ggcaagcaag cgctcgaaag cattgtggcc    2220
cagctgagcc ggcctgatcc ggcgttggcc gcgttgacca acgacgacca cctcgtcgcc    2280
ttggcctgcc tcggcggacg tcctgccatg gatgcagtga aaaagggatt gccgcacgcg    2340
ccggaattga tcagaagagt caatcgccgt attggcgaac gcacgtccca tcgcgttgcc    2400
ggatccaagg ctagcccgaa aaagaaacgc aaagttgggc gcgccgacgc gctggacgat    2460
ttcgatctcg acatgctggg ttctgatgcc ctcgatgact ttgacctgga tatgttggga    2520
agcgacgcat ggatgacttt gatctggac atgctcggct ccgatgctct ggacgatttc    2580
gatctcgata tgttaattaa ctacccgtac gacgttccgg actacgcttc ttga          2634
```

<210> SEQ ID NO 98
<211> LENGTH: 877
<212> TYPE: PRT
<213> ORGANISM: Unknown
<220> FEATURE:
<223> OTHER INFORMATION: Synthetic peptide

<400> SEQUENCE: 98

```
Met Asp Tyr Lys Asp His Asp Gly Asp Tyr Lys Asp His Asp Ile Asp
1               5                   10                  15

Tyr Lys Asp Asp Asp Asp Lys Met Ala Pro Lys Lys Arg Lys Val
            20                  25                  30

Gly Arg Gly Ser Val Asp Leu Arg Thr Leu Gly Tyr Ser Gln Gln Gln
        35                  40                  45

Gln Glu Lys Ile Lys Pro Lys Val Arg Ser Thr Val Ala Gln His His
    50                  55                  60

Glu Ala Leu Val Gly His Gly Phe Thr His Ala His Ile Val Ala Leu
65                  70                  75                  80

Ser Gln His Pro Ala Ala Leu Gly Thr Val Ala Val Thr Tyr Gln His
                85                  90                  95

Ile Ile Thr Ala Leu Pro Glu Ala Thr His Glu Asp Ile Val Gly Val
            100                 105                 110

Gly Lys Gln Trp Ser Gly Ala Arg Ala Leu Glu Ala Leu Leu Thr Asp
        115                 120                 125

Ala Gly Glu Leu Arg Gly Pro Pro Leu Gln Leu Asp Thr Gly Gln Leu
    130                 135                 140

Val Lys Ile Ala Lys Arg Gly Gly Val Thr Ala Met Glu Ala Val His
145                 150                 155                 160

Ala Ser Arg Asn Ala Leu Thr Gly Ala Pro Leu Asn Leu Thr Pro Asp
                165                 170                 175

Gln Val Val Ala Ile Ala Ser His Asp Gly Gly Lys Gln Ala Leu Glu
            180                 185                 190

Thr Val Gln Arg Leu Leu Pro Val Leu Cys Gln Asp His Gly Leu Thr
        195                 200                 205

Pro Asp Gln Val Val Ala Ile Ala Ser Asn Asn Gly Gly Lys Gln Ala
    210                 215                 220

Leu Glu Thr Val Gln Arg Leu Leu Pro Val Leu Cys Gln Asp His Gly
225                 230                 235                 240

Leu Thr Pro Asp Gln Val Val Ala Ile Ala Ser Asn Ile Gly Gly Lys
                245                 250                 255

Gln Ala Leu Glu Thr Val Gln Arg Leu Leu Pro Val Leu Cys Gln Asp
            260                 265                 270
```

```
His Gly Leu Thr Pro Asp Gln Val Ala Ile Ala Ser Asn Gly Gly
            275                 280                 285

Gly Lys Gln Ala Leu Glu Thr Val Gln Arg Leu Leu Pro Val Cys
        290                 295                 300

Gln Asp His Gly Leu Thr Pro Asp Gln Val Val Ala Ile Ala Ser Asn
305                 310                 315                 320

Asn Gly Gly Lys Gln Ala Leu Glu Thr Val Gln Arg Leu Leu Pro Val
                325                 330                 335

Leu Cys Gln Asp His Gly Leu Thr Pro Asp Gln Val Val Ala Ile Ala
                340                 345                 350

Ser Asn Gly Gly Lys Gln Ala Leu Glu Thr Val Gln Arg Leu Leu
        355                 360                 365

Pro Val Leu Cys Gln Asp His Gly Leu Thr Pro Asp Gln Val Val Ala
        370                 375                 380

Ile Ala Ser Asn Asn Gly Gly Lys Gln Ala Leu Glu Thr Val Gln Arg
385                 390                 395                 400

Leu Leu Pro Val Leu Cys Gln Asp His Gly Leu Thr Pro Asp Gln Val
                405                 410                 415

Val Ala Ile Ala Ser Asn Ile Gly Gly Lys Gln Ala Leu Glu Thr Val
                420                 425                 430

Gln Arg Leu Leu Pro Val Leu Cys Gln Asp His Gly Leu Thr Pro Asp
        435                 440                 445

Gln Val Val Ala Ile Ala Ser His Asp Gly Gly Lys Gln Ala Leu Glu
        450                 455                 460

Thr Val Gln Arg Leu Leu Pro Val Leu Cys Gln Asp His Gly Leu Thr
465                 470                 475                 480

Pro Asp Gln Val Val Ala Ile Ala Ser Asn Gly Gly Lys Gln Ala
                485                 490                 495

Leu Glu Thr Val Gln Arg Leu Leu Pro Val Leu Cys Gln Asp His Gly
                500                 505                 510

Leu Thr Pro Asp Gln Val Val Ala Ile Ala Ser Asn Asn Gly Gly Lys
        515                 520                 525

Gln Ala Leu Glu Thr Val Gln Arg Leu Leu Pro Val Leu Cys Gln Asp
        530                 535                 540

His Gly Leu Thr Pro Asp Gln Val Val Ala Ile Ala Ser Asn Gly Gly
545                 550                 555                 560

Gly Lys Gln Ala Leu Glu Thr Val Gln Arg Leu Leu Pro Val Leu Cys
                565                 570                 575

Gln Asp His Gly Leu Thr Pro Asp Gln Val Val Ala Ile Ala Ser His
                580                 585                 590

Asp Gly Gly Lys Gln Ala Leu Glu Thr Val Gln Arg Leu Leu Pro Val
        595                 600                 605

Leu Cys Gln Asp His Gly Leu Thr Pro Asp Gln Val Val Ala Ile Ala
        610                 615                 620

Ser Asn Gly Gly Gly Lys Gln Ala Leu Glu Thr Val Gln Arg Leu Leu
625                 630                 635                 640

Pro Val Leu Cys Gln Asp His Gly Leu Thr Pro Asp Gln Val Val Ala
                645                 650                 655

Ile Ala Ser His Asp Gly Gly Lys Gln Ala Leu Glu Thr Val Gln Arg
                660                 665                 670

Leu Leu Pro Val Leu Cys Gln Asp His Gly Leu Thr Pro Asp Gln Val
        675                 680                 685
```

-continued

```
Val Ala Ile Ala Ser His Asp Gly Gly Lys Gln Ala Leu Glu Thr Val
    690             695                 700
Gln Arg Leu Leu Pro Val Leu Cys Gln Asp His Gly Leu Thr Pro Asp
705             710                 715                 720
Gln Val Val Ala Ile Ala Ser Asn Gly Gly Gly Lys Gln Ala Leu Glu
                725                 730                 735
Ser Ile Val Ala Gln Leu Ser Arg Pro Asp Pro Ala Leu Ala Ala Leu
                740             745                 750
Thr Asn Asp His Leu Val Ala Leu Ala Cys Leu Gly Gly Arg Pro
        755                 760                 765
Ala Met Asp Ala Val Lys Lys Gly Leu Pro His Ala Pro Glu Leu Ile
        770                 775                 780
Arg Arg Val Asn Arg Arg Ile Gly Glu Arg Thr Ser His Arg Val Ala
785                 790                 795                 800
Gly Ser Lys Ala Ser Pro Lys Lys Lys Arg Lys Val Gly Arg Ala Asp
                805                 810                 815
Ala Leu Asp Asp Phe Asp Leu Asp Met Leu Gly Ser Asp Ala Leu Asp
            820                 825                 830
Asp Phe Asp Leu Asp Met Leu Gly Ser Asp Ala Leu Asp Asp Phe Asp
        835                 840                 845
Leu Asp Met Leu Gly Ser Asp Ala Leu Asp Asp Phe Asp Leu Asp Met
    850                 855                 860
Leu Ile Asn Tyr Pro Tyr Asp Val Pro Asp Tyr Ala Ser
865                 870                 875
```

COMPOSITIONS AND METHODS FOR THE INDUCTION AND TUNING OF GENE EXPRESSION

CROSS-REFERENCE TO RELATED APPLICATION

This application claims priority to U.S. Provisional Application No. 61/803,254, filed Mar. 19, 2013, which is incorporated herein by reference in its entirety.

STATEMENT OF GOVERNMENT INTEREST

This invention was made with government support under federal grant number DP2OD008586 awarded by the National Institutes of Health and CBET-1151035 awarded by the National Science Foundation. The U.S. Government has certain rights to this invention.

SEQUENCE LISTING

The sequence listing is filed with the application in electronic format only and is incorporated by reference herein. The sequence listing text file "028193-9177-US01 As Filed Sequence List" was created on Jun. 5, 2014 and is 322,213 bytes in size.

TECHNICAL FIELD

The present disclosure relates to the field of inducing mammalian gene expression using combinations of engineered transcription activator-like effectors transcription factors (TALE-TFs).

BACKGROUND

Synthetic biology aims to study the control of gene expression by constructing gene regulation systems from the "bottom-up" in order to better understand natural biological systems and develop useful tools for biotechnology. Despite many significant accomplishments, this field has largely been limited to studying artificial promoter transgene systems with one or two transactivators, typically in microorganisms. In contrast, the natural regulation of mammalian gene expression is extraordinarily complex. This level of complexity has not yet been achieved in synthetic gene regulation systems and has not been possible for the regulation of endogenous genes.

Several TALE-TFs have recently been reported to regulate native mammalian gene expression. However, the recent emergence of technologies for engineering transcription activator-like effectors (TALEs) targeted to almost any DNA sequence provides a unique opportunity for recapitulating this natural complexity. However, the levels of gene activation in these studies were modest and several genes could not be induced (Table 1). Therefore there is clear need for improvements to gene activation strategies that capitalize on the synthetic TALE-TF technology.

TABLE 1

Published TALE-TFs Targeting Human Genes.

| Reference | Gene | Activation Domain | Assay | Fold-Increase |
|---|---|---|---|---|
| Zhang et al., Nature Biotechnology (2011) | SOX2 | VP64 | qRT-PCR | 5.5 |
| | KLF4 | VP64 | qRT-PCR | 2.2 |
| | MYC | VP64 | qRT-PCR | n.d. |
| | OCT4 | VP64 | qRT-PCR | n.d. |
| Miller et al., Nature Biotechnology (2011) | NTF3 | VP16 | qRT-PCR | 30 |
| Geissler et al., PLoS One (2011) | PUMA | VP16 | qRT-PCR | 1.5 |
| | IFNA1 | VP16 | qRT-PCR | 3 |
| | IFNB1 | VP16 | qRT-PCR | 3.5 |
| Bultmann et al., Nucleic Acids Research (2012) | OCT4 | VP16 | qRT-PCR | n.d.[1] |
| Cong et al., Nature Communications (2012) | CACNA1C | VP64 | qRT-PCR | 3-5 |
| Tremblay et al., Human Gene Therapy (2012) | FXN | VP64 | qRT-PCR | 1.1-3.1 |
| Garg et al., Nucleic Acids Research (2012) | OSGIN2 | VP64 | qRT-PCR | 4.8 |
| | ZC3H10 | VP64 | qRT-PCR | 1.3 | n.d. = not detected
[1] undetectable in control, induced only with chromatin-modifying drugs

SUMMARY

The present invention is directed to a method of modulating mammalian gene expression in a cell. The method comprises contacting the cell with two or more transcription activator-like effector transcription factors (TALE-TFs) that bind to a target gene. The method further comprises contacting the cell with a chromatin modifying drug. The TALE-TFs may bind to different target regions within the target gene. The target regions may be separated by at least one nucleotide. The target regions may be separated by about 15 to about 700 base pairs. At least one target region may be within a non-open chromatin region. At least one target region may be within an open chromatin region. At least one target region may be within the promoter region of the target gene. At least one target region may be within the enhancer region of the target gene. At least one target region may be within the transcribed region of the target gene. At least one target region may be within a region upstream of the transcription start site of the target gene. At least one target region may be located between about 1 to about 1000 base pairs upstream of the transcription start site of the target gene. At least one target region may be located between about 1 to about 600 base pairs upstream of the transcription start site of the target gene. The target regions may be within a region upstream of the transcription start site of the target gene. The gene expression may be induced. The TALE-TFs may each comprise a transcription activation domain. The TALE-TFs may comprise the same transcription activation domain. The TALE-TFs may comprise different transcription activation domains. The transcription activation domain may comprise at least one VP16 transcription activation domain repeat. The transcription activation domain comprises at least one of VP16 transcription activation domain repeat, VP64 transcription activation domain, p65 transcription activation domain, or combinations thereof. The TALE-TFs may each comprise about 15 to about 19 RVD modules. Between about two to about ten TALE-TFs may be used. Three TALE-TFs may be used. Four TALE-TFs may be used. Five TALE-TFs may be used. Six TALE-TFs may be used. The TALE-TFs may binds to a nucleotide sequence comprising one of SEQ ID NOs: 1-29, or the complement thereof. The TALE-TFs may comprise an amino acid sequence selected from the group consisting of SEQ ID NOs: 44, 46, 48, 50, 52, 54, 56, 58, 60, 62, 64, 66, 68, 70, 72, 74, 76, 78, 80, 82, 84, 86, 88, 90, 92, 94, 96, or 98, or variants thereof. The TALE-TFs may be encoded by a polynucleotide sequence selected from the group consisting of SEQ ID NOs: 43, 45, 47, 49, 51, 53, 55, 57, 59, 61, 63, 65, 67, 69, 71, 73, 75, 77, 79, 81, 83, 85, 87, 89, 91, 93, 95, or 97, or variants thereof. The target gene may be IL1RN, KLK3, CEACAM5, and ERBB2.

The present invention is directed to a method of modulating mammalian gene expression in a cell without the use of chromatin modifying drug. The method comprises contacting the cell with two or more transcription activator-like effector transcription factors (TALE-TFs) that bind to a target gene. The TALE-TFs may bind to different target regions within the target gene. The target regions may be separated by at least one nucleotide. The target regions may be separated by about 15 to about 700 base pairs. At least one target region may be within a non-open chromatin region. At least one target region may be within an open chromatin region. At least one target region may be within the promoter region of the target gene. At least one target region may be within the enhancer region of the target gene. At least one target region may be within the transcribed region of the target gene. At least one target region may be within a region upstream of the transcription start site of the target gene. At least one target region may be located between about 1 to about 1000 base pairs upstream of the transcription start site of the target gene. At least one target region may be located between about 1 to about 600 base pairs upstream of the transcription start site of the target gene. The target regions may be within a region upstream of the transcription start site of the target gene. The gene expression may be induced. The TALE-TFs may each comprise a transcription activation domain. The TALE-TFs may comprise the same transcription activation domain. The TALE-TFs may comprise different transcription activation domains. The transcription activation domain may comprise at least one VP16 transcription activation domain repeat. The transcription activation domain comprises at least one of VP16 transcription activation domain repeat, VP64 transcription activation domain, p65 transcription activation domain, or combinations thereof. The TALE-TFs may each comprise about 15 to about 19 RVD modules. Between about two to about ten TALE-TFs may be used. Three TALE-TFs may be used. Four TALE-TFs may be used. Five TALE-TFs may be used. Six TALE-TFs may be used. The TALE-TFs may binds to a nucleotide sequence comprising one of SEQ ID NOs: 1-29, or the complement thereof. The TALE-TFs may comprise an amino acid sequence selected from the group consisting of SEQ ID NOs: 44, 46, 48, 50, 52, 54, 56, 58, 60, 62, 64, 66, 68, 70, 72, 74, 76, 78, 80, 82, 84, 86, 88, 90, 92, 94, 96, or 98, or variants thereof. The TALE-TFs may be encoded by a polynucleotide sequence selected from the group consisting of SEQ ID NOs: 43, 45, 47, 49, 51, 53, 55, 57, 59, 61, 63, 65, 67, 69, 71, 73, 75, 77, 79, 81, 83, 85, 87, 89, 91, 93, 95, or 97, or variants thereof. The target gene may be IL1RN, KLK3, CEACAM5, and ERBB2.

The present invention is directed to a composition for inducing mammalian gene expression in a cell. The composition comprises two or more transcription activator-like effector transcription factors (TALE-TFs) that bind to a target gene. The TALE-TFs may bind to a nucleotide sequence comprising one of SEQ ID NOs: 1-28, or the complement thereof. The TALE-TFs may comprise an amino acid sequence selected from the group consisting of SEQ ID NO: 44, 46, 48, 50, 52, 54, 56, 58, 60, 62, 64, 66, 68, 70, 72, 74, 76, 78, 80, 82, 84, 86, 88, 90, 92, 94, 96, or 98, or variants thereof. The TALE-TFs may be encoded by a polynucleotide sequence selected from the group consisting of SEQ ID NOs: 43, 45, 47, 49, 51, 53, 55, 57, 59, 61, 63, 65, 67, 69, 71, 73, 75, 77, 79, 81, 83, 85, 87, 89, 91, 93, 95, or 97, or variants thereof. The target gene may be IL1RN, KLK3, CEACAM5, and ERBB2.

The present invention is directed to a composition for inducing mammalian gene expression in a cell. The composition comprises an isolated polynucleotide sequence encoding at least one transcription activator-like effector transcription factor (TALE-TF) that binds to a target gene. The more than one TALE-TF may be encoded by the isolated polynucleotide sequence. The two or more TALE-TFs may be encoded by two or more polynucleotide sequences. The TALE-TFs may bind to a nucleotide sequence comprising one of SEQ ID NOs: 1-28, or the complement thereof. The TALE-TFs may comprise an amino acid sequence selected from the group consisting of SEQ ID NO: 44, 46, 48, 50, 52, 54, 56, 58, 60, 62, 64, 66, 68, 70, 72, 74, 76, 78, 80, 82, 84, 86, 88, 90, 92, 94, 96, or 98, or variants thereof. The TALE-TFs may be encoded by a polynucleotide sequence selected from the group consisting of SEQ ID NOs: 43, 45, 47, 49, 51, 53, 55, 57, 59, 61, 63, 65, 67, 69, 71, 73, 75, 77, 79, 81, 83, 85, 87, 89, 91, 93, 95, or 97, or variants thereof. The target gene may be IL1RN, KLK3, CEACAM5, and ERBB2.

The present invention is directed to a cell comprising said composition.

The present invention is directed to a kit comprising said composition or said cell.

The present invention is directed to a kit for inducing mammalian gene expression in a cell. The kit comprises said composition or said cell.

BRIEF DESCRIPTION OF THE DRAWINGS

FIG. 3 shows the TALE-TFs, the target sequence, RVDs, length, percent RVD composition and distance to the TSS of the target genes: IL1RN (a), KLK3 (b), CEACAM5 (c), and ERBB2 (d). The underlined target sequences are located in the minus strand.

FIG. 5A shows the relative luciferase activities and FIG. 5B shows a Western blot of the cell lysates analyzed with anti-HA and anti-GAPDH antibodies.

DETAILED DESCRIPTION

Figure 1:
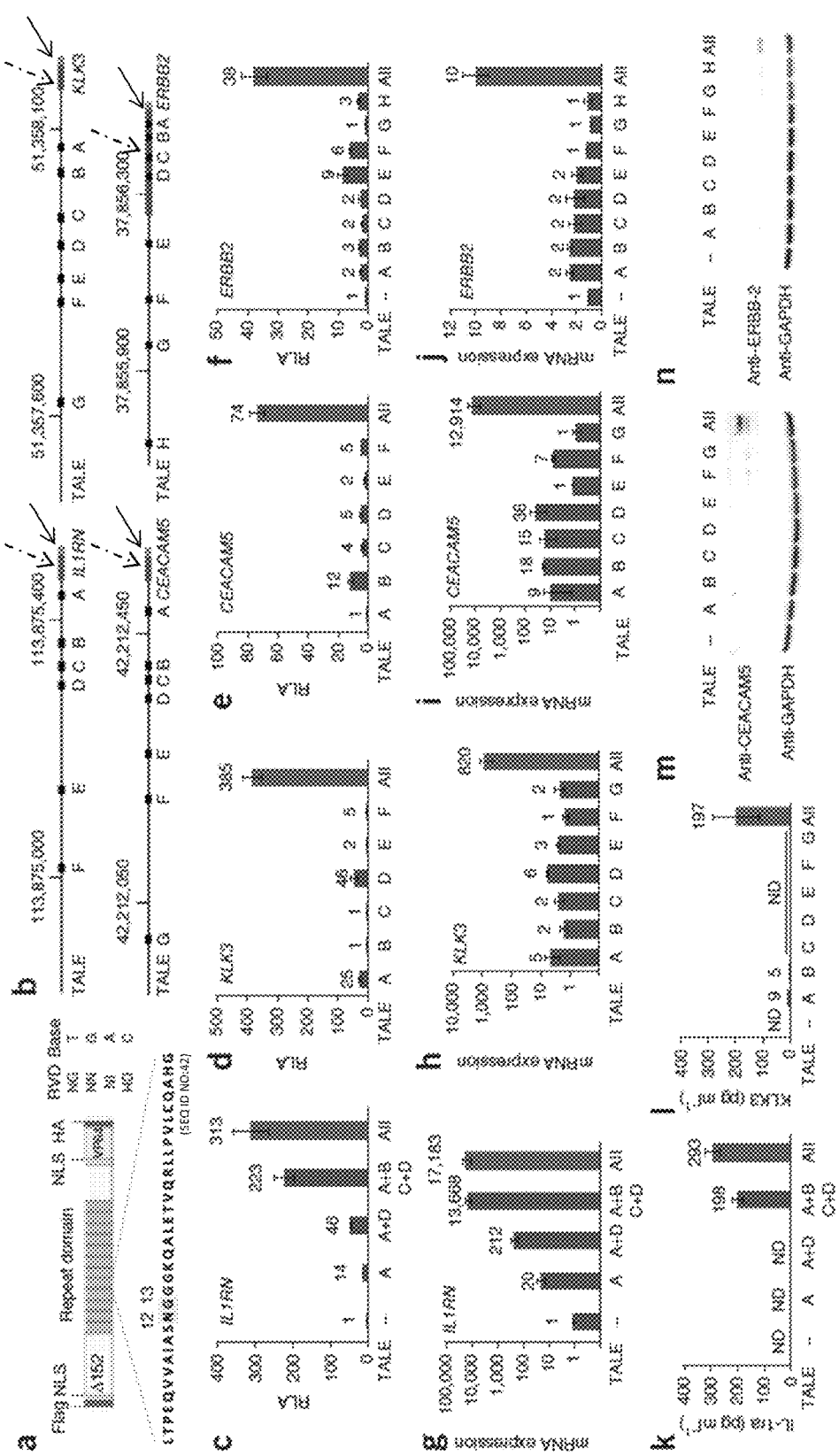
FIG. 1 shows synergistic activation of gene expression by combinations of TALE-TFs. (a) Structure and sequence of TALE-TFs in this study. (b) Genomic positions of TALE-TF target sites in the CEACAM5, KLK3, IL1RN, and ERBB2 genes (hg19 coordinates) are indicated by black boxes. Transcribed and coding regions are indicated by dashed arrow and solid arrow, respectively. (c-f) Relative luciferase activity (RLA) in promoter reporter assays. (g-j) Relative mRNA expression levels measured by quantitative RT-PCR and (k-n) protein expression levels assayed by ELISA or Western blot for each target gene in human cells transfected with the indicated TALE-TFs. Each gene is organized by column. n=3 unless indicated otherwise in the online methods Examples. Mean±SEM and P<0.0001 by ANOVA for all bar graphs.

The present disclosure provides compositions and methods of modulating gene expression that include combinations of engineered TALE-TFs. The combinations of engineered TALE-TFs target endogenous gene promoters, including regions of closed chromatin upstream of silenced genes, and induce substantial gene activation. The combinations also allow tuning of gene expression levels that broadly enables synthetic biology, gene therapy and biotechnology.

The combinatorial regulation of endogenous mammalian genes in their natural chromosomal context is achieved by engineering several TALE-TFs to bind nearby sites upstream of the transcriptional start site (TSS) for a target gene. These combinations of independent TALE-TFs can be manipulated to control gene activation. Synergistic regulation of gene expression by multiple transcriptional activators occurs via simultaneous binding and stabilization of components of the pre-initiation complex. Endogenous genes were activated with combinations of engineered transcription factors. Gene expression levels were tuned by systematically varying these combinations.

1. Definitions

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "and" and "the" include plural references unless the context clearly dictates otherwise. The present disclosure also contemplates other embodiments "comprising," "consisting of" and "consisting essentially of," the embodiments or elements presented herein, whether explicitly set forth or not.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

"Binding region," "target region," or "target sequence" as used interchangeably herein refers to the region within the target gene that is recognized and bound by a TALE-TF. The TALE DNA-binding domain of the TALE-TF recognizes and binds to the binding region. The binding region may include a nucleotide sequence of SEQ ID NO: 1-28, or a complement thereof.

"Chromatin" as used herein refers to an organized complex of chromosomal DNA associated with histones. "Closed chromatin" or "heterochromatin" as used interchangeably herein refers to a tightly packed form of DNA. Closed chromatin may be inaccessible to DNaseI. "Open chromatin" or "euchromatin" as used interchangeably herein refers to a lightly packed form of chromatin that is rich in gene concentration and is often under active transcription. Open chromatin may be accessible to DNaseI.

"Chromatin modifying drug" as used herein refers to drugs that cause chromatin remodeling, i.e., dynamic modification of chromatin architecture, and allow access of condensed genomic DNA to the regulatory transcription machinery proteins, and thereby helps to control gene expression. Chromatin modifying drug function by 1) covalent histone modifications by specific enzymes, i.e., histone acetyltransferases (HATs), deacetylases, methyltransferases, and kinases, and 2) ATP-dependent chromatin remodeling complexes which either move, eject or restructure nucleosomes.

"Coding sequence", "coding region" or "encoding nucleic acid" as used herein means the nucleic acids (RNA or DNA molecule) that comprise a nucleotide sequence which encodes a protein. The coding sequence can further include initiation and termination signals operably linked to regulatory elements including a promoter and polyadenylation signal capable of directing expression in the cells of an individual or mammal to which the nucleic acid is administered. The coding sequence may be codon optimized.

"Complement" or "complementary" as used herein means a nucleic acid can mean Watson-Crick (e.g., A-T/U and C-G) or Hoogsteen base pairing between nucleotides or nucleotide analogs of nucleic acid molecules. "Complementarity" refers to a property shared between two nucleic acid sequences, such that when they are aligned antiparallel to each other, the nucleotide bases at each position will be complementary.

"DNase I hypersensitive sites" are regions of chromatin that are sensitive to cleavage by the DNase I enzyme. In these specific regions of the genome, chromatin has lost its condensed structure, thus exposing the DNA and making it accessible. These accessible chromatin zones are functionally related to transcriptional activity, since this remodeled state is necessary for the binding of proteins such as transcription factors.

"Genetic construct" as used herein refers to the DNA or RNA molecules that comprise a nucleotide sequence that encodes a protein. The coding sequence includes initiation and termination signals operably linked to regulatory elements including a promoter and polyadenylation signal capable of directing expression in the cells of the individual to whom the nucleic acid molecule is administered. As used herein, the term "expressible form" refers to gene constructs that contain the necessary regulatory elements operable linked to a coding sequence that encodes a protein such that when present in the cell of the individual, the coding sequence will be expressed.

"Genetic disease" as used herein refers to a disease, partially or completely, directly or indirectly, caused by one or more abnormalities in the genome, especially a condition that is present from birth. The abnormality may affect the regulatory sequence. The genetic disease may be, but not limited to DMD, cystic fibrosis, Huntington's chorea, familial hypercholesterolemia (LDL receptor defect), hepatoblastoma, Wilson's disease, congenital hepatic porphyria, inherited disorders of hepatic metabolism, Lesch Nyhan syndrome, sickle cell anemia, thalassaemias, xeroderma pigmentosum, Fanconi's anemia, retinitis pigmentosa, ataxia telangiectasia, Bloom's syndrome, retinoblastoma, Friedreich's ataxia, choroidal neovascularization, cancer, amyotrophic lateral sclerosis, diabetic wounds, and Tay-Sachs disease.

"Identical" or "identity" as used herein in the context of two or more nucleic acids or polypeptide sequences means that the sequences have a specified percentage of residues that are the same over a specified region. The percentage may be calculated by optimally aligning the two sequences, comparing the two sequences over the specified region, determining the number of positions at which the identical residue occurs in both sequences to yield the number of matched positions, dividing the number of matched positions by the total number of positions in the specified region, and multiplying the result by 100 to yield the percentage of sequence identity. In cases where the two sequences are of different lengths or the alignment produces one or more staggered ends and the specified region of comparison includes only a single sequence, the residues of single sequence are included in the denominator but not the numerator of the calculation. When comparing DNA and RNA, thymine (T) and uracil (U) may be considered equivalent. Identity may be performed manually or by using a computer sequence algorithm such as BLAST or BLAST 2.0.

"Nucleic acid" or "oligonucleotide" or "polynucleotide" as used herein means at least two nucleotides covalently linked together. The depiction of a single strand also defines the sequence of the complementary strand. Thus, a nucleic acid also encompasses the complementary strand of a depicted single strand. Many variants of a nucleic acid may be used for the same purpose as a given nucleic acid. Thus, a nucleic acid also encompasses substantially identical nucleic acids and complements thereof. A single strand provides a probe that may hybridize to a target sequence under stringent hybridization conditions. Thus, a nucleic acid also encompasses a probe that hybridizes under stringent hybridization conditions.

Nucleic acids may be single stranded or double stranded, or may contain portions of both double stranded and single stranded sequence. The nucleic acid may be DNA, both genomic and cDNA, RNA, or a hybrid, where the nucleic acid may contain combinations of deoxyribo- and ribonucleotides, and combinations of bases including uracil, adenine, thymine, cytosine, guanine, inosine, xanthine hypoxanthine, isocytosine and isoguanine Nucleic acids may be obtained by chemical synthesis methods or by recombinant methods.

"Operably linked" as used herein means that expression of a gene is under the control of a promoter with which it is spatially connected. A promoter may be positioned 5' (upstream) or 3' (downstream) of a gene under its control. The distance between the promoter and a gene may be approximately the same as the distance between that promoter and the gene it controls in the gene from which the promoter is derived. As is known in the art, variation in this distance may be accommodated without loss of promoter function.

"Promoter" as used herein means a synthetic or naturally-derived molecule which is capable of conferring, activating or enhancing expression of a nucleic acid in a cell. A promoter may comprise one or more specific transcriptional regulatory sequences to further enhance expression and/or to alter the spatial expression and/or temporal expression of same. A promoter may also comprise distal enhancer or repressor elements, which may be located as much as several thousand base pairs from the start site of transcription. A promoter may be derived from sources including viral, bacterial, fungal, plants, insects, and animals. A promoter may regulate the expression of a gene component constitutively, or differentially with respect to cell, the tissue or organ in which expression occurs or, with respect to the developmental stage at which expression occurs, or in response to external stimuli such as physiological stresses, pathogens, metal ions, or inducing agents. Representative examples of promoters include the bacteriophage T7 promoter, bacteriophage T3 promoter, SP6 promoter, lac operator-promoter, tac promoter, SV40 late promoter, SV40 early promoter, RSV-LTR promoter, CMV IE promoter, SV40 early promoter or SV40 late promoter and the CMV IE promoter.

"Repeat variable diresidue" or "RVD" as used interchangeably herein refers to a pair of adjacent amino acid residues within the DNA recognition motif (also known as "RVD module"), which includes 33-35 amino acids, of the TALE DNA-binding domain. The RVD determines the nucleotide specificity of the RVD module. RVD modules may be combined to produce an RVD array. The "RVD array length" as used herein refers to the number of RVD modules that corresponds to the length of the nucleotide sequence within the target region that is recognized by the TALE-TF, i.e., the binding region.

"Silenced gene" as used herein refers to a gene that is turned off or prevented from being expressed, i.e., transcribed. Gene silencing may occur when large sections of chromosomal DNA are shut down, such as by incorporating the DNA to be silenced into heterochromatin, that is already silent. A gene may be transcriptional silenced by DNA methylation, wherein a methyl group is attached to certain points on a nucleic acid strand and can prevent transcription.

"Subject" and "patient" as used herein interchangeably refers to any vertebrate, including, but not limited to, a mammal (e.g., cow, pig, camel, llama, horse, goat, rabbit, sheep, hamsters, guinea pig, cat, dog, rat, and mouse, a non-human primate (for example, a monkey, such as a cynomolgous or rhesus monkey, chimpanzee, etc.) and a human). In some embodiments, the subject may be a human or a non-human. The subject or patient may be undergoing other forms of treatment.

"Target gene" as used herein refers to any nucleotide sequence encoding a known or putative gene product. The target gene includes the regulatory regions, such as the promoter and enhancer regions, the transcribed regions, which include the coding regions, and other function sequence regions.

"Transcribed region" as used herein refers to the region of DNA that is transcribed into single-stranded RNA molecule, known as messenger RNA, resulting in the transfer of genetic information from the DNA molecule to the messenger RNA. During transcription, RNA polymerase reads the template strand in the 3' to 5' direction and synthesizes the RNA from 5' to 3'. The mRNA sequence is complementary to the DNA strand.

"Transcription activator-like effector" or "TALE" as used herein refers to a protein structure that recognizes and binds to a particular DNA sequence. The "TALE DNA-binding domain" refers to a DNA-binding domain that includes an array of tandem 33-35 amino acid repeats, also known as RVD modules, each of which specifically recognizes a single base pair of DNA. RVD modules may be arranged in any order to assemble an array that recognizes a defined sequence.

A binding specificity of a TALE DNA-binding domain is determined by the RVD array followed by a single truncated repeat of 20 amino acids. A TALE DNA-binding domain may have 12 to 27 RVD modules, each of which contains an RVD and recognizes a single base pair of DNA. Specific RVDs have been identified that recognize each of the four possible DNA nucleotides (A, T, C, and G). Because the TALE DNA-binding domains are modular, repeats that recognize the four different DNA nucleotides may be linked together to recognize any particular DNA sequence. These targeted DNA-binding domains may then be combined with catalytic domains to create functional enzymes, including artificial transcription factors.

"Transcription activator-like effector transcription factors" or "TALE-TFs" as used interchangeably herein refers to engineered fusion proteins of the transcription activation domain of a transcription factors, such as VP64, and a designed TALE DNA-binding domain that may be targeted to a custom DNA sequence.

"Transcriptional Start Site" or "TSS" as used interchangeably herein refers to the first nucleotide of a transcribed DNA sequence where RNA polymerase begins synthesizing the RNA transcript.

"Variant" used herein with respect to a nucleic acid means (i) a portion or fragment of a referenced nucleotide sequence; (ii) the complement of a referenced nucleotide sequence or portion thereof; (iii) a nucleic acid that is substantially identical to a referenced nucleic acid or the complement thereof; or (iv) a nucleic acid that hybridizes under stringent conditions to the referenced nucleic acid, complement thereof, or a sequences substantially identical thereto.

"Variant" with respect to a peptide or polypeptide that differs in amino acid sequence by the insertion, deletion, or conservative substitution of amino acids, but retain at least one biological activity. Variant may also mean a protein with an amino acid sequence that is substantially identical to a referenced protein with an amino acid sequence that retains at least one biological activity. A conservative substitution of an amino acid, i.e., replacing an amino acid with a different amino acid of similar properties (e.g., hydrophilicity, degree and distribution of charged regions) is recognized in the art as typically involving a minor change. These minor changes may be identified, in part, by considering the hydropathic index of amino acids, as understood in the art. Kyte et al., *J. Mol. Biol.* 157:105-132 (1982). The hydropathic index of an amino acid is based on a consideration of its hydrophobicity and charge. It is known in the art that amino acids of similar hydropathic indexes may be substituted and still retain protein function. In one aspect, amino acids having hydropathic indexes of ±2 are substituted. The hydrophilicity of amino acids may also be used to reveal substitutions that would result in proteins retaining biological function. A consideration of the hydrophilicity of amino acids in the context of a peptide permits calculation of the greatest local average hydrophilicity of that peptide. Substitutions may be performed with amino acids having hydrophilicity values within ±2 of each other. Both the hydrophobicity index and the hydrophilicity value of amino acids are influenced by the particular side chain of that amino acid. Consistent with that observation, amino acid substitutions that are compatible with biological function are understood to depend on the relative similarity of the amino acids, and particularly the side chains of those amino acids, as revealed by the hydrophobicity, hydrophilicity, charge, size, and other properties.

"Vector" as used herein means a nucleic acid sequence containing an origin of replication. A vector may be a viral vector, bacteriophage, bacterial artificial chromosome or yeast artificial chromosome. A vector may be a DNA or RNA vector. A vector may be a self-replicating extrachromosomal vector, and preferably, is a DNA plasmid. For example, the vector may encode a TALE-TF protein comprising the polypeptide sequence of one of SEQ ID NOs: 44, 46, 48, 50, 52, 54, 56, 58, 60, 62, 64, 66, 68, 70, 72, 74, 76, 78, 80, 82, 84, 86, 88, 90, 92, 94, 96, or 98, or variants thereof. The vector may include a polynucleotide sequence of one of SEQ ID NOs: 43, 45, 47, 49, 51, 53, 55, 57, 59, 61, 63, 65, 67, 69, 71, 73, 75, 77, 79, 81, 83, 85, 87, 89, 91, 93, 95, or 97, or variants thereof.

Unless otherwise defined herein, scientific and technical terms used in connection with the present disclosure shall have the meanings that are commonly understood by those of ordinary skill in the art. For example, any nomenclatures used in connection with, and techniques of, cell and tissue culture, molecular biology, immunology, microbiology, genetics and protein and nucleic acid chemistry and hybridization described herein are those that are well known and commonly used in the art. The meaning and scope of the terms should be clear; in the event however of any latent ambiguity, definitions provided herein take precedent over any dictionary or extrinsic definition. Further, unless otherwise required by context, singular terms shall include pluralities and plural terms shall include the singular.

2. TALE-TFs

Provided herein are TALE-TFs for use in modulating gene expression of a target gene. Each TALE-TF has two distinct protein domains that carry out individual molecular functions: (i) a repeat variable diresidue region that binds to DNA at user-specified sequences (i.e., the DNA binding domain), and (ii) a transcription activation domain, such as VP64 effector domain, that recruits the basal transcriptional machinery (FIG. 1a). This design permits rapid construction of synthetic transcription factors that function as autonomous units. The TALE-TFs may be designed to target any gene, including genes involved in a genetic disease. The target gene may be in a region of open or closed chromatin.

(a) TALE DNA Binding Domain

The TALE DNA-binding domain may have an RVD array length from 1 to 30 modules, from 1 to 25 modules, from 1 to 20 modules, from 1 to 15 modules, from 5 to 30 modules, from 5 to 25 modules, from 5 to 20 modules, from 5 to 15 modules, from 7 to 25 modules, from 7 to 23 modules, from 7 to 20 modules, from 10 to 30 modules, from 10 to 25 modules, from 10 to 20 modules, from 10 to 15 modules, from 15 to 30 modules, from 15 to 25 modules, from 15 to 20 modules, from 15 to 19 modules, from 16 to 26 modules, from 16 to 41 modules, from 20 to 30 modules, or from 20 to 25 modules in length. The RVD array length may be 5 modules, 8 modules, 10 modules, 11 modules, 12 modules, 13 modules, 14 modules, 15 modules, 16 modules, 17 modules, 18 modules, 19 modules, 20 modules, 22 modules, 25 modules or 30 modules.

The TALE-TF may target at least one of a promoter region, an enhancer region or a transcribed region of a target gene. The TALE-TF may target a binding region comprising the nucleic acid sequence of one of SEQ ID NOs:1-28, or variants thereof. The TALE-TF may include a polypeptide sequence of at least one of SEQ ID NOs: 44, 46, 48, 50, 52, 54, 56, 58, 60, 62, 64, 66, 68, 70, 72, 74, 76, 78, 80, 82, 84, 86, 88, 90, 92, 94, 96, or 98, or variants thereof. The TALE-TF may include a polynucleotide sequence of at least one of SEQ ID NOs: 43, 45, 47, 49, 51, 53, 55, 57, 59, 61, 63, 65, 67, 69, 71, 73, 75, 77, 79, 81, 83, 85, 87, 89, 91, 93, 95, or 97, or variants thereof.

The TALE-TF may target a region that is at least about 1 base pair to about 1000 base pairs, at least about 10 base pairs to about 1000 base pairs, at least about 50 base pairs to about 1000 base pairs, 100 base pair to about 1000 base pairs, at least about 150 base pairs to about 1000 base pairs, at least about 200 base pairs to about 1000 base pairs, 250 base pair to about 1000 base pairs, at least about 300 base pairs to about 1000 base pairs, at least about 350 base pairs to about 1000 base pairs, 400 base pair to about 1000 base pairs, at least about 450 base pairs to about 1000 base pairs, at least about 500 base pairs to about 1000 base pairs, 550 base pair to about 1000 base pairs, at least about 600 base pairs to about 1000 base pairs, at least about 650 base pairs to about 1000 base pairs, at least about 1 base pair to about 900 base pairs, at least about 10 base pairs to about 900 base pairs, at least about 50 base pairs to about 900 base pairs, 100 base pair to about 900 base pairs, at least about 150 base pairs to about 900 base pairs, at least about 200 base pairs to about 900 base pairs, 250 base pair to about 900 base pairs, at least about 300 base pairs to about 900 base pairs, at least about 350 base pairs to about 900 base pairs, 400 base pair to about 900 base pairs, at least about 450 base pairs to about 900 base pairs, at least about 500 base pairs to about 900 base pairs, 550 base pair to about 900 base pairs, at least about 600 base pairs to about 900 base pairs, at least about 650 base pairs to about 900 base pairs, at least about 1 base pair to about 800 base pairs, at least about 10 base pairs to about 800 base pairs, at least about 50 base pairs to about 800 base pairs, 100 base pair to about 800 base pairs, at least about 150 base pairs to about 800 base pairs, at least about 200 base pairs to about 800 base pairs, 250 base pair to about 800 base pairs, at least about 300 base pairs to about 800 base pairs, at least about 350 base pairs to about 800 base pairs, 400 base pair to about 800 base pairs, at least about 450 base pairs to about 800 base pairs, at least about 500 base pairs to about 800 base pairs, 550 base pair to about 800 base pairs, at least about 600 base pairs to about 800 base pairs, at least about 1 base pair to about 700 base pairs, at least about 10 base pairs to about 700 base pairs, at least about 50 base pairs to about 700 base pairs, 100 base pair to about 700 base pairs, at least about 150 base pairs to about 700 base pairs, at least about 200 base pairs to about 700 base pairs, 250 base pair to about 700 base pairs, at least about 300 base pairs to about 700 base pairs, at least about 350 base pairs to about 700 base pairs, 400 base pair to about 700 base pairs, at least about 450 base pairs to about 700 base pairs, at least about 500 base pairs to about 700 base pairs, at least about 1 base pair to about 600 base pairs, at least about 10 base pairs to about 600 base pairs, at least about 50 base pairs to about 600 base pairs, 100 base pair to about 600 base pairs, at least about 150 base pairs to about 600 base pairs, at least about 200 base pairs to about 600 base pairs, 250 base pair to about 600 base pairs, at least about 300 base pairs to about 600 base pairs, at least about 350 base pairs to about 600 base pairs, or at least about 400 base pair to about 600 base pairs upstream from the TSS. The TALE-TF may target a region that is at least about 1 base pair, at least about 2 base pairs, at least about 3 base pairs, at least about 4 base pairs, at least about 5 base pairs, at least about 10 base pairs, at least about 15 base pairs, at least about 20 base pairs, at least about 25 base pairs, at least about 30 base pairs, at least about 40 base pairs, at least about 50 base pairs, at least about 60 base pairs, at least about 70 base pairs, at least about 80 base pairs, at least about 90 base pairs, at least about 100 base pairs, at least about 110 base pairs, at least about 120, at least about 130, at least about 140 base pairs, at least about 150 base pairs, at least about 160 base pairs, at least about 170 base pairs, at least about 180 base pairs, at least about 190 base pairs, at least about 200 base pairs, at least about 210 base pairs, at least about 220, at least about 230, at least about 240 base pairs, at least about 250 base pairs, at least about 260 base pairs, at least about 270 base pairs, at least about 280 base pairs, at least about 290 base pairs, at least about 300 base pairs, at least about 310 base pairs, at least about 320, at least about 330, at least about 340 base pairs, at least about 350 base pairs, at least about 360 base pairs, at least about 370 base pairs, at least about 380 base pairs, at least about 390 base pairs, at least about 400 base pairs upstream, at least about 410 base pairs, at least about 420, at least about 430, at least about 440 base pairs, at least about 450 base pairs, at least about 460 base pairs, at least about 470 base pairs, at least about 480 base pairs, at least about 490 base pairs, at least about 500 base pairs, at least about 510 base pairs, at least about 520, at least about 530, at least about 540 base pairs, at least about 550 base pairs, at least about 560 base pairs, at least about 570 base pairs, at least about 180 base pairs, at least about 590 base pairs, at least about 600 base pairs, at least about 610 base pairs, at least about 620, at least about 130, at least about 640 base pairs, at least about 650 base pairs, at least about 660 base pairs, at least about 670 base pairs, at least about 680 base pairs, at least about 690 base pairs, at least about 700 base pairs, at least about 710 base pairs, at least about 720, at least about 730, at least about 740 base pairs, at least about 750 base pairs, at least about 760 base pairs, at least about 770 base pairs, at least about 780 base pairs, at least about 790 base pairs, at least about 800 base pairs, at least about 810 base pairs, at least about 820, at least about 830, at least about 840 base pairs, at least about 850 base pairs, at least about 860 base pairs, at least about 870 base pairs, at least about 880 base pairs, at least about 890 base pairs, at least about 900 base pairs, at least about 910 base pairs, at least about 920, at least about 930, at least about 940 base pairs, at least about 950 base pairs, at least about 960 base pairs, at least about 970 base pairs, at least about 980 base pairs, at least about 990 base pairs, or at least about 1000 base pairs upstream from the TSS.

The TALE-TF may target a region that is at least about 1 base pair to at least about 250 base pairs, at least about 50 base pairs to at least about 200 base pairs, or at least about 100 base pair to at least about 200 base pairs downstream from the TSS. The TALE-TF may target a region that is at least about 1 base pair, at least about 2 base pairs, at least about 3 base pairs, at least about 4 base pairs, at least about 5 base pairs, at least about 10 base pairs, at least about 15 base pairs, at least about 20 base pairs, at least about 25 base pairs, at least about 30 base pairs, at least about 40 base pairs, at least about 50 base pairs, at least about 60 base pairs, at least about 70 base pairs, at least about 80 base pairs, at least about 90 base pairs, at least about 100 base pairs, at least about 110 base pairs, at least about 120, at least about 130, at least about 140 base pairs, at least about 150 base pairs, at least about 160 base pairs, at least about 170 base pairs, at least about 180 base pairs, at least about 190 base pairs, at least about 200 base pairs, at least about 210 base pairs, at least about 220, at least about 230, at least about 240 base pairs, or at least about 250 base pairs downstream from the TSS.

(b) Transcriptional Activation Activity

The TALE-TFs includes a polypeptide domain having transcription activation activity, i.e., a transactivation domain or transcriptional activation domain. The transcriptional activation domains activate transcription from a promoter by contacting the transcriptional machinery (general transcription factors and RNA polymerase) either directly or through other proteins known as co-activations. Transcription activation domains include acidic domains, which are rich in acidic amino acids (e.g., DDD, EEE), glutamine-rich domains, and proline-rich domains. The transactivation domain may include a VP16 protein, multiple VP16 proteins, such as a VP64 domain, or p65 domain of NF kappa B transcription activator activity. The TALE-TF may include at least one of VP16 transcription activation domain repeat, VP64 transcription activation domain, p65 transcription activation domain, or combinations thereof.

(c) Gene targets

The TALE-TFs may be designed to target and modulate the expression of any target gene. The target gene may be any mammalian gene. For example, the TALE-TFs may target a mammalian gene, such as IL1RN, KLK3, CEACAM5, ERBB2, ASCL1, NANOG, VEGFA, TERT, IL1B, IL1R2, HBG1, HBG2, MYOD1, HBG1/2, UTRN, FXN, SERPINF1, BAX, SERPINB5, VEFGA, POU5F1, and DMD.

3. Compositions

The present disclosure also provides compositions of at least two TALE-TFs, as described above, or polynucleotide sequences encoding said TALE-TFs, that are administered to a mammalian cell to induce and modulate gene expression of a target gene. These combinations of TALE-TFs may target a closed or open chromatin gene region. These combinations of TALE-TFs may be used with or without chromatin modifying drug. These combinations of TALE-TFs may target DNaseI sensitive regions or DNaseI insensitive regions.

In some embodiments, the composition induces the gene expression of a target gene by at least about 1 fold, at least about 2 fold, at least about 3 fold, at least about 4 fold, at least about 5 fold, at least about 6 fold, at least about 7 fold, at least about 8 fold, at least about 9 fold, at least about 10 fold, at least 15 fold, at least 20 fold, at least 30 fold, at least 40 fold, at least 50 fold, at least 60 fold, at least 70 fold, at least 80 fold, at least 90 fold, at least 100 fold, at least about 110 fold, at least 120 fold, at least 130 fold, at least 140 fold, at least 150 fold, at least 160 fold, at least 170 fold, at least 180 fold, at least 190 fold, at least 200 fold, at least about 300 fold, at least 400 fold, at least 500 fold, at least 600 fold, at least 700 fold, at least 800 fold, at least 900 fold, or at least 1000 fold compared to a control level of gene expression. A control level of gene expression of the target gene may be the level of gene expression of the target gene in a cell that is not treated with any TALE-TF or is treated with only one TALE-TF.

The compositions may include from at least about two TALE-TFs to at least about fifty TALE-TFs, from at least about three TALE-TFs to at least about fifty TALE-TFs, from at least about four TALE-TFs to at least about fifty TALE-TFs, from at least about five TALE-TFs to at least about fifty TALE-TFs, from at least about ten TALE-TFs to at least about fifty TALE-TFs, from at least about fifteen TALE-TFs to at least about fifty TALE-TFs, from at least about twenty TALE-TFs to at least about fifty TALE-TFs, from at least about twenty-five TALE-TFs to at least about fifty TALE-TFs, from at least about two TALE-TFs to at least about twenty-five TALE-TFs, from at least about three TALE-TFs to at least about twenty-five TALE-TFs, from at least about four TALE-TFs to at least about twenty-five TALE-TFs, from at least about five TALE-TFs to at least about twenty-five TALE-TFs, from at least about ten TALE-TFs to at least about twenty-five TALE-TFs, from at least about fifteen TALE-TFs to at least about twenty-five TALE-TFs, from at least about twenty TALE-TFs to at least about twenty-five TALE-TFs, from at least about twenty-five TALE-TFs to at least about twenty-five TALE-TFs. The compositions may include at least two, at least three, at least four, at least five, at least six, at least seven, at least eight, at least nine, at least ten or at least fifteen TALE-TFs. The number of TALE-TFs administered to the cell may be at least two TALE-TFs, at least three TALE-TFs at least four TALE-TFs, at least five TALE-TFs, at least six TALE-TFs, at least seven TALE-TFs, at least eight TALE-TFs, at least nine TALE-TFs, at least ten TALE-TFs, at least fifteen TALE-TFs, at least twenty TALE-TFs, at least thirty TALE-TFs, or at least fifty TALE-TFs.

The TALE-TFs of the composition may have the same and/or different transcriptional activation domain. In some embodiments, the TALE-TFs may have the same transcriptional activation domains. In some embodiments, at least two, at least three, at least four, at least five, at least six, at least seven, at least eight, at least nine, at least ten, at least fifteen, at least twenty, at least thirty, at least forty or at least fifty of the TALE-TFs have the same transcriptional activation domains. In some embodiments, the TALE-TFs may have different transcriptional activation domains. In some embodiments, at least two, at least three, at least four, at least five, at least six, at least seven, at least eight, at least nine, or at least ten of the TALE-TFs have different transcriptional activation domains.

In some embodiments, the TALE-TFs in the composition may bind different target regions that are either upstream or downstream from the TSS. In some embodiments, all of the TALE-TF in the composition may bind to different target regions that are upstream from the TSS. In some embodiments, all of the TALE-TF in the composition may bind to different target regions that are downstream from the TSS. In some embodiments, the TALE-TFs in the composition may bind different target regions, wherein at least one of the target regions is upstream from the TSS and at least one of the target regions is downstream from the TSS.

The target regions of the TALE-TFs may be separated by at least about 1 nucleotide to about 1000 base pairs. For example, the target regions may be separated by at least about 1 base pair, at least about 2 base pairs, at least about 3 base pairs, at least about 4 base pairs, at least about 5 base pairs, at least about 6 base pairs, at least about 7 base pairs, at least about 8 base pairs, at least about 9 base pairs, at least about 10 base pairs, at least about 20 base pairs, at least about 30 base pairs, at least about 40 base pairs, at least about 50 base pairs, at least about 60 base pairs, at least about 70 base pairs, at least about 80 base pairs, at least about 90 base pairs, at least about 100 base pairs, at least about 110 base pairs, at least about 120 base pairs, at least about 130 base pairs, at least about 140 base pairs, at least about 150 base pairs, at least about 160 base pairs, at least about 170 base pairs, at least about 180 base pairs, at least about 190 base pairs, at least about 200 base pairs, at least about 210 base pairs, at least about 220 base pairs, at least about 230 base pairs, at least about 240 base pairs, at least about 250 base pairs, at least about 260 base pairs, at least about 270 base pairs, at least about 280 base pairs, at least about 290 base pairs, at least about 300 base pairs, at least about 310 base pairs, at least about 320 base pairs, at least about 330 base pairs, at least about 340 base pairs, at least about 350 base pairs, at least about 360 base pairs, at least about 370 base pairs, at least about 380 base pairs, at least about 390 base pairs, at least about 400 base pairs, at least about 410 base pairs, at least about 420 base pairs, at least about 430 base pairs, at least about 440 base pairs, at least about 450 base pairs, at least about 460 base pairs, at least about 470 base pairs, at least about 480 base pairs, at least about 490 base pairs, at least about 500 base pairs, at least about 510 base pairs, at least about 520 base pairs, at least about 530 base pairs, at least about 540 base pairs, at least about 550 base pairs, at least about 560 base pairs, at least about 570 base pairs, at least about 580 base pairs, at least about 590 base pairs, at least about 600 base pairs, at least about 700 base pairs, at least about 800 base pairs, at least about 900 base pairs, or at least about 1000 base pairs.

4. Constructs and Plasmids

The genetic constructs may comprise a nucleic acid sequence that encodes the TALE-TFs disclosed herein. The genetic construct, such as a plasmid, may comprise a nucleic acid that encodes the TALE-TFs. The genetic construct may be present in the cell as a functioning extrachromosomal molecule. The genetic construct may be a linear minichromosome including centromere, telomeres or plasmids or cosmids.

The genetic construct may also be part of a genome of a recombinant viral vector, including recombinant lentivirus, recombinant adenovirus, and recombinant adeno-associated virus. The genetic construct may be part of the genetic material in attenuated live microorganisms or recombinant microbial vectors which live in cells. The genetic constructs may comprise regulatory elements for gene expression of the coding sequences of the nucleic acid. The regulatory elements may be a promoter, an enhancer an initiation codon, a stop codon, or a polyadenylation signal.

The nucleic acid sequences may make up a genetic construct that may be a vector. The vector may be capable of expressing the TALE-TFs in the cell of a mammal. The vector may be recombinant. The vector may comprise heterologous nucleic acid encoding the TALE-TFs. The vector may be a plasmid. The vector may be useful for transfecting cells with nucleic acid encoding the TALE-TFs, which the transformed host cell is cultured and maintained under conditions wherein expression of the TALE-TFs takes place.

Coding sequences may be optimized for stability and high levels of expression. In some instances, codons are selected to reduce secondary structure formation of the RNA such as that formed due to intramolecular bonding.

The vector may comprise heterologous nucleic acid encoding the TALE-TFs and may further comprise an initiation codon, which may be upstream of the TALE-TFs coding sequence, and a stop codon, which may be downstream of the TALE-TFs. The initiation and termination codon may be in frame with the TALE-TFs coding sequence.

The vector may also comprise a promoter that is operably linked to the TALE-TFs coding sequence TALE-TFs. The promoter operably linked to the TALE-TFs coding sequence may be a promoter from simian virus 40 (SV40), a mouse mammary tumor virus (MMTV) promoter, a human immunodeficiency virus (HIV) promoter such as the bovine immunodeficiency virus (BIV) long terminal repeat (LTR) promoter, a Moloney virus promoter, an avian leukosis virus (ALV) promoter, a cytomegalovirus (CMV) promoter such as the CMV immediate early promoter, Epstein Barr virus (EBV) promoter, or a Rous sarcoma virus (RSV) promoter. The promoter may also be a promoter from a human gene such as human actin, human myosin, human hemoglobin, human muscle creatine, or human metalothionein. The promoter may also be a tissue specific promoter, such as a muscle or skin specific promoter, natural or synthetic. Examples of such promoters are described in US Patent Application Publication No. US20040175727, the contents of which are incorporated herein in its entirety.

The vector may also comprise a polyadenylation signal, which may be downstream of the TALE-TFs coding sequence. The polyadenylation signal may be a SV40 polyadenylation signal, LTR polyadenylation signal, bovine growth hormone (bGH) polyadenylation signal, human growth hormone (hGH) polyadenylation signal, or human β-globin polyadenylation signal. The SV40 polyadenylation signal may be a polyadenylation signal from a pCEP4 vector (Invitrogen, San Diego, Calif.).

The vector may also comprise an enhancer upstream of the TALE-TFs coding sequence. The enhancer may be necessary for DNA expression. The enhancer may be human actin, human myosin, human hemoglobin, human muscle creatine or a viral enhancer such as one from CMV, HA, RSV or EBV. Polynucleotide function enhancers are described in U.S. Pat. Nos. 5,593,972, 5,962,428, and WO94/016737, the contents of each are fully incorporated by reference. The vector may also comprise a mammalian origin of replication in order to maintain the vector extrachromosomally and produce multiple copies of the vector in a cell. The vector may also comprise a regulatory sequence, which may be well suited for gene expression in a mammalian or human cell into which the vector is administered. The vector may also comprise a reporter gene, such as green fluorescent protein ("GFP") and/or a selectable marker, such as hygromycin ("Hygro").

The vector may be expression vectors or systems to produce protein by routine techniques and readily available starting materials including Sambrook et al., Molecular Cloning and Laboratory Manual, Second Ed., Cold Spring Harbor (1989), which is incorporated fully by reference. In some embodiments the vector may comprise the nucleic acid sequence encoding the TALE-TFs, such as the nucleic acid sequence of at least one of SEQ ID NOs: 43, 45, 47, 49, 51, 53, 55, 57, 59, 61, 63, 65, 67, 69, 71, 73, 75, 77, 79, 81, 83, 85, 87, 89, 91, 93, 95, or 97, or variants thereof.

5. Methods of Use

Potential applications of the combination of TALE-TFs are diverse across many areas of science and biotechnology. The combination of TALE-TFs may be used to induce and modulate mammalian gene expression. The combination of TALE-TFs may be used to transdifferentiate a cell and/or activate genes related to cell and gene therapy, genetic reprogramming, and regenerative medicine. The combination of TALE-TFs may be used to reprogram cell lineage specification. Activation of endogenous genes encoding the key regulators of cell fate, rather than forced overexpression of these factors, may potentially lead to more rapid, efficient, stable, or specific methods for genetic reprogramming and transdifferentiation. Combination of TALE-TFs could provide a greater diversity of transcriptional activators to complement other tools for modulating mammalian gene expression. The combination of TALE-TFs may be used to compensate for genetic defects, suppress angiogenesis, inactivate oncogenes, activate silenced tumor suppressors, regenerate tissue or reprogram genes.

6. Methods of Activating Gene Expression

The present disclosure provides a mechanism for activating the expression of endogenous mammalian genes based on targeting a transcriptional activator to promoters via combinations of TALE-TF, as described above. The combination of TALE-TFs may activate silenced genes without the use of chromatin modifying drugs. The combination of TALE-TFs target regions upstream of the TSS of the target gene substantially induced gene expression of the target gene. The combination of polynucleotides encoding the TALE-TFs can also be transfected directly to cells. Combination of TALE-TFs targeted to a single promoter as well as simultaneous targeting of multiple promoters by different combination of TALE-TFs targeting different target genes is also envisioned.

The method may include administering to a cell or subject a combination of TALE-TFs, compositions of TALE-TFs, or one or more polynucleotides or vectors encoding said combination of TALE-TFs, as described above. The method may include administering a combination of TALE-TFs, compositions of TALE-TFs, or one or more polynucleotides or vectors encoding said combination of TALE-TFs, as described above, to a mammalian cell or subject.

7. Pharmaceutical Compositions

The TALE-TFs may be in a pharmaceutical composition. The pharmaceutical composition may comprise about 1 ng to about 10 mg of DNA encoding each of the TALE-TFs. The pharmaceutical compositions according to the present invention are formulated according to the mode of administration to be used. In cases where pharmaceutical compositions are injectable pharmaceutical compositions, they are sterile, pyrogen free and particulate free. An isotonic formulation is preferably used. Generally, additives for isotonicity may include sodium chloride, dextrose, mannitol, sorbitol and lactose. In some cases, isotonic solutions such as phosphate buffered saline are preferred. Stabilizers include gelatin and albumin. In some embodiments, a vasoconstriction agent is added to the formulation.

The pharmaceutical composition containing the TALE-TFs may further comprise a pharmaceutically acceptable excipient. The pharmaceutically acceptable excipient may be functional molecules as vehicles, adjuvants, carriers, or diluents. The pharmaceutically acceptable excipient may be a transfection facilitating agent, which may include surface active agents, such as immune-stimulating complexes (ISCOMS), Freunds incomplete adjuvant, LPS analog including monophosphoryl lipid A, muramyl peptides, quinone analogs, vesicles such as squalene and squalene, hyaluronic acid, lipids, liposomes, calcium ions, viral proteins, polyanions, polycations, or nanoparticles, or other known transfection facilitating agents.

The transfection facilitating agent is a polyanion, polycation, including poly-L-glutamate (LGS), or lipid. The transfection facilitating agent is poly-L-glutamate, and more preferably, the poly-L-glutamate is present in the pharmaceutical composition containing the TALE-TFs at a concentration less than 6 mg/ml. The transfection facilitating agent may also include surface active agents such as immune-stimulating complexes (ISCOMS), Freunds incomplete adjuvant, LPS analog including monophosphoryl lipid A, muramyl peptides, quinone analogs and vesicles such as squalene and squalene, and hyaluronic acid may also be used administered in conjunction with the genetic construct. In some embodiments, the DNA vector encoding the TALE-TFs may also include a transfection facilitating agent such as lipids, liposomes, including lecithin liposomes or other liposomes known in the art, as a DNA-liposome mixture (see for example WO9324640), calcium ions, viral proteins, polyanions, polycations, or nanoparticles, or other known transfection facilitating agents. Preferably, the transfection facilitating agent is a polyanion, polycation, including poly-L-glutamate (LGS), or lipid.

8. Methods of Delivery

Provided herein is a method for delivering the pharmaceutical formulations, preferably two or more TALE-TF, for providing genetic constructs and/or proteins of the TALE-TFs. The delivery of the TALE-TFs may be the transfection or electroporation of the TALE-TFs as one or more nucleic acid molecules that is expressed in the cell and delivered to the surface of the cell. The TALE-TF protein may be delivered to the cell. The nucleic acid molecules may be electroporated using BioRad Gene Pulser Xcell or Amaxa Nucleofector IIb devices or other electroporation device. Several different buffers may be used, including BioRad electroporation solution, Sigma phosphate-buffered saline product #D8537 (PBS), Invitrogen OptiMEM I (OM), or Amaxa Nucleofector solution V (N.V.). Transfections may include a transfection reagent, such as Lipofectamine 2000.

The vector encoding a TALE-TFs protein may be delivered to the mammal by DNA injection (also referred to as DNA vaccination) with and without in vivo electroporation, liposome mediated, nanoparticle facilitated, and/or recombinant vectors. The recombinant vector may be delivered by any viral mode. The viral mode may be recombinant lentivirus, recombinant adenovirus, and/or recombinant adeno-associated virus.

The nucleotide encoding a TALE-TFs protein may be introduced into a cell to induce gene expression of the target gene. For example, one or more nucleotide sequences encoding one or more TALE-TFs directed towards a target gene may be introduced into a mammalian cell. Upon delivery of the TALE-TFs to the cell, and thereupon the vector into the cells of the mammal, the transfected cells will express the TALE-TFs. The TALE-TFs may be administered to a mammal to induce or modulate gene expression of the target gene in a mammal. The mammal may be human, non-human primate, cow, pig, sheep, goat, antelope, bison, water buffalo, bovids, deer, hedgehogs, elephants, llama, alpaca, mice, rats, or chicken, and preferably human, cow, pig, or chicken.

9. Routes of Administration

The TALE-TFs and compositions thereof may be administered to a subject by different routes including orally, parenterally, sublingually, transdermally, rectally, transmucosally, topically, via inhalation, via buccal administration, intrapleurally, intravenous, intraarterial, intraperitoneal, subcutaneous, intramuscular, intranasal intrathecal, and intraarticular or combinations thereof. For veterinary use, the composition may be administered as a suitably acceptable formulation in accordance with normal veterinary practice. The veterinarian may readily determine the dosing regimen and route of administration that is most appropriate for a particular animal. The TALE-TFs and compositions thereof may be administered by traditional syringes, needleless injection devices, "microprojectile bombardment gone guns", or other physical methods such as electroporation ("EP"), "hydrodynamic method", or ultrasound.

10. Cell Types

Any of these delivery methods and/or routes of administration could be utilized with a myriad of cell types, for example, those cell types currently under investigation for cell-based therapies. The cell may be any mammalian cell, such as a HEK293T cell.

11. Kits

Provided herein is a kit, which may be used to induce mammalian gene expression in a cell. The kit comprises the above-described compositions or a cell that comprises said compositions, as well as instructions for using the compositions. Instructions included in kits may be affixed to packaging material or may be included as a package insert. While the instructions are typically written or printed materials they are not limited to such. Any medium capable of storing such instructions and communicating them to an end user is contemplated by this disclosure. Such media include, but are not limited to, electronic storage media (e.g., magnetic discs, tapes, cartridges, chips), optical media (e.g., CD ROM), and the like. As used herein, the term "instructions" may include the address of an internet site that provides the instructions.

At least one component may include at least two TALE-TFs, as described above, which specifically targets a gene. The TALE-TFs, as described above, may be included in the kit to specifically bind and target a particular target region upstream, within or downstream of the TSS of the target gene. For example, the TALE-TFs may be specific for a promoter region of a target gene.

The present invention has multiple aspects, illustrated by the following non-limiting examples.

12. Examples

The foregoing may be better understood by reference to the following examples, which are presented for purposes of illustration and are not intended to limit the scope of the invention.

EXAMPLE 1

Methods

Cell culture and transfection. HEK293T cells were obtained from the American Tissue Collection Center (ATCC) through the Duke University Cancer Center Facilities and were maintained in Dulbecco's Modified Eagle's Medium supplemented with 10% fetal bovine serum and 1% penicillin and streptomycin at 37° C. with 5% $CO_2$. HEK293T cells were transfected with Lipofectamine 2000 (Invitrogen) according to the manufacturer's instructions. Transfection efficiencies were routinely >95% as determined by flow cytometry after delivery of a control enhanced GFP expression plasmid. The amount of DNA used for lipofection was 800 ng per well in 24-well plates or 200 ng per well in 96-well plates. For luciferase reporter assays in 24-well plates, 100 ng of reporter plasmid was included with 700 ng of TALE-TF expression plasmid. When comparing single TALE-TFs to the combination of all TALE-TFs (FIG. 1), the total amount of TALE-TF expression plasmid was held constant (800 ng of single TALE-TFs and 800 ng of total TALE-TF expression plasmid divided equally amongst each factor). When assessing the individual contribution of each TALE-TF (FIG. 2), the amount of each TALE-TF was held constant at 116 ng, with empty expression plasmid added to a total of 700 ng. Amounts of DNA for transfections in 96-well plates were scaled accordingly.

Plasmids and TALE-TF. Tale-TFs were assembled using the Golden Gate TALEN and TAL effector kit obtained from Addgene (Cermak et al. Nucleic Acids Res 39:e82 (2011)). A destination vector for the final assembly step was created to include a Flag epitope tag and an SV40 NLS at the N terminus, a 152 residue deletion from the N terminus of the wild type TALE proteins that preserves the DNA binding ability of TALEs (Miller et al. Nat. Biotechnol. 29:143-148 (2011)), 63 wild type TAL amino acids after the repeat domain (Zhang et al., Nat. Biotechnol. 29: 149-153 (2011)), a C-terminal SV40 NLS, a VP64 domain that contains four repeats of the minimal activation domain of VP 16, and an HA tag at the C terminus (FIG. 1a). TALE-TFs were designed to target within the 600 bp upstream of the transcriptional start site (FIG. 1b) on the basis of the criteria described by Cermak et al. TALE-TFs were designed downstream of the transcription start site for ERBB2, but upstream of the translation start site, on the basis of previous studies showing high activity of synthetic zinc finger transcription factors targeting this region (Beerli et al., PNAS 97:1495-1500 (2000)). The compositions of the TALE-TFs are provided in FIG. 3.

The reporter plasmids were built by cloning PCR-amplified genomic DNA sequences upstream of the genes of interest IL1RN (chromosome 2, 113874366-113875462), KLK3 (chromosome 19, 51357466-51358177); CEACAM5 (chromosome 19, 42211804-42212651) and ERBB2 (chromosome 17, 37855857-37856492), in the vector pGL3-Basic (Promega). Coordinates are provided based on the hg19 reference genome.

Luciferase assays. Forty-eight hours after transfection, cells were collected into 96-well plates, washed with PBS once and lysed with 100 mM monobasic sodium phosphate and 0.2% Triton X-100. The lysate was incubated with Bright-Glo™ Substrate (Promega) in a 1:1 ratio and luciferase activity was measured using a Synergy 2 Multi-Mode Microplate Reader (BioTek). The results are expressed as relative luciferase activity (RLA), which is the average luciferase activity normalized to the luciferase activity in samples transfected with the reporter vector and the empty TALE-TF expression vector. Data are presented from three independent experiments performed with two biological replicates per experiment.

Western blot analysis Cells were lysed in 50 mM Tris-Cl (pH 7.4), 150 mM NaCl, 0.5% Triton X-100 and 0.1% SDS. Protein concentrations in cell lysates were measured by the BCA Protein Assay (Pierce). Lysates were mixed with loading buffer, boiled for 5 min, and equal amounts of protein were run in NuPAGE® Novex 4-12% Bis-Tris Gel polyacrylamide gels and transferred to nitrocellulose membranes. Non-specific antibody binding was blocked with 50 mM Tris/150 mM NaCl/0.1% Tween-20 (TBS-T) with 5% nonfat milk for 30 min. The membranes were incubated with primary antibodies (horseradish peroxidase (HRP)-conjugated anti-HA (Roche, clone 3F10) in 5% milk in TBS-T diluted 1:5000 for 30 min; anti-CEACAM5 (Cell Signaling Technology, clone CB30) in 5% milk in TBS-T diluted 1:1000 overnight; anti-GAPDH (Cell Signaling Technology, clone 14C10) in 5% milk in TBS-T diluted 1:5000 for 30 min; anti-ERBB2 (Cell Signaling Technology, clone 29D8) in 5% BSA in TBS-T diluted 1:2000 for 2 h). The membranes were then washed with TBS-T for 30 min. Membranes labeled with primary antibodies were incubated with rabbit HRP-conjugated antibody (Sigma-Aldrich, catalog number A6154) diluted 1:5000 for 30 min, and washed with TBS-T for 30 minutes. Membranes were visualized using the Immun-Star WesternC™ Chemiluminescence Kit (Bio- Rad) and images were captured using a ChemiDoc™ XRS+ System and processed using ImageLab software (Bio-Rad).

Enzyme-linked immunosorbent assay. Serum-free culture media (OPTI-MEM) was collected and frozen at −80° C. Human IL-1ra and KLK3 secretion into culture media was quantified via ELISA, according to the manufacturer's protocols (R&D Systems, Cat. No. DY280 and DKK300, respectively). For the IL-1Ra ELISA, the standard curve was prepared by diluting recombinant human IL-1ra in OPTI-MEM and the IL-1ra in culture media was measured undiluted. For the KLK3 ELISA, the standard curve was prepared by diluting recombinant KLK3 in the manufacturer's calibrator diluent and the samples were concentrated approximately eightfold by centrifugation through 3 k-Da MWCO filters for 20 minutes (Amicon Ultra, catalog number UFC500396). Reported values were corrected by the concentration factor for each sample.

For both assays, optical density was measured at 450 nm with a wavelength correction at 540 nm. Each standard and sample was assayed in duplicate. The duplicate readings were averaged and normalized by subtracting the average zero standard optical density. A standard curve was generated by log transforming the data and performing a linear regression of the IL-1ra or KLK3 concentration versus the optical density. The lower limit of detection was 50 pg/ml for human IL-1ra and 32 pg/ml for human KLK3. Data reported are the mean and s.e.m. of these individual values combined from multiple experiments (n=6 biological replicates for IL-1ra, n=4 biological replicates for KLK3).

Quantitative RT-PCR. Total RNA was isolated using the RNEASY® Plus RNA isolation kit (Qiagen). cDNA synthesis was performed using the SuperScript® VILO™ cDNA Synthesis Kit (Invitrogen). Realtime PCR using SsoFast™ EvaGreen® Supermix (Bio-Rad) was performed with the CFX96 Real-Time PCR Detection System (Bio-Rad) with 45 cycles, melting for 2 s at 95° C., and annealing and extension for 2 s at 55° C. Real-time PCR oligonucleotide primers (ERBB2, 5-AGCCGCGAGCACCCAAGT-3 (SEQ ID NO: 29), 5'-TTGGTGGGCAGGTAGGTGAGTT-3' (SEQ ID NO: 30); CEACAM5, 5'-TCCCCACAGATG-GTGCAT-3 (SEQ ID NO: 31), 5-GAACGGCGTGGAT-TCAATAG-3' (SEQ ID NO: 32); KLK3, 5'-CTCGTGGCAGGGCAGTCT-3 (SEQ ID NO: 33), 5'-AGCTGTGGCTGACCTGAAAT-3' (SEQ ID NO: 34); IL1RN, 5'-GACCCTCTGGGAGAAAATCC-3 (SEQ ID NO: 35), 5'-GTCCTTGCAAGTATCCAGCA-3'(SEQ ID NO: 36); PSD4, 5'-GCAGCACCTCCTGGTCAC-3 (SEQ ID NO: 37), 5'-ATCCGACACATCCTGATTCC-3' (SEQ ID NO: 38); IL1F10, 5'-CCTCCCCATGGCAAGATACT-3 (SEQ ID NO: 39), 5-AGCAGTTGTCTGCAACAGGA-3' (SEQ ID NO: 40); and GAPDH, 5'-CAATGACCCCT-TCATTGACC-3'(SEQ ID NO: 41); 5'-TTGATTTTG-GAGGGATCTCG-3' (SEQ ID NO: 42)) were designed using Primer3Plus software and purchased from IDT. Primer specificity was confirmed by agarose gel electrophoresis and melting curve analysis. Reaction efficiencies over the appropriate dynamic range were calculated to ensure linearity of the standard curve. Data are presented from three independent experiments performed with two biological replicates per experiment.

Statistics. Statistical analysis were performed by single factor ANOVA with α=0.05 in Microsoft Office Excel 2007. Effect coefficients (Table 3) were determined using the regression tool in the data analysis add-in to Microsoft Office Excel 2007, with the relative luciferase activities (FIG. 2a-c, Table 2) serving as the y input and an array of zeros and ones representing each TALE-TF combination as the x input.

EXAMPLE 2

Combinations of TALE-TFs

Figure 3:
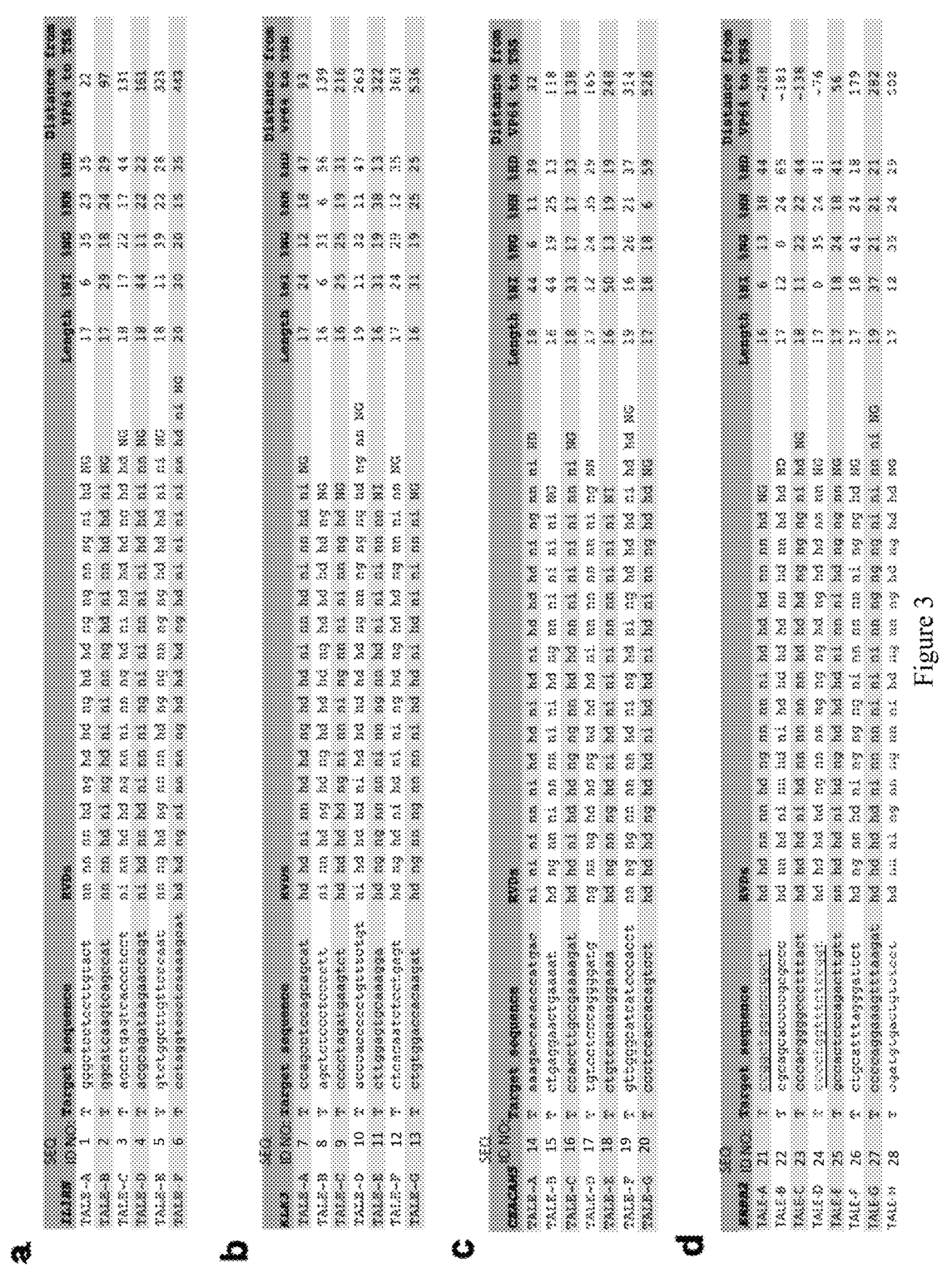
Figure 4:
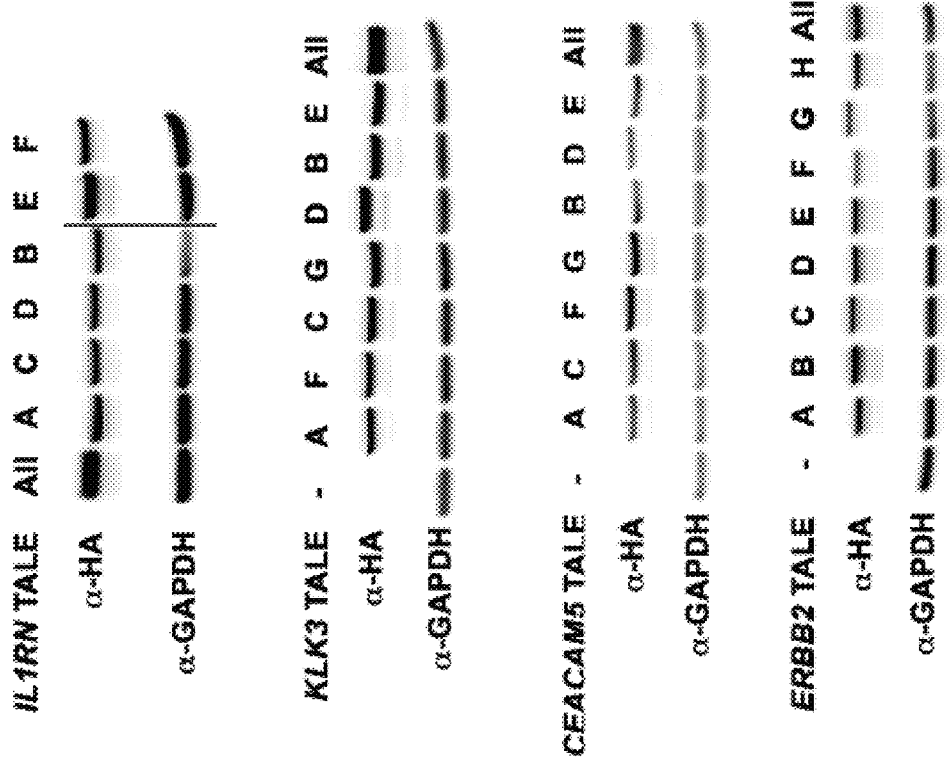
FIG. 4 shows the expression of TALE-TFs targeting ILIRN, KLK3, CEACAM5 and ERBB2 transfected into HEK293T cells.

Six, seven or eight TALE-TFs were targeted to the promoter regions of the IL1RN, KLK3 (also known as prostate-specific antigen (PSA)), CEACAM5 (also known as CEA), and ERBB2 which are implicated in immunomodulation, inflammation, and cancer (FIG. 3). The target sites for these TALE-TFs were distributed within 600 by of the TSS (FIG. 1b). TALE-TF expression plasmids were transfected into HEK293T cells either individually or as a combination of all the TALE-TFs targeted to a particular promoter. After 2 days, cell lysates were analyzed by Western blot with anti-HA for TALE-TF expression and anti-GADPH as a loading control. The anti-HA antibody recognizes an HA tag fused to the VP64 domain at the C-terminus of the TALE-TF. The expression of the TALE-TFs was confirmed by western blot (FIG. 4). TALE-TF activity was measured in reporter assays in which luciferase was under the control of the respective gene promoter (FIG. 1c-f). Most individual TALE-TFs activated the co-transfected plasmid reporters, but only modestly, as in previous studies (Table 1). However, the delivery of combinations of TALE-TFs led to substantial synergistic effects on gene activation. The synergistic activation of the plasmid-based reporters was recapitulated in the upregulation of the native genes in their natural chromosomal context as determined by quantitative reverse transcription PCR (qRT-PCR), including increases in mRNA abundance greater than 10,000-fold (FIG. 1g-j). Detection of induced protein expression of IL-1ra, (encoded by IL1RN), KLK3, CEACAM5, and ERBB-2 by ELISA and western blot validated the functional outcome of the activation of these genes (FIG. 1k-n). In particular, expression of IL-1ra, KLK3 and CEACAM5 protein was reproducibly detected in samples with combinations of TALE-TFs. Low expression of ERBB-2 was found in control samples and cells transfected with single TALE-TFs, but its expression was substantially enhanced in cells transfected with all TALE-TFs (FIG. 1n).

Figure 5:
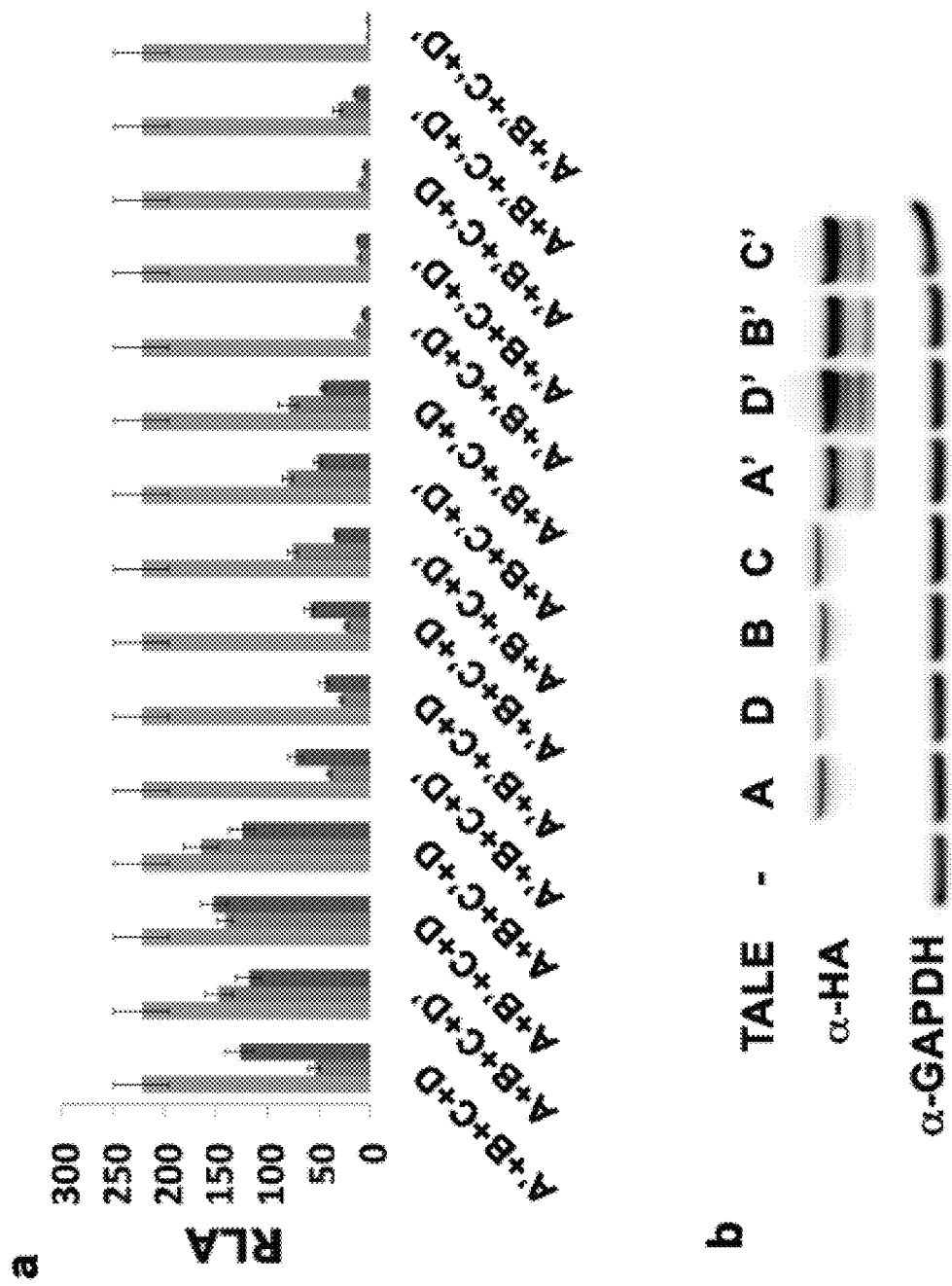
FIG. 5 shows the requirement of transactivation domain for synergistic gene regulation.

These results are consistent with a mechanism in which the VP64 acidic activation domain of multiple transcription factors is simultaneously interacting with and stabilizing components of the pre-initiation complex. This mechanism was confirmed by demonstrating that the VP64 domain, i.e., the transactivation domain, rather than nucleosome displacement by TALEs, was essential to achieving the synergistic effect on gene regulation (FIG. 5). The VP64 transcriptional activation domain was removed from the TALE-TF destination expression plasmid and TALE A, B, C and D targeting the ILIRN gene were recloned and designated A', B', C' and D'. HEK293T cells were transfected with the ILIRN reporter vector and all combinations of four TALE-TFs in which one, two, three or four TALE-TFs were replaced with a TALE-TF lacking the VP64 domain. In FIG. 5A, the relative luciferase activities (RLAs) are shown in groups for each indicated combination (middle bar), the RLA for transfection of all four TALE-TFs with VP64 (left bar), and the RLA for transfection of only the one, two, or three TALE-TFs that contain VP64 (right bar). The total amount of transfected plasmid DNA was maintained constant with empty expression vector. The results indicate that removing the VP64 domain from one or more TALE-TFs is similar to not including that TALE-TF in the transfection, indicating that binding and stabilization of preinitiation complex components by VP64, and not simply DNA-binding by the TALE, is necessary for synergistic activation. HEK293T cells were transfected with TALE-TFs A, B, C, D and the corresponding TALE-TF variants lacking VP64 targeting ILIRN. The cell lysates were analyzed by Western blot with anti-HA and anti-GAPDH antibodies.

Figure 6:
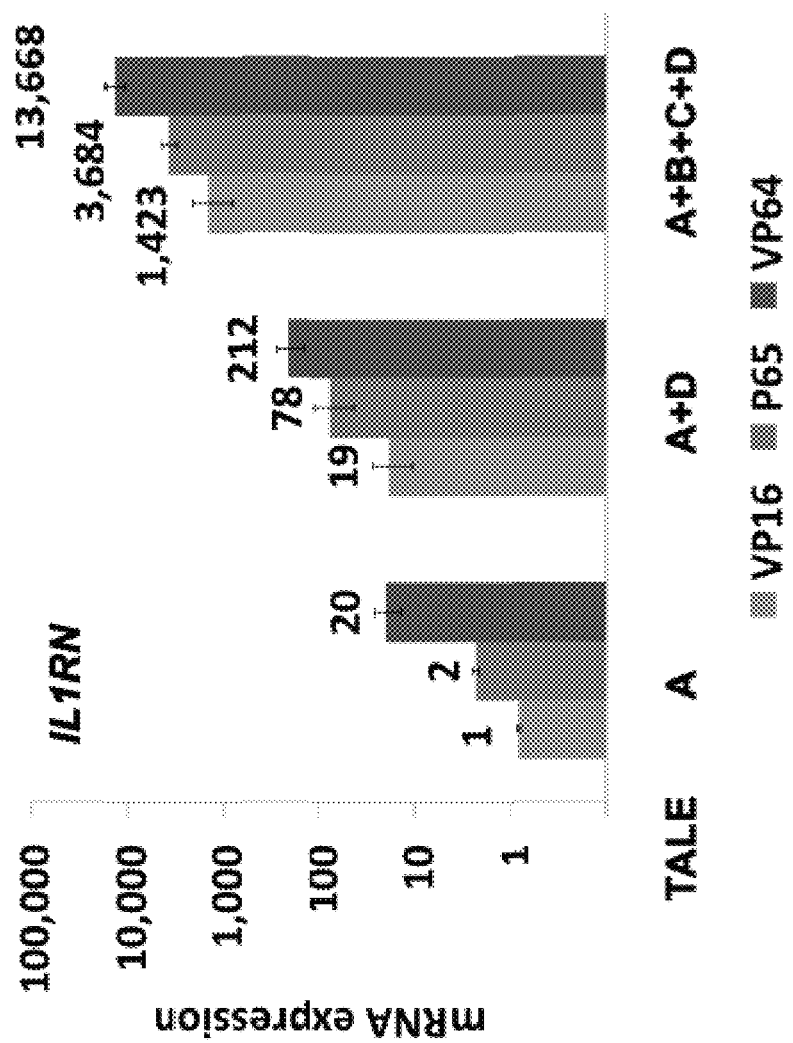
FIG. 6 shows the synergistic gene activation with multiple acidic activation domains as shown by quantitative RT-PCR to determine the levels of ILIRN transcripts.

Alternative acidic activation domains could also synergistically activate gene expression (FIG. 6). The VP64 transcriptional activation domain in the TALE-TF destination plasmid was replaced with two other well characterized acidic transcriptional activators: VP16 and P65. TALE-TFs A, B, C, and D targeting the ILIRN gene were recloned into these vectors. HEK293T cells were transfected with either TALE-TF A alone, TALE-TFs A and D, TALE-TFs A, B, C, and D together, or an empty vector as control. The RNA was analyzed using quantitative RT-PCR to determine the levels of ILIRN transcripts. The results are represented as relative levels of expression of ILIRN induced by each combination of TALE-TF with different activation domains normalized to GAPDH expression and control samples transfected with the empty vector only.

EXAMPLE 3

Specificity of TALE-TFs

Figure 7:
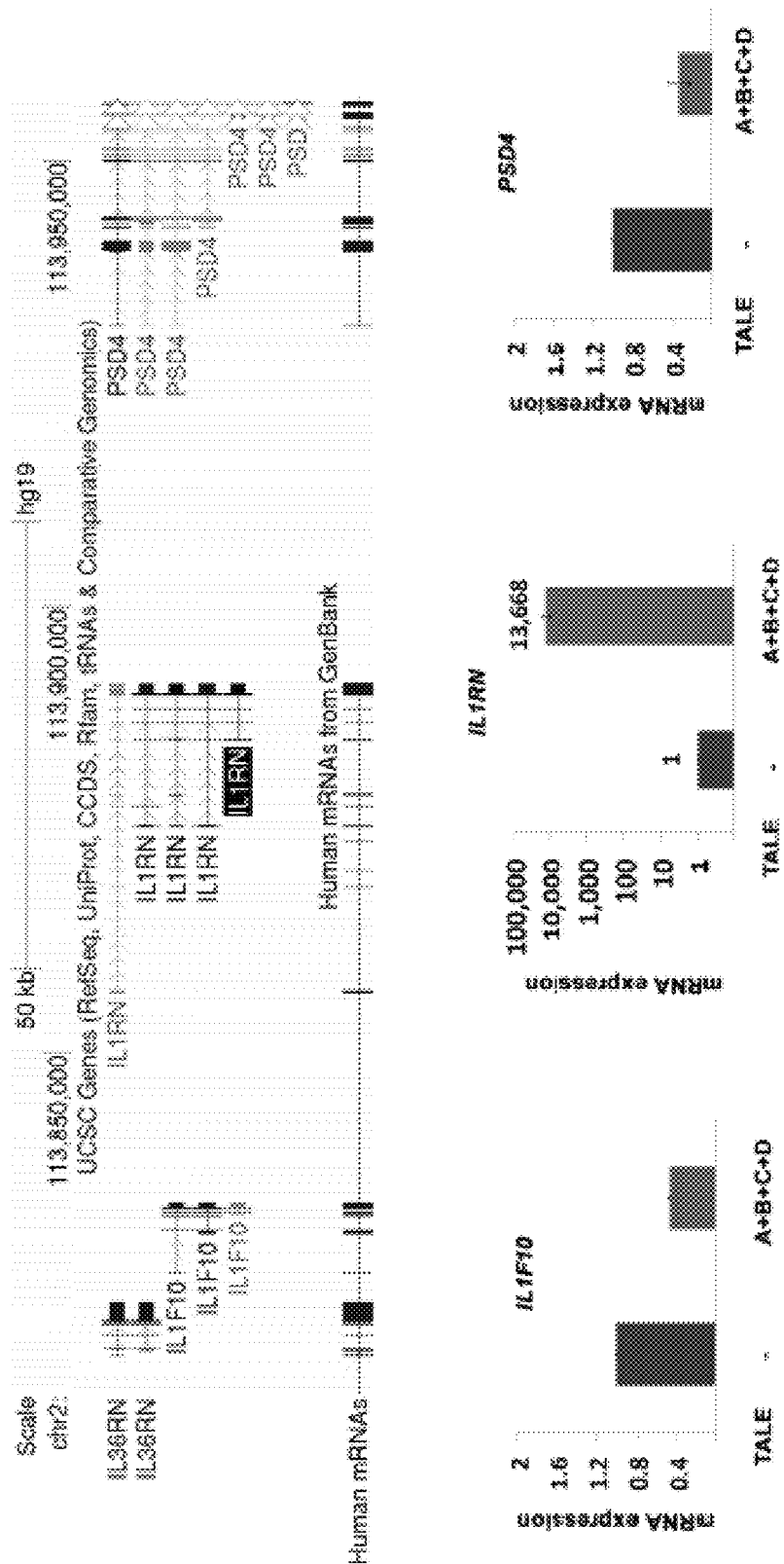
FIG. 7 shows the effect of synergistic gene activation by TALE-TFs on neighboring genes as shown by quantitative RT-PCR to determine the levels of ILIRN transcripts.

The expression of other genes near IL1RN did not increase, indicating that this large synergistic activation was specific to the target gene (FIG. 7). The ILIRN locus is flanked by genes ILIF10 and PSD4. To test whether transcriptional activation of the ILIRN gene caused changes in expression of nearby genes, quantitative RT-PCR was performed with cDNA prepared from cells transfected with TALE-TFs A, B, C, and D. The results are represented as levels of expression relative to GAPDH and normalized to samples transfected with an empty expression plasmid.

Figure 2:
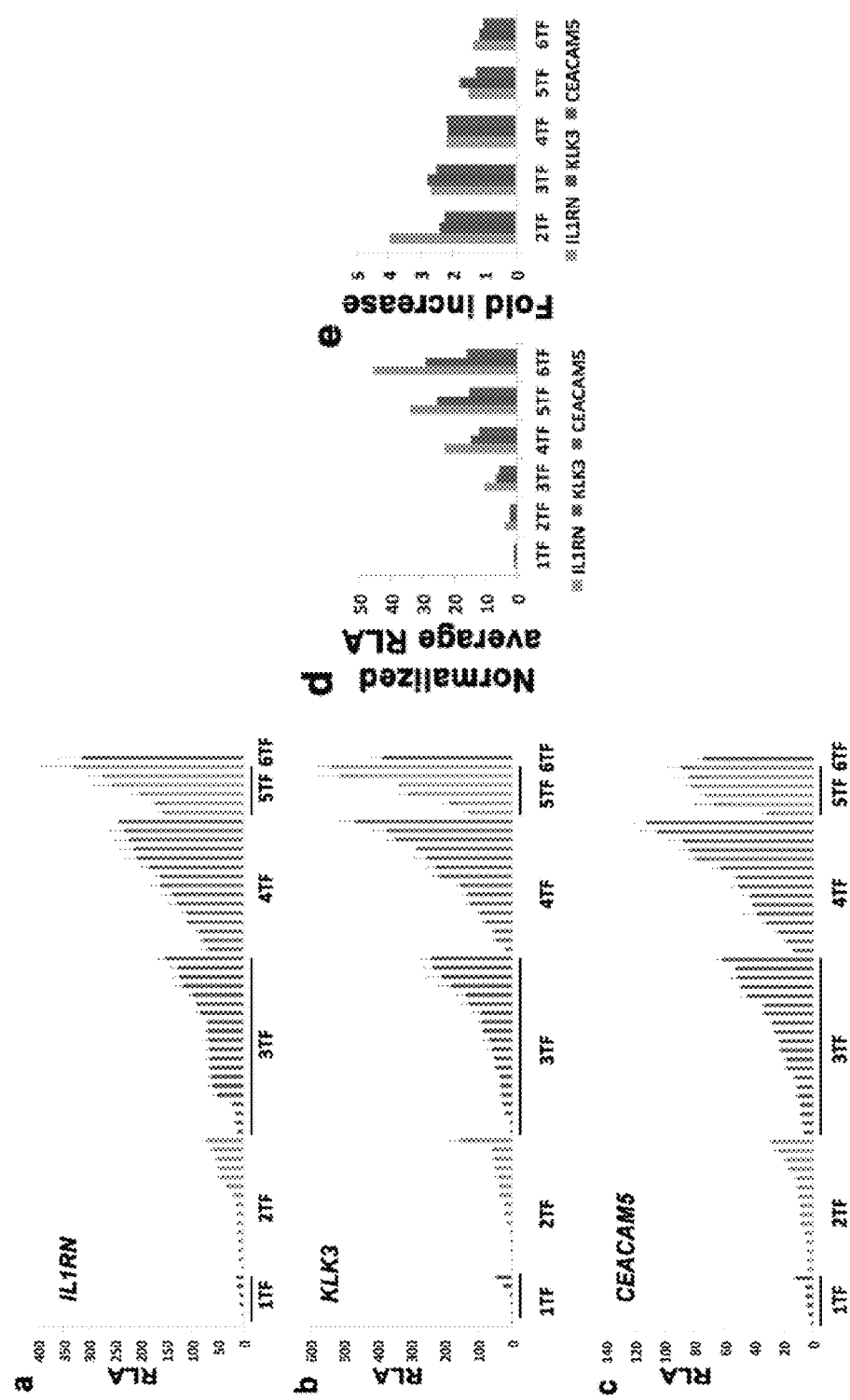
FIG. 2 shows combinatorial regulation of gene expression by TALE-TFs. (a-c) All possible 63 combinations of six TALE-TFs targeting the IL1RN, KLK3, and CEACAM5 genes were tested for activation of a luciferase reporter plasmid and ordered according to number of TALE-TFs and magnitude of relative luciferase activity (RLA). Samples receiving the same number of TALE-TFs are indicated by line or no line. Data are shown as the mean±SEM (n=3) independent experiments. P<0.0001 by ANOVA for all three data sets (Table 2). (d) The average RLA for the indicated number of TALE-TFs for each gene. (e) The fold increase of RLA for each number of TALE-TFs relative to the average RLA for one less TALE-TF is presented for each gene. (f-h) The measured values for all 63 combinations of TALE-TFs are plotted versus the values fit by the polynomial model, along with y=x (solid line).
Figure 2:
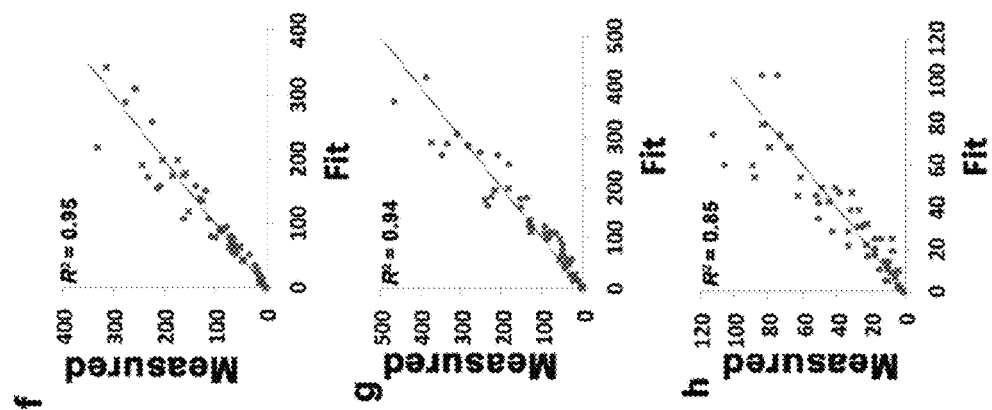
Figure 8:
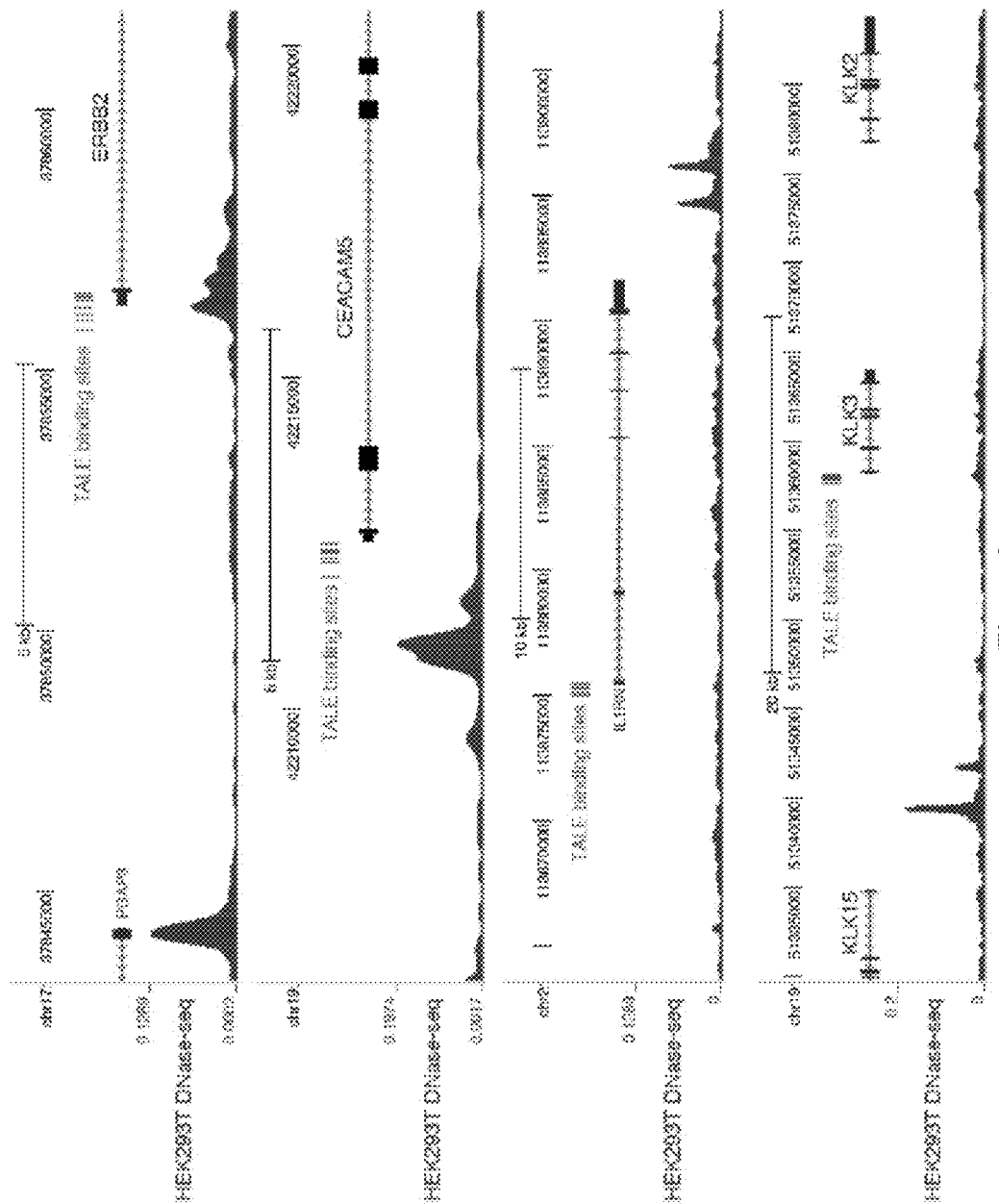
FIG. 8 shows the DNase hypersensitive regions of ERBB2, CEACAM5, ILIRN, and KLK3 genes.

The TALE-TFs were not specifically designed to target DNase-hypersensitive regions (FIG. 8). DNase-seq was performed in HEK293T cells to identify DNase hypersensitive regions as previously described (Song et al., *Genome Res* 21(10):1757 (2011); Song and Crawford, *Cold Spring Harbor Protocols* (2010)). The results show that open chromatin was not a requirement for gene activation by combinations of TALE-TFs. In fact, IL1RN, KLK3, and CEACAM5 are not expressed in HEK293T cells. Notably, targeting chromatin that is inaccessible to DNase did not prevent gene activation by the engineered TALE-TFs (FIG. 1 *g-i*). These results suggest that targeting open chromatin may not be a prerequisite to successful TALE-TF engineering and that activation of silenced genes is possible in the absence of chromatin modifying drugs, particularly when using combinations of TALE-TFs. In contrast to these three genes, ERBB2 is moderately expressed in HEK293 cells and the TALE-TFs for ERBB2 regulation were targeted to open chromatin (FIG. 8). Combinations of these TALE-TFs also led to synergistic ERBB2 activation although the effect was not as substantial relative to the other genes as a result of higher levels of basal expression (FIG. 1*f,j,n*).

EXAMPLE 4

Combinatorial Regulation of Mammalian Genes by TALE-TFs

To comprehensively characterize the effects of combinatorial regulation of mammalian genes by engineered TALE-TFs, all 63 combinations of six TALE-TFs targeting three different genes with a corresponding luciferase reporter were co-transfected in HEK293T cells (FIG. 2*a-c*). Various combinations of TALE-TFs could be used to reproducibly achieve tunable levels of gene expression over a large dynamic range. Many TALE-TFs that did not activate the reporter when delivered alone contributed to synergistic activation of expression when combined with other TALE-TFs (Table 2). In some cases, the addition of a TALE-TF decreased gene expression. However, for all three genes there was an increase in the average gene expression with increasing numbers of TALE-TFs (FIG. 2*d*), and the average contribution of each additional TALE-TF decreased as the number of TALE-TFs increased (FIG. 2*e*).

TABLE 2

Relative Luciferase Activity for combinations of TALE-TFs.
SEM = standard error of the mean.

| IL1RN | | | KLK3 | | | CEACAM5 | | |
|---|---|---|---|---|---|---|---|---|
| | RLA | SEM | | RLA | SEM | | RLA | SEM |
| E | 1.09 | 0.03 | C | 0.88 | 0.14 | A | 1.01 | 0.04 |
| F | 1.22 | 0.03 | B | 1.03 | 0.15 | E | 2.41 | 0.19 |
| D | 5.76 | 0.35 | E | 2.17 | 0.35 | C | 3.74 | 0.64 |
| C | 6.75 | 0.33 | F | 4.57 | 0.48 | D | 4.59 | 0.78 |
| B | 11.96 | 1.26 | A | 25.07 | 3.20 | F | 4.70 | 0.18 |
| A | 14.41 | 0.36 | D | 45.80 | 9.31 | B | 11.64 | 1.52 |
| E + F | 2.00 | 0.13 | C + B | 1.14 | 0.12 | A + E | 3.06 | 0.10 |
| C + F | 8.06 | 1.16 | C + E | 1.44 | 0.10 | A + C | 3.41 | 0.44 |
| D + F | 8.97 | 0.50 | B + E | 2.04 | 0.17 | A + D | 3.65 | 0.20 |
| A + E | 11.47 | 0.96 | F + B | 3.29 | 0.28 | A + F | 4.03 | 0.17 |
| E + C | 12.36 | 1.58 | C + F | 5.66 | 0.24 | C + E | 5.26 | 0.62 |
| D + E | 12.42 | 0.74 | F + E | 11.77 | 2.04 | F + E | 7.45 | 0.49 |
| A + F | 13.56 | 0.62 | A + C | 19.17 | 3.94 | F + D | 7.74 | 0.92 |
| B + F | 13.97 | 1.07 | A + B | 19.46 | 2.96 | D + E | 7.77 | 0.92 |
| E + B | 18.11 | 1.99 | B + D | 34.64 | 4.17 | C + B | 9.40 | 1.02 |
| A + C | 32.59 | 1.70 | C + D | 34.98 | 4.54 | A + B | 9.72 | 1.40 |
| D + C | 45.00 | 4.67 | A + F | 40.17 | 8.27 | B + E | 10.90 | 1.44 |
| A + D | 46.42 | 2.18 | A + E | 45.95 | 4.75 | C + F | 15.43 | 1.34 |
| A + B | 51.05 | 3.36 | D + E | 50.08 | 9.11 | F + B | 18.05 | 1.36 |
| D + B | 58.79 | 4.30 | F + D | 56.06 | 9.47 | C + D | 22.90 | 3.37 |
| B + C | 71.78 | 6.54 | A + D | 152.91 | 34.41 | B + D | 27.62 | 1.19 |
| D + E + F | 11.89 | 0.36 | C + B + E | 4.01 | 0.33 | A + C + E | 5.87 | 0.11 |
| E + C + F | 14.79 | 3.64 | C + F + B | 4.85 | 0.97 | A + D + E | 7.00 | 0.40 |
| A + E + F | 15.47 | 0.23 | C + F + E | 18.14 | 2.24 | A + F + D | 7.78 | 0.83 |
| E + B + F | 21.13 | 3.93 | F + B + E | 25.22 | 0.97 | A + F + E | 7.92 | 0.87 |
| A + D + E | 52.26 | 7.11 | A + B + E | 28.08 | 4.65 | A + C + F | 10.09 | 1.55 |
| A + C + F | 61.57 | 5.32 | A + C + B | 31.73 | 3.46 | A + B + E | 10.40 | 0.85 |

TABLE 2-continued

Relative Luciferase Activity for combinations of TALE-TFs.
SEM = standard error of the mean.

| IL1RN | | | KLK3 | | | CEACAM5 | | |
|---|---|---|---|---|---|---|---|---|
| | RLA | SEM | | RLA | SEM | | RLA | SEM |
| A + D + F | 62.86 | 6.23 | A + C + E | 34.01 | 8.92 | A + C + B | 12.19 | 0.73 |
| D + E + B | 63.74 | 2.92 | A + C + F | 47.13 | 5.69 | C + F + E | 17.67 | 1.28 |
| D + C + F | 64.91 | 8.48 | A + F + B | 51.75 | 9.41 | C + B + E | 18.05 | 2.59 |
| A + E + C | 65.87 | 5.77 | C + B + D | 58.13 | 15.67 | A + F + B | 21.81 | 2.38 |
| D + B + F | 67.75 | 11.26 | C + F + D | 66.90 | 16.42 | C + F + B | 22.16 | 1.95 |
| B + C + F | 68.43 | 5.02 | B + D + E | 84.46 | 6.84 | A + B + D | 25.63 | 1.13 |
| D + E + C | 68.74 | 2.29 | C + D + E | 89.15 | 8.43 | F + D + E | 27.28 | 1.40 |
| E + B + C | 84.19 | 9.28 | A + F + E | 93.34 | 27.51 | A + C + D | 33.30 | 1.78 |
| A + E + B | 90.14 | 1.21 | F + B + D | 129.09 | 23.93 | F + B + E | 33.40 | 2.07 |
| A + B + F | 99.39 | 5.19 | A + B + D | 137.64 | 29.66 | C + F + D | 44.71 | 4.66 |
| A + B + C | 118.47 | 11.71 | A + D + E | 181.23 | 36.26 | C + B + D | 48.82 | 0.91 |
| A + D + B | 124.43 | 12.23 | A + F + D | 208.90 | 45.84 | C + D + E | 51.02 | 4.10 |
| D + B + C | 127.18 | 13.20 | F + D + E | 234.64 | 26.66 | B + D + E | 52.22 | 0.78 |
| A + D + C | 151.52 | 12.87 | A + C + D | 240.72 | 37.19 | F + B + D | 61.45 | 2.95 |
| A + D + E + F | 69.05 | 15.29 | C + F + B + E | 19.38 | 3.21 | A + C + B + E | 13.77 | 1.40 |
| D + E + B + F | 77.85 | 6.07 | A + C + B + E | 47.83 | 3.68 | A + C + F + E | 17.93 | 1.79 |
| A + E + C + F | 86.78 | 5.91 | A + C + F + B | 50.99 | 5.52 | A + C + F + B | 23.56 | 2.26 |
| D + E + C + F | 107.60 | 8.92 | C + B + D + E | 77.91 | 7.42 | A + F + D + E | 31.94 | 1.68 |
| E + B + C + F | 110.89 | 9.61 | C + F + B + D | 93.54 | 5.79 | C + F + B + E | 38.24 | 9.11 |
| A + D + C + F | 128.88 | 16.78 | A + C + F + E | 124.04 | 15.39 | A + C + B + D | 40.97 | 1.64 |
| A + D + B + F | 138.25 | 19.88 | A + F + B + E | 131.46 | 13.41 | A + F + B + E | 42.93 | 4.57 |
| A + B + C + F | 161.75 | 17.78 | C + F + D + E | 154.91 | 15.96 | A + C + F + D | 50.64 | 4.41 |
| A + E + B + F | 161.90 | 10.25 | A + C + B + D | 217.21 | 24.85 | A + C + D + E | 51.35 | 2.52 |
| D + E + B + C | 183.28 | 13.62 | F + B + D + E | 225.37 | 27.23 | A + B + D + E | 63.08 | 5.62 |
| D + B + C + F | 206.73 | 24.31 | A + B + D + E | 252.84 | 37.27 | C + B + D + E | 79.15 | 5.86 |
| A + D + E + C | 213.39 | 27.30 | A + C + F + D | 281.45 | 12.10 | C + F + B + D | 83.07 | 6.02 |
| A + D + B + C | 223.14 | 26.85 | A + C + D + E | 347.17 | 24.04 | A + F + B + D | 87.62 | 9.63 |
| A + D + E + B | 231.11 | 27.32 | A + F + B + D | 371.94 | 38.64 | C + F + D + E | 105.23 | 10.75 |
| A + E + B + C | 242.59 | 8.96 | A + F + D + E | 465.06 | 53.26 | F + B + D + E | 112.50 | 7.69 |
| A + D + E + C + F | 156.95 | 12.86 | A + C + F + B + E | 130.16 | 13.44 | A + C + F + B + E | 31.17 | 4.76 |
| A + D + E + B + F | 172.57 | 22.95 | C + F + B + D + E | 183.75 | 20.22 | A + C + B + D + E | 67.69 | 11.42 |
| D + E + B + C + F | 202.99 | 15.63 | A + C + F + B + D | 308.92 | 24.92 | A + F + B + D + E | 73.06 | 4.11 |
| A + D + E + B + C | 256.14 | 37.49 | A + C + B + D + E | 334.67 | 8.54 | A + C + F + B + D | 81.95 | 5.44 |
| A + D + B + C + F | 275.31 | 25.38 | A + C + F + D + E | 511.60 | 72.91 | C + F + B + D + E | 83.69 | 12.00 |
| A + E + B + C + F | 330.26 | 62.33 | A + F + B + D + E | 540.35 | 44.96 | A + C + F + D + E | 89.03 | 8.65 |
| A + D + E + B + C + F | 313.00 | 47.33 | A + C + F + B + D + E | 385.24 | 31.31 | A + C + F + B + D + E | 74.12 | 4.47 |

To assign quantitative parameters to the relative contribution of each TALE-TF to the synergistic effect across the 63 data points in these experiments, polynomial model was applied to the data set of each gene of the form $$y_j = \left(\sum_{i=1}^{6} w_i x_{i,j}\right)^2$$

where $y_j$ is the relative luciferase activity for the jth combination of the six TALE-TFs. The value of $x_{i,j}$ is 0 if the ith TALE-TF is not included in the jth combination and it is 1 if it is included. The effect coefficient $w_i$ is a fit parameter that represents the relative contribution of the ith TALE-TF to the regulation of its target promoter in the context of all permutations of the six TALE-TFs. Multiple regression was used to solve for values of $w_i$ for all TALEs for each of the three target genes. These coefficients generate an excellent fit of the experimental data (FIG. 2f-h) and were highly significant ($P<2\times10^{-3}$) in accurately describing the relative contribution of each TALE-TF (Table 3).

TABLE 3

Effect coefficients and corresponding P-values resulting
from multiple regression of the polynomial model.

| | IL1RN | | KLK3 | | CEACAM5 | |
|---|---|---|---|---|---|---|
| | Effect coefficient | P-value | Effect coefficient | P-value | Effect coefficient | P-value |
| Intercept | −1.7 | 8.82e−5 | 2.4 | 3.02e−05 | −0.1 | 0.8 |
| TALE A | 4.4 | 6.15e−22 | 6.4 | 3.16e−23 | 0.0 | 1.0 |

TABLE 3-continued

Effect coefficients and corresponding P-values resulting from multiple regression of the polynomial model.

| | IL1RN | | KLK3 | | CEACAM5 | |
|---|---|---|---|---|---|---|
| | Effect coefficient | P-value | Effect coefficient | P-value | Effect coefficient | P-value |
| TALE B | 5.1 | 4.40e−2 | 0.7 | 0.1 | 2.4 | 1.67e−12 |
| TALE C | 4.4 | 4.59e−22 | 0.5 | 0.2 | 1.5 | 3.65e−07 |
| TALE D | 3.7 | 7.83e−19 | 8.8 | 6.00e−30 | 3.3 | 1.19e−17 |
| TALE E | 1.5 | 1.47e−06 | 3.0 | 3.21e−10 | 1.2 | 1.86e−05 |
| TALE F | 0.9 | 1.69e−03 | 3.5 | 1.27e−12 | 1.9 | 2.98e−09 |

In order to represent the contribution of each TALE-TF to the synergistic activation of gene expression, additive, multiplicative, and polynomial models of the form $$y_j = \sum_{i=1}^{6} w_i x_{i,j} \quad \text{additive}$$

$$y_j = 10 \sum_{i=1}^{6} w_i x_{i,j} \quad \text{multiplication}$$

$$y_j = \left(\sum_{i=1}^{6} w_i x_{i,j}\right)^2 \quad \text{polynomial}$$

were tested for best fit of the data in FIG. 2a-c and Table 2, where $y_j$ is the relative luciferase activity for the $j^{th}$ combination of i TALE-TFs. The value of $x_{ij}$ is 0 if the $i^{th}$ TALE-TF is not included in $j^{th}$ combination and is 1 if it is included. The effect coefficient $w_i$ is a fit parameter that represents the relative contribution of that particular TALE-TF to the regulation of its target promoter in the context of all permutations of the six TALE-TFs. Multiple regression was used to solve for values of $w_i$ for all TALEs for each gene. The resulting fits for IL1RN (a-c), KLK3 (d-f) and CEACAM5 (g-i) are shown here, as well as x=y (solid line). The additive model does not account for synergy between TALE-TFs and therefore underestimates the data as the number of TALE-TFs and corresponding level of gene activation increases (a,d,g). The multiplicative model does not account for the diminishing effect of extra TALE-TFs as the number of TALE-TFs increases (FIG. 2e), and therefore overestimates the data as the number of TALE-TFs and corresponding level of gene activation increases (b,e,h). The polynomial model generally provides the best fit of the data (c,f,i), which mechanistically can be explained by its inclusion of second-order terms that account for interactions between TALE-TFs.

Figure 9:
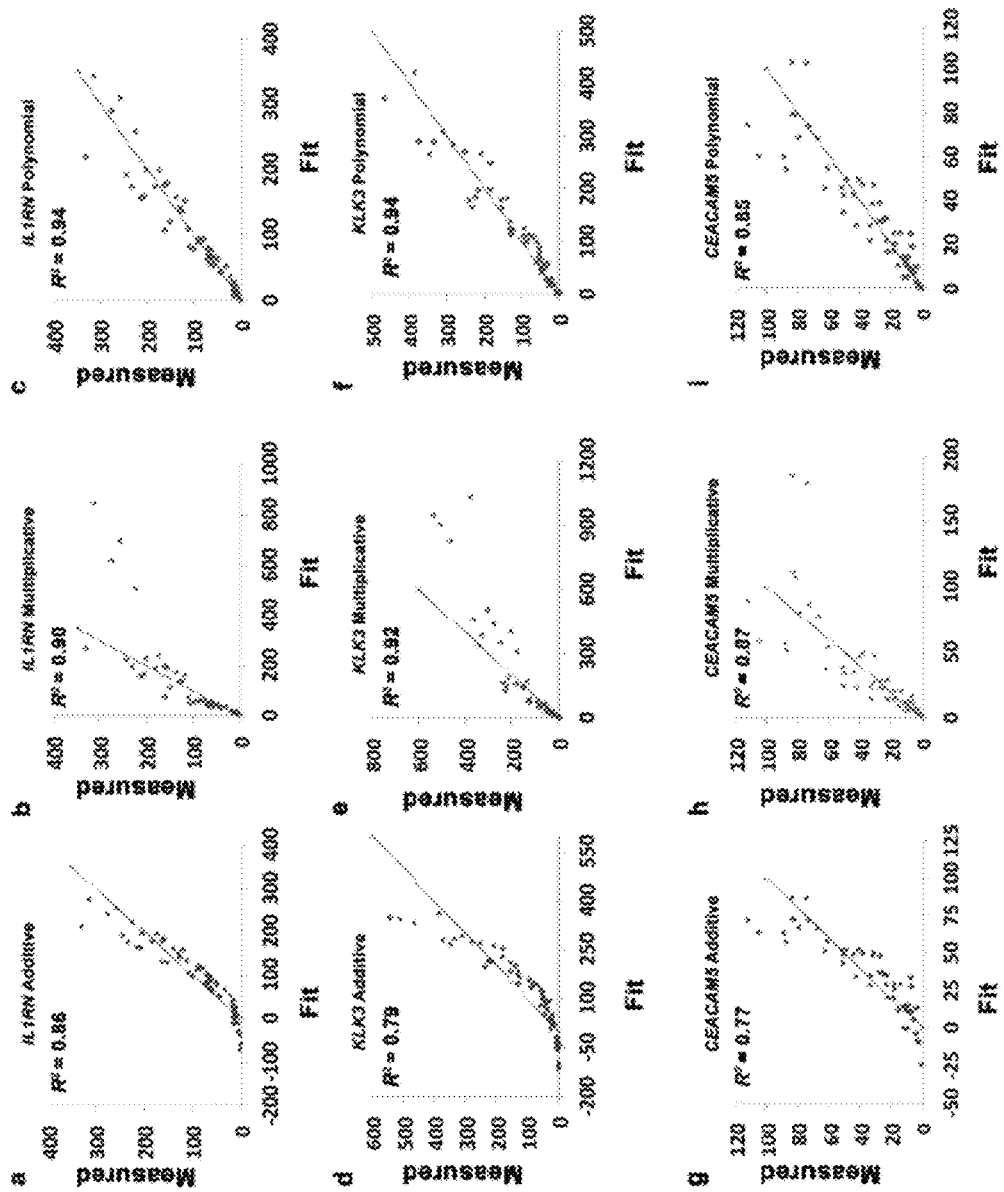
FIG. 9(a-i) shows the mathematical expression of combinatorial regulation of gene activation by TALE-TFs.

The polynomial model provided a stronger description of the data than the corresponding additive and multiplicative models (FIG. 9). The additive model does not account for the synergy of TALE-TF activity (FIG. 2d) and the multiplicative model does not account for the diminishing contribution of each additional TALE-TF (FIG. 2e). The superior fit of the polynomial model relative to the additive model can be mathematically explained by the second-order terms that are the product of effect coefficients for different TALE-TFs. This suggests the presence of some form of cooperativity, but does not reveal the underlying mechanism. As discussed above, the simultaneous binding and stabilization of components of the pre-initiation complex by VP64 probably has a role, in addition to other secondary effects of VP64-mediated gene activation on local epigenetics and chromatin structure.

No clear correlation coefficient with TALE array length, composition, or distance to the TSS was found that was consistent for all genes (FIG. 3). This suggests that these TALE-TF design parameters cannot be used independently to predict highly effective TALE-TFs. It is probable that other biological and structural components of these gene promoters, including genome folding and competition with endogenous regulatory factors, have a dominant role in determining the activity of single TALE-TFs and TALE-TF combinations.

The cooperative activity of TALE-TFs enables the control of gene expression without the need for small molecules used in conventional chemically regulated systems. The use of TALE-TF combinations that target endogenous promoters recapitulates the complexity of natural systems in a precise and controlled manner. This approach constitutes a powerful experimental system for elucidating the fundamental mechanisms of natural gene regulation. The capacity for combinatorial regulation also provides a new framework for engineering biocomputation systems that control endogenous genes in mammalian cells, similarly to recently developed genetic logic gates that control engineered transgenes. Precise control of gene expression with multiple tunable inputs may lead to greater potency, robustness and predictability in bioengineered systems in the context of cell-machine interfaces and gene and cell-based therapies.

It is understood that the foregoing detailed description and accompanying examples are merely illustrative and are not to be taken as limitations upon the scope of the invention, which is defined solely by the appended claims and their equivalents.

Various changes and modifications to the disclosed embodiments will be apparent to those skilled in the art. Such changes and modifications, including without limitation those relating to the chemical structures, substituents, derivatives, intermediates, syntheses, compositions, formulations, or methods of use of the invention, may be made without departing from the spirit and scope thereof.

TALE-TF SEQUENCES

SEQ ID NO: 43: IL1RN TALE-A nucleotide
ATGGACTACAAAGACCATGACGGTGATTATAAAGATCATGACATCGATTACAAGGATGACGATGACAAGa
tggcccccaagaagaagaggaaggtgggccgcGgatcTgtggatctacgcacgctcggctacagtcagca
gcagcaagagaagatcaaaccgaaggtgcgttcgacagtggcgcagcaccacgaggcactggtgggccat
gggtttacacacgcgcacatcgttgcgctcagccaacacccggcagcgttagggaccgtcgctgtcacgt
atcagcacataatcacggcgttgccagaggcgacacacgaagacatcgttggcgtcggcaaacagtggtc
cggcgcacgcgcccggaggccttgctcacggatgcgggggagttgagaggtccgccgttacagttggac
acaggccaacttgtgaagattgcaaaacgtggcggcgtgaccgcaatggaggcagtgcatgcatcgcgca
atgcactgacgggtgcccccctgAACCTGACCCCGGACCAAGTGGTGGCTATCGCCAGCAACAATGGCGG
CAAGCAAGCGCTCGAAACGGTGCAGCGGCTGTTGCCGGTGCTGTGCCAGGACCATGGCCTGACCCCGGAC
CAAGTGGTGGCTATCGCCAGCAACAATGGCGGCAAGCAAGCGCTCGAAACGGTGCAGCGGCTGTTGCCGG
TGCTGTGCCAGGACCATGGCCTGACCCCGGACCAAGTGGTGGCTATCGCCAGCAACAATGGCGGCAAGCA
AGCGCTCGAAACGGTGCAGCGGCTGTTGCCGGTGCTGTGCCAGGACCATGGCCTGACCCCGGACCAAGTG
GTGGCTATCGCCAGCCACGATGGCGGCAAGCAAGCGCTCGAAACGGTGCAGCGGCTGTTGCCGGTGCTGT
GCCAGGACCATGGCCTGACCCCGGACCAAGTGGTGGCTATCGCCAGCAACGGTGGCGGCAAGCAAGCGCT
CGAAACGGTGCAGCGGCTGTTGCCGGTGCTGTGCCAGGACCATGGCCTGACCCCGGACCAAGTGGTGGCT
ATCGCCAGCCACGATGGCGGCAAGCAAGCGCTCGAAACGGTGCAGCGGCTGTTGCCGGTGCTGTGCCAGG
ACCATGGCCTGACCCCGGACCAAGTGGTGGCTATCGCCAGCCACGATGGCGGCAAGCAAGCGCTCGAAAC
GGTGCAGCGGCTGTTGCCGGTGCTGTGCCAGGACCATGGCCTGACCCCGGACCAAGTGGTGGCTATCGCC
AGCAACGGTGGCGGCAAGCAAGCGCTCGAAACGGTGCAGCGGCTGTTGCCGGTGCTGTGCCAGGACCATG
GCCTGACCCCGGACCAAGTGGTGGCTATCGCCAGCCACGATGGCGGCAAGCAAGCGCTCGAAACGGTGCA
GCGGCTGTTGCCGGTGCTGTGCCAGGACCATGGCCTGACCCCGGACCAAGTGGTGGCTATCGCCAGCCAC
GATGGCGGCAAGCAAGCGCTCGAAACGGTGCAGCGGCTGTTGCCGGTGCTGTGCCAGGACCATGGCCTGA
CTCCGGACCAAGTGGTGGCTATCGCCAGCAACGGTGGCGGCAAGCAAGCGCTCGAAACGGTGCAGCGGCT
GTTGCCGGTGCTGTGCCAGGACCATGGCCTGACCCCGGACCAAGTGGTGGCTATCGCCAGCAACGGTGGC
GGCAAGCAAGCGCTCGAAACGGTGCAGCGGCTGTTGCCGGTGCTGTGCCAGGACCAtggcCTGACCCCGG
ACCAAGTGGTGGCTATCGCCAGCAACAATGGCGGCAAGCAAGCGCTCGAAACGGTGCAGCGGCTGTTGCC
GGTGCTGTGCCAGGACCATGGCCTGACCCCGGACCAAGTGGTGGCTATCGCCAGCAACGGTGGCGGCAAG
CAAGCGCTCGAAACGGTGCAGCGGCTGTTGCCGGTGCTGTGCCAGGACCATGGCCTGACCCCGGACCAAG
TGGTGGCTATCGCCAGCAACATTGGCGGCAAGCAAGCGCTCGAAACGGTGCAGCGGCTGTTGCCGGTGCT
GTGCCAGGACCATGGCCTGACCCCGGACCAAGTGGTGGCTATCGCCAGCCACGATGGCGGCAAGCAAGCG
CTCGAAACGGTGCAGCGGCTGTTGCCGGTGCTGTGCCAGGACCATGGCCTGACCCCGGACCAAGTGGTGG
ctatcgccagcAACGGTggcggcaagcaagcgctcgaaagcattgtggcccagctgagccggcctgatcc
ggcgttggccgcgttgaccaacgacgaccacctcgtcgccttggcctgcctcggcggacgtcctgccatg
gatgcagtgaaaaagggattgccgcacgcgccggaattgatcagaagagtcaatcgccgtattggcgaac
gcacgtcccatcgcgttgccGgatcCaAGGCTAGCCCGAAAAAGAAACGCAAAGTTGGGCGCCGCGACGC
GCTGGACGATTTCGATCTCGACATGCTGGGTTCTGATGCCCTCGATGACTTTGACCTGGATATGTTGGGA
AGCGACGCATTGGATGACTTTGATCTCGACATGCTCGGCTCCGATGCTCTGGACGATTTCGATCTCGATA
TGTTAATTAACTACCCGTACGACGTTCCGGACTACGCTTCTTGA SEQ ID NO: 44: IL1RN TALE-A polypeptide
MDYKDHDGDYKDHDIDYKDDDDKMAPKKKRKVGRGSVDLRTLGYSQQQQEKIKPKVRSTVAQHHEALVGH
GFTHAHIVALSQHPAALGTVAVTYQHIITALPEATHEDIVGVKQWSGARALEALLTDAGELRGPPLQLD
TGQLVKIAKRGGVTAMEAVHASRNALTGAPLNLTPDQVVAIASNNGGKQALETVQRLLPVLCQDHGLTPD
QVVAIASNNGGKQALETVQRLLPVLCQDHGLTPDQVVAIASNNGGKQALETVQRLLPVLCQDHGLTPDQV
VAIASHDGGKQALETVQRLLPVLCQDHGLTPDQVVAIASNGGGKQALETVQRLLPVLCQDHGLTPDQVVA
IASHDGGKQALETVQRLLPVLCQDHGLTPDQVVAIASHDGGKQALETVQRLLPVLCQDHGLTPDQVVAIA
SNGGGKQALETVQRLLPVLCQDHGLTPDQVVAIASHDGGKQALETVQRLLPVLCQDHGLTPDQVVAIASH
DGGKQALETVQRLLPVLCQDHGLTPDQVVAIASNGGGKQALETVQRLLPVLCQDHGLTPDQVVAIASNGG
GKQALETVQRLLPVLCQDHGLTPDQVVAIASNNGGKQALETVQRLLPVLCQDHGLTPDQVVAIASNGGGK
QALETVQRLLPVLCQDHGLTPDQVVAIASNIGGKQALETVQRLLPVLCQDHGLTPDQVVAIASHDGGKQA
LETVQRLLPVLCQDHGLTPDQVVAIASNGGGKQALESIVAQLSRPDPALAALTNDDHLVALACLGGRPAM
DAVKKGLPHAPELIRRVNRRIGERTSHRVAGSKASPKKKRKVGRADALDDFDLDMLGSDALDDFDLDMLG
SDALDDFDLDMLGSDALDDFDLDMLINYPYDVPDYAS SEQ ID NO: 45: IL1RN TALE-B nucleotide
ATGGACTACAAAGACCATGACGGTGATTATAAAGATCATGACATCGATTACAAGGATGACGATGACAAGa
tggcccccaagaagaagaggaaggtgggccgcGgatcTgtggatctacgcacgctcggctacagtcagca
gcagcaagagaagatcaaaccgaaggtgcgttcgacagtggcgcagcaccacgaggcactggtgggccat
gggtttacacacgcgcacatcgttgcgctcagccaacacccggcagcgttagggaccgtcgctgtcacgt
atcagcacataatcacggcgttgccagaggcgacacacgaagacatcgttggcgtcggcaaacagtggtc
cggcgcacgcgcccggaggccttgctcacggatgcgggggagttgagaggtccgccgttacagttggac
acaggccaacttgtgaagattgcaaaacgtggcggcgtgaccgcaatggaggcagtgcatgcatcgcgca
atgcactgacgggtgcccccctgAACCTGACCCCGGACCAAGTGGTGGCTATCGCCAGCAACAATGGCGG
CAAGCAAGCGCTCGAAACGGTGCAGCGGCTGTTGCCGGTGCTGTGCCAGGACCATGGCCTGACCCCGGAC
CAAGTGGTGGCTATCGCCAGCAACAATGGCGGCAAGCAAGCGCTCGAAACGGTGCAGCGGCTGTTGCCGG
TGCTGTGCCAGGACCATGGCCTGACCCCGGACCAAGTGGTGGCTATCGCCAGCCACGATGGCGGCAAGCA
AGCGCTCGAAACGGTGCAGCGGCTGTTGCCGGTGCTGTGCCAGGACCATGGCCTGACCCCGGACCAAGTG
GTGGCTATCGCCAGCAACATTGGCGGCAAGCAAGCGCTCGAAACGGTGCAGCGGCTGTTGCCGGTGCTGT
GCCAGGACCATGGCCTGACCCCGGACCAAGTGGTGGCTATCGCCAGCAACGGTGGCAAGCAAGCGCT
CGAAACGGTGCAGCGGCTGTTGCCGGTGCTGTGCCAGGACCATGGCCTGACCCCGGACCAAGTGGTGGCT
ATCGCCAGCCACGATGGCGGCAAGCAAGCGCTCGAAACGGTGCAGCGGCTGTTGCCGGTGCTGTGCCAGG
ACCATGGCCTGACCCCGGACCAAGTGGTGGCTATCGCCAGCAACATTGGCGGCAAGCAAGCGCTCGAAAC
GGTGCAGCGGCTGTTGCCGGTGCTGTGCCAGGACCATGGCCTGACCCCGGACCAAGTGGTGGCTATCGCC
AGCAACATTGGCGGCAAGCAAGCGCTCGAAACGGTGCAGCGGCTGTTGCCGGTGCTGTGCCAGGACCATG
GCCTGACCCCGGACCAAGTGGTGGCTATCGCCAGCAACAATGGCGGCAAGCAAGCGCTCGAAACGGTGCA
GCGGCTGTTGCCGGTGCTGTGCCAGGACCATGGCCTGACCCCGGACCAAGTGGTGGCTATCGCCAGCAAC
GGTGGCGGCAAGCAAGCGCTCGAAACGGTGCAGCGGCTGTTGCCGGTGCTGTGCCAGGACCATGGCCTGA
CTCCGGACCAAGTGGTGGCTATCGCCAGCCACGATGGCGGCAAGCAAGCGCTCGAAACGGTGCAGCGGCT

TALE-TF SEQUENCES

GTTGCCGGTGCTGTGCCAGGACCATGGCCTGACCCCGGACCAAGTGGTGGCTATCGCCAGCAACATTGGC
GGCAAGCAAGCGCTCGAAACGGTGCAGCGGCTGTTGCCGGTGCTGTGCCAGGACCAtggcCTGACCCCGG
ACCAAGTGGTGGCTATCGCCAGCAACAATGGCGGCAAGCAAGCGCTCGAAACGGTGCAGCGGCTGTTGCC
GGTGCTGTGCCAGGACCATGGCCTGACCCCGGACCAAGTGGTGGCTATCGCCAGCCACGATGGCGGCAAG
CAAGCGCTCGAAACGGTGCAGCGGCTGTTGCCGGTGCTGTGCCAGGACCATGGCCTGACCCCGGACCAAG
TGGTGGCTATCGCCAGCCACGATGGCGGCAAGCAAGCGCTCGAAACGGTGCAGCGGCTGTTGCCGGTGCT
GTGCCAGGACCATGGCCTGACCCCGGACCAAGTGGTGGCTATCGCCAGCAACATTGGCGGCAAGCAAGCG
CTCGAAACGGTGCAGCGGCTGTTGCCGGTGCTGTGCCAGGACCATGGCCTGACCCCGGACCAAGTGGTGG
ctatcgccagcaacggtggcggcaagcaagcgctcgaaagcattgtgggcccagctgagccggcctgatcc
ggcgttggccgcgttgaccaacgacgaccacctcgtcgccttggcctgcctcggcggacgtcctgccatg
gatgcagtgaaaaagggattgccgcacgcgccggaattgatcagaagagtcaatcgccgtattggcgaac
gcacgtcccatcgcgttgccGgatcCaAGGCTAGCCCGAAAAAGAAACGCAAAGTTGGGCGCGCCGACGC
GCTGGACGATTTCGATCTCGACATGCTGGGTTCTGATGCCCTCGATGACTTTGACCTGGATATGTTGGGA
AGCGACGCATTGGATGACTTTGATCTGGACATGCTCGGCTCCGATGCTCTGGACGATTTCGATCTCGATA
TGTTAATTAACTACCCGTACGACGTTCCGGACTACGCTTCTTGA SEQ ID NO: 46: IL1RN TALE-B polypeptide
MDYKDHDGDYKDHDIDYKDDDDKMAPKKKRKVGRGSVDLRTLGYSQQQQEKIKPKVRSTVAQHHEALVGH
GFTHAHIVALSQHPAALGTVAVTYQHIITALPEATHEDIVGKQWSGARALEALLTDAGELRGPPLQLD
TGQLVKIAKRGGVTAMEAVHASRNALTGAPLNLTPDQVVAIASNNGGKQALETVQRLLPVLCQDHGLTPD
QVVAIASNNGGKQALETVQRLLPVLCQDHGLTPDQVVAIASHDGGKQALETVQRLLPVLCQDHGLTPDQV
VAIASNIGGKQALETVQRLLPVLCQDHGLTPDQVVAIASNGGGKQALETVQRLLPVLCQDHGLTPDQVVA
IASHDGGKQALETVQRLLPVLCQDHGLTPDQVVAIASNIGGKQALETVQRLLPVLCQDHGLTPDQVVAIA
SNIGGKQALETVQRLLPVLCQDHGLTPDQVVAIASNNGGKQALETVQRLLPVLCQDHGLTPDQVVAIASN
GGGKQALETVQRLLPVLCQDHGLTPDQVVAIASHDGGKQALETVQRLLPVLCQDHGLTPDQVVAIASNIG
GKQALETVQRLLPVLCQDHGLTPDQVVAIASNNGGKQALETVQRLLPVLCQDHGLTPDQVVAIASHDGGK
QALETVQRLLPVLCQDHGLTPDQVVAIASHDGGKQALETVQRLLPVLCQDHGLTPDQVVAIASNIGGKQA
LETVQRLLPVLCQDHGLTPDQVVAIASNGGGKQALESIVAQLSRPDPALAALTNDDHLVALACLGGRPAM
DAVKKGLPHAPELIRRVNRRIGERTSHRVAGSKASPKKKRKVGRADALDDFDLDMLGSDALDDFDLDMLG
SDALDDFDLDMLGSDALDDFDLDMLINYPYDVPDYAS SEQ ID NO: 47: IL1RN TALE-C nucleotide
ATGGACTACAAGACCATGACGGTGATTATAAAGATCATGACATCGATTACAAGGATGACGATGACAAGa
tggcccccaagaagaagaggaaggtgggccgcGgatcTgtggatctacgcacgctcggctacagtcagca
gcagcaagagaagatcaaaccgaaggtgcgttcgacagtggcgcagcaccacgaggcactggtgggccat
gggtttacacacgcgcacatcgttgcgctcagccaacaccggcagcgttagggaccgtcgctgtcacgt
atcagcacataatcacggcgttgccagaggcgacacaacgaagacatcgttggcgtcggcaaacagtggtc
cggcgcacgcgccctggaggccttgctcacggatgcggggagttgagaggtccgccgttacagttggac
acaggccaacttgtgaagattgcaaaacgtggcggcgtgaccgcaatggaggcagtgcatgcatcgcgca
atgcactgacgggtgccccctgAACCTGACCCCGGACCAAGTGGTGGCTATCGCCAGCAACATTGGCGG
CAAGCAAGCGCTCGAAACGGTGCAGCGGCTGTTGCCGGTGCTGTGCCAGGACCATGGCCTGACCCCGGAC
CAAGTGGTGGCTATCGCCAGCAACAATGGCGGCAAGCAAGCGCTCGAAACGGTGCAGCGGCTGTTGCCGG
TGCTGTGCCAGGACCATGGCCTGACCCCGGACCAAGTGGTGGCTATCGCCAGCCACGATGGCGGCAAGCA
AGCGCTCGAAACGGTGCAGCGGCTGTTGCCGGTGCTGTGCCAGGACCATGGCCTGACCCCGGACCAAGTG
GTGGCTATCGCCAGCCACGATGGCGGCAAGCAAGCGCTCGAAACGGTGCAGCGGCTGTTGCCGGTGCTGT
GCCAGGACCATGGCCTGACCCCGGACCAAGTGGTGGCTATCGCCAGCAACGGTGGCGGCAAGCAAGCGCT
CGAAACGGTGCAGCGGCTGTTGCCGGTGCTGTGCCAGGACCATGGCCTGACCCCGGACCAAGTGGTGGCT
ATCGCCAGCAACAATGGCGGCAAGCAAGCGCTCGAAACGGTGCAGCGGCTGTTGCCGGTGCTGTGCCAGG
ACCATGGCCTGACCCCGGACCAAGTGGTGGCTATCGCCAGCAACATTGGCGGCAAGCAAGCGCTCGAAAC
GGTGCAGCGGCTGTTGCCGGTGCTGTGCCAGGACCATGGCCTGACCCCGGACCAAGTGGTGGCTATCGCC
AGCAACAATGGCGGCAAGCAAGCGCTCGAAACGGTGCAGCGGCTGTTGCCGGTGCTGTGCCAGGACCATG
GCCTGACCCCGGACCAAGTGGTGGCTATCGCCAGCAACGGTGGCGGCAAGCAAGCGCTCGAAACGGTGCA
GCGGCTGTTGCCGGTGCTGTGCCAGGACCATGGCCTGACCCCGGACCAAGTGGTGGCTATCGCCAGCCAC
GATGGCGGCAAGCAAGCGCTCGAAACGGTGCAGCGGCTGTTGCCGGTGCTGTGCCAGGACCATGGCCTGA
CCCCGGACCAAGTGGTGGCTATCGCCAGCAACATTGGCGGCAAGCAAGCGCTCGAAACGGTGCAGCGGCT
GTTGCCGGTGCTGTGCCAGGACCATGGCCTGACTCCGGACCAAGTGGTGGCTATCGCCAGCCACGATGGC
GGCAAGCAAGCGCTCGAAACGGTGCAGCGGCTGTTGCCGGTGCTGTGCCAGGACCATGGCCTGACCCCGG
ACCAAGTGGTGGCTATCGCCAGCCACGATGGCGGCAAGCAAGCGCTCGAAACGGTGCAGCGGCTGTTGCC
GGTGCTGTGCCAGGACCAtggcCTGACCCCGGACCAAGTGGTGGCTATCGCCAGCCACGATGGCGGCAAG
CAAGCGCTCGAAACGGTGCAGCGGCTGTTGCCGGTGCTGTGCCAGGACCATGGCCTGACCCCGGACCAAG
TGGTGGCTATCGCCAGCAACGGTGGCGGCAAGCAAGCGCTCGAGCGGCTGTTGCCGGTGCT
GTGCCAGGACCATGGCCTGACCCCGGACCAAGTGGTGGCTATCGCCAGCCACGATGGCGGCAAGCAAGCG
CTCGAAACGGTGCAGCGGCTGTTGCCGGTGCTGTGCCAGGACCATGGCCTGACCCCGGACCAAGTGGTGG
CTATCGCCAGCCACGATGGCGGCAAGCAAGCGCTCGAAACGGTGCAGCGGCTGTTGCCGGTGCTGTGCCA
GGACCATGGCCTGACCCCGGACCAAGTGGTGGctatcgccagcaacggtggcggcaagcaagcgctcgaa
agcattgtgggcccagctgagccggcctgatccggcgttggccgcgttgaccaacgacgaccacctcgtcg
ccttggcctgcctcggcggacgtcctgccatggatgcagtgaaaaagggattgccgcacgcgccggaatt
gatcagaagagtcaatcgccgtattggcgaacgcacgtcccatcgcgttgccGgatcCaAGGCTAGCCCG
AAAAAGAAACGCAAAGTTGGGCGCGCCGACGCGCTGGACGATTTCGATCTCGACATGCTGGGTTCTGATG
CCCTCGATGACTTTGACCTGGATATGTTGGGAAGCGACGCATTGGATGACTTTGATCTGGACATGCTCGG
CTCCGATGCTCTGGACGATTTCGATCTCGATATGTTAATTAACTACCCGTACGACGTTCCGGACTACGCT
TCTTGA SEQ ID NO: 48: IL1RN TALE-C polypeptide
MDYKDHDGDYKDHDIDYKDDDDKMAPKKKRKVGRGSVDLRTLGYSQQQQEKIKPKVRSTVAQHHEALVGH
GFTHAHIVALSQHPAALGTVAVTYQHIITALPEATHEDIVGKQWSGARALEALLTDAGELRGPPLQLD
TGQLVKIAKRGGVTAMEAVHASRNALTGAPLNLTPDQVVAIASNIGGKQALETVQRLLPVLCQDHGLTPD

TALE-TF SEQUENCES

QVVAIASNNGGKQALETVQRLLPVLCQDHGLTPDQVVAIASHDGGKQALETVQRLLPVLCQDHGLTPDQV
VAIASHDGGKQALETVQRLLPVLCQDHGLTPDQVVAIASNGGGKQALETVQRLLPVLCQDHGLTPDQVVA
IASNNGGKQALETVQRLLPVLCQDHGLTPDQVVAIASNIGGKQALETVQRLLPVLCQDHGLTPDQVVAIA
SNNGGKQALETVQRLLPVLCQDHGLTPDQVVAIASNGGGKQALETVQRLLPVLCQDHGLTPDQVVAIASH
DGGKQALETVQRLLPVLCQDHGLTPDQVVAIASNIGGKQALETVQRLLPVLCQDHGLTPDQVVAIASHDG
GKQALETVQRLLPVLCQDHGLTPDQVVAIASHDGGKQALETVQRLLPVLCQDHGLTPDQVVAIASHDGGK
QALETVQRLLPVLCQDHGLTPDQVVAIASNGGGKQALETVQRLLPVLCQDHGLTPDQVVAIASHDGGKQA
LETVQRLLPVLCQDHGLTPDQVVAIASHDGGKQALETVQRLLPVLCQDHGLTPDQVVAIASNGGGKQALE
SIVAQLSRPDPALAALTNDDHLVALACLGGRPAMDAVKKGLPHAPELIRRVNRRIGERTSHRVAGSKASP
KKKRKVGRADALDDFDLDMLGSDALDDFDLDMLGSDALDDFDLDMLGSDALDDFDLDMLINYPYDVPDYA
S

SEQ ID NO: 49: IL1RN TALE-D nucleotide
ATGGACTACAAAGACCATGACGGTGATTATAAAGATCATGACATCGATTACAAGGATGACGATGACAAGa
tggcccccaagaagaagaggaaggtgggccgcGgatcTgtggatctacgcacgctcggctacagtcagca
gcagcaagagaagatcaaaccgaaggtgcgttcgacagtggcgcagcaccacgaggcactggtgggccat
gggtttacacacgcgcacatcgttgcgctcagccaacacccggcagcgttagggaccgtcgctgtcacgt
atcagcacataatcacggcgttgccagaggcgacacacgaagacatcgttggcgtcggcaaacagtggtc
cggcgcacgcgccctggaggccttgctcacggatgcgggggagttgagaggtccgccgttacagttggac
acaggccaacttgtgaagattgcaaaacgtggcggcgtcaatggaggcagtgcatgcatcgcgca
atgcactgacgggtgcccccctgAACCTGACCCCGGACCAAGTGGTGGCTATCGCCAGCAACATTGGCGG
CAAGCAAGCGCTCGAAACGGTGCAGCGGCTGTTGCCGGTGCTGTGCCAGGACCATGGCCTGACCCCGGAC
CAAGTGGTGGCTATCGCCAGCCACGATGGCGGCAAGCAAGCGCTCGAAACGGTGCAGCGGCTGTTGCCGG
TGCTGTGCCAGGACCATGGCCTGACCCCGGACCAAGTGGTGGCTATCGCCAGCAACAATGGCGGCAAGCA
AGCGCTCGAAACGGTGCAGCGGCTGTTGCCGGTGCTGTGCCAGGACCATGGCCTGACCCCGGACCAAGTG
GTGGCTATCGCCAGCCACGATGGCGGCAAGCAAGCGCTCGAAACGGTGCAGCGGCTGTTGCCGGTGCTGT
GCCAGGACCATGGCCTGACCCCGGACCAAGTGGTGGCTATCGCCAGCAACATTGGCGGCAAGCAAGCGCT
CGAAACGGTGCAGCGGCTGTTGCCGGTGCTGTGCCAGGACCATGGCCTGACCCCGGACCAAGTGGTGGCT
ATCGCCAGCAACAATGGCGGCAAGCAAGCGCTCGAAACGGTGCAGCGGCTGTTGCCGGTGCTGTGCCAGG
ACCATGGCCTGACCCCGGACCAAGTGGTGGCTATCGCCAGCAACATTGGCGGCAAGCAAGCGCTCGAAAC
GGTGCAGCGGCTGTTGCCGGTGCTGTGCCAGGACCATGGCCTGACCCCGGACCAAGTGGTGGCTATCGCC
AGCAACGGTGGCGGCAAGCAAGCGCTCGAAACGGTGCAGCGGCTGTTGCCGGTGCTGTGCCAGGACCATG
GCCTGACCCCGGACCAAGTGGTGGCTATCGCCAGCAACATTGGCGGCAAGCAAGCGCTCGAAACGGTGCA
GCGGCTGTTGCCGGTGCTGTGCCAGGACCATGGCCTGACCCCGGACCAAGTGGTGGCTATCGCCAGCAAC
ATTGGCGGCAAGCAAGCGCTCGAAACGGTGCAGCGGCTGTTGCCGGTGCTGTGCCAGGACCATGGCCTGA
CCCCGGACCAAGTGGTGGCTATCGCCAGCAACAATGGCGGCAAGCAAGCGCTCGAAACGGTGCAGCGGCT
GTTGCCGGTGCTGTGCCAGGACCATGGCCTGACTCCGGACCAAGTGGTGGCTATCGCCAGCAACATTGGC
GGCAAGCAAGCGCTCGAAACGGTGCAGCGGCTGTTGCCGGTGCTGTGCCAGGACCATGGCCTGACCCCGG
ACCAAGTGGTGGCTATCGCCAGCAACATTGGCGGCAAGCAAGCGCTCGAAACGGTGCAGCGGCTGTTGCC
GGTGCTGTGCCAGGACCAtggcCTGACCCCGGACCAAGTGGTGGCTATCGCCAGCCACGATGGCGGCAAG
CAAGCGCTCGAAACGGTGCAGCGGCTGTTGCCGGTGCTGTGCCAGGACCATGGCCTGACCCCGGACCAAG
TGGTGGCTATCGCCAGCCACGATGGCGGCAAGCAAGCGCTCGAAACGGTGCAGCGGCTGTTGCCGGTGCT
GTGCCAGGACCATGGCCTGACCCCGGACCAAGTGGTGGCTATCGCCAGCAACATTGGCGGCAAGCAAGCG
CTCGAAACGGTGCAGCGGCTGTTGCCGGTGCTGTGCCAGGACCATGGCCTGACCCCGGACCAAGTGGTGG
CTATCGCCAGCAACAATGGCGGCAAGCAAGCGCTCGAAACGGTGCAGCGGCTGTTGCCGGTGCTGTGCCA
GGACCATGGCCTGACCCCGGACCAAGTGGTGGctatcgccagcaacggtggcggcaagcaagcgctcgaa
agcattgtggcccagctgagccggcctgatccggcgttggccgcgttgaccaacgacgaccacctcgtcg
ccttggcctgcctcggcggacgtcctgccatggatgcagtgaaaaagggattgccgcacgcgccggaatt
gatcagaagagtcaatcgccgtattggcgaacgcacgtcccatcgcGgatcCaAGGCTAGCCCG
AAAAAGAAACGCAAAGTTGGGCGCGCCGACGCGCTGGACGATTTCGATCTCGACATGCTGGGTTCTGATG
CCCTCGATGACTTTGACCTGGATATGTTGGGAAGCGACGCATTGATGACTTTGATCTGGACATGCTCGG
CTCCGATGCTCTGGACGATTTCGATCTCGATATGTTAATTAACTACCCGTACGACGTTCCGGACTACGCT
TCTTGA SEQ ID NO: 50: IL1RN TALE-D polypeptide
MDYKDHDGDYKDHDIDYKDDDDKMAPKKKRKVGRGSVDLRTLGYSQQQQEKIKPKVRSTVAQHHEALVGH
GFTHAHIVALSQHPAALGTVAVTYQHIITALPEATHEDIVGVGKQWSGARALEALLTDAGELRGPPLQLD
TGQLVKIAKRGGVTAMEAVHASRNALTGAPLNLTPDQVVAIASNIGGKQALETVQRLLPVLCQDHGLTPD
QVVAIASHDGGKQALETVQRLLPVLCQDHGLTPDQVVAIASNNGGKQALETVQRLLPVLCQDHGLTPDQV
VAIASHDGGKQALETVQRLLPVLCQDHGLTPDQVVAIASNIGGKQALETVQRLLPVLCQDHGLTPDQVVA
IASNNGGKQALETVQRLLPVLCQDHGLTPDQVVAIASNIGGKQALETVQRLLPVLCQDHGLTPDQVVAIA
SNGGGKQALETVQRLLPVLCQDHGLTPDQVVAIASNIGGKQALETVQRLLPVLCQDHGLTPDQVVAIASN
IGGKQALETVQRLLPVLCQDHGLTPDQVVAIASNNGGKQALETVQRLLPVLCQDHGLTPDQVVAIASNIG
GKQALETVQRLLPVLCQDHGLTPDQVVAIASNIGGKQALETVQRLLPVLCQDHGLTPDQVVAIASHDGGK
QALETVQRLLPVLCQDHGLTPDQVVAIASHDGGKQALETVQRLLPVLCQDHGLTPDQVVAIASNIGGKQA
LETVQRLLPVLCQDHGLTPDQVVAIASNNGGKQALETVQRLLPVLCQDHGLTPDQVVAIASNGGGKQALE
SIVAQLSRPDPALAALTNDDHLVALACLGGRPAMDAVKKGLPHAPELIRRVNRRIGERTSHRVAGSKASP
KKKRKVGRADALDDFDLDMLGSDALDDFDLDMLGSDALDDFDLDMLGSDALDDFDLDMLINYPYDVPDYA
S SEQ ID NO: 51: IL1RN TALE-E nucleotide
ATGGACTACAAAGACCATGACGGTGATTATAAAGATCATGACATCGATTACAAGGATGACGATGACAAGa
tggcccccaagaagaagaggaaggtgggccgcGgatcTgtggatctacgcacgctcggctacagtcagca
gcagcaagagaagatcaaaccgaaggtgcgttcgacagtggcgcagcaccacgaggcactggtgggccat
gggtttacacacgcgcacatcgttgcgctcagccaacacccggcagcgttagggaccgtcgctgtcacgt
atcagcacataatcacggcgttgccagaggcgacacacgaagacatcgttggcgtcggcaaacagtggtc
cggcgcacgcgccctggaggccttgctcacggatgcgggggagttgagaggtccgccgttacagttggac

TALE-TF SEQUENCES

```
acaggccaacttgtgaagattgcaaaacgtggcggcgtgaccgcaatggaggcagtgcatgcatcgcgca
atgcactgacgggtgcccccctgAACCTGACCCCGGACCAAGTGGTGGCTATCGCCAGCAACAATGGCGG
CAAGCAAGCGCTCGAAACGGTGCAGCGGCTGTTGCCGGTGCTGTGCCAGGACCATGGCCTGACCCCGGAC
CAAGTGGTGGCTATCGCCAGCAACGGTGGCGGCAAGCAAGCGCTCGAAACGGTGCAGCGGCTGTTGCCGG
TGCTGTGCCAGGACCATGGCCTGACCCCGGACCAAGTGGTGGCTATCGCCAGCCACGATGGCGGCAAGCA
AGCGCTCGAAACGGTGCAGCGGCTGTTGCCGGTGCTGTGCCAGGACCATGGCCTGACCCCGGACCAAGTG
GTGGCTATCGCCAGCAACGGTGGCGGCAAGCAAGCGCTCGAAACGGTGCAGCGGCTGTTGCCGGTGCTGT
GCCAGGACCATGGCCTGACCCCGGACCAAGTGGTGGCTATCGCCAGCAACAATGGCGGCAAGCAAGCGCT
CGAAACGGTGCAGCGGCTGTTGCCGGTGCTGTGCCAGGACCATGGCCTGACCCCGGACCAAGTGGTGGCT
ATCGCCAGCAACAATGGCGGCAAGCAAGCGCTCGAAACGGTGCAGCGGCTGTTGCCGGTGCTGTGCCAGG
ACCATGGCCTGACCCCGGACCAAGTGGTGGCTATCGCCAGCCACGATGGCGGCAAGCAAGCGCTCGAAAC
GGTGCAGCGGCTGTTGCCGGTGCTGTGCCAGGACCATGGCCTGACCCCGGACCAAGTGGTGGCTATCGCC
AGCAACGGTGGCGGCAAGCAAGCGCTCGAAACGGTGCAGCGGCTGTTGCCGGTGCTGTGCCAGGACCATG
GCCTGACCCCGGACCAAGTGGTGGCTATCGCCAGCAACGGTGGCGGCAAGCAAGCGCTCGAAACGGTGCA
GCGGCTGTTGCCGGTGCTGTGCCAGGACCATGGCCTGACCCCGGACCAAGTGGTGGCTATCGCCAGCAAC
AATGGCGGCAAGCAAGCGCTCGAAACGGTGCAGCGGCTGTTGCCGGTGCTGTGCCAGGACCATGGCCTGA
CCCCGGACCAAGTGGTGGCTATCGCCAGCAACGGTGGCGGCAAGCAAGCGCTCGAAACGGTGCAGCGGCT
GTTGCCGGTGCTGTGCCAGGACCATGGCCTGACTCCGGACCAAGTGGTGGCTATCGCCAGCAACGGTGGC
GGCAAGCAAGCGCTCGAAACGGTGCAGCGGCTGTTGCCGGTGCTGTGCCAGGACCATGGCCTGACCCCGG
ACCAAGTGGTGGCTATCGCCAGCCACGATGGCGGCAAGCAAGCGCTCGAAACGGTGCAGCGGCTGTTGCC
GGTGCTGTGCCAGGACCAtggcCTGACCCCGGACCAAGTGGTGGCTATCGCCAGCCACGATGGCGGCAAG
CAAGCGCTCGAAACGGTGCAGCGGCTGTTGCCGGTGCTGTGCCAGGACCATGGCCTGACCCCGGACCAAG
TGGTGGCTATCGCCAGCCACGATGGCGGCAAGCAAGCGCTCGAAACGGTGCAGCGGCTGTTGCCGGTGCT
GTGCCAGGACCATGGCCTGACCCCGGACCAAGTGGTGGCTATCGCCAGCAACATTGGCGGCAAGCAAGCG
CTCGAAACGGTGCAGCGGCTGTTGCCGGTGCTGTGCCAGGACCATGGCCTGACCCCGGACCAAGTGGTGG
CTATCGCCAGCAACATTGGCGGCAAGCAAGCGCTCGAAACGGTGCAGCGGCTGTTGCCGGTGCTGTGCCA
GGACCATGGCCTGACCCCGGACCAAGTGGTGGctatcgccagcaacggtggcggcaagcaagcgctcgaa
agcattgtgacccagctgagccggcctgatccggcgttggccgcgttgaccaacgacgaccacctcgtcg
ccttggcctgcctcggcggacgtcctgccatggatgcagtgaaaaagggattgccgcacgcgccggaatt
gatcagaagagtcaatcgccgtattggcgaacgcacgtccatcgcgttgccGgatcCaAGGCTAGCCCG
AAAAAGAAACGCAAAGTTGGGCGCGCCGACGCGCTGGACGATTTCGATCTCGACATGCTGGGTTCTGATG
CCCTCGATGACTTTGACCTGGATATGTTGGGAAGCGACGCATTGGATGACTTTGATCTGGACATGCTCGG
CTCCGATGCTCTGGACGATTTCGATCTCGATATGTTAATTAACTACCCGTACGACGTTCCGGACTACGCT
TCTTGA
```

SEQ ID NO: 52: IL1RN TALE-E polypeptide
MDYKDHDGDYKDHDIDYKDDDDKMAPKKKRKVGRGSVDLRTLGYSQQQQEKIKPKVRSTVAQHHEALVGH
GFTHAHIVALSQHPAALGTVAVTYQHIITALPEATHEDIVGVGKQWSGARALEALLTDAGELRGPPLQLD
TGQLVKIAKRGGVTAMEAVHASRNALTGAPLNLTPDQVVAIASNNGGKQALETVQRLLPVLCQDHGLTPD
QVVAIASNGGGKQALETVQRLLPVLCQDHGLTPDQVVAIASHDGGKQALETVQRLLPVLCQDHGLTPDQV
VAIASNGGGKQALETVQRLLPVLCQDHGLTPDQVVAIASNNGGKQALETVQRLLPVLCQDHGLTPDQVVA
IASNNGGKQALETVQRLLPVLCQDHGLTPDQVVAIASHDGGKQALETVQRLLPVLCQDHGLTPDQVVAIA
SNGGGKQALETVQRLLPVLCQDHGLTPDQVVAIASNGGGKQALETVQRLLPVLCQDHGLTPDQVVAIASN
NGGKQALETVQRLLPVLCQDHGLTPDQVVAIASNGGGKQALETVQRLLPVLCQDHGLTPDQVVAIASNGG
GKQALETVQRLLPVLCQDHGLTPDQVVAIASHDGGKQALETVQRLLPVLCQDHGLTPDQVVAIASHDGGK
QALETVQRLLPVLCQDHGLTPDQVVAIASHDGGKQALETVQRLLPVLCQDHGLTPDQVVAIASNIGGKQA
LETVQRLLPVLCQDHGLTPDQVVAIASNIGGKQALETVQRLLPVLCQDHGLTPDQVVAIASNGGGKQALE
SIVAQLSRPDPALAALTNDDHLVALACLGGRPAMDAVKKGLPHAPELIRRVNRRIGERTSHRVAGSKASP
KKKRKVGRADALDDFDLDMLGSDALDDFDLDMLGSDALDDFDLDMLGSDALDDFDLDMLINYPYDVPDYA
S SEQ ID NO: 53: IL1RN TALE-F nucleotide
```
ATGGACTACAAAGACCATGACGGTGATTATAAAGATCATGACATCGATTACAAGGATGACGATGACAAGa
tggccccccaagaagaagaggaaggtgggccgcGgatcTgtggatctacgcacgctcggctacagtcagca
gcagcaagagaagatcaaaccgaaggtgcgttcgacagtggcgcagcaccacgaggcactggtgggccat
gggtttacacacgcgcacatcgttgcgctcagccaacacccggcagcgttagggaccgtcgctgtcacgt
atcagcacataatcacggcgttgccagaggcgacacacgaagacatcgttggcgtcggcaaacagtggtc
cggcgcacgcgccctggaggccttgctcacggatgcggggggagttgagaggtccgccgttacagttggac
acaggccaacttgtgaagattgcaaaacgtggcggcgtgaccgcaatggaggcagtgcatgcatcgcgca
atgcactgacgggtgcccccctgAACCTGACCCCGGACCAAGTGGTGGCTATCGCCAGCCACGATGGCGG
CAAGCAAGCGCTCGAAACGGTGCAGCGGCTGTTGCCGGTGCTGTGCCAGGACCATGGCCTGACCCCGGAC
CAAGTGGTGGCTATCGCCAGCCACGATGGCGGCAAGCAAGCGCTCGAAACGGTGCAGCGGCTGTTGCCGG
TGCTGTGCCAGGACCATGGCCTGACCCCGGACCAAGTGGTGGCTATCGCCAGCAACGGTGGCGGCAAGCA
AGCGCTCGAAACGGTGCAGCGGCTGTTGCCGGTGCTGTGCCAGGACCATGGCCTGACCCCGGACCAAGTG
GTGGCTATCGCCAGCAACATTGGCGGCAAGCAAGCGCTCGAAACGGTGCAGCGGCTGTTGCCGGTGCTGT
GCCAGGACCATGGCCTGACCCCGGACCAAGTGGTGGCTATCGCCAGCAACAATGGCGGCAAGCAAGCGCT
CGAAACGGTGCAGCGGCTGTTGCCGGTGCTGTGCCAGGACCATGGCCTGACCCCGGACCAAGTGGTGGCT
ATCGCCAGCAACAATGGCGGCAAGCAAGCGCTCGAAACGGTGCAGCGGCTGTTGCCGGTGCTGTGCCAGG
ACCATGGCCTGACCCCGGACCAAGTGGTGGCTATCGCCAGCAACGGTGGCGGCAAGCAAGCGCTCGAAAC
GGTGCAGCGGCTGTTGCCGGTGCTGTGCCAGGACCATGGCCTGACCCCGGACCAAGTGGTGGCTATCGCC
AGCCACGATGGCGGCAAGCAAGCGCTCGAAACGGTGCAGCGGCTGTTGCCGGTGCTGTGCCAGGACCATG
GCCTGACCCCGGACCAAGTGGTGGCTATCGCCAGCCACGATGGCGGCAAGCAAGCGCTCGAAACGGTGCA
GCGGCTGTTGCCGGTGCTGTGCCAGGACCATGGCCTGACCCCGGACCAAGTGGTGGCTATCGCCAGCCAC
GATGGCGGCAAGCAAGCGCTCGAAACGGTGCAGCGGCTGTTGCCGGTGCTGTGCCAGGACCATGGCCTGA
CCCCGGACCAAGTGGTGGCTATCGCCAGCAACGGTGGCGGCAAGCAAGCGCTCGAAACGGTGCAGCGGCT
GTTGCCGGTGCTGTGCCAGGACCATGGCCTGACCCCGGACCAAGTGGTGGCTATCGCCAGCCACGATGGC
GGCAAGCAAGCGCTCGAAACGGTGCAGCGGCTGTTGCCGGTGCTGTGCCAGGACCATGGCCTGACCCCGG
```

TALE-TF SEQUENCES

```
ACCAAGTGGTGGCTATCGCCAGCAACATTGGCGGCAAGCAAGCGCTCGAAACGGTGCAGCGGCTGTTGCC
GGTGCTGTGCCAGGACCATGGCCTGACTCCCGACCAAGTGGTGGCTATCGCCAGCAACATTGGCGGCAAG
CAAGCGCTCGAAACGGTGCAGCGGCTGTTGCCGGTGCTGTGCCAGGACCATGGCCTGACCCCGGACCAAG
TGGTGGCTATCGCCAGCAACATTGGCGGCAAGCAAGCGCTCGAAACGGTGCAGCGGCTGTTGCCGGTGCT
GTGCCAGGACCAtggcCTGACCCCGGACCAAGTGGTGGCTATCGCCAGCAACATTGGCGGCAAGCAAGCG
CTCGAAACGGTGCAGCGGCTGTTGCCGGTGCTGTGCCAGGACCATGGCCTGACCCCGGACCAAGTGGTGG
CTATCGCCAGCAACAATGGCGGCAAGCAAGCGCTCGAAACGGTGCAGCGGCTGTTGCCGGTGCTGTGCCA
GGACCATGGCCTGACCCCGGACCAAGTGGTGGCTATCGCCAGCCACGATGGCGGCAAGCAAGCGCTCGAA
ACGGTGCAGCGGCTGTTGCCGGTGCTGTGCCAGGACCATGGCCTGACCCCGGACCAAGTGGTGGCTATCG
CCAGCAACATTGGCGGCAAGCAAGCGCTCGAAACGGTGCAGCGGCTGTTGCCGGTGCTGTGCCAGGACCA
TGGCCTGACCCCGGACCAAGTGGTGGctatcgccagcAACGGTGgcggcaagcaagcgctcgaaagcatt
gtggcccagctgagccggcctgatccggcgttggccgcgttgaccaacgacgaccacctcgtcgccttgg
cctgcctcggcggacgtcctgccatggatgcagtgaaaaagggattgccgcacgcgccggaattgatcag
aagagtcaatcgccgtattggcgaacgcacgtcccatcgcgttgccGgatcCaAGGCTAGCCCGAAAAAG
AAACGCAAAGTTGGGCGCGCCGACGCGCTGGACGATTTCGATCTCGACATGCTGGGTTCTGATGCCCTCG
ATGACTTTGACCTGGATATGTTGGGAAGCGACGCATTGGATGACTTTGATCTGGACATGCTCGGCTCCGA
TGCTCTGGACGATTTCGATCTCGATATGTTAATTAACTACCCGTACGACGTTCCGGACTACGCTTCTTGA
```

SEQ ID NO: 54: IL1RN TALE-F polypeptide
MDYKDHDGDYKDHDIDYKDDDDKMAPKKKRKVGRGSVDLRTLGYSQQQQEKIKPKVRSTVAQHHEALVGH
GFTHAHIVALSQHPAALGTVAVTYQHIITALPEATHEDIVGVGKQWSGARALEALLTDAGELRGPPLQLD
TGQLVKIAKRGGVTAMEAVHASRNALTGAPLNLTPDQVVAIASHDGGKQALETVQRLLPVLCQDHGLTPD
QVVAIASHDGGKQALETVQRLLPVLCQDHGLTPDQVVAIASNGGGKQALETVQRLLPVLCQDHGLTPDQV
VAIASNIGGKQALETVQRLLPVLCQDHGLTPDQVVAIASNNGGKQALETVQRLLPVLCQDHGLTPDQVVA
IASNNGGKQALETVQRLLPVLCQDHGLTPDQVVAIASNGGGKQALETVQRLLPVLCQDHGLTPDQVVAIA
SHDGGKQALETVQRLLPVLCQDHGLTPDQVVAIASHDGGKQALETVQRLLPVLCQDHGLTPDQVVAIASH
DGGKQALETVQRLLPVLCQDHGLTPDQVVAIASNGGGKQALETVQRLLPVLCQDHGLTPDQVVAIASHDG
GKQALETVQRLLPVLCQDHGLTPDQVVAIASNIGGKQALETVQRLLPVLCQDHGLTPDQVVAIASNIGGK
QALETVQRLLPVLCQDHGLTPDQVVAIASNIGGKQALETVQRLLPVLCQDHGLTPDQVVAIASNIGGKQA
LETVQRLLPVLCQDHGLTPDQVVAIASNNGGKQALETVQRLLPVLCQDHGLTPDQVVAIASHDGGKQALE
TVQRLLPVLCQDHGLTPDQVVAIASNIGGKQALETVQRLLPVLCQDHGLTPDQVVAIASNGGGKQALESI
VAQLSRPDPALAALTNDDHLVALACLGGRPAMDAVKKGLPHAPELIRRVNRRIGERTSHRVAGSKASPKK
KRKVGRADALDDFDLDMLGSDALDDFDLDMLGSDALDDFDLDMLGSDALDDFDLDMLINYPYDVPDYAS SEQ ID NO: 55: KLK3 TALE-A nucleotide
```
ATGGACTACAAAGACCATGACGGTGATTATAAAGATCATGACATCGATTACAAGGATGACGATGACAAGa
tggccccccaagaagaagaggaaggtgggccgcGgatcTgtggatctacgcacgctcggctacagtcagca
gcagcaagagaagatcaaaccgaaggtgcgttcgacagtggcgcagcaccacgaggcactggtgggccat
gggtttacacacgcgcacatcgttgcgctcagccaacaccoggcagcgttagggaccgtcgctgtcacgt
atcagcacataatcacggcgttgccagaggcgacacacgaagacatcgttggcgtcggcaaacagtggtc
cggcgcacgcgccctggaggccttgctcacggatgcgggggagttgagaggtccgccgttacagttggac
acaggccaacttgtgaagattgcaaaacgtggcggcgtgaccgcaatggaggcagtgcatgcatcgcgca
atgcactgacgggtgccccctgAACCTGACCCCGGACCAAGTGGTGGCTATCGCCAGCCACGATGGCGG
CAAGCAAGCGCTCGAAACGGTGCAGCGGCTGTTGCCGGTGCTGTGCCAGGACCATGGCCTGACCCCGGAC
CAAGTGGTGGCTATCGCCAGCCACGATGGCGGCAAGCAAGCGCTCGAAACGGTGCAGCGGCTGTTGCCGG
TGCTGTGCCAGGACCATGGCCTGACCCCGGACCAAGTGGTGGCTATCGCCAGCAACATTGGCGGCAAGCA
AGCGCTCGAAACGGTGCAGCGGCTGTTGCCGGTGCTGTGCCAGGACCATGGCCTGACCCCGGACCAAGTG
GTGGCTATCGCCAGCAACAATGGCGGCAAGCAAGCGCTCGAAACGGTGCAGCGGCTGTTGCCGGTGCTGT
GCCAGGACCATGGCCTGACCCCGGACCAAGTGGTGGCTATCGCCAGCCACGATGGCGGCAAGCAAGCGCT
CGAAACGGTGCAGCGGCTGTTGCCGGTGCTGTGCCAGGACCATGGCCTGACCCCGGACCAAGTGGTGGCT
ATCGCCAGCCACGATGGCGGCAAGCAAGCGCTCGAAACGGTGCAGCGGCTGTTGCCGGTGCTGTGCCAGG
ACCATGGCCTGACCCCGGACCAAGTGGTGGCTATCGCCAGCAACGGTGGCGGCAAGCAAGCGCTCGAAAC
GGTGCAGCGGCTGTTGCCGGTGCTGTGCCAGGACCATGGCCTGACCCCGGACCAAGTGGTGGCTATCGCC
AGCCACGATGGCGGCAAGCAAGCGCTCGAAACGGTGCAGCGGCTGTTGCCGGTGCTGTGCCAGGACCATG
GCCTGACCCCGGACCAAGTGGTGGCTATCGCCAGCCACGATGGCGGCAAGCAAGCGCTCGAAACGGTGCA
GCGGCTGTTGCCGGTGCTGTGCCAGGACCATGGCCTGACCCCGGACCAAGTGGTGGCTATCGCCAGCAAC
ATTGGCGGCAAGCAAGCGCTCGAAACGGTGCAGCGGCTGTTGCCGGTGCTGTGCCAGGACCATGGCCTGA
CCCCGGACCAAGTGGTGGCTATCGCCAGCAACAATGGCGGCAAGCAAGCGCTCGAAACGGTGCAGCGGCT
GTTGCCGGTGCTGTGCCAGGACCATGGCCTGACCCCGGACCAAGTGGTGGCTATCGCCAGCCACGATGGC
GGCAAGCAAGCGCTCGAAACGGTGCAGCGGCTGTTGCCGGTGCTGTGCCAGGACCATGGCCTGACCCCGG
ACCAAGTGGTGGCTATCGCCAGCAACATTGGCGGCAAGCAAGCGCTCGAAACGGTGCAGCGGCTGTTGCC
GGTGCTGTGCCAGGACCATGGCCTGACCCCGGACCAAGTGGTGGCTATCGCCAGCAACAATGGCGGCAAG
CAAGCGCTCGAAACGGTGCAGCGGCTGTTGCCGGTGCTGTGCCAGGACCATGGCCTGACCCCGGACCAAG
TGGTGGCTATCGCCAGCCACGATGGCGGCAAGCAAGCGCTCGAAACGGTGCAGCGGCTGTTGCCGGTGCT
GTGCCAGGACCATGGCCTGACCCCGGACCAAGTGGTGGCTATCGCCAGCAACATTGGCGGCAAGCAAGCG
CTCGAAACGGTGCAGCGGCTGTTGCCGGTGCTGTGCCAGGACCATGGCCTGACCCCGGACCAAGTGGTGG
ctatcgccagcaacggtggcggcaagcaagcgctcgaaagcattgtggcccagctgagccggcctgatcc
ggcgttggccgcgttgaccaacgacgaccacctcgtcgccttggcctgcctcggcggacgtcctgccatg
gatgcagtgaaaaagggattgccgcacgcgccggaattgatcagaagagtcaatcgccgtattggcgaac
gcacgtcccatcgcgttgccGgatcCaAGGCTAGCCCGAAAAAGAAACGCAAAGTTGGGCGCGCCGACGC
GCTGGACGATTTCGATCTCGACATGCTGGGTTCTGATGCCCTCGATGACTTTGACCTGGATATGTTGGGA
AGCGACGCATTGGATGACTTTGATCTCGGCTCCGATGCTCTGGACGATTTCGATCTCGATA
TGTTAATTAACTACCCGTACGACGTTCCGGACTACGCTTCTTGA
```

SEQ ID NO: 56: KLK3 TALE-A polypeptide
MDYKDHDGDYKDHDIDYKDDDDKMAPKKKRKVGRGSVDLRTLGYSQQQQEKIKPKVRSTVAQHHEALVGH
GFTHAHIVALSQHPAALGTVAVTYQHIITALPEATHEDIVGVGKQWSGARALEALLTDAGELRGPPLQLD

| TALE-TF SEQUENCES |
|---|
| TGQLVKIAKRGGVTAMEAVHASRNALTGAPLNLTPDQVVAIASHDGGKQALETVQRLLPVLCQDHGLTPD
QVVAIASHDGGKQALETVQRLLPVLCQDHGLTPDQVVAIASNIGGKQALETVQRLLPVLCQDHGLTPDQV
VAIASNNGGKQALETVQRLLPVLCQDHGLTPDQVVAIASHDGGKQALETVQRLLPVLCQDHGLTPDQVVA
IASHDGGKQALETVQRLLPVLCQDHGLTPDQVVAIASNGGGKQALETVQRLLPVLCQDHGLTPDQVVAIA
SHDGGKQALETVQRLLPVLCQDHGLTPDQVVAIASHDGGKQALETVQRLLPVLCQDHGLTPDQVVAIASN
IGGKQALETVQRLLPVLCQDHGLTPDQVVAIASNNGGKQALETVQRLLPVLCQDHGLTPDQVVAIASHDG
GKQALETVQRLLPVLCQDHGLTPDQVVAIASNIGGKQALETVQRLLPVLCQDHGLTPDQVVAIASNNGGK
QALETVQRLLPVLCQDHGLTPDQVVAIASHDGGKQALETVQRLLPVLCQDHGLTPDQVVAIASNIGGKQA
LETVQRLLPVLCQDHGLTPDQVVAIASNGGGKQALESIVAQLSRPDPALAALTNDDHLVALACLGGRPAM
DAVKKGLPHAPELIRRVNRRIGERTSHRVAGSKASPKKKRKVGRADALDDFDLDMLGSDALDDFDLDMLG
SDALDDFDLDMLGSDALDDFDLDMLINYPYDVPDYAS

SEQ ID NO: 57: KLK3 TALE B nucleotide
ATGGACTACAAAGACCATGACGGTGATTATAAAGATCATGACATCGATTACAAGGATGACGATGACAAGa
tggcccccaagaagaagaggaaggtgggccgcGgatcTgtggatctacgcacgctcggctacagtcagca
gcagcaagagaagatcaaaccgaaggtgcgttcgacagtggcgcagcaccacgaggcactggtgggccat
gggtttacacacgcgcacatcgttgcgctcagccaacacccggcagcgttagggaccgtcgctgtcacgt
atcagcacataatcacggcgttgccagaggcgacacacgaagacatcgttggcgtcggcaaacagtggtc
cggcgcacgcgcctggaggccttgctcacggatgcgggggagttgagaggtccgccgttacagttggac
acaggccaacttgtgaagattgcaaaacgtggcggcgtgaccgcaatggaggcagtgcatgcatcgcgca
atgcactgacgggtgcccccctgAACCTGACCCCGGACCAAGTGGTGGCTATCGCCAGCAACATTGGCGG
CAAGCAAGCGCTCGAAACGGTGCAGCGGCTGTTGCCGGTGCTGTGCCAGGACCATGGCCTGACCCCGGAC
CAAGTGGTGGCTATCGCCAGCAACAATGGCGGCAAGCAAGCGCTCGAAACGGTGCAGCGGCTGTTGCCGG
TGCTGTGCCAGGACCATGGCCTGACCCCGGACCAAGTGGTGCTATCGCCAGCCACGATGGCGGCAAGCA
AGCGCTCGAAACGGTGCAGCGGCTGTTGCCGGTGCTGTGCCAGGACCATGGCCTGACCCCGGACCAAGTG
GTGGCTATCGCCAGCAACGGTGGCGGCAAGCAAGCGCTCGAAACGGTGCAGCGGCTGTTGCCGGTGCTGT
GCCAGGACCATGGCCTGACCCCGGACCAAGTGGTGGCTATCGCCAGCCACGATGGCGGCAAGCAAGCGCT
CGAAACGGTGCAGCGGCTGTTGCCGGTGCTGTGCCAGGACCATGGCCTGACCCCGGACCAAGTGGTGGCT
ATCGCCAGCAACGGTGGCGGCAAGCAAGCGCTCGAAACGGTGCAGCGGCTGTTGCCGGTGCTGTGCCAGG
ACCATGGCCTGACCCCGGACCAAGTGGTGGCTATCGCCAGCCACGATGGCGGCAAGCAAGCGCTCGAAAC
GGTGCAGCGGCTGTTGCCGGTGCTGTGCCAGGACCATGGCCTGACCCCGGACCAAGTGGTGGCTATCGCC
AGCCACGATGGCGGCAAGCAAGCGCTCGAAACGGTGCAGCGGCTGTTGCCGGTGCTGTGCCAGGACCATG
GCCTGACCCCGGACCAAGTGGTGGCTATCGCCAGCCACGATGGCGGCAAGCAAGCGCTCGAAACGGTGCA
GCGGCTGTTGCCGGTGCTGTGCCAGGACCATGGCCTGACCCCGGACCAAGTGGTGGCTATCGCCAGCAAC
GGTGGCGGCAAGCAAGCGCTCGAAACGGTGCAGCGGCTGTTGCCGGTGCTGTGCCAGGACCATGGCCTGA
CCCCGGACCAAGTGGTGGCTATCGCCAGCCACGATGGCGGCAAGCAAGCGCTCGAAACGGTGCAGCGGCT
GTTGCCGGTGCTGTGCCAGGACCATGGCCTGACCCCGGACCAAGTGGTGGCTATCGCCAGCCACGATGGC
GGCAAGCAAGCGCTCGAAACGGTGCAGCGGCTGTTGCCGGTGCTGTGCCAGGACCATGGCCTGACCCCGG
ACCAAGTGGTGGCTATCGCCAGCCACGATGGCGGCAAGCAAGCGCTCGAAACGGTGCAGCGGCTGTTGCC
GGTGCTGTGCCAGGACCATGGCCTGACCCCGGACCAAGTGGTGGCTATCGCCAGCCACGATGGCGGCAAG
CAAGCGCTCGAAACGGTGCAGCGGCTGTTGCCGGTGCTGTGCCAGGACCATGGCCTGACCCCGGACCAAG
TGGTGGCTATCGCCAGCAACGGTGGCGGCAAGCAAGCGCTCGAAACGGTGCAGCGGCTGTTGCCGGTGCT
GTGCCAGGACCATGGCCTGACCCCGGACCAAGTGGTGGctatcgccagcaacggtggcggcaagcaagcg
ctcgaaagcattgtgggcccagctgagccggcctgatccggcgttggccgcgttgaccaacgacgaccac
tcgtcgccctggcctgcctcggcggacgtcctgccatggatgcagtggaaaagggattgccgcacgcgcc
ggaattgatcagaagagtcaatcgccgtattggcgaacgcacgtccatcgcgttgccGgatcCaAGGCT
AGCCCGAAAAAGAAACGCAAAGTTGGGCGCGCCGACGCGCTGGACGATTTCGATCTCGACATGCTGGGTT
CTGATGCCCTCGATGACTTTGACCTGGATATGTTGGGAAGCGACGCATTGGATGACTTTGATCTGGACAT
GCTCGGCTCCGATGCTCTGGACGATTTCGATCTCGATATGTTAATTAACTACCCGTACGACGTTCCGGAC
TACGCTTCTTGA SEQ ID NO: 58: KLK3 TALE B polypeptide
MDYKDHDGDYKDHDIDYKDDDDKMAPKKKRKVGRGSVDLRTLGYSQQQQEKIKPKVRSTVAQHHEALVGH
GFTHAHIVALSQHPAALGTVAVTYQHIITALPEATHEDIVGVGKQWSGARALEAALLTDAGELRGPPLQLD
TGQLVKIAKRGGVTAMEAVHASRNALTGAPLNLTPDQVVAIASNIGGKQALETVQRLLPVLCQDHGLTPD
QVVAIASNNGGKQALETVQRLLPVLCQDHGLTPDQVVAIASHDGGKQALETVQRLLPVLCQDHGLTPDQV
VAIASNGGGKQALETVQRLLPVLCQDHGLTPDQVVAIASHDGGKQALETVQRLLPVLCQDHGLTPDQVVA
IASNGGGKQALETVQRLLPVLCQDHGLTPDQVVAIASHDGGKQALETVQRLLPVLCQDHGLTPDQVVAIA
SHDGGKQALETVQRLLPVLCQDHGLTPDQVVAIASHDGGKQALETVQRLLPVLCQDHGLTPDQVVAIASN
GGGKQALETVQRLLPVLCQDHGLTPDQVVAIASHDGGKQALETVQRLLPVLCQDHGLTPDQVVAIASHDG
GKQALETVQRLLPVLCQDHGLTPDQVVAIASHDGGKQALETVQRLLPVLCQDHGLTPDQVVAIASHDGGK
QALETVQRLLPVLCQDHGLTPDQVVAIASNGGGKQALETVQRLLPVLCQDHGLTPDQVVAIASNGGGKQA
LESIVAQLSRPDPALAALTNDDHLVALACLGGRPAMDAVKKGLPHAPELIRRVNRRIGERTSHRVAGSKA
SPKKKRKVGRADALDDFDLDMLGSDALDDFDLDMLGSDALDDFDLDMLGSDALDDFDLDMLINYPYDVPD
YAS SEQ ID NO: 59: KLK3 TALE C nucleotide
ATGGACTACAAAGACCATGACGGTGATTATAAAGATCATGACATCGATTACAAGGATGACGATGACAAGa
tggcccccaagaagaagaggaaggtgggccgcGgatcTgtggatctacgcacgctcggctacagtcagca
gcagcaagagaagatcaaaccgaaggtgcgttcgacagtggcgcagcaccacgaggcactggtgggccat
gggtttacacacgcgcacatcgttgcgctcagccaacacccggcagcgttagggaccgtcgctgtcacgt
atcagcacataatcacggcgttgccagaggcgacacacgaagacatcgttggcgtcggcaaacagtggtc
cggcgcacgcgcctggaggccttgctcacggatgcgggggagttgagaggtccgccgttacagttggac
acaggccaacttgtgaagattgcaaaacgtggcggcgtgaccgcaatggaggcagtgcatgcatcgcgca
atgcactgacgggtgcccccctgAACCTGACCCCGGACCAAGTGGTGGCTATCGCCAGCCACGATGGCGG
CAAGCAAGCGCTCGAAACGGTGCAGCGGCTGTTGCCGGTGCTGTGCCAGGACCATGGCCTGACCCCGGAC
CAAGTGGTGGCTATCGCCAGCCACGATGGCGGCAAGCAAGCGCTCGAAACGGTGCAGCGGCTGTTGCCGG |

TALE-TF SEQUENCES

```
TGCTGTGCCAGGACCATGGCCTGACCCCGGACCAAGTGGTGGCTATCGCCAGCCACGATGGCGGCAAGCA
AGCGCTCGAAACGGTGCAGCGGCTGTTGCCGGTGCTGTGCCAGGACCATGGCCTGACCCCGGACCAAGTG
GTGGCTATCGCCAGCCACGATGGCGGCAAGCAAGCGCTCGAAACGGTGCAGCGGCTGTTGCCGGTGCTGT
GCCAGGACCATGGCCTGACCCCGGACCAAGTGGTGGCTATCGCCAGCAACGGTGGCGGCAAGCAAGCGCT
CGAAACGGTGCAGCGGCTGTTGCCGGTGCTGTGCCAGGACCATGGCCTGACCCCGGACCAAGTGGTGGCT
ATCGCCAGCAACATTGGCGGCAAGCAAGCGCTCGAAACGGTGCAGCGGCTGTTGCCGGTGCTGTGCCAGG
ACCATGGCCTGACCCCGGACCAAGTGGTGGCTATCGCCAGCAACAATGGCGGCAAGCAAGCGCTCGAAAC
GGTGCAGCGGCTGTTGCCGGTGCTGTGCCAGGACCATGGCCTGACCCCGGACCAAGTGGTGGCTATCGCC
AGCAACATTGGCGGCAAGCAAGCGCTCGAAACGGTGCAGCGGCTGTTGCCGGTGCTGTGCCAGGACCATG
GCCTGACCCCGGACCAAGTGGTGGCTATCGCCAGCAACGGTGGCGGCAAGCAAGCGCTCGAAACGGTGCA
GCGGCTGTTGCCGGTGCTGTGCCAGGACCATGGCCTGACCCCGGACCAAGTGGTGGCTATCGCCAGCAAC
AATGGCGGCAAGCAAGCGCTCGAAACGGTGCAGCGGCTGTTGCCGGTGCTGTGCCAGGACCATGGCCTGA
CCCCGGACCAAGTGGTGGCTATCGCCAGCAACATTGGCGGCAAGCAAGCGCTCGAAACGGTGCAGCGGCT
GTTGCCGGTGCTGTGCCAGGACCATGGCCTGACCCCGGACCAAGTGGTGGCTATCGCCAGCAACATTGGC
GGCAAGCAAGCGCTCGAAACGGTGCAGCGGCTGTTGCCGGTGCTGTGCCAGGACCATGGCCTGACCCCGG
ACCAAGTGGTGGCTATCGCCAGCAACAATGGCGGCAAGCAAGCGCTCGAAACGGTGCAGCGGCTGTTGCC
GGTGCTGTGCCAGGACCATGGCCTGACCCCGGACCAAGTGGTGGCTATCGCCAGCAACGGTGGCGGCAAG
CAAGCGCTCGAAACGGTGCAGCGGCTGTTGCCGGTGCTGTGCCAGGACCATGGCCTGACCCCGGACCAAG
TGGTGGCTATCGCCAGCCACGATGGCGGCAAGCAAGCGCTCGAAACGGTGCAGCGGCTGTTGCCGGTGCT
GTGCCAGGACCATGGCCTGACCCCGGACCAAGTGGTGGctatcgccagcaacggtggcggcaagcaagcg
ctcgaaagcattgtggcccagctgagccggcctgatccggcgttggccgcgttgaccaacgacgaccacc
tcgtcgccttggcctgcctcggcggacgtcctgccatggatgcagtgaaaaagggattgccgcacgcgcc
ggaattgatcagaagagtcaatcgccgtattggcgaacgcacgtcccatcgcgttgccGgatcCaAGGCT
AGCCCGAAAAAGAAACGCAAAGTTGGGCGCGCCGACGCGCTGGACGATTTCGATCTCGACATGCTGGGTT
CTGATGCCCTCGATGACTTTGACCTGGATATGTTGGGAAGCGACGCATTGGATGACTTTGATCTGGACAT
GCTCGGCTCCGATGCTCTGGACGATTTCGATCTCGATATGTTAATTAACTACCCGTACGACGTTCCGGAC
TACGCTTCTTGA
```

SEQ ID NO: 60: KLK3 TALE C polypeptide

```
MDYKDHDGDYKDHDIDYKDDDDKMAPKKKRKVGRGSVDLRTLGYSQQQQEKIKPKVRSTVAQHHEALVGH
GFTHAHIVALSQHPAALGTVAVTYQHIITALPEATHEDIVGVGKQWSGARALEALLTDAGELRGPPLQLD
TGQLVKIAKRGGVTAMEAVHASRNALTGAPLNLTPDQVVAIASHDGGKQALETVQRLLPVLCQDHGLTPD
QVVAIASHDGGKQALETVQRLLPVLCQDHGLTPDQVVAIASHDGGKQALETVQRLLPVLCQDHGLTPDQV
VAIASHDGGKQALETVQRLLPVLCQDHGLTPDQVVAIASNGGGKQALETVQRLLPVLCQDHGLTPDQVVA
IASNIGGKQALETVQRLLPVLCQDHGLTPDQVVAIASNNGGKQALETVQRLLPVLCQDHGLTPDQVVAIA
SNIGGKQALETVQRLLPVLCQDHGLTPDQVVAIASNGGGKQALETVQRLLPVLCQDHGLTPDQVVAIASN
NGGKQALETVQRLLPVLCQDHGLTPDQVVAIASNIGGKQALETVQRLLPVLCQDHGLTPDQVVAIASNIG
GKQALETVQRLLPVLCQDHGLTPDQVVAIASNNGGKQALETVQRLLPVLCQDHGLTPDQVVAIASNGGGK
QALETVQRLLPVLCQDHGLTPDQVVAIASHDGGKQALETVQRLLPVLCQDHGLTPDQVVAIASNGGGKQA
LESIVAQLSRPDPALAALTNDDHLVALACLGGRPAMDAVKKGLPHAPELIRRVNRRIGERTSHRVAGSKA
SPKKKRKVGRADALDDFDLDMLGSDALDDFDLDMLGSDALDDFDLDMLGSDALDDFDLDMLINYPYDVPD
YAS
```

SEQ ID NO: 61: KLK3 TALE D nucleotide

```
ATGGACTACAAAGACCATGACGGTGATTATAAAGATCATGACATCGATTACAAGGATGACGATGACAAGa
tggcccccaagaagaagaggaaggtgggccgcGgatcTgtggatctacgcacgctcggctacagtcagca
gcagcaagagaagatcaaaccgaaggtgcgttcgacagtggcgcagcaccacgaggcactggtgggccat
gggtttacacacgcgcacatcgttgcgctcagccaacacccggcagcgttagggaccgtcgctgtcacgt
atcagcacataatcacggcgttgccagaggcgacacaacgaagacatcgttggcgtcggcaaacagtggtc
cggcgcacgcgccctggaggccttgctcacggatgcggggagttgagaggtccgccgttacagttggac
acaggccaacttgtgaagattgcaaaacgtggcggcgtgaccgcaatggaggcagtgcatgcatcgcgca
atgcactgacgggtgccccctgAACCTGACCCCGGACCAAGTGGTGGCTATCGCCAGCAACATTGGCGG
CAAGCAAGCGCTCGAAACGGTGCAGCGGCTGTTGCCGGTGCTGTGCCAGGACCATGGCCTGACCCCGGAC
CAAGTGGTGGCTATCGCCAGCCACGATGGCGGCAAGCAAGCGCTCGAAACGGTGCAGCGGCTGTTGCCGG
TGCTGTGCCAGGACCATGGCCTGACCCCGGACCAAGTGGTGGCTATCGCCAGCCACGATGGCGGCAAGCA
AGCGCTCGAAACGGTGCAGCGGCTGTTGCCGGTGCTGTGCCAGGACCATGGCCTGACCCCGGACCAAGTG
GTGGCTATCGCCAGCCACGATGGCGGCAAGCAAGCGCTCGAAACGGTGCAGCGGCTGTTGCCGGTGCTGT
GCCAGGACCATGGCCTGACCCCGGACCAAGTGGTGGCTATCGCCAGCAACATTGGCGGCAAGCAAGCGCT
CGAAACGGTGCAGCGGCTGTTGCCGGTGCTGTGCCAGGACCATGGCCTGACCCCGGACCAAGTGGTGGCT
ATCGCCAGCCACGATGGCGGCAAGCAAGCGCTCGAAACGGTGCAGCGGCTGTTGCCGGTGCTGTGCCAGG
ACCATGGCCTGACCCCGGACCAAGTGGTGGCTATCGCCAGCCACGATGGCGGCAAGCAAGCGCTCGAAAC
GGTGCAGCGGCTGTTGCCGGTGCTGTGCCAGGACCATGGCCTGACCCCGGACCAAGTGGTGGCTATCGCC
AGCCACGATGGCGGCAAGCAAGCGCTCGAAACGGTGCAGCGGCTGTTGCCGGTGCTGTGCCAGGACCATG
GCCTGACCCCGGACCAAGTGGTGGCTATCGCCAGCCACGATGGCGGCAAGCAAGCGCTCGAAACGGTGCA
GCGGCTGTTGCCGGTGCTGTGCCAGGACCATGGCCTGACCCCGGACCAAGTGGTGGCTATCGCCAGCCAC
GATGGCGGCAAGCAAGCGCTCGAAACGGTGCAGCGGCTGTTGCCGGTGCTGTGCCAGGACCATGGCCTGA
CCCCGGACCAAGTGGTGGCTATCGCCAGCAACGGTGGCGGCAAGCAAGCGCTCGAAACGGTGCAGCGGCT
GTTGCCGGTGCTGTGCCAGGACCATGGCCTGACCCCGGACCAAGTGGTGGCTATCGCCAGCAACAATGGC
GGCAAGCAAGCGCTCGAAACGGTGCAGCGGCTGTTGCCGGTGCTGTGCCAGGACCATGGCCTGACCCCGG
ACCAAGTGGTGGCTATCGCCAGCAACGGTGGCGGCAAGCAAGCGCTCGAAACGGTGCAGCGGCTGTTGCC
GGTGCTGTGCCAGGACCATGGCCTGACCCCGGACCAAGTGGTGGCTATCGCCAGCAACGGTGGCGGCAAG
CAAGCGCTCGAAACGGTGCAGCGGCTGTTGCCGGTGCTGTGCCAGGACCATGGCCTGACCCCGGACCAAG
TGGTGGCTATCGCCAGCAACGGTGGCGGCAAGCAAGCGCTCGAAACGGTGCAGCGGCTGTTGCCGGTGCT
GTGCCAGGACCATGGCCTGACCCCGGACCAAGTGGTGGCTATCGCCAGCCACGATGGCGGCAAGCAAGCG
CTCGAAACGGTGCAGCGGCTGTTGCCGGTGCTGTGCCAGGACCATGGCCTGACCCCGGACCAAGTGGTGG
CTATCGCCAGCAACGGTGGCGGCAAGCAAGCGCTCGAAACGGTGCAGCGGCTGTTGCCGGTGCTGTGCCA
GGACCATGGCCTGACCCCGGACCAAGTGGTGGCTATCGCCAGCAACAATGGCGGCAAGCAAGCGCTCGAA
```

| TALE-TF SEQUENCES |
|---|
| ACGGTGCAGCGGCTGTTGCCGGTGCTGTGCCAGGACCATGGCCTGACCCCGGACCAAGTGGTGGctatcg
ccagcaacggtggcggcaagcaagcgctcgaaagcattgtggcccagctgagccggcctgatccggcgtt
ggccgcgttgaccaacgacgaccacctcgtcgccttggcctgcctcggcggacgtcctgccatggatgca
gtgaaaaagggattgccgcacgcgccggaattgatcagaagagtcaatcgccgtattggcgaacgcacgt
cccatcgcgttgccGgatcCaAGGCTAGCCCGAAAAAGAAACGCAAAGTTGGGCGCGCCGACGCGCTGGA
CGATTTCGATCTCGACATGCTGGGTTCTGATGCCCTCGATGACTTTGACCTGGATATGTTGGGAAGCGAC
GCATTGGATGACTTTGATCTGGACATGCTCGGCTCCGATGCTCTGGACGATTTCGATCTCGATATGTTAA
TTAACTACCCGTACGACGTTCCGGACTACGCTTCTTGA SEQ ID NO: 62: KLK3 TALE D polypeptide
MDYKDHDGDYKDHDIDYKDDDDKMAPKKKRKVGRGSVDLRTLGYSQQQQEKIKPKVRSTVAQHHEALVGH
GFTHAHIVALSQHPAALGTVAVTYQHIITALPEATHEDIVGVGKQWSGARALEALLTDAGELRGPPLQLD
TGQLVKIAKRGGVTAMEAVHASRNALTGAPLNLTPDQVVAIASNIGGKQALETVQRLLPVLCQDHGLTPD
QVVAIASHDGGKQALETVQRLLPVLCQDHGLTPDQVVAIASHDGGKQALETVQRLLPVLCQDHGLTPDQV
VAIASHDGGKQALETVQRLLPVLCQDHGLTPDQVVAIASNIGGKQALETVQRLLPVLCQDHGLTPDQVVA
IASHDGGKQALETVQRLLPVLCQDHGLTPDQVVAIASHDGGKQALETVQRLLPVLCQDHGLTPDQVVAIA
SHDGGKQALETVQRLLPVLCQDHGLTPDQVVAIASHDGGKQALETVQRLLPVLCQDHGLTPDQVVAIASH
DGGKQALETVQRLLPVLCQDHGLTPDQVVAIASNGGGKQALETVQRLLPVLCQDHGLTPDQVVAIASNNG
GKQALETVQRLLPVLCQDHGLTPDQVVAIASNGGGKQALETVQRLLPVLCQDHGLTPDQVVAIASNGGGK
QALETVQRLLPVLCQDHGLTPDQVVAIASNGGGKQALETVQRLLPVLCQDHGLTPDQVVAIASHDGGKQA
LETVQRLLPVLCQDHGLTPDQVVAIASNGGGKQALETVQRLLPVLCQDHGLTPDQVVAIASNNGGKQALE
TVQRLLPVLCQDHGLTPDQVVAIASNGGGKQALESIVAQLSRPDPALAALTNDDHLVALACLGGRPAMDA
VKKGLPHAPELIRRVNRRIGERTSHRVAGSKASPKKKRKVGRADALDDFDLDMLGSDALDDFDLDMLGSD
ALDDFDLDMLGSDALDDFDLDMLINYPYDVPDYAS SEQ ID NO: 63: KLK3 TALE E nucleotide
ATGGACTACAAGACCATGACGGTGATTATAAAGATCATGACATCGATTACAAGGATGACGATGACAAGa
tggccccaagaagaagaggaaggtgggccgcGgatcTgtggatctacgcacgctcggctacagtcagca
gcagcaagagaagatcaaaccgaaggtgcgttcgacagtggcgcagcaccacgaggcactggtgggccat
gggtttacacacgcgcacatcgttgcgctcagccaacaccggcagcgttagggaccgtcgctgtcacgt
atcagcacataatcacggcgttgccagaggcgacacacgaagacatcgttggcgtcggcaaacagtggtc
cggcgcacgcgccctggaggcctgctcacggatgcgggggagttgagaggtccgccgttcagttggac
acaggccaacttgtgaagattgcaaaacgtggcggcgtgaccgccaatggaggcagtgcatgcatcgcga
atgcactgacgggtgcccccctgAACCTGACCCCGGACCAAGTGGTGGCTATCGCCAGCCACGATGGCGG
CAAGCAAGCGCTCGAAACGGTGCAGCGGCTGTTGCCGGTGCTGTGCCAGGACCATGGCCTGACCCCGGAC
CAAGTGGTGGCTATCGCCAGCAACGGTGGCGGCAAGCAAGCGCTCGAAACGGTGCAGCGGCTGTTGCCGG
TGCTGTGCCAGGACCATGGCCTGACCCCGGACCAAGTGGTGGCTATCGCCAGCAACGGTGGCGGCAAGCA
AGCGCTCGAAACGGTGCAGCGGCTGTTGCCGGTGCTGTGCCAGGACCATGGCCTGACCCCGGACCAAGTG
GTGGCTATCGCCAGCAACAATGGCGGCAAGCAAGCGCTCGAAACGGTGCAGCGGCTGTTGCCGGTGCTGT
GCCAGGACCATGGCCTGACCCCGGACCAAGTGGTGGCTATCGCCAGCAACAATGGCGGCAAGCAAGCGCT
CGAAACGGTGCAGCGGCTGTTGCCGGTGCTGTGCCAGGACCATGGCCTGACCCCGGACCAAGTGGTGGCT
ATCGCCAGCAACATTGGCGGCAAGCAAGCGCTCGAAACGGTGCAGCGGCTGTTGCCGGTGCTGTGCCAGG
ACCATGGCCTGACCCCGGACCAAGTGGTGGCTATCGCCAGCAACAATGGCGGCAAGCAAGCGCTCGAAAC
GGTGCAGCGGCTGTTGCCGGTGCTGTGCCAGGACCATGGCCTGACCCCGGACCAAGTGGTGGCTATCGCC
AGCAACGGTGGCGGCAAGCAAGCGCTCGAAACGGTGCAGCGGCTGTTGCCGGTGCTGTGCCAGGACCATG
GCCTGACCCCGGACCAAGTGGTGGCTATCGCCAGCAACAATGGCGGCAAGCAAGCGCTCGAAACGGTGCA
GCGGCTGTTGCCGGTGCTGTGCCAGGACCATGGCCTGACCCCGGACCAAGTGGTGGCTATCGCCAGCCAC
GATGGCGGCAAGCAAGCGCTCGAAACGGTGCAGCGGCTGTTGCCGGTGCTGTGCCAGGACCATGGCCTGA
CCCCGGACCAAGTGGTGGCTATCGCCAGCAACATTGGCGGCAAGCAAGCGCTCGAAACGGTGCAGCGGCT
GTTGCCGGTGCTGTGCCAGGACCATGGCCTGACCCCGGACCAAGTGGTGGCTATCGCCAGCAACATTGGC
GGCAAGCAAGCGCTCGAAACGGTGCAGCGGCTGTTGCCGGTGCTGTGCCAGGACCATGGCCTGACCCCGG
ACCAAGTGGTGGCTATCGCCAGCAACATTGGCGGCAAGCAAGCGCTCGAAACGGTGCAGCGGCTGTTGCC
GGTGCTGTGCCAGGACCATGGCCTGACCCCGGACCAAGTGGTGGCTATCGCCAGCAACAATGGCGGCAAG
CAAGCGCTCGAAACGGTGCAGCGGCTGTTGCCGGTGCTGTGCCAGGACCATGGCCTGACCCCGGACCAAG
TGGTGGCTATCGCCAGCAACAATGGCGGCAAGCAAGCGCTCGAAACGGTGCAGCGGCTGTTGCCGGTGCT
GTGCCAGGACCATGGCCTGACCCCGGACCAAGTGGtgctatcgccagcaacattggcggcaagcaagcg
ctcgaaagcattgtggcccagctgagccggcctgatccggcgttggccgcgttgaccaacgacgaccacc
tcgtcgcccttggcctgcctcggcggacgtcctgccatggatgcagtgaaaaagggattgccgcacgcgcc
ggaattgatcagaagagtcaatcgccgtattggcgaacgcacgtcccatcgcgttgccGgatcCaAGGCT
AGCCCGAAAAAGAAACGCAAAGTTGGGCGCGCCGACGCGCTGGACGATTTCGATCTCGACATGCTGGGTT
CTGATGCCCTCGATGACTTTGACCTGGATATGTTGGGAAGCGACGCATTGGATGACTTTGATCTGGACAT
GCTCGGCTCCGATGCTCTGGACGATTTCGATCTCGATATGTTAATTAACTACCCGTACGACGTTCCGGAC
TACGCTTCTTGA SEQ ID NO: 64: KLK3 TALE E polypeptide
MDYKDHDGDYKDHDIDYKDDDDKMAPKKKRKVGRGSVDLRTLGYSQQQQEKIKPKVRSTVAQHHEALVGH
GFTHAHIVALSQHPAALGTVAVTYQHIITALPEATHEDIVGVGKQWSGARALEALLTDAGELRGPPLQLD
TGQLVKIAKRGGVTAMEAVHASRNALTGAPLNLTPDQVVAIASHDGGKQALETVQRLLPVLCQDHGLTPD
QVVAIASNGGGKQALETVQRLLPVLCQDHGLTPDQVVAIASNGGGKQALETVQRLLPVLCQDHGLTPDQV
VAIASNNGGKQALETVQRLLPVLCQDHGLTPDQVVAIASNNGGKQALETVQRLLPVLCQDHGLTPDQVVA
IASNIGGKQALETVQRLLPVLCQDHGLTPDQVVAIASNNGGKQALETVQRLLPVLCQDHGLTPDQVVAIA
SNGGGKQALETVQRLLPVLCQDHGLTPDQVVAIASNNGGKQALETVQRLLPVLCQDHGLTPDQVVAIASH
DGGKQALETVQRLLPVLCQDHGLTPDQVVAIASNIGGKQALETVQRLLPVLCQDHGLTPDQVVAIASNIG
GKQALETVQRLLPVLCQDHGLTPDQVVAIASNIGGKQALETVQRLLPVLCQDHGLTPDQVVAIASNNGGK
QALETVQRLLPVLCQDHGLTPDQVVAIASNNGGKQALETVQRLLPVLCQDHGLTPDQVVAIASNIGGKQA
LESIVAQLSRPDPALAALTNDDHLVALACLGGRPAMDAVKKGLPHAPELIRRVNRRIGERTSHRVAGSKA |

TALE-TF SEQUENCES

SPKKKRKVGRADALDDFDLDMLGSDALDDFDLDMLGSDALDDFDLDMLGSDALDDFDLDMLINYPYDVPD
YAS

SEQ ID NO: 65: KLK3 TALE F nucleotide
ATGGACTACAAAGACCATGACGGTGATTATAAAGATCATGACATCGATTACAAGGATGACGATGACAAGa
tggcccccaagaagaagaggaaggtgggccgcGgatcTgtggatctacgcacgctcggctacagtcagca
gcagcaagagaagatcaaaccgaaggtgcgttcgacagtggcgcagcaccacgaggcactggtgggccat
gggtttacacacgcgcacatcgttgcgctcagccaacacccggcagcgttagggaccgtcgctgtcacgt
atcagcacataatcacggcgttgccagaggcgacacacgaagacatcgttggcgtcggcaaacagtggtc
cggcgcacgcgccctggaggccttgctcacggatgcgggggagttgagaggtccgccgttacagttggac
acaggccaacttgtgaagattgcaaaacgtggcggcgtgaccgcaatggaggcagtgcatgcatcgcgca
atgcactgacgggtgccccctgAACCTGACCCCGGACCAAGTGGTGGCTATCGCCAGCCACGATGGCGG
CAAGCAAGCGCTCGAAACGGTGCAGCGGCTGTTGCCGGTGCTGTGCCAGGACCATGGCCTGACCCCGGAC
CAAGTGGTGGCTATCGCCAGCAACGGTGGCGGCAAGCAAGCGCTCGAAACGGTGCAGCGGCTGTTGCCGG
TGCTGTGCCAGGACCATGGCCTGACCCCGGACCAAGTGGTGGCTATCGCCAGCAACGGTGGCGGCAAGCA
AGCGCTCGAAACGGTGCAGCGGCTGTTGCCGGTGCTGTGCCAGGACCATGGCCTGACCCCGGACCAAGTG
GTGGCTATCGCCAGCAACAATGGCGGCAAGCAAGCGCTCGAAACGGTGCAGCGGCTGTTGCCGGTGCTGT
GCCAGGACCATGGCCTGACCCCGGACCAAGTGGTGGCTATCGCCAGCAACAATGGCGGCAAGCAAGCGCT
CGAAACGGTGCAGCGGCTGTTGCCGGTGCTGTGCCAGGACCATGGCCTGACCCCGGACCAAGTGGTGGCT
ATCGCCAGCAACATTGGCGGCAAGCAAGCGCTCGAAACGGTGCAGCGGCTGTTGCCGGTGCTGTGCCAGG
ACCATGGCCTGACCCCGGACCAAGTGGTGGCTATCGCCAGCAACAATGGCGGCAAGCAAGCGCTCGAAAC
GGTGCAGCGGCTGTTGCCGGTGCTGTGCCAGGACCATGGCCTGACCCCGGACCAAGTGGTGGCTATCGCC
AGCAACGGTGGCGGCAAGCAAGCGCTCGAAACGGTGCAGCGGCTGTTGCCGGTGCTGTGCCAGGACCATG
GCCTGACCCCGGACCAAGTGGTGGCTATCGCCAGCAACAATGGCGGCAAGCAAGCGCTCGAAACGGTGCA
GCGGCTGTTGCCGGTGCTGTGCCAGGACCATGGCCTGACCCCGGACCAAGTGGTGGCTATCGCCAGCCAC
GATGGCGGCAAGCAAGCGCTCGAAACGGTGCAGCGGCTGTTGCCGGTGCTGTGCCAGGACCATGGCCTGA
CCCCGGACCAAGTGGTGGCTATCGCCAGCAACATTGGCGGCAAGCAAGCGCTCGAAACGGTGCAGCGGCT
GTTGCCGGTGCTGTGCCAGGACCATGGCCTGACCCCGGACCAAGTGGTGGCTATCGCCAGCAACATTGGC
GGCAAGCAAGCGCTCGAAACGGTGCAGCGGCTGTTGCCGGTGCTGTGCCAGGACCATGGCCTGACCCCGG
ACCAAGTGGTGGCTATCGCCAGCAACATTGGCGGCAAGCAAGCGCTCGAAACGGTGCAGCGGCTGTTGCC
GGTGCTGTGCCAGGACCATGGCCTGACCCCGGACCAAGTGGTGGCTATCGCCAGCAACAATGGCGGCAAG
CAAGCGCTCGAAACGGTGCAGCGGCTGTTGCCGGTGCTGTGCCAGGACCATGGCCTGACCCCGGACCAAG
TGGTGGCTATCGCCAGCAACAATGGCGGCAAGCAAGCGCTCGAAACGGTGCAGCGGCTGTTGCCGGTGCT
GTGCCAGGACCATGGCCTGACCCCGGACCAAGTGGTGGctatcgccagcaacggtggcggcaagcaagcg
ctcgaaagcattgtggcccagctgagccggcctgatccggcgttggccgcgttgaccaacgacgaccacc
tcgtcgccttggcctgcctcggcggacgtcctgccatggatgcagtgaaaaaggggattgccgcacgcgcc
ggaattgatcagaagagtcaatcgccgtattggcgaacgcacgtcccatcgcgttgccGgatcCaAGGCT
AGCCCGAAAAAGAAACGCAAAGTTGGGCGCGCCGACGCGCTGGACGATTTCGATCTCGACATGCTGGGTT
CTGATGCCCTCGATGACTTTGACCTGGATATGTTGGGAAGCGACGCATTGGATGACTTTGATCTGGACAT
GCTCGGCTCCGATGCTCTGGACGATTTCGATCTCGATATGTTAATTAACTACCCGTACGACGTTCCGGAC
TACGCTTCTTGA SEQ ID NO: 66: KLK3 TALE F polypeptide
MDYKDHDGDYKDHDIDYKDDDDKMAPKKKRKVGRGSVDLRTLGYSQQQQEKIKPKVRSTVAQHHEALVGH
GFTHAHIVALSQHPAALGTVAVTYQHIITALPEATHEDIVGVGKQWSGARALEALLTDAGELRGPPLQLD
TGQLVKIAKRGGVTAMEAVHASRNALTGAPLNLTPDQVVAIASHDGGKQALETVQRLLPVLCQDHGLTPD
QVVAIASNGGGKQALETVQRLLPVLCQDHGLTPDQVVAIASNGGGKQALETVQRLLPVLCQDHGLTPDQV
VAIASNNGGKQALETVQRLLPVLCQDHGLTPDQVVAIASNNGGKQALETVQRLLPVLCQDHGLTPDQVVA
IASNIGGKQALETVQRLLPVLCQDHGLTPDQVVAIASNNGGKQALETVQRLLPVLCQDHGLTPDQVVAIA
SNGGGKQALETVQRLLPVLCQDHGLTPDQVVAIASNNGGKQALETVQRLLPVLCQDHGLTPDQVVAIASH
DGGKQALETVQRLLPVLCQDHGLTPDQVVAIASNIGGKQALETVQRLLPVLCQDHGLTPDQVVAIASNIG
GKQALETVQRLLPVLCQDHGLTPDQVVAIASNIGGKQALETVQRLLPVLCQDHGLTPDQVVAIASNNGGK
QALETVQRLLPVLCQDHGLTPDQVVAIASNNGGKQALETVQRLLPVLCQDHGLTPDQVVAIASNGGGKQA
LESIVAQLSRPDPALAALTNDDHLVALACLGGRPAMDAVKKGLPHAPELIRRVNRRIGERTSHRVAGSKA
SPKKKRKVGRADALDDFDLDMLGSDALDDFDLDMLGSDALDDFDLDMLGSDALDDFDLDMLINYPYDVPD
YAS SEQ ID NO: 67: KLK3 TALE G nucleotide
ATGGACTACAAAGACCATGACGGTGATTATAAAGATCATGACATCGATTACAAGGATGACGATGACAAGa
tggcccccaagaagaagaggaaggtgggccgcGgatcTgtggatctacgcacgctcggctacagtcagca
gcagcaagagaagatcaaaccgaaggtgcgttcgacagtggcgcagcaccacgaggcactggtgggccat
gggtttacacacgcgcacatcgttgcgctcagccaacacccggcagcgttagggaccgtcgctgtcacgt
atcagcacataatcacggcgttgccagaggcgacacacgaagacatcgttggcgtcggcaaacagtggtc
cggcgcacgcgccctggaggccttgctcacggatgcgggggagttgagaggtccgccgttacagttggac
acaggccaacttgtgaagattgcaaaacgtggcggcgtgaccgcaatggaggcagtgcatgcatcgcgca
atgcactgacgggtgccccctgAACCTGACCCCGGACCAAGTGGTGGCTATCGCCAGCCACGATGGCGG
CAAGCAAGCGCTCGAAACGGTGCAGCGGCTGTTGCCGGTGCTGTGCCAGGACCATGGCCTGACCCCGGAC
CAAGTGGTGGCTATCGCCAGCAACGGTGGCGGCAAGCAAGCGCTCGAAACGGTGCAGCGGCTGTTGCCGG
TGCTGTGCCAGGACCATGGCCTGACCCCGGACCAAGTGGTGGCTATCGCCAGCAACAATGGCGGCAAGCA
AGCGCTCGAAACGGTGCAGCGGCTGTTGCCGGTGCTGTGCCAGGACCATGGCCTGACCCCGGACCAAGTG
GTGGCTATCGCCAGCAACGGTGGCGGCAAGCAAGCGCTCGAAACGGTGCAGCGGCTGTTGCCGGTGCTGT
GCCAGGACCATGGCCTGACCCCGGACCAAGTGGTGGCTATCGCCAGCAACAATGGCGGCAAGCAAGCGCT
CGAAACGGTGCAGCGGCTGTTGCCGGTGCTGTGCCAGGACCATGGCCTGACCCCGGACCAAGTGGTGGCT
ATCGCCAGCAACAATGGCGGCAAGCAAGCGCTCGAAACGGTGCAGCGGCTGTTGCCGGTGCTGTGCCAGG
ACCATGGCCTGACCCCGGACCAAGTGGTGGCTATCGCCAGCAACATTGGCGGCAAGCAAGCGCTCGAAAC
GGTGCAGCGGCTGTTGCCGGTGCTGTGCCAGGACCATGGCCTGACCCCGGACCAAGTGGTGGCTATCGCC
AGCCACGATGGCGGCAAGCAAGCGCTCGAAACGGTGCAGCGGCTGTTGCCGGTGCTGTGCCAGGACCATG

TALE-TF SEQUENCES

```
GCCTGACCCCGGACCAAGTGGTGGCTATCGCCAGCCACGATGGCGGCAAGCAAGCGCTCGAAACGGTGCA
GCGGCTGTTGCCGGTGCTGTGCCAGGACCATGGCCTGACCCCGGACCAAGTGGTGGCTATCGCCAGCAAC
ATTGGCGGCAAGCAAGCGCTCGAAACGGTGCAGCGGCTGTTGCCGGTGCTGTGCCAGGACCATGGCCTGA
CCCCGGACCAAGTGGTGGCTATCGCCAGCCACGATGGCGGCAAGCAAGCGCTCGAAACGGTGCAGCGGCT
GTTGCCGGTGCTGTGCCAGGACCATGGCCTGACCCCGGACCAAGTGGTGGCTATCGCCAGCAACATTGGC
GGCAAGCAAGCGCTCGAAACGGTGCAGCGGCTGTTGCCGGTGCTGTGCCAGGACCATGGCCTGACCCCGG
ACCAAGTGGTGGCTATCGCCAGCAACATTGGCGGCAAGCAAGCGCTCGAAACGGTGCAGCGGCTGTTGCC
GGTGCTGTGCCAGGACCATGGCCTGACCCCGGACCAAGTGGTGGCTATCGCCAGCAACAATGGCGGCAAG
CAAGCGCTCGAAACGGTGCAGCGGCTGTTGCCGGTGCTGTGCCAGGACCATGGCCTGACCCCGGACCAAG
TGGTGGCTATCGCCAGCAACATTGGCGGCAAGCAAGCGCTCGAAACGGTGCAGCGGCTGTTGCCGGTGCT
GTGCCAGGACCATGGCCTGACCCCGGACCAAGTGGTGGctatcgccagcaacggtggcggcaagcaagcg
ctcgaaagcattgtggcccagctgagccggcctgatccggcgttggccgcgttgaccaacgacgaccacc
tcgtcgccttggcctgcctcggcggacgtcctgccatggatgcagtgaaaaaggattgccgcacgcgcc
ggaattgatcagaagagtcaatcgccgtattggcgaacgcacgtcccatcgcgttgccGgatcCaAGGCT
AGCCCGAAAAAGAAACGCAAAGTTGGGCGCGCCGACGCGCTGGACGATTTCGATCTCGACATGCTGGGTT
CTGATGCCCTCGATGACTTTGACCTGGATATGTTGGGAAGCGACGCATTGGATGACTTTGATCTGGACAT
GCTCGGCTCCGATGCTCTGGACGATTTCGATCTCGATATGTTAATTAACTACCCGTACGACGTTCCGGAC
TACGCTTCTTGA
```

SEQ ID NO: 68: KLK3 TALE G polypeptide
```
MDYKDHDGDYKDHDIDYKDDDDKMAPKKKRKVGRGSVDLRTLGYSQQQQEKIKPKVRSTVAQHHEALVGH
GFTHAHIVALSQHPAALGTVAVTYQHIITALPEATHEDIVGVKQWSGARALEALLTDAGELRGPPLQLD
TGQLVKIAKRGGVTAMEAVHASRNALTGAPLNLTPDQVVAIASHDGGKQALETVQRLLPVLCQDHGLTPD
QVVAIASNGGGKQALETVQRLLPVLCQDHGLTPDQVVAIASNGGGKQALETVQRLLPVLCQDHGLTPDQV
VAIASNGGGKQALETVQRLLPVLCQDHGLTPDQVVAIASNNGGKQALETVQRLLPVLCQDHGLTPDQVVA
IASNNGGKQALETVQRLLPVLCQDHGLTPDQVVAIASNIGGKQALETVQRLLPVLCQDHGLTPDQVVAIA
SHDGGKQALETVQRLLPVLCQDHGLTPDQVVAIASHDGGKQALETVQRLLPVLCQDHGLTPDQVVAIASN
IGGKQALETVQRLLPVLCQDHGLTPDQVVAIASHDGGKQALETVQRLLPVLCQDHGLTPDQVVAIASNIG
GKQALETVQRLLPVLCQDHGLTPDQVVAIASNIGGKQALETVQRLLPVLCQDHGLTPDQVVAIASNNGGK
QALETVQRLLPVLCQDHGLTPDQVVAIASNIGGKQALETVQRLLPVLCQDHGLTPDQVVAIASNGGGKQA
LESIVAQLSRPDPALAALTNDDHLVALACLGGRPAMDAVKKGLPHAPELIRRVNRRIGERTSHRVAGSKA
SPKKKRKVGRADALDDFDLDMLGSDALDDFDLDMLGSDALDDFDLDMLGSDALDDFDLDMLINYPYDVPD
YAS
```

SEQ ID NO: 69: CEACAM5 TALE A nucleotide
```
ATGGACTACAAGACCATGACGGTGATTATAAAGATCATGACATCGATTACAAGGATGACGATGACAAGa
tggccccaagaagaagaggaaggtggggccgcGgatcTgtggatctacgcacgctcggctacagtcagca
gcagcaagagaagatcaaaccgaaggtgcgttcgacagtggcgcagcaccacgaggcactggtgggccat
gggtttacacacgcgcacatcgttgcgctcagccaacacccggcagcgttagggaccgtcgctgtcacgt
atcagcacataatcacggcgttgccagaggcgacacacgaagacatcgttggcgtcggcaaacagtggtc
cggcgcacgcgcctggaggccttgctcacggatgcggggagttgagaggtccgccgttacagttggac
acaggccaacttgtgaagattgcaaaacgtggcggcgtgaccgcaatggaggcagtgcatgcatcgcgca
atgcactgacgggtgccccctgAACCTGACCCCGGACCAAGTGGTGGCTATCGCCAGCAACATTGGCGG
CAAGCAAGCGCTCGAAACGGTGCAGCGGCTGTTGCCGGTGCTGTGCCAGGACCATGGCCTGACCCCGGAC
CAAGTGGTGGCTATCGCCAGCAACATTGGCGGCAAGCAAGCGCTCGAAACGGTGCAGCGGCTGTTGCCGG
TGCTGTGCCAGGACCATGGCCTGACCCCGGACCAAGTGGTGGCTATCGCCAGCAACATTGGCGGCAAGCA
AGCGCTCGAAACGGTGCAGCGGCTGTTGCCGGTGCTGTGCCAGGACCATGGCCTGACCCCGGACCAAGTG
GTGGCTATCGCCAGCAACAATGGCGGCAAGCAAGCGCTCGAAACGGTGCAGCGGCTGTTGCCGGTGCTGT
GCCAGGACCATGGCCTGACCCCGGACCAAGTGGTGGCTATCGCCAGCAACATTGGCGGCAAGCAAGCGCT
CGAAACGGTGCAGCGGCTGTTGCCGGTGCTGTGCCAGGACCATGGCCTGACCCCGGACCAAGTGGTGGCT
ATCGCCAGCCACGATGGCGGCAAGCAAGCGCTCGAAACGGTGCAGCGGCTGTTGCCGGTGCTGTGCCAGG
ACCATGGCCTGACCCCGGACCAAGTGGTGGCTATCGCCAGCCACGATGGCGGCAAGCAAGCGCTCGAAAC
GGTGCAGCGGCTGTTGCCGGTGCTGTGCCAGGACCATGGCCTGACCCCGGACCAAGTGGTGGCTATCGCC
AGCAACATTGGCGGCAAGCAAGCGCTCGAAACGGTGCAGCGGCTGTTGCCGGTGCTGTGCCAGGACCATG
GCCTGACCCCGGACCAAGTGGTGGCTATCGCCAGCCACGATGGCGGCAAGCAAGCGCTCGAAACGGTGCA
GCGGCTGTTGCCGGTGCTGTGCCAGGACCATGGCCTGACCCCGGACCAAGTGGTGGCTATCGCCAGCAAC
ATTGGCGGCAAGCAAGCGCTCGAAACGGTGCAGCGGCTGTTGCCGGTGCTGTGCCAGGACCATGGCCTGA
CCCCGGACCAAGTGGTGGCTATCGCCAGCCACGATGGCGGCAAGCAAGCGCTCGAAACGGTGCAGCGGCT
GTTGCCGGTGCTGTGCCAGGACCATGGCCTGACCCCGGACCAAGTGGTGGCTATCGCCAGCCACGATGGC
GGCAAGCAAGCGCTCGAAACGGTGCAGCGGCTGTTGCCGGTGCTGTGCCAGGACCATGGCCTGACCCCGG
ACCAAGTGGTGGCTATCGCCAGCCACGATGGCGGCAAGCAAGCGCTCGAAACGGTGCAGCGGCTGTTGCC
GGTGCTGTGCCAGGACCATGGCCTGACCCCGGACCAAGTGGTGGCTATCGCCAGCAACATTGGCGGCAAG
CAAGCGCTCGAAACGGTGCAGCGGCTGTTGCCGGTGCTGTGCCAGGACCATGGCCTGACCCCGGACCAAG
TGGTGGCTATCGCCAGCAACGGTGGCGGCAAGCAAGCGCTCGAAACGGTGCAGCGGCTGTTGCCGGTGCT
GTGCCAGGACCATGGCCTGACCCCGGACCAAGTGGTGGCTATCGCCAGCAACAATGGCGGCAAGCAAGCG
CTCGAAACGGTGCAGCGGCTGTTGCCGGTGCTGTGCCAGGACCATGGCCTGACCCCGGACCAAGTGGTGG
CTATCGCCAGCAACATTGGCGGCAAGCAAGCGCTCGAAACGGTGCAGCGGCTGTTGCCGGTGCTGTGCCA
GGACCATGGCCTGACCCCGGACCAAGTGGTGGctatcgccagcCACGATggcggcaagcaagcgctcgaa
agcattgtggcccagctgagccggcctgatccggcgttggccgcgttgaccaacgacgaccacctcgtcg
ccttggcctgcctcggcggacgtcctgccatggatgcagtgaaaaaggattgccgcacgcgccggaatt
gatcagaagagtcaatcgccgtattggcgaacgcacgtcccatcgcgttgccGgatcCaAGGCTAGCCCG
AAAAAGAAACGCAAAGTTGGGCGCGCCGACGCGCTGGACGATTTCGATCTCGACATGCTGGGTTCTGATG
CCCTCGATGACTTTGACCTGGATATGTTGGGAAGCGACGCATTGGATGACTTTGATCTGGACATGCTCGG
CTCCGATGCTCTGGACGATTTCGATCTCGATATGTTAATTAACTACCCGTACGACGTTCCGGACTACGCT
TCTTGA
```

| TALE-TF SEQUENCES |
| --- |

SEQ ID NO: 70: CEACAM5 TALE A polypeptide
MDYKDHDGDYKDHDIDYKDDDDKMAPKKKRKVGRGSVDLRTLGYSQQQQEKIKPKVRSTVAQHHEALVGH
GFTHAHIVALSQHPAALGTVAVTYQHIITALPEATHEDIVGVGKQWSGARALEALLTDAGELRGPPLQLD
TGQLVKIAKRGGVTAMEAVHASRNALTGAPLNLTPDQVVAIASNIGGKQALETVQRLLPVLCQDHGLTPD
QVVAIASNIGGKQALETVQRLLPVLCQDHGLTPDQVVAIASNIGGKQALETVQRLLPVLCQDHGLTPDQV
VAIASNNGGKQALETVQRLLPVLCQDHGLTPDQVVAIASNIGGKQALETVQRLLPVLCQDHGLTPDQVVA
IASHDGGKQALETVQRLLPVLCQDHGLTPDQVVAIASHDGGKQALETVQRLLPVLCQDHGLTPDQVVAIA
SNIGGKQALETVQRLLPVLCQDHGLTPDQVVAIASHDGGKQALETVQRLLPVLCQDHGLTPDQVVAIASN
IGGKQALETVQRLLPVLCQDHGLTPDQVVAIASHDGGKQALETVQRLLPVLCQDHGLTPDQVVAIASHDG
GKQALETVQRLLPVLCQDHGLTPDQVVAIASHDGGKQALETVQRLLPVLCQDHGLTPDQVVAIASNIGGK
QALETVQRLLPVLCQDHGLTPDQVVAIASNGGGKQALETVQRLLPVLCQDHGLTPDQVVAIASNGGGKQA
LETVQRLLPVLCQDHGLTPDQVVAIASNIGGKQALETVQRLLPVLCQDHGLTPDQVVAIASHDGGKQALE
SIVAQLSRPDPALAALTNDDHLVALACLGGRPAMDAVKKGLPHAPELIRRVNRRIGERTSHRVAGSKASP
KKKRKVGRADALDDFDLDMLGSDALDDFDLDMLGSDALDDFDLDMLGSDALDDFDLDMLINYPYDVPDYA
S SEQ ID NO: 71: CEACAM5 TALE B nucleotide
ATGGACTACAAAGACCATGACGGTGATTATAAAGATCATGACATCGATTACAAGGATGACGATGACAAGa
tggcccccaagaagaagaggaaggtgggccgcGgatcTgtggatctacgcacgctcggctacagtcagca
gcagcaagagaagatcaaaccgaaggtgcgttcgacagtggcgcagcaccacgaggcactggtgggccat
gggtttacacacgcgcacatcgttgcgctcagccaacacccggcagcgttagggaccgtcgctgtcacgt
atcagcacataatcacggcgttgccagaggcgacacacgaagacatcgttggcgtcggcaaacagtggtc
cggcgcacgcgccctggaggccttgctcacggatgcggggggagttgagaggtccgccgttacagttggac
acaggccaacttgtgaagattgcaaaacgtggcggcgtgcaatggaggcagtgcatgcatcgcgca
atgcactgacgggtgcccccctgAACCTGACCCCGGACCAAGTGGTGGCTATCGCCAGCCACGATGGCGG
CAAGCAAGCGCTCGAAACGGTGCAGCGGCTGTTGCCGGTGCTGTGCCAGGACCATGGCCTGACCCCGGAC
CAAGTGGTGGCTATCGCCAGCAACGGTGGCGGCAAGCAAGCGCTCGAAACGGTGCAGCGGCTGTTGCCGG
TGCTGTGCCAGGACCATGGCCTGACCCCGGACCAAGTGGTGGCTATCGCCAGCAACAATGGCGGCAAGCA
AGCGCTCGAAACGGTGCAGCGGCTGTTGCCGGTGCTGTGCCAGGACCATGGCCTGACCCCGGACCAAGTG
GTGGCTATCGCCAGCAACATTGGCGGCAAGCAAGCGCTCGAAACGGTGCAGCGGCTGTTGCCGGTGCTGT
GCCAGGACCATGGCCTGACCCCGGACCAAGTGGTGGCTATCGCCAGCAACAATGGCGGCAAGCAAGCGCT
CGAAACGGTGCAGCGGCTGTTGCCGGTGCTGTGCCAGGACCATGGCCTGACCCCGGACCAAGTGGTGGCT
ATCGCCAGCAACAATGGCGGCAAGCAAGCGCTCGAAACGGTGCAGCGGCTGTTGCCGGTGCTGTGCCAGG
ACCATGGCCTGACCCCGGACCAAGTGGTGGCTATCGCCAGCAACATTGGCGGCAAGCAAGCGCTCGAAAC
GGTGCAGCGGCTGTTGCCGGTGCTGTGCCAGGACCATGGCCTGACCCCGGACCAAGTGGTGGCTATCGCC
AGCAACATTGGCGGCAAGCAAGCGCTCGAAACGGTGCAGCGGCTGTTGCCGGTGCTGTGCCAGGACCATG
GCCTGACCCCGGACCAAGTGGTGGCTATCGCCAGCCACGATGGCGGCAAGCAAGCGCTCGAAACGGTGCA
GCGGCTGTTGCCGGTGCTGTGCCAGGACCATGGCCTGACCCCGGACCAAGTGGTGGCTATCGCCAGCAAC
GGTGGCGGCAAGCAAGCGCTCGAAACGGTGCAGCGGCTGTTGCCGGTGCTGTGCCAGGACCATGGCCTGA
CCCCGGACCAAGTGGTGGCTATCGCCAGCAACAATGGCGGCAAGCAAGCGCTCGAAACGGTGCAGCGGCT
GTTGCCGGTGCTGTGCCAGGACCATGGCCTGACCCCGGACCAAGTGGTGGCTATCGCCAGCAACATTGGC
GGCAAGCAAGCGCTCGAAACGGTGCAGCGGCTGTTGCCGGTGCTGTGCCAGGACCATGGCCTGACCCCGG
ACCAAGTGGTGGCTATCGCCAGCAACATTGGCGGCAAGCAAGCGCTCGAAACGGTGCAGCGGCTGTTGCC
GGTGCTGTGCCAGGACCATGGCCTGACCCCGGACCAAGTGGTGGCTATCGCCAGCAACATTGGCGGCAAG
CAAGCGCTCGAAACGGTGCAGCGGCTGTTGCCGGTGCTGTGCCAGGACCATGGCCTGACCCCGGACCAAG
TGGTGGCTATCGCCAGCAACATTGGCGGCAAGCAAGCGCTCGAAACGGTGCAGCGGCTGTTGCCGGTGCT
GTGCCAGGACCATGGCCTGACCCCGGACCAAGTGGTGGctatcgccagcaacggtggcggcaagcaagcg
ctcgaaagcattgtggcccagctgagccggcctgatccggcgttggccgcgttgaccaacgacgaccacc
tcgtcgctttggcctgcctcggcggacgtcctgccatggatgcagtgaaaaagggattgccgcacgcgcc
ggaattgatcagaagagtcaatcgccgtattggcgaacgcacgtcccatcgcgttgccGgatcCaAGGCT
AGCCCGAAAAAGAAACGCAAAGTTGGGCGCGCCGACGCGCTGGACGATTTCGATCTCGACATGCTGGGTT
CTGATGCCCTCGATGACTTTGACCTGGATATGTTGGGAAGCGACGCATTGGATGACTTTGATCTGGACAT
GCTCGGCTCCGATGCTCTGGACGATTTCGATCTCGATATGTTAATTAACTACCCGTACGACGTTCCGGAC
TACGCTTCTTGA SEQ ID NO: 72: CEACAM5 TALE B polypeptide
MDYKDHDGDYKDHDIDYKDDDDKMAPKKKRKVGRGSVDLRTLGYSQQQQEKIKPKVRSTVAQHHEALVGH
GFTHAHIVALSQHPAALGTVAVTYQHIITALPEATHEDIVGVGKQWSGARALEALLTDAGELRGPPLQLD
TGQLVKIAKRGGVTAMEAVHASRNALTGAPLNLTPDQVVAIASHDGGKQALETVQRLLPVLCQDHGLTPD
QVVAIASNGGGKQALETVQRLLPVLCQDHGLTPDQVVAIASNNGGKQALETVQRLLPVLCQDHGLTPDQV
VAIASNIGGKQALETVQRLLPVLCQDHGLTPDQVVAIASNNGGKQALETVQRLLPVLCQDHGLTPDQVVA
IASNNGGKQALETVQRLLPVLCQDHGLTPDQVVAIASNIGGKQALETVQRLLPVLCQDHGLTPDQVVAIA
SNIGGKQALETVQRLLPVLCQDHGLTPDQVVAIASHDGGKQALETVQRLLPVLCQDHGLTPDQVVAIASN
GGGKQALETVQRLLPVLCQDHGLTPDQVVAIASNNGGKQALETVQRLLPVLCQDHGLTPDQVVAIASNIG
GKQALETVQRLLPVLCQDHGLTPDQVVAIASNIGGKQALETVQRLLPVLCQDHGLTPDQVVAIASNIGGK
QALETVQRLLPVLCQDHGLTPDQVVAIASNIGGKQALETVQRLLPVLCQDHGLTPDQVVAIASNGGGKQA
LESIVAQLSRPDPALAALTNDDHLVALACLGGRPAMDAVKKGLPHAPELIRRVNRRIGERTSHRVAGSKA
SPKKKRKVGRADALDDFDLDMLGSDALDDFDLDMLGSDALDDFDLDMLGSDALDDFDLDMLINYPYDVPD
YAS SEQ ID NO: 73: CEACAM5 TALE C nucleotide
ATGGACTACAAAGACCATGACGGTGATTATAAAGATCATGACATCGATTACAAGGATGACGATGACAAGa
tggcccccaagaagaagaggaaggtgggccgcGgatcTgtggatctacgcacgctcggctacagtcagca
gcagcaagagaagatcaaaccgaaggtgcgttcgacagtggcgcagcaccacgaggcactggtgggccat
gggtttacacacgcgcacatcgttgcgctcagccaacacccggcagcgttagggaccgtcgctgtcacgt
atcagcacataatcacggcgttgccagaggcgacacacgaagacatcgttggcgtcggcaaacagtggtc
cggcgcacgcgccctggaggccttgctcacggatgcggggggagttgagaggtccgccgttacagttggac

TALE-TF SEQUENCES acaggccaacttgtgaagattgcaaaacgtggcggcgtgaccgcaatggaggcagtgcatgcatcgcgca
atgcactgacgggtgcccccctgAACCTGACCCCGGACCAAGTGGTGGCTATCGCCAGCCACGATGGCGG
CAAGCAAGCGCTCGAAACGGTGCAGCGGCTGTTGCCGGTGCTGTGCCAGGACCATGGCCTGACCCCGGAC
CAAGTGGTGGCTATCGCCAGCCACGATGGCGGCAAGCAAGCGCTCGAAACGGTGCAGCGGCTGTTGCCGG
TGCTGTGCCAGGACCATGGCCTGACCCCGGACCAAGTGGTGGCTATCGCCAGCAACATTGGCGGCAAGCA
AGCGCTCGAAACGGTGCAGCGGCTGTTGCCGGTGCTGTGCCAGGACCATGGCCTGACCCCGGACCAAGTG
GTGGCTATCGCCAGCCACGATGGCGGCAAGCAAGCGCTCGAAACGGTGCAGCGGCTGTTGCCGGTGCTGT
GCCAGGACCATGGCCTGACCCCGGACCAAGTGGTGGCTATCGCCAGCCACGATGGCGGCAAGCAAGCGCT
CGAAACGGTGCAGCGGCTGTTGCCGGTGCTGTGCCAGGACCATGGCCTGACCCCGGACCAAGTGGTGGCT
ATCGCCAGCAACGGTGGCGGCAAGCAAGCGCTCGAAACGGTGCAGCGGCTGTTGCCGGTGCTGTGCCAGG
ACCATGGCCTGACCCCGGACCAAGTGGTGGCTATCGCCAGCAACGGTGGCGGCAAGCAAGCGCTCGAAAC
GGTGCAGCGGCTGTTGCCGGTGCTGTGCCAGGACCATGGCCTGACCCCGGACCAAGTGGTGGCTATCGCC
AGCAACAATGGCGGCAAGCAAGCGCTCGAAACGGTGCAGCGGCTGTTGCCGGTGCTGTGCCAGGACCATG
GCCTGACCCCGGACCAAGTGGTGGCTATCGCCAGCCACGATGGCGGCAAGCAAGCGCTCGAAACGGTGCA
GCGGCTGTTGCCGGTGCTGTGCCAGGACCATGGCCTGACCCCGGACCAAGTGGTGGCTATCGCCAGCCAC
GATGGCGGCAAGCAAGCGCTCGAAACGGTGCAGCGGCTGTTGCCGGTGCTGTGCCAGGACCATGGCCTGA
CCCCGGACCAAGTGGTGGCTATCGCCAGCAACAATGGCGGCAAGCAAGCGCTCGAAACGGTGCAGCGGCT
GTTGCCGGTGCTGTGCCAGGACCATGGCCTGACCCCGGACCAAGTGGTGGCTATCGCCAGCAACATTGGC
GGCAAGCAAGCGCTCGAAACGGTGCAGCGGCTGTTGCCGGTGCTGTGCCAGGACCATGGCCTGACCCCGG
ACCAAGTGGTGGCTATCGCCAGCAACATTGGCGGCAAGCAAGCGCTCGAAACGGTGCAGCGGCTGTTGCC
GGTGCTGTGCCAGGACCATGGCCTGACCCCGGACCAAGTGGTGGCTATCGCCAGCAACATTGGCGGCAAG
CAAGCGCTCGAAACGGTGCAGCGGCTGTTGCCGGTGCTGTGCCAGGACCATGGCCTGACCCCGGACCAAG
TGGTGGCTATCGCCAGCAACATTGGCGGCAAGCAAGCGCTCGAAACGGTGCAGCGGCTGTTGCCGGTGCT
GTGCCAGGACCATGGCCTGACCCCGGACCAAGTGGTGGCTATCGCCAGCAACATTGGCGGCAAGCAAGCG
CTCGAAACGGTGCAGCGGCTGTTGCCGGTGCTGTGCCAGGACCATGGCCTGACCCCGGACCAAGTGGTGG
CTATCGCCAGCAACAATGGCGGCAAGCAAGCGCTCGAAACGGTGCAGCGGCTGTTGCCGGTGCTGTGCCA
GGACCATGGCCTGACCCCGGACCAAGTGGTGGCTATCGCCAGCAACATTGGCGGCAAGCAAGCGCTCGAA
ACGGTGCAGCGGCTGTTGCCGGTGCTGTGCCAGGACCATGGCCTGACCCCGGACCAAGTGGTGGctatcg
ccagcaacggtggcggcaagcaagcgctcgaaagcattgtggcccagctgagccggcctgatccggcgtt
ggccgcgttgaccaacgacgaccacctcgtcgccttggcctgcctcggcggacgtcctgccatggatgca
gtgaaaaagggattgccgcacgcgccggaattgatcagaagagtcaatcgccgtattggcgaacgcacgt
cccatcgcgttgccGgatcCaAGGCTAGCCCGAAAAAGAAACGCAAAGTTGGGCGCGCCGACGCGCTGGA
CGATTTCGATCTCGACATGCTGGGTTCTGATGCCCTCGATGACTTTGACCTGGATATGTTGGGAAGCGAC
GCATTGGATGACTTTGATCTGGACATGCTCGGCTCCGATGCTCTGGACGATTTCGATCTCGATATGTTAA
TTAACTACCCGTACGACGTTCCGGACTACGCTTCTTGA SEQ ID NO: 74: CEACAM5 TALE C polypeptide
MDYKDHDGDYKDHDIDYKDDDDKMAPKKKRKVGRGSVDLRTLGYSQQQQEKIKPKVRSTVAQHHEALVGH
GFTHAHIVALSQHPAALGTVAVTYQHIITALPEATHEDIVGVGKQWSGARALEALLTDAGELRGPPLQLD
TGQLVKIAKRGGVTAMEAVHASRNALTGAPLNLTPDQVVAIASHDGGKQALETVQRLLPVLCQDHGLTPD
QVVAIASHDGGKQALETVQRLLPVLCQDHGLTPDQVVAIASNIGGKQALETVQRLLPVLCQDHGLTPDQV
VAIASHDGGKQALETVQRLLPVLCQDHGLTPDQVVAIASHDGGKQALETVQRLLPVLCQDHGLTPDQVVA
IASNGGGKQALETVQRLLPVLCQDHGLTPDQVVAIASNGGGKQALETVQRLLPVLCQDHGLTPDQVVAIA
SNNGGKQALETVQRLLPVLCQDHGLTPDQVVAIASHDGGKQALETVQRLLPVLCQDHGLTPDQVVAIASH
DGGKQALETVQRLLPVLCQDHGLTPDQVVAIASNNGGKQALETVQRLLPVLCQDHGLTPDQVVAIASNIG
GKQALETVQRLLPVLCQDHGLTPDQVVAIASNIGGKQALETVQRLLPVLCQDHGLTPDQVVAIASNIGGK
QALETVQRLLPVLCQDHGLTPDQVVAIASNIGGKQALETVQRLLPVLCQDHGLTPDQVVAIASNIGGKQA
LETVQRLLPVLCQDHGLTPDQVVAIASNNGGKQALETVQRLLPVLCQDHGLTPDQVVAIASNIGGKQALE
TVQRLLPVLCQDHGLTPDQVVAIASNGGGKQALESIVAQLSRPDPALAALTNDDHLVALACLGGRPAMDA
VKKGLPHAPELIRRVNRRIGERTSHRVAGSKASPKKKRKVGRADALDDFDLDMLGSDALDDFDLDMLGSD
ALDDFDLDMLGSDALDDFDLDMLINYPYDVPDYAS SEQ ID NO: 75: CEACAM5 TALE D nucleotide
ATGGACTACAAAGACCATGACGGTGATTATAAAGATCATGACATCGATTACAAGGATGACGATGACAAGa
tggcccccaagaagaagaggaaggtgggccgcGgatcTgtggatctacgcacgctcggctacagtcagca
gcagcaagagaagatcaaaccgaaggtgcgttcgacagtggcgcagcaccacgaggcactggtgggccat
gggtttacacacgcgcacatcgttgcgctcagccaacacccggcagcgttagggaccgtcgctgtcacgt
atcagcacataatcacggcgttgccagaggcgacacacgaagacatcgttggcgtcggcaaacagtggtc
cggcgcacgcgccctggaggccttgctcacgcgatgcgggggagttgagaggtccgccgttacagttggac
acaggccaacttgtgaagattgcaaaacgtggcggcgtgaccgcaatggaggcagtgcatgcatcgcgca
atgcactgacgggtgcccccctgAACCTGACCCCGGACCAAGTGGTGGCTATCGCCAGCCACGATGGCGG
CAAGCAAGCGCTCGAAACGGTGCAGCGGCTGTTGCCGGTGCTGTGCCAGGACCATGGCCTGACCCCGGAC
CAAGTGGTGGCTATCGCCAGCAACAATGGCGGCAAGCAAGCGCTCGAAACGGTGCAGCGGCTGTTGCCGG
TGCTGTGCCAGGACCATGGCCTGACCCCGGACCAAGTGGTGGCTATCGCCAGCCACGATGGCGGCAAGCA
AGCGCTCGAAACGGTGCAGCGGCTGTTGCCGGTGCTGTGCCAGGACCATGGCCTGACCCCGGACCAAGTG
GTGGCTATCGCCAGCCACGATGGCGGCAAGCAAGCGCTCGAAACGGTGCAGCGGCTGTTGCCGGTGCTGT
GCCAGGACCATGGCCTGACCCCGGACCAAGTGGTGGCTATCGCCAGCAACATTGGCGGCAAGCAAGCGCT
CGAAACGGTGCAGCGGCTGTTGCCGGTGCTGTGCCAGGACCATGGCCTGACCCCGGACCAAGTGGTGGCT
ATCGCCAGCCACGATGGCGGCAAGCAAGCGCTCGAAACGGTGCAGCGGCTGTTGCCGGTGCTGTGCCAGG
ACCATGGCCTGACCCCGGACCAAGTGGTGGCTATCGCCAGCCACGATGGCGGCAAGCAAGCGCTCGAAAC
GGTGCAGCGGCTGTTGCCGGTGCTGTGCCAGGACCATGGCCTGACCCCGGACCAAGTGGTGGCTATCGCC
AGCCACGATGGCGGCAAGCAAGCGCTCGAAACGGTGCAGCGGCTGTTGCCGGTGCTGTGCCAGGACCATG
GCCTGACCCCGGACCAAGTGGTGGCTATCGCCAGCAACATTGGCGGCAAGCAAGCGCTCGAAACGGTGCA
GCGGCTGTTGCCGGTGCTGTGCCAGGACCATGGCCTGACCCCGGACCAAGTGGTGGCTATCGCCAGCAAC
AATGGCGGCAAGCAAGCGCTCGAAACGGTGCAGCGGCTGTTGCCGGTGCTGTGCCAGGACCATGGCCTGA
CCCCGGACCAAGTGGTGGCTATCGCCAGCAACAATGGCGGCAAGCAAGCGCTCGAAACGGTGCAGCGGCT
GTTGCCGGTGCTGTGCCAGGACCATGGCCTGACCCCGGACCAAGTGGTGGCTATCGCCAGCAACAATGGC

| TALE-TF SEQUENCES |
| --- |
| GGCAAGCAAGCGCTCGAAACGGTGCAGCGGCTGTTGCCGGTGCTGTGCCAGGACCATGGCCTGACCCCGG
ACCAAGTGGTGGCTATCGCCAGCAACAATGGCGGCAAGCAAGCGCTCGAAACGGTGCAGCGGCTGTTGCC
GGTGCTGTGCCAGGACCATGGCCTGACCCCGGACCAAGTGGTGGCTATCGCCAGCAACATTGGCGGCAAG
CAAGCGCTCGAAACGGTGCAGCGGCTGTTGCCGGTGCTGTGCCAGGACCATGGCCTGACCCCGGACCAAG
TGGTGGCTATCGCCAGCAACGGTGGCGGCAAGCAAGCGCTCGAAACGGTGCAGCGGCTGTTGCCGGTGCT
GTGCCAGGACCATGGCCTGACCCCGGACCAAGTGGTGGctatcgccagcaacggtggcggcaagcaagcg
ctcgaaagcattgtggcccagctgagccggcctgatccggcgttggccgcgttgaccaacgacgaccacc
tcgtcgcctttggcctgcctcggcggacgtcctgccatggatgcagtgaaaaaggggattgccgcacgcgcc
ggaattgatcagaagagtcaatcgccgtattggcgaacgcacgtcccatcgcgttgccGgatcCaAGGCT
AGCCCGAAAAAGAAACGCAAAGTTGGGCGCGCCGACGCGCTGGACGATTTCGATCTCGACATGCTGGGTT
CTGATGCCCTCGATGACTTTGACCTGGATATGTTGGGAAGCGACGCATTGGATGACTTTGATCTGGACAT
GCTCGGCTCCGATGCTCTGGACGATTTCGATCTCGATATGTTAATTAACTACCCGTACGACGTTCCGGAC
TACGCTTCTTGA |

SEQ ID NO: 76: CEACAM5 TALE D polypeptide
MDYKDHDGDYKDHDIDYKDDDDKMAPKKKRKVGRGSVDLRTLGYSQQQQEKIKPKVRSTVAQHHEALVGH
GFTHAHIVALSQHPAALGTVAVTYQHIITALPEATHEDIVGVGKQWSGARALEALLTDAGELRGPPLQLD
TGQLVKIAKRGGVTAMEAVHASRNALTGAPLNLTPDQVVAIASNGGGKQALETVQRLLPVLCQDHGLTPD
QVVAIASNNGGKQALETVQRLLPVLCQDHGLTPDQVVAIASHDGGKQALETVQRLLPVLCQDHGLTPDQV
VAIASHDGGKQALETVQRLLPVLCQDHGLTPDQVVAIASNGGGKQALETVQRLLPVLCQDHGLTPDQVVA
IASHDGGKQALETVQRLLPVLCQDHGLTPDQVVAIASHDGGKQALETVQRLLPVLCQDHGLTPDQVVAIA
SHDGGKQALETVQRLLPVLCQDHGLTPDQVVAIASNIGGKQALETVQRLLPVLCQDHGLTPDQVVAIASN
NGGKQALETVQRLLPVLCQDHGLTPDQVVAIASNNGGKQALETVQRLLPVLCQDHGLTPDQVVAIASNNG
GKQALETVQRLLPVLCQDHGLTPDQVVAIASNNGGKQALETVQRLLPVLCQDHGLTPDQVVAIASNIGGK
QALETVQRLLPVLCQDHGLTPDQVVAIASNGGGKQALETVQRLLPVLCQDHGLTPDQVVAIASNGGGKQA
LESIVAQLSRPDPALAALTNDDHLVALACLGGRPAMDAVKKGLPHAPELIRRVNRRIGERTSHRVAGSKA
SPKKKRKVGRADALDDFDLDMLGSDALDDFDLDMLGSDALDDFDLDMLGSDALDDFDLDMLINYPYDVPD
YAS SEQ ID NO: 77: CEACAM5 TALE E nucleotide
ATGGACTACAAAGACCATGACGGTGATTATAAAGATCATGACATCGATTACAAGGATGACGATGACAAGa
tggcccccaagaagaagaggaaggtgggccgcGgatcTgtggatctacgcacgctcggctacagtcagca
gcagcaagagaagatcaaaccgaaggtgcgttcgacagtggcgcagcaccacgaggcactggtgggccat
gggtttacacacgcgcacatcgttgcgctcagccaacacccggcagcgttagggaccgtcgctgtcacgt
atcagcacataatcacggcgttgccagaggcgacacacgaagacatcgttggcgtcggcaaacagtggtc
cggcgcacgcgccctggaggccttgctcacggatgcgggggagttgagaggtccgccgttacagttggac
acaggccaacttgtgaagattgcaaaacgtggcggcgtgaccgccaatggaggcagtgcattgcatcgcgca
atgcactgacgggtgcccccctgAACCTGACCCCGGACCAAGTGGTGGCTATCGCCAGCCACGATGGCGG
CAAGCAAGCGCTCGAAACGGTGCAGCGGCTGTTGCCGGTGCTGTGCCAGGACCATGGCCTGACCCCGGAC
CAAGTGGTGGCTATCGCCAGCAACGGTGGCGGCAAGCAAGCGCTCGAAACGGTGCAGCGGCTGTTGCCGG
TGCTGTGCCAGGACCATGGCCTGACCCCGGACCAAGTGGTGGCTATCGCCAGCAACAATGGCGGCAAGCA
AGCGCTCGAAACGGTGCAGCGGCTGTTGCCGGTGCTGTGCCAGGACCATGGCCTGACCCCGGACCAAGTG
GTGGCTATCGCCAGCAACGGTGGCGGCAAGCAAGCGCTCGAAACGGTGCAGCGGCTGTTGCCGGTGCTGT
GCCAGGACCATGGCCTGACCCCGGACCAAGTGGTGGCTATCGCCAGCCACGATGGCGGCAAGCAAGCGCT
CGAAACGGTGCAGCGGCTGTTGCCGGTGCTGTGCCAGGACCATGGCCTGACCCCGGACCAAGTGGTGGCT
ATCGCCAGCAACATTGGCGGCAAGCAAGCGCTCGAAACGGTGCAGCGGCTGTTGCCGGTGCTGTGCCAGG
ACCATGGCCTGACCCCGGACCAAGTGGTGGCTATCGCCAGCCACGATGGCGGCAAGCAAGCGCTCGAAAC
GGTGCAGCGGCTGTTGCCGGTGCTGTGCCAGGACCATGGCCTGACCCCGGACCAAGTGGTGGCTATCGCC
AGCAACATTGGCGGCAAGCAAGCGCTCGAAACGGTGCAGCGGCTGTTGCCGGTGCTGTGCCAGGACCATG
GCCTGACCCCGGACCAAGTGGTGGCTATCGCCAGCAACATTGGCGGCAAGCAAGCGCTCGAAACGGTGCA
GCGGCTGTTGCCGGTGCTGTGCCAGGACCATGGCCTGACCCCGGACCAAGTGGTGGCTATCGCCAGCAAC
ATTGGCGGCAAGCAAGCGCTCGAAACGGTGCAGCGGCTGTTGCCGGTGCTGTGCCAGGACCATGGCCTGA
CCCCGGACCAAGTGGTGGCTATCGCCAGCAACAATGGCGGCAAGCAAGCGCTCGAAACGGTGCAGCGGCT
GTTGCCGGTGCTGTGCCAGGACCATGGCCTGACCCCGGACCAAGTGGTGGCTATCGCCAGCAACAATGGC
GGCAAGCAAGCGCTCGAAACGGTGCAGCGGCTGTTGCCGGTGCTGTGCCAGGACCATGGCCTGACCCCGG
ACCAAGTGGTGGCTATCGCCAGCAACATTGGCGGCAAGCAAGCGCTCGAAACGGTGCAGCGGCTGTTGCC
GGTGCTGTGCCAGGACCATGGCCTGACCCCGGACCAAGTGGTGGCTATCGCCAGCAACATTGGCGGCAAG
CAAGCGCTCGAAACGGTGCAGCGGCTGTTGCCGGTGCTGTGCCAGGACCATGGCCTGACCCCGGACCAAG
TGGTGGCTATCGCCAGCAACATTGGCGGCAAGCAAGCGCTCGAAACGGTGCAGCGGCTGTTGCCGGTGCT
GTGCCAGGACCATGGCCTGACCCCGGACCAAGTGGTGGctatcgccagcaacattggcggcaagcaagcg
ctcgaaagcattgtggcccagctgagccggcctgatccggcgttggccgcgttgaccaacgacgaccacc
tcgtcgcctttggcctgcctcggcggacgtcctgccatggatgcagtgaaaaaggggattgccgcacgcgcc
ggaattgatcagaagagtcaatcgccgtattggcgaacgcacgtcccatcgcgttgccGgatcCaAGGCT
AGCCCGAAAAAGAAACGCAAAGTTGGGCGCGCCGACGCGCTGGACGATTTCGATCTCGACATGCTGGGTT
CTGATGCCCTCGATGACTTTGACCTGGATATGTTGGGAAGCGACGCATTGGATGACTTTGATCTGGACAT
GCTCGGCTCCGATGCTCTGGACGATTTCGATCTCGATATGTTAATTAACTACCCGTACGACGTTCCGGAC
TACGCTTCTTGA SEQ ID NO: 78: CEACAM5 TALE E polypeptide
MDYKDHDGDYKDHDIDYKDDDDKMAPKKKRKVGRGSVDLRTLGYSQQQQEKIKPKVRSTVAQHHEALVGH
GFTHAHIVALSQHPAALGTVAVTYQHIITALPEATHEDIVGVGKQWSGARALEALLTDAGELRGPPLQLD
TGQLVKIAKRGGVTAMEAVHASRNALTGAPLNLTPDQVVAIASHDGGKQALETVQRLLPVLCQDHGLTPD
QVVAIASNGGGKQALETVQRLLPVLCQDHGLTPDQVVAIASNNGGKQALETVQRLLPVLCQDHGLTPDQV
VAIASNGGGKQALETVQRLLPVLCQDHGLTPDQVVAIASHDGGKQALETVQRLLPVLCQDHGLTPDQVVA
IASNIGGKQALETVQRLLPVLCQDHGLTPDQVVAIASHDGGKQALETVQRLLPVLCQDHGLTPDQVVAIA
SNIGGKQALETVQRLLPVLCQDHGLTPDQVVAIASNIGGKQALETVQRLLPVLCQDHGLTPDQVVAIASN
IGGKQALETVQRLLPVLCQDHGLTPDQVVAIASNNGGKQALETVQRLLPVLCQDHGLTPDQVVAIASNNG

TALE-TF SEQUENCES

GKQALETVQRLLPVLCQDHGLTPDQVVAIASNIGGKQALETVQRLLPVLCQDHGLTPDQVVAIASNIGGK
QALETVQRLLPVLCQDHGLTPDQVVAIASNIGGKQALETVQRLLPVLCQDHGLTPDQVVAIASNIGGKQA
LESIVAQLSRPDPALAALTNDDHLVALACLGGRPAMDAVKKGLPHAPELIRRVNRRIGERTSHRVAGSKA
SPKKKRKVGRADALDDFDLDMLGSDALDDFDLDMLGSDALDDFDLDMLGSDALDDFDLDMLINYPYDVPD
YAS

SEQ ID NO: 79: CEACAM5 TALE F nucleotide
ATGGACTACAAAGACCATGACGGTGATTATAAAGATCATGACATCGATTACAAGGATGACGATGACAAGa
tggcccccaagaagaagaggaaggtgggccgcGgatcTgtggatctacgcacgctcggctacagtcagca
gcagcaagagaagatcaaaccgaaggtgcgttcgacagtggcgcagcaccacgaggcactggtgggccat
gggtttacacacgcgcacatcgttgcgctcagccaacacccggcagcgttagggaccgtcgctgtcacgt
atcagcacataatcacggcgttgccagaggcgacacacgaagacatcgttggcgtcggcaaacagtggtc
cggcgcacgcgccctggaggccttgctcacggatgcgggggagttgagaggtccgccgttacagttggac
acaggccaacttgtgaagattgcaaaacgtggcggcgtgaccgcaatggaggcagtgcatgcatcgcgca
atgcactgacgggtgccccctgAACCTGACCCCGGACCAAGTGGTGGCTATCGCCAGCAACAATGGCGG
CAAGCAAGCGCTCGAAACGGTGCAGCGGCTGTTGCCGGTGCTGTGCCAGGACCATGGCCTGACCCCGGAC
CAAGTGGTGGCTATCGCCAGCAACGGTGGCGGCAAGCAAGCGCTCGAAACGGTGCAGCGGCTGTTGCCGG
TGCTGTGCCAGGACCATGGCCTGACCCCGGACCAAGTGGTGGCTATCGCCAGCAACGGTGGCGGCAAGCA
AGCGCTCGAAACGGTGCAGCGGCTGTTGCCGGTGCTGTGCCAGGACCATGGCCTGACCCCGGACCAAGTG
GTGGCTATCGCCAGCAACAATGGCGGCAAGCAAGCGCTCGAAACGGTGCAGCGGCTGTTGCCGGTGCTGT
GCCAGGACCATGGCCTGACCCCGGACCAAGTGGTGGCTATCGCCAGCAACAATGGCGGCAAGCAAGCGCT
CGAAACGGTGCAGCGGCTGTTGCCGGTGCTGTGCCAGGACCATGGCCTGACCCCGGACCAAGTGGTGGCT
ATCGCCAGCAACAATGGCGGCAAGCAAGCGCTCGAAACGGTGCAGCGGCTGTTGCCGGTGCTGTGCCAGG
ACCATGGCCTGACCCCGGACCAAGTGGTGGCTATCGCCAGCCACGATGGCGGCAAGCAAGCGCTCGAAAC
GGTGCAGCGGCTGTTGCCGGTGCTGTGCCAGGACCATGGCCTGACCCCGGACCAAGTGGTGGCTATCGCC
AGCAACATTGGCGGCAAGCAAGCGCTCGAAACGGTGCAGCGGCTGTTGCCGGTGCTGTGCCAGGACCATG
GCCTGACCCCGGACCAAGTGGTGGCTATCGCCAGCAACGGTGGCGGCAAGCAAGCGCTCGAAACGGTGCA
GCGGCTGTTGCCGGTGCTGTGCCAGGACCATGGCCTGACCCCGGACCAAGTGGTGGCTATCGCCAGCCAC
GATGGCGGCAAGCAAGCGCTCGAAACGGTGCAGCGGCTGTTGCCGGTGCTGTGCCAGGACCATGGCCTGA
CCCCGGACCAAGTGGTGGCTATCGCCAGCAACATTGGCGGCAAGCAAGCGCTCGAAACGGTGCAGCGGCT
GTTGCCGGTGCTGTGCCAGGACCATGGCCTGACCCCGGACCAAGTGGTGGCTATCGCCAGCAACGGTGGC
GGCAAGCAAGCGCTCGAAACGGTGCAGCGGCTGTTGCCGGTGCTGTGCCAGGACCATGGCCTGACCCCGG
ACCAAGTGGTGGCTATCGCCAGCCACGATGGCGGCAAGCAAGCGCTCGAAACGGTGCAGCGGCTGTTGCC
GGTGCTGTGCCAGGACCATGGCCTGACCCCGGACCAAGTGGTGGCTATCGCCAGCCACGATGGCGGCAAG
CAAGCGCTCGAAACGGTGCAGCGGCTGTTGCCGGTGCTGTGCCAGGACCATGGCCTGACCCCGGACCAAG
TGGTGGCTATCGCCAGCCACGATGGCGGCAAGCAAGCGCTCGAAACGGTGCAGCGGCTGTTGCCGGTGCT
GTGCCAGGACCATGGCCTGACCCCGGACCAAGTGGTGGCTATCGCCAGCAACATTGGCGGCAAGCAAGCG
CTCGAAACGGTGCAGCGGCTGTTGCCGGTGCTGTGCCAGGACCATGGCCTGACCCCGGACCAAGTGGTGG
CTATCGCCAGCCACGATGGCGGCAAGCAAGCGCTCGAAACGGTGCAGCGGCTGTTGCCGGTGCTGTGCCA
GGACCATGGCCTGACCCCGGACCAAGTGGTGGCTATCGCCAGCCACGATGGCGGCAAGCAAGCGCTCGAA
ACGGTGCAGCGGCTGTTGCCGGTGCTGTGCCAGGACCATGGCCTGACCCCGGACCAAGTGGTGGCtatcg
ccagcaacggtggcggcaagcaagcgctcgaaagcattgtggcccagctgagccggcctgatccggcgtt
ggccgcgttgaccaacgacgaccacctcgtcgcctttggcctgcctcggcggacgtcctgccatggatgca
gtgaaaaagggattgccgcacgcgccggaattgatcagaagagtcaatcgccgtattggcgaacgcacgt
cccatcgcgttgccGgatcCaAGGCTAGCCCGAAAAAGAAACGCAAAGTTGGGCGCGCCGACGCGCTGGA
CGATTTCGATCTCGACATGCTGGGTTCTGATGCCCTCGATGACTTTGACCTGGATATGTTGGGAAGCGAC
GCATTGGATGACTTTGATCTGGACATGCTCGGCTCCGATGCTCTGGACGATTTCGATCTCGATATGTTAA
TTAACTACCCGTACGACGTTCCGGACTACGCTTCTTGA SEQ ID NO: 80: CEACAM5 TALE F polypeptide
MDYKDHDGDYKDHDIDYKDDDDKMAPKKKRKVGRGSVDLRTLGYSQQQQEKIKPKVRSTVAQHHEALVGH
GFTHAHIVALSQHPAALGTVAVTYQHIITALPEATHEDIVGVKQWSGARALEALLTDAGELRGPPLQLD
TGQLVKIAKRGGVTAMEAVHASRNALTGAPLNLTPDQVVAIASNGGGKQALETVQRLLPVLCQDHGLTPD
QVVAIASNGGGKQALETVQRLLPVLCQDHGLTPDQVVAIASNGGGKQALETVQRLLPVLCQDHGLTPDQV
VAIASNNGGKQALETVQRLLPVLCQDHGLTPDQVVAIASNNGGKQALETVQRLLPVLCQDHGLTPDQVVA
IASNNGGKQALETVQRLLPVLCQDHGLTPDQVVAIASHDGGKQALETVQRLLPVLCQDHGLTPDQVVAIA
SNIGGKQALETVQRLLPVLCQDHGLTPDQVVAIASNGGGKQALETVQRLLPVLCQDHGLTPDQVVAIASH
DGGKQALETVQRLLPVLCQDHGLTPDQVVAIASNIGGKQALETVQRLLPVLCQDHGLTPDQVVAIASNGG
GKQALETVQRLLPVLCQDHGLTPDQVVAIASHDGGKQALETVQRLLPVLCQDHGLTPDQVVAIASHDGGK
QALETVQRLLPVLCQDHGLTPDQVVAIASHDGGKQALETVQRLLPVLCQDHGLTPDQVVAIASNIGGKQA
LETVQRLLPVLCQDHGLTPDQVVAIASHDGGKQALETVQRLLPVLCQDHGLTPDQVVAIASHDGGKQALE
TVQRLLPVLCQDHGLTPDQVVAIASNGGGKQALESIVAQLSRPDPALAALTNDDHLVALACLGGRPAMDA
VKKGLPHAPELIRRVNRRIGERTSHRVAGSKASPKKKRKVGRADALDDFDLDMLGSDALDDFDLDMLGSD
ALDDFDLDMLGSDALDDFDLDMLINYPYDVPDYAS SEQ ID NO: 81: CEACAM5 TALE G nucleotide
ATGGACTACAAAGACCATGACGGTGATTATAAAGATCATGACATCGATTACAAGGATGACGATGACAAGa
tggcccccaagaagaagaggaaggtgggccgcGgatcTgtggatctacgcacgctcggctacagtcagca
gcagcaagagaagatcaaaccgaaggtgcgttcgacagtggcgcagcaccacgaggcactggtgggccat
gggtttacacacgcgcacatcgttgcgctcagccaacacccggcagcgttagggaccgtcgctgtcacgt
atcagcacataatcacggcgttgccagaggcgacacacgaagacatcgttggcgtcggcaaacagtggtc
cggcgcacgcgccctggaggccttgctcacggatgcgggggagttgagaggtccgccgttacagttggac
acaggccaacttgtgaagattgcaaaacgtggcggcgtgaccgcaatggaggcagtgcatgcatcgcgca
atgcactgacgggtgccccctgAACCTGACCCCGGACCAAGTGGTGGCTATCGCCAGCCACGATGGCGG
CAAGCAAGCGCTCGAAACGGTGCAGCGGCTGTTGCCGGTGCTGTGCCAGGACCATGGCCTGACCCCGGAC
CAAGTGGTGGCTATCGCCAGCCACGATGGCGGCAAGCA

TALE-TF SEQUENCES

AGCGCTCGAAACGGTGCAGCGGCTGTTGCCGGTGCTGTGCCAGGACCATGGCCTGACCCCGGACCAAGTG
GTGGCTATCGCCAGCAACGGTGGCGGCAAGCAAGCGCTCGAAACGGTGCAGCGGCTGTTGCCGGTGCTGT
GCCAGGACCATGGCCTGACCCCGGACCAAGTGGTGGCTATCGCCACGATGGCGGCAAGCAAGCGCT
CGAAACGGTGCAGCGGCTGTTGCCGGTGCTGTGCCAGGACCATGGCCTGACCCCGGACCAAGTGGTGGCT
ATCGCCAGCCACGATGGCGGCAAGCAAGCGCTCGAAACGGTGCAGCGGCTGTTGCCGGTGCTGTGCCAGG
ACCATGGCCTGACCCCGGACCAAGTGGTGGCTATCGCCAGCAACATTGGCGGCAAGCAAGCGCTCGAAAC
GGTGCAGCGGCTGTTGCCGGTGCTGTGCCAGGACCATGGCCTGACCCCGGACCAAGTGGTGGCTATCGCC
AGCCACGATGGCGGCAAGCAAGCGCTCGAAACGGTGCAGCGGCTGTTGCCGGTGCTGTGCCAGGACCATG
GCCTGACCCCGGACCAAGTGGTGGCTATCGCCAGCCACGATGGCGGCAAGCAAGCGCTCGAAACGGTGCA
GCGGCTGTTGCCGGTGCTGTGCCAGGACCATGGCCTGACCCCGGACCAAGTGGTGGCTATCGCCAGCAAC
ATTGGCGGCAAGCAAGCGCTCGAAACGGTGCAGCGGCTGTTGCCGGTGCTGTGCCAGGACCATGGCTGA
CCCCGGACCAAGTGGTGGCTATCGCCAGCCACGATGGCGGCAAGCAAGCGCTCGAAACGGTGCAGCGGCT
GTTGCCGGTGCTGTGCCAGGACCATGGCCTGACCCCGGACCAAGTGGTGGCTATCGCCAGCAACATTGGC
GGCAAGCAAGCGCTCGAAACGGTGCAGCGGCTGTTGCCGGTGCTGTGCCAGGACCATGGCCTGACCCCGG
ACCAAGTGGTGGCTATCGCCAGCAACAATGGCGGCAAGCAAGCGCTCGAAACGGTGCAGCGGCTGTTGCC
GGTGCTGTGCCAGGACCATGGCCTGACCCCGGACCAAGTGGTGGCTATCGCCAGCAACGGTGGCGGCAAG
CAAGCGCTCGAAACGGTGCAGCGGCTGTTGCCGGTGCTGTGCCAGGACCATGGCCTGACCCCGGACCAAG
TGGTGGCTATCGCCAGCCACGATGGCGGCAAGCAAGCGCTCGAAACGGTGCAGCGGCTGTTGCCGGTGCT
GTGCCAGGACCATGGCCTGACCCCGGACCAAGTGGTGGCTATCGCCAGCCACGATGGCGGCAAGCAAGCG
CTCGAAACGGTGCAGCGGCTGTTGCCGGTGCTGTGCCAGGACCATGGCCTGACCCCGGACCAAGTGGTGG
ctatcgccagcaacggtggcggcaagcaagcgctcgaaagcattgtgggcccagctgagccggcctgatcc
ggcgttggccgcgttgaccaacgacgaccaccctcgtcgccttggcctgcctcggcggacgtcctgccatg
gatgcagtgaaaaagggattgccgcacgcgccggaattgatcagaagagtcaatcgccgtattggcgaac
gcacgtcccatcgcgttgccGgatcCaAGGCTAGCCCGAAAAAGAAACGCAAAGTTGGGCGCGCCGACGC
GCTGGACGATTTCGATCTCGACATGCTGGGTTCTGATGCCCTCGATGACTTTGACCTGGATATGTTGGGA
AGCGACGCATTGGATGACTTTGATCTGGACATGCTCGGCTCCGATGCTCTGGACGATTTCGATCTCGATA
TGTTAATTAACTACCCGTACGACGTTCCGGACTACGCTTCTTGA SEQ ID NO: 82: CEACAM5 TALE G polypeptide
MDYKDHDGDYKDHDIDYKDDDDKMAPKKKRKVGRGSVDLRTLGYSQQQQEKIKPKVRSTVAQHHEALVGH
GFTHAHIVALSQHPAALGTVAVTYQHIITALPEATHEDIVGVGKQWSGARALEALLTDAGELRGPPLQLD
TGQLVKIAKRGGVTAMEAVHASRNALTGAPLNLTPDQVVAIASHDGGKQALETVQRLLPVLCQDHGLTPD
QVVAIASHDGGKQALETVQRLLPVLCQDHGLTPDQVVAIASHDGGKQALETVQRLLPVLCQDHGLTPDQV
VAIASNGGGKQALETVQRLLPVLCQDHGLTPDQVVAIASHDGGKQALETVQRLLPVLCQDHGLTPDQVVA
IASHDGGKQALETVQRLLPVLCQDHGLTPDQVVAIASNIGGKQALETVQRLLPVLCQDHGLTPDQVVAIA
SHDGGKQALETVQRLLPVLCQDHGLTPDQVVAIASHDGGKQALETVQRLLPVLCQDHGLTPDQVVAIASN
IGGKQALETVQRLLPVLCQDHGLTPDQVVAIASHDGGKQALETVQRLLPVLCQDHGLTPDQVVAIASNIG
GKQALETVQRLLPVLCQDHGLTPDQVVAIASNNGGKQALETVQRLLPVLCQDHGLTPDQVVAIASNGGGK
QALETVQRLLPVLCQDHGLTPDQVVAIASHDGGKQALETVQRLLPVLCQDHGLTPDQVVAIASHDGGKQA
LETVQRLLPVLCQDHGLTPDQVVAIASNGGGKQALESIVAQLSRPDPALAALTNDDHLVALACLGGRPAM
DAVKKGLPHAPELIRRVNRRIGERTSHRVAGSKASPKKKRKVGRADALDDFDLDMLGSDALDDFDLDMLG
SDALDDFDLDMLGSDALDDFDLDMLINYPYDVPDYAS SEQ ID NO: 83: ERBB2 TALE A nucleotide
ATGGACTACAAAGACCATGACGGTGATTATAAAGATCATGACATCGATTACAAGGATGACGATGACAAGa
tggccccccaagaagaagaggaaggtgggccgcGgatcTgtggatctacgcacgctcggctacagtcagca
gcagcaagagaagatcaaaccgaaggtgcgttcgacagtggcgcagcaccacgaggcactggtgggccat
gggtttacacacgcgcacatcgttgcgctcagccaacacccggcagcgttagggaccgtcgctgtcacgt
atcagcacataatcacggcgttgccagaggcgacacaacgaagacatcgttggcgtcggcaaacagtggtc
cggcgcacgcgccctggaggccttgctcacggatgcggggggagttgagaggtccgccgttacagttggac
acaggccaacttgtgaagattgcaaaacgtggcggcgtgaccgcaatggaggcagtgcatgcatcgcgca
atgcactgacgggtgcccccctgAACCTGACCCCGGACCAAGTGGTGGCTATCGCCAGCCACGATGGCGG
CAAGCAAGCGCTCGAAACGGTGCAGCGGCTGTTGCCGGTGCTGTGCCAGGACCATGGCCTGACCCCGGAC
CAAGTGGTGGCTATCGCCAGCCACGATGGCGGCAAGCAAGCGCTCGAAACGGTGCAGCGGCTGTTGCCGG
TGCTGTGCCAGGACCATGGCCTGACCCCGGACCAAGTGGTGGCTATCGCCAGCAACAATGGCGGCAAGCA
AGCGCTCGAAACGGTGCAGCGGCTGTTGCCGGTGCTGTGCCAGGACCATGGCCTGACCCCGGACCAAGTG
GTGGCTATCGCCAGCAACAATGGCGGCAAGCAAGCGCTCGAAACGGTGCAGCGGCTGTTGCCGGTGCTGT
GCCAGGACCATGGCCTGACCCCGGACCAAGTGGTGGCTATCGCCAGCCACGATGGCGGCAAGCAAGCGCT
CGAAACGGTGCAGCGGCTGTTGCCGGTGCTGTGCCAGGACCATGGCCTGACCCCGGACCAAGTGGTGGCT
ATCGCCAGCAACGGTGGCGGCAAGCAAGCGCTCGAAACGGTGCAGCGGCTGTTGCCGGTGCTGTGCCAGG
ACCATGGCCTGACCCCGGACCAAGTGGTGGCTATCGCCAGCAACAATGGCGGCAAGCAAGCGCTCGAAAC
GGTGCAGCGGCTGTTGCCGGTGCTGTGCCAGGACCATGGCCTGACCCCGGACCAAGTGGTGGCTATCGCC
AGCAACAATGGCGGCAAGCAAGCGCTCGAAACGGTGCAGCGGCTGTTGCCGGTGCTGTGCCAGGACCATG
GCCTGACCCCGGACCAAGTGGTGGCTATCGCCAGCAACATTGGCGGCAAGCAAGCGCTCGAAACGGTGCA
GCGGCTGTTGCCGGTGCTGTGCCAGGACCATGGCCTGACCCCGGACCAAGTGGTGGCTATCGCCAGCCAC
GATGGCGGCAAGCAAGCGCTCGAAACGGTGCAGCGGCTGTTGCCGGTGCTGTGCCAGGACCATGGCCTGA
CCCCGGACCAAGTGGTGGCTATCGCCAGCCACGATGGCGGCAAGCAAGCGCTCGAAACGGTGCAGCGGCT
GTTGCCGGTGCTGTGCCAGGACCATGGCCTGACCCCGGACCAAGTGGTGGCTATCGCCAGCCACGATGGC
GGCAAGCAAGCGCTCGAAACGGTGCAGCGGCTGTTGCCGGTGCTGTGCCAGGACCATGGCCTGACCCCGG
ACCAAGTGGTGGCTATCGCCAGCAACAATGGCGGCAAGCAAGCGCTCGAAACGGTGCAGCGGCTGTTGCC
GGTGCTGTGCCAGGACCATGGCCTGACCCCGGACCAAGTGGTGGCTATCGCCAGCAACAATGGCGGCAAG
CAAGCGCTCGAAACGGTGCAGCGGCTGTTGCCGGTGCTGTGCCAGGACCATGGCCTGACCCCGGACCAAG
TGGTGGCTATCGCCAGCCACGATGGCGGCAAGCAAGCGCTCGAAACGGTGCAGCGGCTGTTGCCGGTGCT
GTGCCAGGACCATGGCCTGACCCCGGACCAAGTGGTGGctatcgccagcaacggtggcggcaagcaagcg
ctcgaaagcattgtgggcccagctgagccggcctgatccggcgttggccgcgttgaccaacgacgaccacc
tcgtcgccttggcctgcctcggcggacgtcctgccatggatgcagtgaaaaagggattgccgcacgcgcc
ggaattgatcagaagagtcaatcgccgtattggcgaacgcacgtcccatcgcgttgccGgatcCaAGGCT

| TALE-TF SEQUENCES |
| --- |
| AGCCCGAAAAAGAAACGCAAAGTTGGGCGCGCCGACGCGCTGGACGATTTCGATCTCGACATGCTGGGTT
CTGATGCCCTCGATGACTTTGACCTGGATATGTTGGGAAGCGACGCATTGGATGACTTTGATCTGGACAT
GCTCGGCTCCGATGCTCTGGACGATTTCGATCTCGATATGTTAATTAACTACCCGTACGACGTTCCGGAC
TACGCTTCTTGA

SEQ ID NO: 84: ERBB2 TALE A polypeptide
MDYKDHDGDYKDHDIDYKDDDDKMAPKKKRKVGRGSVDLRTLGYSQQQQEKIKPKVRSTVAQHHEALVGH
GFTHAHIVALSQHPAALGTVAVTYQHIITALPEATHEDIVGVGKQWSGARALEALLTDAGELRGPPLQLD
TGQLVKIAKRGGVTAMEAVHASRNALTGAPLNLTPDQVVAIASHDGGKQALETVQRLLPVLCQDHGLTPD
QVVAIASHDGGKQALETVQRLLPVLCQDHGLTPDQVVAIASNNGGKQALETVQRLLPVLCQDHGLTPDQV
VAIASNNGGKQALETVQRLLPVLCQDHGLTPDQVVAIASHDGGKQALETVQRLLPVLCQDHGLTPDQVVA
IASNGGGKQALETVQRLLPVLCQDHGLTPDQVVAIASNNGGKQALETVQRLLPVLCQDHGLTPDQVVAIA
SNNGGKQALETVQRLLPVLCQDHGLTPDQVVAIASNIGGKQALETVQRLLPVLCQDHGLTPDQVVAIASH
DGGKQALETVQRLLPVLCQDHGLTPDQVVAIASHDGGKQALETVQRLLPVLCQDHGLTPDQVVAIASHDG
GKQALETVQRLLPVLCQDHGLTPDQVVAIASNNGGKQALETVQRLLPVLCQDHGLTPDQVVAIASNNGGK
QALETVQRLLPVLCQDHGLTPDQVVAIASHDGGKQALETVQRLLPVLCQDHGLTPDQVVAIASNGGGKQA
LESIVAQLSRPDPALAALTNDDHLVALACLGGRPAMDAVKKGLPHAPELIRRVNRRIGERTSHRVAGSKA
SPKKKRKVGRADALDDFDLDMLGSDALDDFDLDMLGSDALDDFDLDMLGSDALDDFDLDMLINYPYDVPD
YAS SEQ ID NO: 85: ERBB2 TALE B nucleotide
ATGGACTACAAAGACCATGACGGTGATTATAAAGATCATGACATCGATTACAAGGATGACGATGACAAGa
tggccccaagaagaagaggaaggtgggccgcGgatcTgtggatctacgcacgctcggctacagtcagca
gcagcaagagaagatcaaaccgaaggtgcgttcgacagtggcgcagcaccacgaggcactggtgggccat
gggtttacacacgcgcacatcgttgcgctcagccaacacccggcagcgttagggaccgtcgctgtcacgt
atcagcacataatcacggcgttgccagaggcgacacacgaagacatcgttggcgtcggcaaacagtggtc
cggcgcacgcgccctggaggccttgctcacggatgcggggagttgagaggtccgccgttacagtttggac
acaggccaacttgtgaagattgcaaaacgtggcggcgtgaccgcaatggaggcagtgcatgcatcgcgca
atgcactgacgggtgccccctgAACCTGACCCCGGACCAAGTGGTGGCTATCGCCAGCCACGATGGCGG
CAAGCAAGCGCTCGAAACGGTGCAGCGGCTGTTGCCGGTGCTGTGCCAGGACCATGGCCTGACCCCGGAC
CAAGTGGTGGCTATCGCCAGCAACAATGGCGGCAAGCAAGCGCTCGAAACGGTGCAGCGGCTGTTGCCGG
TGCTGTGCCAGGACCATGGCCTGACCCCGGACCAAGTGGTGGCTATCGCCACGATGGCGGCAAGCA
AGCGCTCGAAACGGTGCAGCGGCTGTTGCCGGTGCTGTGCCAGGACCATGGCCTGACCCCGGACCAAGTG
GTGGCTATCGCCAGCAACATTGGCGGCAAGCAAGCGCTCGAAACGGTGCAGCGGCTGTTGCCGGTGCTGT
GCCAGGACCATGGCCTGACCCCGGACCAAGTGGTGGCTATCGCCAGCAACAATGGCGGCAAGCAAGCGCT
CGAAACGGTGCAGCGGCTGTTGCCGGTGCTGTGCCAGGACCATGGCCTGACCCCGGACCAAGTGGTGGCT
ATCGCCAGCCACGATGGCGGCAAGCAAGCGCTCGAAACGGTGCAGCGGCTGTTGCCGGTGCTGTGCCAGG
ACCATGGCCTGACCCCGGACCAAGTGGTGGCTATCGCCAGCAACATTGGCGGCAAGCAAGCGCTCGAAAC
GGTGCAGCGGCTGTTGCCGGTGCTGTGCCAGGACCATGGCCTGACCCCGGACCAAGTGGTGGCTATCGCC
AGCCACGATGGCGGCAAGCAAGCGCTCGAAACGGTGCAGCGGCTGTTGCCGGTGCTGTGCCAGGACCATG
GCCTGACCCCGGACCAAGTGGTGGCTATCGCCAGCCACGATGGCGGCAAGCAAGCGCTCGAAACGGTGCA
GCGGCTGTTGCCGGTGCTGTGCCAGGACCATGGCCTGACCCCGGACCAAGTGGTGGCTATCGCCAGCCAC
GATGGCGGCAAGCAAGCGCTCGAAACGGTGCAGCGGCTGTTGCCGGTGCTGTGCCAGGACCATGGCCTGA
CCCCGGACCAAGTGGTGGCTATCGCCAGCCACGATGGCGGCAAGCAAGCGCTCGAAACGGTGCAGCGGCT
GTTGCCGGTGCTGTGCCAGGACCATGGCCTGACCCCGGACCAAGTGGTGGCTATCGCCAGCAACAATGGC
GGCAAGCAAGCGCTCGAAACGGTGCAGCGGCTGTTGCCGGTGCTGTGCCAGGACCATGGCCTGACCCCGG
ACCAAGTGGTGGCTATCGCCAGCCACGATGGCGGCAAGCAAGCGCTCGAAACGGTGCAGCGGCTGTTGCC
GGTGCTGTGCCAGGACCATGGCCTGACCCCGGACCAAGTGGTGGCTATCGCCAGCAACAATGGCGGCAAG
CAAGCGCTCGAAACGGTGCAGCGGCTGTTGCCGGTGCTGTGCCAGGACCATGGCCTGACCCCGGACCAAG
TGGTGGCTATCGCCAGCCACGATGGCGGCAAGCAAGCGCTCGAAACGGTGCAGCGGCTGTTGCCGGTGCT
GTGCCAGGACCATGGCCTGACCCCGGACCAAGTGGTGGCTATCGCCAGCCACGATGGCGGCAAGCAAGCG
CTCGAAACGGTGCAGCGGCTGTTGCCGGTGCTGTGCCAGGACCATGGCCTGACCCCGGACCAAGTGGTGG
ctatcgccagcCACGATggcggcaagcaagcgctcgaaagtatcgtggcccagctgagccggtcgatcc
ggcgttggccgcgttgaccaacgacgaccacctcgtcgccttggcctgcctcggcggacgtcctgccatg
gatgcagtgaaaaagggattgccgcacgcgccggaattgatcagaagagtcaatcgccgtattggcgaac
gcacgtccatcgcgttgccGgatcCaAGGCTAGCCCGAAAAAGAAACGCAAAGTTGGGCGCGCCGACGC
GCTGGACGATTTCGATCTCGACATGCTGGGTTCTGATGCCCTCGATGACTTTGACCTGGATATGTTGGGA
AGCGACGCATTGGATGACTTTGATCTGGACATGCTCGGCTCCGATGCTCTGGACGATTTCGATCTCGATA
TGTTAATTAACTACCCGTACGACGTTCCGGACTACGCTTCTTGA SEQ ID NO: 86: ERBB2 TALE B polypeptide
MDYKDHDGDYKDHDIDYKDDDDKMAPKKKRKVGRGSVDLRTLGYSQQQQEKIKPKVRSTVAQHHEALVGH
GFTHAHIVALSQHPAALGTVAVTYQHIITALPEATHEDIVGVGKQWSGARALEALLTDAGELRGPPLQLD
TGQLVKIAKRGGVTAMEAVHASRNALTGAPLNLTPDQVVAIASHDGGKQALETVQRLLPVLCQDHGLTPD
QVVAIASNNGGKQALETVQRLLPVLCQDHGLTPDQVVAIASHDGGKQALETVQRLLPVLCQDHGLTPDQV
VAIASNIGGKQALETVQRLLPVLCQDHGLTPDQVVAIASNNGGKQALETVQRLLPVLCQDHGLTPDQVVA
IASHDGGKQALETVQRLLPVLCQDHGLTPDQVVAIASNIGGKQALETVQRLLPVLCQDHGLTPDQVVAIA
SHDGGKQALETVQRLLPVLCQDHGLTPDQVVAIASHDGGKQALETVQRLLPVLCQDHGLTPDQVVAIASH
DGGKQALETVQRLLPVLCQDHGLTPDQVVAIASHDGGKQALETVQRLLPVLCQDHGLTPDQVVAIASNNG
GKQALETVQRLLPVLCQDHGLTPDQVVAIASHDGGKQALETVQRLLPVLCQDHGLTPDQVVAIASNNGGK
QALETVQRLLPVLCQDHGLTPDQVVAIASHDGGKQALETVQRLLPVLCQDHGLTPDQVVAIASHDGGKQA
LETVQRLLPVLCQDHGLTPDQVVAIASHDGGKQALESIVAQLSRPDPALAALTNDDHLVALACLGGRPAM
DAVKKGLPHAPELIRRVNRRIGERTSHRVAGSKASPKKKRKVGRADALDDFDLDMLGSDALDDFDLDMLG
SDALDDFDLDMLGSDALDDFDLDMLINYPYDVPDYAS |

TALE-TF SEQUENCES

SEQ ID NO: 87: ERBB2 TALE C nucleotide
ATGGACTACAAAGACCATGACGGTGATTATAAAGATCATGACATCGATTACAAGGATGACGATGACAAGa
tggcccccaagaagaagaggaaggtgggccgcGgatcTgtggatctacgcacgctcggctacagtcagca
gcagcaagagaagatcaaaccgaaggtgcgttcgacagtggcgcagcaccacgaggcactggtgggccat
gggtttacacacgcgcacatcgttgcgctcagccaacacccggcagcgttagggaccgtcgctgtcacgt
atcagcacataatcacggcgttgccagaggcgacacacgaagacatcgttggcgtcggcaaacagtggtc
cggcgcacgcgcctggaggccttgctcacggatgcgggggagttgagaggtccgccgttacagttggac
acaggccaacttgtgaagattgcaaaacgtggcggcgtgaccgcaatggaggcagtgcatgcatcgcgca
atgcactgacgggtgcccccctgAACCTGACCCCGGACCAAGTGGTGGCTATCGCCAGCCACGATGGCGG
CAAGCAAGCGCTCGAAACGGTGCAGCGGCTGTTGCCGGTGCTGTGCCAGGACCATGGCCTGACCCCGGAC
CAAGTGGTGGCTATCGCCAGCCACGATGGCGGCAAGCAAGCGCTCGAAACGGTGCAGCGGCTGTTGCCGG
TGCTGTGCCAGGACCATGGCCTGACCCCGGACCAAGTGGTGGCTATCGCCAGCCACGATGGCGGCAAGCA
AGCGCTCGAAACGGTGCAGCGGCTGTTGCCGGTGCTGTGCCAGGACCATGGCCTGACCCCGGACCAAGTG
GTGGCTATCGCCAGCAACATTGGCGGCAAGCAAGCGCTCGAAACGGTGCAGCGGCTGTTGCCGGTGCTGT
GCCAGGACCATGGCCTGACCCCGGACCAAGTGGTGGCTATCGCCAGCCACGATGGCGGCAAGCAAGCGCT
CGAAACGGTGCAGCGGCTGTTGCCGGTGCTGTGCCAGGACCATGGCCTGACCCCGGACCAAGTGGTGGCT
ATCGCCAGCAACAATGGCGGCAAGCAAGCGCTCGAAACGGTGCAGCGGCTGTTGCCGGTGCTGTGCCAGG
ACCATGGCCTGACCCCGGACCAAGTGGTGGCTATCGCCAGCAACAATGGCGGCAAGCAAGCGCTCGAAAC
GGTGCAGCGGCTGTTGCCGGTGCTGTGCCAGGACCATGGCCTGACCCCGGACCAAGTGGTGGCTATCGCC
AGCAACAATGGCGGCAAGCAAGCGCTCGAAACGGTGCAGCGGCTGTTGCCGGTGCTGTGCCAGGACCATG
GCCTGACCCCGGACCAAGTGGTGGCTATCGCCAGCAACAATGGCGGCAAGCAAGCGCTCGAAACGGTGCA
GCGGCTGTTGCCGGTGCTGTGCCAGGACCATGGCCTGACCCCGGACCAAGTGGTGGCTATCGCCAGCCAC
GATGGCGGCAAGCAAGCGCTCGAAACGGTGCAGCGGCTGTTGCCGGTGCTGTGCCAGGACCATGGCCTGA
CCCCGGACCAAGTGGTGGCTATCGCCAGCCACGATGGCGGCAAGCAAGCGCTCGAAACGGTGCAGCGGCT
GTTGCCGGTGCTGTGCCAGGACCATGGCCTGACCCCGGACCAAGTGGTGGCTATCGCCAGCCACGATGGC
GGCAAGCAAGCGCTCGAAACGGTGCAGCGGCTGTTGCCGGTGCTGTGCCAGGACCATGGCCTGACCCCGG
ACCAAGTGGTGGCTATCGCCAGCAACGGTGGCGGCAAGCAAGCGCTCGAAACGGTGCAGCGGCTGTTGCC
GGTGCTGTGCCAGGACCATGGCCTGACCCCGGACCAAGTGGTGGCTATCGCCAGCAACGGTGGCGGCAAG
CAAGCGCTCGAAACGGTGCAGCGGCTGTTGCCGGTGCTGTGCCAGGACCATGGCCTGACCCCGGACCAAG
TGGTGGCTATCGCCAGCAACGGTGGCGGCAAGCAAGCGCTCGAAACGGTGCAGCGGCTGTTGCCGGTGCT
GTGCCAGGACCATGGCCTGACCCCGGACCAAGTGGTGGCTATCGCCAGCAACATTGGCGGCAAGCAAGCG
CTCGAAACGGTGCAGCGGCTGTTGCCGGTGCTGTGCCAGGACCATGGCCTGACCCCGGACCAAGTGGTGG
CTATCGCCAGCCACGATGGCGGCAAGCAAGCGCTCGAAACGGTGCAGCGGCTGTTGCCGGTGCTGTGCCA
GGACCATGGCCTGACCCCGGACCAAGTGGTGGctatcgccagcaacggtggcggcaagcaagcgctcgaa
agcattgtggcccagctgagccggcctgatccggcgttggccgcgttgaccaacgacgaccacctcgtcg
ccttggcctgcctcggcggacgtcctgccatggatgcagtgaaaaagggattgccgcacgcgccggaatt
gatcagaagagtcaatcgccgtattggcgaacgcacgtcccatcgccgtgccGgatcCaAGGCTAGCCCG
AAAAAGAAACGCAAAGTTGGGCGCGCCGACGCGCTGGACGATTTCGATCTCGACATGCTGGGTTCTGATG
CCCTCGATGACTTTGACCTGGATATGTTGGGAAGCGACGCATTGGATGACTTTGATCTGGACATGCTCGG
CTCCGATGCTCTGGACGATTTCGATCTCGATATGTTAATTAACTACCCGTACGACGTTCCGGACTACGCT
TCTTGA SEQ ID NO: 88: ERBB2 TALE C polypeptide
MDYKDHDGDYKDHDIDYKDDDDKMAPKKKRKVGRGSVDLRTLGYSQQQQEKIKPKVRSTVAQHHEALVGH
GFTHAHIVALSQHPAALGTVAVTYQHIITALPEATHEDIVGVGKQWSGARALEALLTDAGELRGPPLQLD
TGQLVKIAKRGGVTAMEAVHASRNALTGAPLNLTPDQVVAIASHDGGKQALETVQRLLPVLCQDHGLTPD
QVVAIASHDGGKQALETVQRLLPVLCQDHGLTPDQVVAIASHDGGKQALETVQRLLPVLCQDHGLTPDQV
VAIASNIGGKQALETVQRLLPVLCQDHGLTPDQVVAIASHDGGKQALETVQRLLPVLCQDHGLTPDQVVA
IASNNGGKQALETVQRLLPVLCQDHGLTPDQVVAIASNNGGKQALETVQRLLPVLCQDHGLTPDQVVAIA
SNNGGKQALETVQRLLPVLCQDHGLTPDQVVAIASNNGGKQALETVQRLLPVLCQDHGLTPDQVVAIASH
DGGKQALETVQRLLPVLCQDHGLTPDQVVAIASHDGGKQALETVQRLLPVLCQDHGLTPDQVVAIASHDG
GKQALETVQRLLPVLCQDHGLTPDQVVAIASNGGGKQALETVQRLLPVLCQDHGLTPDQVVAIASNGGGK
QALETVQRLLPVLCQDHGLTPDQVVAIASNGGGKQALETVQRLLPVLCQDHGLTPDQVVAIASNIGGKQA
LETVQRLLPVLCQDHGLTPDQVVAIASHDGGKQALETVQRLLPVLCQDHGLTPDQVVAIASNGGGKQALE
SIVAQLSRPDPALAALTNDDHLVALACLGGRPAMDAVKKGLPHAPELIRRVNRRIGERTSHRVAGSKASP
KKKRKVGRADALDDFDLDMLGSDALDDFDLDMLGSDALDDFDLDMLGSDALDDFDLDMLINYPYDVPDYA
S SEQ ID NO: 89: ERBB2 TALE D nucleotide
ATGGACTACAAAGACCATGACGGTGATTATAAAGATCATGACATCGATTACAAGGATGACGATGACAAGa
tggcccccaagaagaagaggaaggtgggccgcGgatcTgtggatctacgcacgctcggctacagtcagca
gcagcaagagaagatcaaaccgaaggtgcgttcgacagtggcgcagcaccacgaggcactggtgggccat
gggtttacacacgcgcacatcgttgcgctcagccaacacccggcagcgttagggaccgtcgctgtcacgt
atcagcacataatcacggcgttgccagaggcgacacacgaagacatcgttggcgtcggcaaacagtggtc
cggcgcacgcgcctggaggccttgctcacggatgcgggggagttgagaggtccgccgttacagttggac
acaggccaacttgtgaagattgcaaaacgtggcggcgtgaccgcaatggaggcagtgcatgcatcgcgca
atgcactgacgggtgcccccctgAACCTGACCCCGGACCAAGTGGTGGCTATCGCCAGCCACGATGGCGG
CAAGCAAGCGCTCGAAACGGTGCAGCGGCTGTTGCCGGTGCTGTGCCAGGACCATGGCCTGACCCCGGAC
CAAGTGGTGGCTATCGCCAGCCACGATGGCGGCAAGCAAGCGCTCGAAACGGTGCAGCGGCTGTTGCCGG
TGCTGTGCCAGGACCATGGCCTGACCCCGGACCAAGTGGTGGCTATCGCCAGCCACGATGGCGGCAAGCA
AGCGCTCGAAACGGTGCAGCGGCTGTTGCCGGTGCTGTGCCAGGACCATGGCCTGACCCCGGACCAAGTG
GTGGCTATCGCCAGCCACGATGGCGGCAAGCAAGCGCTCGAAACGGTGCAGCGGCTGTTGCCGGTGCTGT
GCCAGGACCATGGCCTGACCCCGGACCAAGTGGTGGCTATCGCCAGCAACGGTGGCGGCAAGCAAGCGCT
CGAAACGGTGCAGCGGCTGTTGCCGGTGCTGTGCCAGGACCATGGCCTGACCCCGGACCAAGTGGTGGCT
ATCGCCAGCAACAATGGCGGCAAGCAAGCGCTCGAAACGGTGCAGCGGCTGTTGCCGGTGCTGTGCCAGG
ACCATGGCCTGACCCCGGACCAAGTGGTGGCTATCGCCAGCAACAATGGCGGCAAGCAAGCGCTCGAAAC
GGTGCAGCGGCTGTTGCCGGTGCTGTGCCAGGACCATGGCCTGACCCCGGACCAAGTGGTGGCTATCGCC

TALE-TF SEQUENCES

AGCAACGGTGGCGGCAAGCAAGCGCTCGAAACGGTGCAGCGGCTGTTGCCGGTGCTGTGCCAGGACCATG
GCCTGACCCCGGACCAAGTGGTGGCTATCGCCAGCAACGGTGGCGGCAAGCAAGCGCTCGAAACGGTGCA
GCGGCTGTTGCCGGTGCTGTGCCAGGACCATGGCCTGACCCCGGACCAAGTGGTGGCTATCGCCAGCAAC
GGTGGCGGCAAGCAAGCGCTCGAAACGGTGCAGCGGCTGTTGCCGGTGCTGTGCCAGGACCATGGCCTGA
CCCCGGACCAAGTGGTGGCTATCGCCAGCCACGATGGCGGCAAGCAAGCGCTCGAAACGGTGCAGCGGCT
GTTGCCGGTGCTGTGCCAGGACCATGGCCTGACCCCGGACCAAGTGGTGGCTATCGCCAGCAACGGTGGC
GGCAAGCAAGCGCTCGAAACGGTGCAGCGGCTGTTGCCGGTGCTGTGCCAGGACCATGGCCTGACCCCGG
ACCAAGTGGTGGCTATCGCCAGCCACGATGGCGGCAAGCAAGCGCTCGAAACGGTGCAGCGGCTGTTGCC
GGTGCTGTGCCAGGACCATGGCCTGACCCCGGACCAAGTGGTGGCTATCGCCAGCCACGATGGCGGCAAG
CAAGCGCTCGAAACGGTGCAGCGGCTGTTGCCGGTGCTGTGCCAGGACCATGGCCTGACCCCGGACCAAG
TGGTGGCTATCGCCAGCAACATGGCGGCAAGCAAGCGCTCGAAACGGTGCAGCGGCTGTTGCCGGTGCT
GTGCCAGGACCATGGCCTGACCCCGGACCAAGTGGTGGCTATCGCCAGCAACAATGGCGGCAAGCAAGCG
CTCGAAACGGTGCAGCGGCTGTTGCCGGTGCTGTGCCAGGACCATGGCCTGACCCCGGACCAAGTGGTGG
ctatcgccagcaacggtggcggcaagcaagcgctcgaaagcattgtgcccagctgagccggcctgatcc
ggcgttggccgcgttgaccaacgacgaccacctcgtcgccttggcctgcctcggcggacgtcctgccatg
gatgcagtgaaaaagggattgccgcacgcgccggaattgatcagaagagtcaatcgccgtattggcgaac
gcacgtcccatcgcgttgccGgatcCaAGGCTAGCCCGAAAAAGAAACGCAAAGTTGGGCGCGCCGACGC
GCTGGACGATTTCGATCTCGACATGCTGGGTTCTGATGCCCTCGATGACTTTGACCTGGATATGTTGGGA
AGCGACGCATTGGATGACTTTGATCTGGACATGCTCGGCTCCGATGCTCTGGACGATTTCGATCTCGATA
TGTTAATTAACTACCCGTACGACGTTCCGGACTACGCTTCTTGA SEQ ID NO: 90: ERBB2 TALE D polypeptide
MDYKDHDGDYKDHDIDYKDDDDKMAPKKKRKVGRGSVDLRTLGYSQQQQEKIKPKVRSTVAQHHEALVGH
GFTHAHIVALSQHPAALGTVAVTYQHIITALPEATHEDIVGVGKQWSGARALEALLTDAGELRGPPLQLD
TGQLVKIAKRGGVTAMEAVHASRNALTGAPLNLTPDQVVAIASHDGGKQALETVQRLLPVLCQDHGLTPD
QVVAIASHDGGKQALETVQRLLPVLCQDHGLTPDQVVAIASHDGGKQALETVQRLLPVLCQDHGLTPDQV
VAIASHDGGKQALETVQRLLPVLCQDHGLTPDQVVAIASNGGGKQALETVQRLLPVLCQDHGLTPDQVVA
IASNNGGKQALETVQRLLPVLCQDHGLTPDQVVAIASNNGGKQALETVQRLLPVLCQDHGLTPDQVVAIA
SNGGGKQALETVQRLLPVLCQDHGLTPDQVVAIASNGGGKQALETVQRLLPVLCQDHGLTPDQVVAIASN
GGGKQALETVQRLLPVLCQDHGLTPDQVVAIASHDGGKQALETVQRLLPVLCQDHGLTPDQVVAIASNGG
GKQALETVQRLLPVLCQDHGLTPDQVVAIASHDGGKQALETVQRLLPVLCQDHGLTPDQVVAIASHDGGK
QALETVQRLLPVLCQDHGLTPDQVVAIASNNGGKQALETVQRLLPVLCQDHGLTPDQVVAIASNNGGKQA
LETVQRLLPVLCQDHGLTPDQVVAIASNGGGKQALESIVAQLSRPDPALAALTNDDHLVALACLGGRPAM
DAVKKGLPHAPELIRRVNRRIGERTSHRVAGSKASPKKKRKVGRADALDDFDLDMLGSDALDDFDLDMLG
SDALDDFDLDMLGSDALDDFDLDMLINYPYDVPDYAS SEQ ID NO: 91: ERBB2 TALE E nucleotide
ATGGACTACAAAGACCATGACGGTGATTATAAAGATCATGACATCGATTACAAGGATGACGATGACAAGa
tggcccccaagaagaagaggaaggtgggccgcGgatcTgtggatctacgcacgctcggctacagtcagca
gcagcaagagaagatcaaaccgaaggtgcgttcgacagtggcgcagcaccacgaggcactggtgggccat
gggtttacacacgcgcacatcgttgcgctcagccaacaccggcagcgttagggaccgtcgctgtcacgt
atcagcacataatcacggcgttgccagaggcgacacacgaagacatcgttggcgtcggcaaacagtggtc
cggcgcacgcgccctggaggccttgctcacggatgcgggggagttgagaggtccgccgttacagttggac
acaggccaacttgtgaagattgcaaaacgtggcggcgtgaccgcaatggaggcagtgcatgcatcgcgca
atgcactgacgggtgccccctgAACCTGACCCCGGACCAAGTGGTGGCTATCGCCAGCAACAATGGCGG
CAAGCAAGCGCTCGAAACGGTGCAGCGGCTGTTGCCGGTGCTGTGCCAGGACCATGGCCTGACCCCGGAC
CAAGTGGTGGCTATCGCCAGCCACGATGGCGGCAAGCAAGCGCTCGAAACGGTGCAGCGGCTGTTGCCGG
TGCTGTGCCAGGACCATGGCCTGACCCCGGACCAAGTGGTGGCTATCGCCAGCCACGATGGCGGCAAGCA
AGCGCTCGAAACGGTGCAGCGGCTGTTGCCGGTGCTGTGCCAGGACCATGGCCTGACCCCGGACCAAGT
GGTGGCTATCGCCAGCAACATTGGCGGCAAGCAAGCGCTCGAAACGGTGCAGCGGCTGTTGCCGGTGCTGT
GCCAGGACCATGGCCTGACCCCGGACCAAGTGGTGGCTATCGCCAGCCACGATGGCGGCAAGCAAGCGCT
CGAAACGGTGCAGCGGCTGTTGCCGGTGCTGTGCCAGGACCATGGCCTGACCCCGGACCAAGTGGTGGCT
ATCGCCAGCAACGGTGGCGGCAAGCAAGCGCTCGAAACGGTGCAGCGGCTGTTGCCGGTGCTGTGCCAGG
ACCATGGCCTGACCCCGGACCAAGTGGTGGCTATCGCCAGCCACGATGGCGGCAAGCAAGCGCTCGAAAC
GGTGCAGCGGCTGTTGCCGGTGCTGTGCCAGGACCATGGCCTGACCCCGGACCAAGTGGTGGCTATCGCC
AGCCACGATGGCGGCAAGCAAGCGCTCGAAACGGTGCAGCGGCTGTTGCCGGTGCTGTGCCAGGACCATG
GCCTGACCCCGGACCAAGTGGTGGCTATCGCCAGCAACGGTGGCGGCAAGCAAGCGCTCGAAACGGTGCA
GCGGCTGTTGCCGGTGCTGTGCCAGGACCATGGCCTGACCCCGGACCAAGTGGTGGCTATCGCCAGCAAC
ATTGGCGGCAAGCAAGCGCTCGAAACGGTGCAGCGGCTGTTGCCGGTGCTGTGCCAGGACCATGGCCTGA
CCCCGGACCAAGTGGTGGCTATCGCCAGCAACAATGGCGGCAAGCAAGCGCTCGAAACGGTGCAGCGGCT
GTTGCCGGTGCTGTGCCAGGACCATGGCCTGACCCCGGACCAAGTGGTGGCTATCGCCAGCAACATTGGC
GGCAAGCAAGCGCTCGAAACGGTGCAGCGGCTGTTGCCGGTGCTGTGCCAGGACCATGGCCTGACCCCGG
ACCAAGTGGTGGCTATCGCCAGCCACGATGGCGGCAAGCAAGCGCTCGAAACGGTGCAGCGGCTGTTGCC
GGTGCTGTGCCAGGACCATGGCCTGACCCCGGACCAAGTGGTGGCTATCGCCAGCAACGGTGGCGGCAAG
CAAGCGCTCGAAACGGTGCAGCGGCTGTTGCCGGTGCTGTGCCAGGACCATGGCCTGACCCCGGACCAAG
TGGTGGCTATCGCCAGCAACGGTGGCGGCAAGCAAGCGCTCGAAACGGTGCAGCGGCTGTTGCCGGTGCT
GTGCCAGGACCATGGCCTGACCCCGGACCAAGTGGTGGCTATCGCCAGCAACAATGGCGGCAAGCAAGCG
CTCGAAACGGTGCAGCGGCTGTTGCCGGTGCTGTGCCAGGACCATGGCCTGACCCCGGACCAAGTGGTGG
ctatcgccagcaacggtggcggcaagcaagcgctcgaaagcattgtgcccagctgagccggcctgatcc
ggcgttggccgcgttgaccaacgacgaccacctcgtcgccttggcctgcctcggcggacgtcctgccatg
gatgcagtgaaaaagggattgccgcacgcgccggaattgatcagaagagtcaatcgccgtattggcgaac
gcacgtcccatcgcgttgccGgatcCaAGGCTAGCCCGAAAAAGAAACGCAAAGTTGGGCGCGCCGACGC
GCTGGACGATTTCGATCTCGACATGCTGGGTTCTGATGCCCTCGATGACTTTGACCTGGATATGTTGGGA
AGCGACGCATTGGATGACTTTGATCTGGACATGCTCGGCTCCGATGCTCTGGACGATTTCGATCTCGATA
TGTTAATTAACTACCCGTACGACGTTCCGGACTACGCTTCTTGA

TALE-TF SEQUENCES

SEQ ID NO: 92: ERBB2 TALE E polypeptide
MDYKDHDGDYKDHDIDYKDDDDKMAPKKKRKVGRGSVDLRTLGYSQQQQEKIKPKVRSTVAQHHEALVGH
GFTHAHIVALSQHPAALGTVAVTYQHIITALPEATHEDIVGVGKQWSGARALEALLTDAGELRGPPLQLD
TGQLVKIAKRGGVTAMEAVHASRNALTGAPLNLTPDQVVAIASNNGGKQALETVQRLLPVLCQDHGLTPD
QVVAIASHDGGKQALETVQRLLPVLCQDHGLTPDQVVAIASHDGGKQALETVQRLLPVLCQDHGLTPDQV
VAIASNIGGKQALETVQRLLPVLCQDHGLTPDQVVAIASHDGGKQALETVQRLLPVLCQDHGLTPDQVVA
IASNGGGKQALETVQRLLPVLCQDHGLTPDQVVAIASHDGGKQALETVQRLLPVLCQDHGLTPDQVVAIA
SHDGGKQALETVQRLLPVLCQDHGLTPDQVVAIASHDGGKQALETVQRLLPVLCQDHGLTPDQVVAIASN
IGGKQALETVQRLLPVLCQDHGLTPDQVVAIASNNGGKQALETVQRLLPVLCQDHGLTPDQVVAIASNIG
GKQALETVQRLLPVLCQDHGLTPDQVVAIASHDGGKQALETVQRLLPVLCQDHGLTPDQVVAIASNGGGK
QALETVQRLLPVLCQDHGLTPDQVVAIASNGGGKQALETVQRLLPVLCQDHGLTPDQVVAIASNGGGKQA
LETVQRLLPVLCQDHGLTPDQVVAIASNGGGKQALESIVAQLSRPDPALAALTNDDHLVALACLGGRPAM
DAVKKGLPHAPELIRRVNRRIGERTSHRVAGSKASPKKKRKVGRADALDDFDLDMLGSDALDDFDLDMLG
SDALDDFDLDMLGSDALDDFDLDMLINYPYDVPDYAS SEQ ID NO: 93: ERBB2 TALE F nucleotide
ATGGACTACAAAGACCATGACGGTGATTATAAAGATCATGACATCGATTACAAGGATGACGATGACAAGa
tggcccccaagaagaagaggaaggtgggccgcGgatcTgtggatctacgcacgctcggctacagtcagca
gcagcaagagaagatcaaaccgaaggtgcgttcgacagtggcgcagcaccacgaggcactggtgggccat
gggtttacacacgcgcacatcgttgcgctcagccaacacccggcagcgttagggaccgtcgctgtcacgt
atcagcacataatcacggcgttgccagaggcgacacacgaagacatcgttggcgtcggcaaacagtggtc
cggcgcacgcgccctggaggccttgctcacggatgcggggagttgagaggtccgccgttacagttggac
acaggccaacttgtgaagattgcaaaacgtggcggcgtgaccgcaatggaggcagtgcatgcatcgcgca
atgcactgacgggtgccccctgAACCTGACCCCGGACCAAGTGGTGGCTATCGCCAGCCACGATGGCGG
CAAGCAAGCGCTCGAAACGGTGCAGCGGCTGTTGCCGGTGCTGTGCCAGGACCATGGCCTGACCCCGGAC
CAAGTGGTGGCTATCGCCAGCAACGGTGGCGGCAAGCAAGCGCTCGAAACGGTGCAGCGGCTGTTGCCGG
TGCTGTGCCAGGACCATGGCCTGACCCCGGACCAAGTGGTGGCTATCGCCAGCAACAATGGCGGCAAGCA
AGCGCTCGAAACGGTGCAGCGGCTGTTGCCGGTGCTGTGCCAGGACCATGGCCTGACCCCGGACCAAGTG
GTGGCTATCGCCAGCCACGATGGCGGCAAGCAAGCGCTCGAAACGGTGCAGCGGCTGTTGCCGGTGCTGT
GCCAGGACCATGGCCTGACCCCGGACCAAGTGGTGGCTATCGCCAGCAACATTGGCGGCAAGCAAGCGCT
CGAAACGGTGCAGCGGCTGTTGCCGGTGCTGTGCCAGGACCATGGCCTGACCCCGGACCAAGTGGTGGCT
ATCGCCAGCAACGGTGGCGGCAAGCAAGCGCTCGAAACGGTGCAGCGGCTGTTGCCGGTGCTGTGCCAGG
ACCATGGCCTGACCCCGGACCAAGTGGTGGCTATCGCCAGCAACGGTGGCGGCAAGCAAGCGCTCGAAAC
GGTGCAGCGGCTGTTGCCGGTGCTGTGCCAGGACCATGGCCTGACCCCGGACCAAGTGGTGGCTATCGCC
AGCAACGGTGGCGGCAAGCAAGCGCTCGAAACGGTGCAGCGGCTGTTGCCGGTGCTGTGCCAGGACCATG
GCCTGACCCCGGACCAAGTGGTGGCTATCGCCAGCAACATTGGCGGCAAGCAAGCGCTCGAAACGGTGCA
GCGGCTGTTGCCGGTGCTGTGCCAGGACCATGGCCTGACCCCGGACCAAGTGGTGGCTATCGCCAGCAAC
AATGGCGGCAAGCAAGCGCTCGAAACGGTGCAGCGGCTGTTGCCGGTGCTGTGCCAGGACCATGGCCTGA
CCCCGGACCAAGTGGTGGCTATCGCCAGCAACAATGGCGGCAAGCAAGCGCTCGAAACGGTGCAGCGGCT
GTTGCCGGTGCTGTGCCAGGACCATGGCCTGACCCCGGACCAAGTGGTGGCTATCGCCAGCAACAATGGC
GGCAAGCAAGCGCTCGAAACGGTGCAGCGGCTGTTGCCGGTGCTGTGCCAGGACCATGGCCTGACCCCGG
ACCAAGTGGTGGCTATCGCCAGCAACATTGGCGGCAAGCAAGCGCTCGAAACGGTGCAGCGGCTGTTGCC
GGTGCTGTGCCAGGACCATGGCCTGACCCCGGACCAAGTGGTGGCTATCGCCAGCAACGGTGGCGGCAAG
CAAGCGCTCGAAACGGTGCAGCGGCTGTTGCCGGTGCTGTGCCAGGACCATGGCCTGACCCCGGACCAAG
TGGTGGCTATCGCCAGCAACGGTGGCGGCAAGCAAGCGCTCGAAACGGTGCAGCGGCTGTTGCCGGTGCT
GTGCCAGGACCATGGCCTGACCCCGGACCAAGTGGTGGCTATCGCCAGCCACGATGGCGGCAAGCAAGCG
CTCGAAACGGTGCAGCGGCTGTTGCCGGTGCTGTGCCAGGACCATGGCCTGACCCCGGACCAAGTGGTGG
ctatcgccagcaacggtggcggcaagcaagcgctcgaaagcattgtggcccagctgagccggcctgatcc
ggcgttggccgcgttgaccaacgacgaccacctcgtcgccttggcctgcctcggcggacgtcctgccatg
gatgcagtgaaaaagggattgccgcacgcgccggaattgatcagaagagtcaatcgccgtattggcgaac
gcacgtccatcgcgttgccGgatcCaAGGCTAGCCCGAAAAAGAAACGCAAAGTTGGGCGCGCCGACGC
GCTGGACGATTTCGATCTCGACATGCTGGGTTCTGATGCCCTCGATGACTTTGACCTGGATATGTTGGGA
AGCGACGCATTGGATGACTTTGATCTGGACATGCTCGGCTCCGATGCTCTGGACGATTTCGATCTCGATA
TGTTAATTAACTACCCGTACGACGTTCCGGACTACGCTTCTTGA SEQ ID NO: 94: ERBB2 TALE F polypeptide
MDYKDHDGDYKDHDIDYKDDDDKMAPKKKRKVGRGSVDLRTLGYSQQQQEKIKPKVRSTVAQHHEALVGH
GFTHAHIVALSQHPAALGTVAVTYQHIITALPEATHEDIVGVGKQWSGARALEALLTDAGELRGPPLQLD
TGQLVKIAKRGGVTAMEAVHASRNALTGAPLNLTPDQVVAIASHDGGKQALETVQRLLPVLCQDHGLTPD
QVVAIASNGGGKQALETVQRLLPVLCQDHGLTPDQVVAIASNNGGKQALETVQRLLPVLCQDHGLTPDQV
VAIASHDGGKQALETVQRLLPVLCQDHGLTPDQVVAIASNIGGKQALETVQRLLPVLCQDHGLTPDQVVA
IASNGGGKQALETVQRLLPVLCQDHGLTPDQVVAIASNGGGKQALETVQRLLPVLCQDHGLTPDQVVAIA
SNGGGKQALETVQRLLPVLCQDHGLTPDQVVAIASNIGGKQALETVQRLLPVLCQDHGLTPDQVVAIASN
NGGKQALETVQRLLPVLCQDHGLTPDQVVAIASNNGGKQALETVQRLLPVLCQDHGLTPDQVVAIASNNG
GKQALETVQRLLPVLCQDHGLTPDQVVAIASNIGGKQALETVQRLLPVLCQDHGLTPDQVVAIASNGGGK
QALETVQRLLPVLCQDHGLTPDQVVAIASNGGGKQALETVQRLLPVLCQDHGLTPDQVVAIASHDGGKQA
LETVQRLLPVLCQDHGLTPDQVVAIASNGGGKQALESIVAQLSRPDPALAALTNDDHLVALACLGGRPAM
DAVKKGLPHAPELIRRVNRRIGERTSHRVAGSKASPKKKRKVGRADALDDFDLDMLGSDALDDFDLDMLG
SDALDDFDLDMLGSDALDDFDLDMLINYPYDVPDYAS SEQ ID NO: 95: ERBB2 TALE G nucleotide
ATGGACTACAAAGACCATGACGGTGATTATAAAGATCATGACATCGATTACAAGGATGACGATGACAAGa
tggcccccaagaagaagaggaaggtgggccgcGgatcTgtggatctacgcacgctcggctacagtcagca
gcagcaagagaagatcaaaccgaaggtgcgttcgacagtggcgcagcaccacgaggcactggtgggccat
gggtttacacacgcgcacatcgttgcgctcagccaacacccggcagcgttagggaccgtcgctgtcacgt
atcagcacataatcacggcgttgccagaggcgacacacgaagacatcgttggcgtcggcaaacagtggtc
cggcgcacgcgccctggaggccttgctcacggatgcggggagttgagaggtccgccgttacagttggac

TALE-TF SEQUENCES

```
acaggccaacttgtgaagattgcaaaacgtggcggcgtgaccgcaatggaggcagtgcatgcatcgcgca
atgcactgacgggtgcccccctgAACCTGACCCCGGACCAAGTGGTGGCTATCGCCAGCCACGATGGCGG
CAAGCAAGCGCTCGAAACGGTGCAGCGGCTGTTGCCGGTGCTGTGCCAGGACCATGGCCTGACCCCGGAC
CAAGTGGTGGCTATCGCCAGCCACGATGGCGGCAAGCAAGCGCTCGAAACGGTGCAGCGGCTGTTGCCGG
TGCTGTGCCAGGACCATGGCCTGACCCCGGACCAAGTGGTGGCTATCGCCAGCCACGATGGCGGCAAGCA
AGCGCTCGAAACGGTGCAGCGGCTGTTGCCGGTGCTGTGCCAGGACCATGGCCTGACCCCGGACCAAGTG
GTGGCTATCGCCAGCCACGATGGCGGCAAGCAAGCGCTCGAGCGGCTGTTGCCGGTGCTGT
GCCAGGACCATGGCCTGACCCCGGACCAAGTGGTGGCTATCGCCAGCAACATTGGCGGCAAGCAAGCGCT
CGAAACGGTGCAGCGGCTGTTGCCGGTGCTGTGCCAGGACCATGGCCTGACCCCGGACCAAGTGGTGGCT
ATCGCCAGCAACAATGGCGGCAAGCAAGCGCTCGAAACGGTGCAGCGGCTGTTGCCGGTGCTGTGCCAGG
ACCATGGCCTGACCCCGGACCAAGTGGTGGCTATCGCCAGCAACAATGGCGGCAAGCAAGCGCTCGAAAC
GGTGCAGCGGCTGTTGCCGGTGCTGTGCCAGGACCATGGCCTGACCCCGGACCAAGTGGTGGCTATCGCC
AGCAACATTGGCGGCAAGCAAGCGCTCGAAACGGTGCAGCGGCTGTTGCCGGTGCTGTGCCAGGACCATG
GCCTGACCCCGGACCAAGTGGTGGCTATCGCCAGCAACATTGGCGGCAAGCAAGCGCTCGAAACGGTGCA
GCGGCTGTTGCCGGTGCTGTGCCAGGACCATGGCCTGACCCCGGACCAAGTGGTGGCTATCGCCAGCAAC
ATTGGCGGCAAGCAAGCGCTCGAAACGGTGCAGCGGCTGTTGCCGGTGCTGTGCCAGGACCATGGCCTGA
CCCCGGACCAAGTGGTGGCTATCGCCAGCAACAATGGCGGCAAGCAAGCGCTCGAAACGGTGCAGCGGCT
GTTGCCGGTGCTGTGCCAGGACCATGGCCTGACCCCGGACCAAGTGGTGGCTATCGCCAGCAACGGTGGC
GGCAAGCAAGCGCTCGAAACGGTGCAGCGGCTGTTGCCGGTGCTGTGCCAGGACCATGGCCTGACCCCGG
ACCAAGTGGTGGCTATCGCCAGCAACGGTGGCGGCAAGCAAGCGCTCGAAACGGTGCAGCGGCTGTTGCC
GGTGCTGTGCCAGGACCATGGCCTGACCCCGGACCAAGTGGTGGCTATCGCCAGCAACGGTGGCGGCAAG
CAAGCGCTCGAAACGGTGCAGCGGCTGTTGCCGGTGCTGTGCCAGGACCATGGCCTGACCCCGGACCAAG
TGGTGGCTATCGCCAGCAACATTGGCGGCAAGCAAGCGCTCGAAACGGTGCAGCGGCTGTTGCCGGTGCT
GTGCCAGGACCATGGCCTGACCCCGGACCAAGTGGTGGCTATCGCCAGCAACATTGGCGGCAAGCAAGCG
CTCGAAACGGTGCAGCGGCTGTTGCCGGTGCTGTGCCAGGACCATGGCCTGACCCCGGACCAAGTGGTGG
CTATCGCCAGCAACAATGGCGGCAAGCAAGCGCTCGAAACGGTGCAGCGGCTGTTGCCGGTGCTGTGCCA
GGACCATGGCCTGACCCCGGACCAAGTGGTGGCTATCGCCAGCAACATTGGCGGCAAGCAAGCGCTCGAA
ACGGTGCAGCGGCTGTTGCCGGTGCTGTGCCAGGACCATGGCCTGACCCCGGACCAAGTGGTGGCtatcg
ccagcaacggtggcggcaagcaagcgctcgaaagcattgtggcccagctgagccggcctgatccggcgtt
ggccgcgttgaccaacgacgaccacctcgtcgccttggcctgcctcggcggacgtcctgccatggatgca
gtgaaaaagggattgccgcacgcgccggaattgatcagaagagtcaatcgccgtattggcgaacgcacgt
cccatcgcgttgccGgatcCaAGGCTAGCCCGAAAAAGAAACGCAAAGTTGGGCGCGCCGACGCGCTGGA
CGATTTCGATCTCGACATGCTGGGTTCTGATGCCCTCGATGACTTTGACCTGGATATGTTGGGAAGCGAC
GCATTGGATGACTTTGATCTGGACATGCTCGGCTCCGATGCTCTGGACGATTTCGATCTCGATATGTTAA
TTAACTACCCGTACGACGTTCCGGACTACGCTTCTTGA SEQ ID NO: 96: ERBB2 TALE G polypeptide
MDYKDHDGDYKDHDIDYKDDDDKMAPKKKRKVGRGSVDLRTLGYSQQQQEKIKPKVRSTVAQHHEALVGH
GFTHAHIVALSQHPAALGTVAVTYQHIITALPEATHEDIVGVKQWSGARALEALLTDAGELRGPPLQLD
TGQLVKIAKRGGVTAMEAVHASRNALTGAPLNLTPDQVVAIASHDGGKQALETVQRLLPVLCQDHGLTPD
QVVAIASHDGGKQALETVQRLLPVLCQDHGLTPDQVVAIASHDGGKQALETVQRLLPVLCQDHGLTPDQV
VAIASHDGGKQALETVQRLLPVLCQDHGLTPDQVVAIASNIGGKQALETVQRLLPVLCQDHGLTPDQVVA
IASNNGGKQALETVQRLLPVLCQDHGLTPDQVVAIASNNGGKQALETVQRLLPVLCQDHGLTPDQVVAIA
SNIGGKQALETVQRLLPVLCQDHGLTPDQVVAIASNIGGKQALETVQRLLPVLCQDHGLTPDQVVAIASN
IGGKQALETVQRLLPVLCQDHGLTPDQVVAIASNNGGKQALETVQRLLPVLCQDHGLTPDQVVAIASNGG
GKQALETVQRLLPVLCQDHGLTPDQVVAIASNGGGKQALETVQRLLPVLCQDHGLTPDQVVAIASNGGGK
QALETVQRLLPVLCQDHGLTPDQVVAIASNIGGKQALETVQRLLPVLCQDHGLTPDQVVAIASNIGGKQA
LETVQRLLPVLCQDHGLTPDQVVAIASNNGGKQALETVQRLLPVLCQDHGLTPDQVVAIASNIGGKQALE
TVQRLLPVLCQDHGLTPDQVVAIASNGGGKQALESIVAQLSRPDPALAALTNDDHLVALACLGGRPAMDA
VKKGLPHAPELIRRVNRRIGERTSHRVAGSKASPKKKRKVGRADALDDFDLDMLGSDALDDFDLDMLGSD
ALDDFDLDMLGSDALDDFDLDMLINYPYDVPDYAS SEQ ID NO: 97: ERBB2 TALE H nucleotide
ATGGACTACAAAGACCATGACGGTGATTATAAAGATCATGACATCGATTACAAGGATGACGATGACAAGa
tggcccccaagaagaagaggaaggtgggccgcGgatcTgtggatctacgcacgctcggctacagtcagca
gcagcaagagaagatcaaaccgaaggtgcgttcgacagtggcgcagcaccacgaggcactggtgggccat
gggtttacacacgcgcacatcgttgcgctcagccaacacccggcagcgttagggaccgtcgctgtcacgt
atcagcacataatcacggcgttgccagaggcgacacacgaagacatcgttggcgtcggcaaacagtggtc
cggcgcacgcgccctggaggccttgctcacgggatgcggggagttgagaggtccgccgttacagttggac
acaggccaacttgtgaagattgcaaaacgtggcggcgtgaccgcaatggaggcagtgcatgcatcgcgca
atgcactgacgggtgcccccctgAACCTGACCCCGGACCAAGTGGTGGCTATCGCCAGCCACGATGGCGG
CAAGCAAGCGCTCGAAACGGTGCAGCGGCTGTTGCCGGTGCTGTGCCAGGACCATGGCCTGACCCCGGAC
CAAGTGGTGGCTATCGCCAGCAACAATGGCGGCAAGCAAGCGCTCGAAACGGTGCAGCGGCTGTTGCCGG
TGCTGTGCCAGGACCATGGCCTGACCCCGGACCAAGTGGTGGCTATCGCCAGCAACATTGGCGGCAAGCA
AGCGCTCGAAACGGTGCAGCGGCTGTTGCCGGTGCTGTGCCAGGACCATGGCCTGACCCCGGACCAAGTG
GTGGCTATCGCCAGCAACGGTGGCGGCAAGCAAGCGCTCGAAACGGTGCAGCGGCTGTTGCCGGTGCTGT
GCCAGGACCATGGCCTGACCCCGGACCAAGTGGTGGCTATCGCCAGCAACAATGGCGGCAAGCAAGCGCT
CGAAACGGTGCAGCGGCTGTTGCCGGTGCTGTGCCAGGACCATGGCCTGACCCCGGACCAAGTGGTGGCT
ATCGCCAGCAACGGTGGCGGCAAGCAAGCGCTCGAAACGGTGCAGCGGCTGTTGCCGGTGCTGTGCCAGG
ACCATGGCCTGACCCCGGACCAAGTGGTGGCTATCGCCAGCAACAATGGCGGCAAGCAAGCGCTCGAAAC
GGTGCAGCGGCTGTTGCCGGTGCTGTGCCAGGACCATGGCCTGACCCCGGACCAAGTGGTGGCTATCGCC
AGCAACATTGGCGGCAAGCAAGCGCTCGAAACGGTGCAGCGGCTGTTGCCGGTGCTGTGCCAGGACCATG
GCCTGACCCCGGACCAAGTGGTGGCTATCGCCAGCCACGATGGCGGCAAGCAAGCGCTCGAAACGGTGCA
GCGGCTGTTGCCGGTGCTGTGCCAGGACCATGGCCTGACCCCGGACCAAGTGGTGGCTATCGCCAGCAAC
GGTGGCGGCAAGCAAGCGCTCGAAACGGTGCAGCGGCTGTTGCCGGTGCTGTGCCAGGACCATGGCCTGA
CCCCGGACCAAGTGGTGGCTATCGCCAGCAACAATGGCGGCAAGCAAGCGCTCGAAACGGTGCAGCGGCT
GTTGCCGGTGCTGTGCCAGGACCATGGCCTGACCCCGGACCAAGTGGTGGCTATCGCCAGCAACGGTGGC
```

| TALE-TF SEQUENCES |
|---|
| GGCAAGCAAGCGCTCGAAACGGTGCAGCGGCTGTTGCCGGTGCTGTGCCAGGACCATGGCCTGACCCCGG<br>ACCAAGTGGTGGCTATCGCCAGCCACGATGGCGGCAAGCAAGCGCTCGAAACGGTGCAGCGGCTGTTGCC<br>GGTGCTGTGCCAGGACCATGGCCTGACCCCGGACCAAGTGGTGGCTATCGCCAGCAACGGTGGCGGCAAG<br>CAAGCGCTCGAAACGGTGCAGCGGCTGTTGCCGGTGCTGTGCCAGGACCATGGCCTGACCCCGGACCAAG<br>TGGTGGCTATCGCCAGCCACGATGGCGGCAAGCAAGCGCTCGAAACGGTGCAGCGGCTGTTGCCGGTGCT<br>GTGCCAGGACCATGGCCTGACCCCGGACCAAGTGGTGGCTATCGCCAGCCACGATGGCGGCAAGCAAGCG<br>CTCGAAACGGTGCAGCGGCTGTTGCCGGTGCTGTGCCAGGACCATGGCCTGACCCCGGACCAAGTGGTGG<br>ctatcgccagcaacggtgagcggcaagcaagcgctcgaaagcattgtggcccagctgagccggcctgatcc<br>ggcgttggccgcgttgaccaacgacgaccacctcgtcgcctggcctgcctcggcggacgtcctgccatg<br>gatgcagtgaaaaagggattgccgcacgcgccggaattgatcagaagagtcaatcgccgtattggcgaac<br>gcacgtccatcgcgttgccGgatcCaAGGCTAGCCCGAAAAAGAAACGCAAAGTTGGGCGCGCCGACGC<br>GCTGGACGATTTCGATCTCGACATGCTGGGTTCTGATGCCCTCGATGACTTTGACCTGGATATGTTGGGA<br>AGCGACGCATTGGATGACTTTGATCTGGACATGCTCGGCTCCGATGCTCTGGACGATTTCGATCTCGATA<br>TGTTAATTAACTACCCGTACGACGTTCCGGACTACGCTTCTTGA<br><br>SEQ ID NO: 98: ERBB2 TALE H polypeptide<br>MDYKDHDGDYKDHDIDYKDDDDKMAPKKKRKVGRGSVDLRTLGYSQQQQEKIKPKVRSTVAQHHEALVGH<br>GFTHAHIVALSQHPAALGTVAVTYQHIITALPEATHEDIVGVGKQWSGARALEALLTDAGELRGPPLQLD<br>TGQLVKIAKRGGVTAMEAVHASRNALTGAPLNLTPDQVVAIASHDGGKQALETVQRLLPVLCQDHGLTPD<br>QVVAIASNNGGKQALETVQRLLPVLCQDHGLTPDQVVAIASNIGGKQALETVQRLLPVLCQDHGLTPDQV<br>VAIASNGGGKQALETVQRLLPVLCQDHGLTPDQVVAIASNNGGKQALETVQRLLPVLCQDHGLTPDQVVA<br>IASNGGGKQALETVQRLLPVLCQDHGLTPDQVVAIASNNGGKQALETVQRLLPVLCQDHGLTPDQVVAIA<br>SNIGGKQALETVQRLLPVLCQDHGLTPDQVVAIASHDGGKQALETVQRLLPVLCQDHGLTPDQVVAIASN<br>GGGKQALETVQRLLPVLCQDHGLTPDQVVAIASNNGGKQALETVQRLLPVLCQDHGLTPDQVVAIASNGG<br>GKQALETVQRLLPVLCQDHGLTPDQVVAIASHDGGKQALETVQRLLPVLCQDHGLTPDQVVAIASNGGGK<br>QALETVQRLLPVLCQDHGLTPDQVVAIASHDGGKQALETVQRLLPVLCQDHGLTPDQVVAIASHDGGKQA<br>LETVQRLLPVLCQDHGLTPDQVVAIASNGGGKQALESIVAQLSRPDPALAALTNDDHLVALACLGGRPAM<br>DAVKKGLPHAPELIRRVNRRIGERTSHRVAGSKASPKKKRKVGRADALDDFDLDMLGSDALDDFDLDMLG<br>SDALDDFDLDMLGSDALDDFDLDMLINYPYDVPDYAS |

What is claimed is:

1. A method of increasing gene expression of a target gene in a mammalian cell, the method comprising administering to the mammalian cell in vitro two or more transcription activator-like effector transcription factors (TALE-TFs) that bind to at least a first target region and a second target region in the target gene, wherein at least one target region is within a non-open chromatin region, and wherein gene expression is increased in the mammalian cell without the use of a chromatin modifying drug, wherein the mammalian cell is a human cell, and wherein the two or more TALE-TFs each comprise an amino acid sequence selected from one of the following groups:
   a) SEQ ID NOs: 44, 46, 48, 50, 52, or 54;
   b) SEQ ID NOs: 56, 58, 60, 62, 64, 66, or 68;
   c) SEQ ID NOs: 70, 72, 74, 76, 78, 80, or 82; and
   d) SEQ ID NOs: 84, 86, 88, 90, 92, 94, 96, or 98.

* * * * *